US008343928B2

(12) United States Patent
Doronina et al.

(10) Patent No.: US 8,343,928 B2
(45) Date of Patent: Jan. 1, 2013

(54) MONOMETHYLVALINE COMPOUNDS HAVING PHENYLALANINE SIDE-CHAIN REPLACEMENTS AT THE C-TERMINUS

(75) Inventors: Svetlana O. Doronina, Snohomish, WA (US); Toni Beth Kline, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 1248 days.

(21) Appl. No.: 11/994,809

(22) PCT Filed: Jul. 7, 2006

(86) PCT No.: PCT/US2006/026352
§ 371 (c)(1),
(2), (4) Date: May 30, 2008

(87) PCT Pub. No.: WO2007/008603
PCT Pub. Date: Jan. 18, 2007

(65) Prior Publication Data
US 2009/0018086 A1    Jan. 15, 2009

Related U.S. Application Data

(60) Provisional application No. 60/697,767, filed on Jul. 7, 2005.

(51) Int. Cl.
*A61K 38/02* (2006.01)
(52) U.S. Cl. .................................................. 514/19.3
(58) Field of Classification Search .................. None
See application file for complete search history.

(56) References Cited

U.S. PATENT DOCUMENTS

| | | | |
|---|---|---|---|
| 4,753,894 A | 6/1988 | Frankel et al. |
| 4,816,397 A | 3/1989 | Boss et al. |
| 4,816,567 A | 3/1989 | Cabilly et al. |
| 4,943,628 A | 7/1990 | Rosen et al. |
| 4,978,744 A | 12/1990 | Pettit et al. |
| 5,047,335 A | 9/1991 | Paulson et al. |
| 5,169,774 A | 12/1992 | Frankel et al. |
| 5,225,539 A | 7/1993 | Winter |
| 5,229,275 A | 7/1993 | Goroff |
| 5,278,299 A | 1/1994 | Wong et al. |
| 5,286,637 A | 2/1994 | Veronese et al. |
| 5,410,024 A | 4/1995 | Petit et al. |
| 5,500,362 A | 3/1996 | Robinson et al. |
| 5,510,261 A | 4/1996 | Goochee et al. |
| 5,530,097 A | 6/1996 | Pettit et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,583,024 A | 12/1996 | McElroy et al. |
| 5,585,089 A | 12/1996 | Queen et al. |
| 5,587,458 A | 12/1996 | King et al. |
| 5,589,369 A | 12/1996 | Seidman et al. |
| 5,591,669 A | 1/1997 | Krimpenfort et al. |
| 5,625,126 A | 4/1997 | Lonberg et al. |
| 5,629,197 A | 5/1997 | Ring et al. |
| 5,633,425 A | 5/1997 | Lonberg et al. |
| 5,635,483 A | 6/1997 | Pettit et al. |
| 5,641,870 A | 6/1997 | Rinderknecht et al. |
| 5,654,399 A | 8/1997 | Sakakibara et al. |
| 5,661,016 A | 8/1997 | Lonberg et al. |
| 5,663,149 A | 9/1997 | Pettit et al. |
| 5,674,713 A | 10/1997 | McElroy et al. |
| 5,700,670 A | 12/1997 | Yamagishi et al. |
| 5,731,168 A | 3/1998 | Carter et al. |
| 5,767,237 A | 6/1998 | Sakakibara et al. |
| 5,780,588 A | 7/1998 | Pettit et al. |
| 5,821,337 A | 10/1998 | Carter et al. |
| 5,840,699 A | 11/1998 | Sakakibara et al. |
| 5,888,809 A | 3/1999 | Allison |
| 5,939,527 A | 8/1999 | Barlozzari et al. |
| 6,004,934 A | 12/1999 | Sakakibara et al. |
| 6,048,720 A | 4/2000 | Dalborg et al. |
| 6,054,297 A | 4/2000 | Carter et al. |
| 6,054,561 A | 4/2000 | Ring |
| 6,124,431 A | 9/2000 | Sakakibara et al. |
| 6,214,345 B1 | 4/2001 | Firestone et al. |
| 6,323,315 B1 | 11/2001 | Pettit et al. |
| 6,407,213 B1 | 6/2002 | Carter et al. |
| 6,569,834 B1 | 5/2003 | Pettit et al. |

(Continued)

FOREIGN PATENT DOCUMENTS

CA      2114156 A1    7/1994

(Continued)

OTHER PUBLICATIONS

Supplementary European Search Report mailed on Sep. 22, 2010, for EP Application No. 06786489.2, 5 pages.
U.S. Appl. No. 11/833,954, filed Aug. 3, 2007, Doronina, et al.
U.S. Appl. No. 11/994,459, Doronina et al.
Alley et al., "Controlling the location of drug attachment in antibody-drug conjugates," *Proceedings of the AACR*, vol. 45, abstract # 627 (2004).
Afar et al., "Preclinical validation of anti-TMEFF2-auristatin E-conjugated antibodies in the treatment of prostate cancer," *Molecular Cancer Therapeutics*, 3(8):921-932 (2004).
Bhaskar et al., "E-Selectin Up-Regulation Allows for Targeted Drug Delivery in Prostate Cancer," *Cancer Research*, 63:6387-6394 (2003).
Carter, "Improving the Efficacy of Antibody-Based Cancer Therapies," *Nature Reviews* 1:118-129 (2001).

(Continued)

*Primary Examiner* — Cecilia J Tsang
*Assistant Examiner* — Ronald Niebauer
(74) *Attorney, Agent, or Firm* — Kilpatrick Townsend & Stockton LLP

(57) ABSTRACT

Auristatin peptide analogs of MeVal-Val-Dil-Dap-Phe (MMAF) are provided having C-terminal phenylalanine residue side chain replacements or modifications which are provided alone or attached to ligands through various linkers. The related conjugates can target specific cell types to provide therapeutic benefit.

26 Claims, No Drawings

U.S. PATENT DOCUMENTS

| | | | |
|---|---|---|---|
| 6,620,911 | B1 | 9/2003 | Petit et al. |
| 6,639,055 | B1 | 10/2003 | Carter et al. |
| 6,884,869 | B2 | 4/2005 | Senter et al. |
| 7,056,942 | B2 * | 6/2006 | Hildesheim et al. ......... 514/411 |
| 7,498,298 | B2 | 3/2009 | Doronina et al. |
| 7,662,387 | B2 | 2/2010 | Law |
| 7,745,394 | B2 | 6/2010 | Doronina et al. |
| 7,964,566 | B2 | 6/2011 | Doronina et al. |
| 7,964,567 | B2 | 6/2011 | Doronina et al. |
| 2002/0001587 | A1 | 1/2002 | Erickson et al. |
| 2003/0096743 | A1 | 5/2003 | Senter et al. |
| 2003/0130189 | A1 | 7/2003 | Senter et al. |
| 2004/0006215 | A1 | 1/2004 | Keler et al. |
| 2004/0018194 | A1 | 1/2004 | Francisco et al. |
| 2004/0235068 | A1 | 11/2004 | Levinson |
| 2005/0106644 | A1 | 5/2005 | Cairns et al. |
| 2005/0107595 | A1 | 5/2005 | Cairns et al. |
| 2005/0232929 | A1 | 10/2005 | Kadkhodayan et al. |
| 2005/0238649 | A1 | 10/2005 | Doronina et al. |
| 2005/0238650 | A1 | 10/2005 | Crowley et al. |
| 2005/0256030 | A1 | 11/2005 | Feng |
| 2006/0073152 | A1 | 4/2006 | Dennis |
| 2006/0182751 | A1 | 8/2006 | Gazzard et al. |
| 2006/0233794 | A1 | 10/2006 | Law et al. |
| 2007/0092520 | A1 | 4/2007 | Dennis et al. |
| 2007/0134243 | A1 | 6/2007 | Gazzard et al. |
| 2007/0212356 | A1 | 9/2007 | Chen et al. |
| 2009/0047296 | A1 | 2/2009 | Doronina et al. |
| 2009/0111756 | A1 | 4/2009 | Doronina et al. |

FOREIGN PATENT DOCUMENTS

| | | |
|---|---|---|
| JP | 06-234790 A | 8/1994 |
| JP | 09-77791 A | 3/1997 |
| WO | WO 99/35164 A1 | 7/1999 |
| WO | WO 01/018032 A2 | 3/2001 |
| WO | WO 01/18032 A2 | 3/2001 |
| WO | WO 02/088172 A2 | 11/2002 |
| WO | WO 03/008378 A1 | 1/2003 |
| WO | WO 03/034903 A2 | 5/2003 |
| WO | WO 03/043583 A2 | 5/2003 |
| WO | WO 2004/010957 A2 | 2/2004 |
| WO | WO 2004/032828 A2 | 4/2004 |
| WO | WO 2004/073656 A2 | 9/2004 |
| WO | WO 2005/001038 A2 | 1/2005 |
| WO | WO 2005/081711 A2 | 9/2005 |
| WO | WO 2006/034488 A3 | 3/2006 |
| WO | WO 2006/083936 A3 | 8/2006 |
| WO | WO 2007/001851 A3 | 1/2007 |
| WO | WO 2007/008848 A2 | 1/2007 |
| WO | WO 2007/109567 A1 | 9/2007 |

OTHER PUBLICATIONS

Dillman, "Monoclonal Antibodies for Treating Cancer," *Annals of Internal Medicine* 111:592-603 (1989).

Doronina et al., "Development of potent monoclonal antibody auristatin conjugates for cancer therapy," *Nature Biotechnology*, 21(7):778-784 (2003) + Erratum, *Nature Biotechnology*, 21(8):941 (2003).

Doronina et al., "Immunoconjugates comprised of drugs with impaired cellular permeability: A new approach to targeted therapy," SciFinder search result, abstract of paper from 228th ACS National Meeting held in Philadelphia, PA, Aug. 22-26, 2004.

Doronina et al., "Enhanced Activity of Monomethylauristatin F through Monoclonal Antibody Delivery: Effects of Linker Technology on Efficacy and Toxicity," *Bioconjugate Chem.*, 17:114-124 (2006).

Emery et al., "Humanized monoclonal antibodies for therapeutic applications," *Exp. Opin. Invest. Drugs* 3(3):241-251 (1994).

Francisco et al., "cAC10-vcMMAE, an anti-CD30-monomethyl auristatin E conjugate with potent and selective antitumor activity," *Blood*, 102(4):1458-1465 (2003).

Gaertner and Offord, "Site-specific attachment of functionalized poly(ethylene glycol) to the amino terminus of proteins." *Bioconj. Chem.*, 7(1):38-44, 1996.

Genet, J. P., "Recent studies on asymmetric hydrogenation. New catalysts and synthetic applications in organic synthesis," *Pure Appl. Chem.*, 74(1):77-83 (2002).

Hamblett et al., "Effect of drug loading on the pharmacology, pharmacokinetics, and toxicity of an anti-CD30 antibody-drug conjugate," *Proceedings of the AACR*, vol. 45, abstract # 624 (2004).

Inada et al., "Modification of proteins with polyethylene glycol derivatives." *Methods Enzymol.*, 242:65-90, 1994.

Kline et al., "Novel Antitumor Prodrugs Designed for Activation by Matrix Metalloproteinases-2 and -9," *Molecular Pharmaceutics*, 1(1):9-22 (2004).

Klussman et al., "Secondary mAb—vcMMAE conjugates are highly sensitive reporters of antibody internalization via the lysosome pathway," *Bioconjug Chem.*, 15(4):765-773 (2004).

Law et al., "CD70 is expressed on renal cell carcinoma and is a potential target for tumor cell elimination by antibody-drug conjugates," *Proceedings of the AACR*, vol. 45, abstract # 625 (2004).

Mao et al., "EphB2 as a Therapeutic Antibody Drug Target for the Treatment of Colorectal Cancer," *Cancer Research*, 64:781-788 (2004).

Meyer et al., "Recent Advances in Antibody Drug Conjugates for Cancer Therapy" *Annual Reports in Medical Chemistry*, 38(chapter 23):229-237 (2003).

Miyazaki et al., "Synthesis and Antitumor Activity of Novel Dolastatin 10 Analogs," *Chem. Pharm. Bull.*, 43(10):1706-1718 (1995).

Natsume et al., "Characterization of the Interaction of TZT-1027, a Potent Antitumor Agent, with Tubulin," *Jpn. J. Cancer*, 91:737-747 (2000).

Petit et al., "Antineoplastic agents 337. Synthesis of dolastatin 10 structural modifications," *Anti-Cancer Drug Design*, 10:529-544 (1995).

Petit et al., "Specific Activities of Dolastatin 10 and Peptide Derivatives against *Cryptococcus neoformans*," *Antimicrobial Agents and Chemotherapy*, 42(11):2961-2965 (1998).

Petit et al., "A Cobalt—Phosphine Complex Directed Reformatsky Approach to a Stereospecific Synthesis of the Dolastatin 10 Unit Dolaproine (Dap)$^1$," *J. Org. Chem.*, 66:8640-8642 (2001).

Pettit et al., "The Absolute Configuration and Synthesis of Natural (−)-Dolastatin 10," *J. Am. Chem. Soc.*, 111:5463-5465 (1989).

Pettit et al., "Dolastatins 24. Synthesis of (−)-dolastatin 10. X-Ray molecular structure of N,N-dimethylvalyl-valyl-dolaisoleuine *tert*-butyl ester," *J. Chem. Soc. Perkin Trans.1*, 5:859-863 (1996).

Pettit et al., "Antineoplastic agents 365. Dolastatin 10 SAR probes," *Anticancer Drug Des.*,13(4):243-277 (1998).

Press Release, "Seattle Genetics, Inc. (SGEN) To Present Advances in Preclinical Research At American Cancer Research Annual Meeting," Mar. 24, 2004, downloaded from internet on Aug. 31, 2004.

Schoffski et al., "Phase I and pharmacokinetic study of TZT-1027, a novel synthetic dolastatin 10 derivative, administered as a 1-hour intravenous infusion every 3 weeks in patients with advanced refractory cancer," *Annals of Oncology*, 15:671-679 (2004).

Senter et al., "Immunoconjugates comprised of drugs with impaired cellular permeability: A new approach to targeted therapy," *Proceedings of the AACR*, vol. 45, abstract # 623 (2004).

Thornber, "Isosterism and Molecular Modification in Drug Design." *Chem. Soc. Rev.*, 8(4):563-580, 1979.

Toki et al., "Protease-Mediated Fragmentation of p-Amidobenzyl Ethers: A New Strategy for the Activation of Anticancer Prodrugs," *J. Org. Chem.*, 67:1866-1872 (2002).

Vippagunta et al., "Crystalline Solids." *Adv. Drug Delivery Rev.*, 48: 3-26, 2001.

Woyke et al., "In Vitro Activities and Postantifungal Effects of the Potent Dolastatin 10 Derivative Auristatin PHE," *Antimicrobial Agents and Chemotherapy*, 45(12):3580-3584 (2001).

Woyke et al., "Effect of auristatin PHE on microtube integrity and nuclear localization in *Cryptococcus neoformans*," *Antimicrobial Agents and Chemotherapy*, 46(12):3802-3808 (2003).

International Search Report of Oct. 2, 2006 for PCT application PCT/US04/38392.

Written Opinion of Oct. 2, 2006 for PCT application PCT/US04/38392.

* cited by examiner

MONOMETHYLVALINE COMPOUNDS HAVING PHENYLALANINE SIDE-CHAIN REPLACEMENTS AT THE C-TERMINUS

CONTINUITY

This application is the U.S. National Phase entry under 35 U.S.C. §371 of International Patent Application No. PCT/US06/26352, filed Jul. 7, 2006 which claims priority from and the benefit of U.S. Provisional Application No. 60/697,767, filed Jul. 7, 2005; the disclosures of which are incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-15-1.TXT, created on Mar. 8, 2012, 4,096 bytes, machine format IBM-PC, MS-Windows operating system, is hereby incorporated by reference in its entirety for all purposes.

FIELD OF THE INVENTION

The present invention is directed to Drug Compounds, to Drug-Linker-Ligand Conjugates, Drug-Linker Compounds, and Drug-Ligand Conjugates; as well as to compositions including the same, and to methods for using the same to treat cancer, an autoimmune disease, an infectious disease and other pathological conditions. The invention also relates to methods of using Antibody-Drug Conjugate compounds in vitro, in situ, and in vivo for the diagnosis or treatment of mammalian cells, or associated pathological conditions.

BACKGROUND OF THE INVENTION

A great deal of interest has surrounded the use of monoclonal antibodies (mAbs) for the selective delivery of cytotoxic agents to tumor cells. MMAF (N-methylvaline-valine-dolaisoleuine-dolaproine-phenylalanine) is an auristatin that is relatively non-toxic, yet is highly potent in activity when conjugated to internalizing mAbs. MMAF has a charged C-terminal phenylalanine residue that attenuates its cytotoxic activity compared to its neutral counterpart, MMAE; this difference is most likely due to impaired intracellular access. However, conjugating MMAF to internalizing antibodies, like AC10 or 1F6, via a protease cleavable linker resulted in conjugates that are >2000 fold more potent on antigen positive cells as compared to unconjugated drug. Active targeting with mAbs facilitates intracellular delivery of MMAF; once MMAF is released from the conjugate inside cells the drug, it is presumably trapped due to its reduced ability to cross cellular membranes thus increasing its intracellular concentration and therefore the potency of the conjugate. Using cytotoxic drugs with impaired passive intracellular uptake can potentially lead to mAb-drug conjugates with reduced systemic toxicity. Indeed, non-specific cleavage of the linker in circulation would release a relatively non-toxic drug.

To expand and improve the auristatin class of drugs, and the corresponding antibody drug conjugates (ADCs), the side chain of the C-terminal phenylalanine residue of MMAF has been modified. This structural modification imparts unexpected properties to the resultant free drug and ADC.

The recitation of any reference in this application is not an admission that the reference is prior art to this application.

SUMMARY OF THE INVENTION

In one aspect, the present invention provides compounds and conjugates represented by the general formula $$L_v\text{-}[(LU)_{0\text{-}1}\text{-}(D)_{1\text{-}4}]_p$$

wherein L is H or a Ligand unit; LU is a Linker unit; v is 0 or 1; p is an integer of from 1 to 20; and D is a drug moiety having the formula:

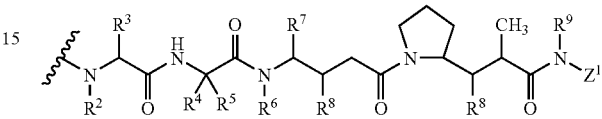

D wherein $R^2$ is selected from H and $C_1$-$C_8$ alkyl; $R^3$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); $R^4$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); $R^5$ is selected from H and methyl; or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6; $R^6$ is selected from H and $C_1$-$C_8$ alkyl; $R^7$ is selected from H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); each $R^8$ is independently selected from H, OH, $C_1$-$C_8$ alkyl, $C_3$-$C_8$ carbocycle and O—($C_1$-$C_8$ alkyl); wherein each $X^1$ is a $C_1$-$C_{10}$ alkylene and the moiety —$NR^9Z^1$ is a phenylalanine bioisostere with a modified amino acid side chain; or a pharmaceutically acceptable salt or solvate thereof.

The compounds of the above formulas are useful for treating disorders, such as cancer, autoimmune disease or infectious disease, in a patient or useful as an intermediate for the synthesis of a Drug-Linker Compound or a Drug-Linker-Ligand Conjugate (e.g., a Drug-Linker-Antibody Conjugate, a Drug-Ligand Conjugate, or a Drug-Ligand Conjugate having a cleavable Drug unit).

In another aspect, compositions are provided that include an effective amount of a compound of the above formulae and a pharmaceutically acceptable carrier or vehicle.

In yet another aspect, methods for killing or inhibiting the multiplication of a tumor cell or cancer cell are provided. In still another aspect, methods for treating cancer are provided. In still another aspect, methods for killing or inhibiting the replication of a cell that expresses an autoimmune antibody are provided. In yet another aspect, methods for treating an autoimmune disease are provided. In still another aspect, methods for treating an infectious disease are provided. In yet another aspect, methods for preventing the multiplication of a tumor cell or cancer cell are provided. In still another aspect, methods for preventing cancer are provided. In still another aspect, methods for preventing the multiplication of a cell that expresses an autoimmune antibody are provided. In yet another aspect, methods for preventing an autoimmune disease are provided. In still another aspect, methods for preventing an infectious disease are provided.

In another aspect, a Drug Compound is provided that can be used as an intermediate for the synthesis of a Drug-Linker Compound having a cleavable Drug unit.

In another aspect, a Drug-Linker Compound is provided that can be used as an intermediate for the synthesis of a Drug-Linker-Ligand Conjugate.

In another aspect, an assay is provided for detecting cancer cells, the assay including:
(a) exposing the cells to an Antibody Drug Conjugate compound; and
(b) determining the extent of binding of the Antibody Drug Conjugate compound to the cells.

The invention will best be understood by reference to the following detailed description of the exemplary embodiments, taken in conjunction with the accompanying drawings, figures, and schemes. The discussion below is descriptive, illustrative and exemplary and is not to be taken as limiting the scope defined by any appended claims.

DETAILED DESCRIPTION OF THE INVENTION

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" herein is used in the broadest sense and specifically covers intact monoclonal antibodies, polyclonal antibodies, monospecific antibodies, multispecific antibodies (e.g., bispecific antibodies) formed from at least two intact antibodies, and antibody fragments, that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, *Immuno. Biology, 5th Ed.*, Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In one aspect, however, the antibody is of human, murine, or rabbit origin. An antibody can be, for example, human, humanized or chimeric, a single chain antibody, an Fv fragment, an Fab fragment, an F(ab') fragment, an F(ab')$_2$ fragment, a fragment(s) produced by a Fab expression library, anti-idiotypic (anti-Id) antibodies, and epitope-binding fragments of any of the above which immunospecifically bind to a target antigen (e.g., a cancer cell antigen, a viral antigen or a microbial antigen).

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Antibody fragments" comprise a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, and multispecific antibodies formed from antibody fragment(s).

An "intact" antibody is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An intact antibody may have one or more "effector functions" which refers to those biological activities attributable to the Fc region (e.g., a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

A "native sequence" polypeptide is one which has the same amino acid sequence as a polypeptide, e.g., a tumor-associated antigen receptor, derived from nature. Such native sequence polypeptides can be isolated from nature or can be produced by recombinant or synthetic means. Thus, a native sequence polypeptide can have the amino acid sequence of a naturally-occurring human polypeptide, a murine polypeptide, or a polypeptide from any other mammalian species.

The term "amino acid sequence variant" refers to polypeptides having amino acid sequences that differ to some extent from a native sequence polypeptide. Ordinarily, amino acid sequence variants will possess at least about 70% homology with at least one receptor binding domain of a native ligand, or with at least one ligand binding domain of a native receptor, such as a tumor-associated antigen. In other aspects, they will be at least about 80%, at least about 90%, or at least 95% homologous with such receptor or ligand binding domains. The amino acid sequence variants possess substitutions, deletions, and/or insertions at certain positions within the amino acid sequence of the native amino acid sequence.

"Sequence identity" is defined as the percentage of residues in the amino acid sequence variant that are identical after aligning the sequences and introducing gaps, if necessary, to achieve the maximum percent sequence identity. A preferred, non-limiting example of a mathematical algorithm utilized for the comparison of two sequences is the algorithm of Karlin and Altschul, 1990, *Proc. Natl. Acad. Sci. USA* 87:2264-2268, modified as in Karlin and Altschul, 1993, *Proc. Natl. Acad. Sci. USA* 90:5873-5877. Such an algorithm is incorporated into the NBLAST and XBLAST programs of Altschul et al., 1990, *J. Mol. Biol.* 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, *Nucleic Acids Res.* 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, *Comput. Appl. Biosci.* 10:3-5; and FASTA described in Pearson and Lipman, 1988, *Proc. Natl. Acad. Sci. USA* 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, *Methods Enzymol.* 266:383-402. In some embodiments, the two sequences that are compared are the same length after gaps are introduced within the sequences, as appropriate (e.g., excluding additional sequence extending beyond the sequences being compared).

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, 1991, *Annu. Rev. Immunol.* 9:457-92. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., 1998, *Proc. Natl. Acad. Sci. USA* 95:652-656.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), that have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in Daëron, 1997, *Annu. Rev. Immunol.* 15:203-234). FcRs are reviewed in Ravetch and Kinet, 1991, *Annu. Rev. Immunol.*, 9:457-92; Capel et al., 1994, *Immunomethods* 4:25-34 (1994); and de Haas et al., 1995, *J. Lab. Clin. Med.* 126:330-41. Other FcRs, including those to be identified in the future, are encompassed by the term "FcR" herein. The term also includes the neonatal receptor, FcRn, which is responsible for the transfer of maternal IgGs to the fetus. (See, e.g., Guyer et al., 1976, *J. Immunol.* 117:587; and Kim et al., 1994, *J. Immunol.* 24:249).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., 1996, *J. Immunol. Methods* 202:163, may be performed.

The term "variable" refers to certain portions of the variable domains of antibodies that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al. (*Sequences of Proteins of Immunological Interest*, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined.

"Single-chain Fv" or "scFv" antibody fragments comprise the $V_H$ and $V_L$ domains of antibody, wherein these domains are present in a single polypeptide chain. Typically, the Fv polypeptide further comprises a polypeptide linker between the $V_H$ and $V_L$ domains which enables the scFv to form the desired structure for antigen binding. For a review of scFv, see Plütckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a variable heavy domain ($V_H$) connected to a variable light domain ($V_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, *Proc. Natl. Acad. Sci. USA* 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, *Nature* 321:522-525; Riechmann et al., 1988, *Nature* 332:323-329; and Presta, 1992, *Curr. Op. Struct. Biol.* 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. >50% of a population, of a collection or a sample.

The term "intracellular metabolite" refers to a compound resulting from a metabolic process or reaction inside a cell on a Drug-Linker-Ligand conjugate (e.g., an antibody drug conjugate (ADC)). The metabolic process or reaction may be an enzymatic process such as proteolytic cleavage of a peptide linker of the ADC, by hydrolysis of a functional group such as a hydrazone, ester, or amide, or by proteolytic degradation of the Drug-Linker-Ligand conjugate (e.g., releasing a cystyl-Linker-Drug fragment). Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an Drug-Ligand Conjugate, a Drug-Linker-Ligand Conjugate, an Antibody Drug Conjugate (ADC) or the like, whereby the covalent attachment, e.g., the linker, between the drug moiety (D) and the antibody (Ab) is broken, resulting in the free Drug, a Drug-Linker Compound or other metabolite of the Conjugate dissociated from the antibody inside the cell. The cleaved moieties of the Drug-Ligand Conjugate, a Drug-Linker-Ligand Conjugate or ADC are thus intracellular metabolites.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or anti-proliferation effect of an antibody drug conjugate compound or an intracellular metabolite of an antibody drug conjugate compound. Cytotoxic activity may be expressed as the $IC_{50}$ value which is the concentration (molar or mass) per unit volume at which half the cells survive.

A "disorder" is any condition that would benefit from treatment. This includes chronic and acute disorders or diseases including those pathological conditions which predispose the mammal to the disorder in question. Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "cytotoxic agent" as used herein refers to a substance that inhibits or prevents the function of cells and/or causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof. In one aspect, the term does not include a radioactive isotope(s).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, and IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as, for example, anti-CD20, CD30, CD33, CD40, CD70, BCMA, or Lewis Y antibodies and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indication(s), usage, dosage, administration, contraindications and/or warnings concerning the use of such therapeutic products.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence, for example, if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers can be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis), respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjogren's syndrome, Stevens-Johnson syndrome, solid organ transplant rejection (including pretreatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic throbocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The term "alkyl" refers to a straight chain or branched, saturated or unsaturated hydrocarbon having the indicated number of carbon atoms (e.g., "$C_1$-$C_8$ alkyl" refers to an alkyl group having from 1 to 8 carbon atoms). When the number of carbon atoms is not indicated, the alkyl group has from 1 to 8 carbon atoms. Representative straight chain "$C_1$-$C_8$ alkyl" groups include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and 2-methylbutyl; unsaturated $C_2$-$C_8$ alkyls include, but are not limited to, vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl and -3-methyl-1 butynyl. An alkyl group can be unsubstituted or substituted with one or more groups including, but not limited to, —O—($C_1$-$C_8$ alkyl), aryl, —C(O)R', —OC(O)R', —C(O)OR', —C(O)$NH_2$, —OH—C(O)NHR', —C(O)N(R')$_2$—NHC(O)R', —$SO_3$R', —S(O)$_2$R', —S(O)R', —SR', -halogen, —$N_3$, —$NH_2$, —NH(R'), —N(R')$_2$ and —CN; where each R' is independently selected from H, unsubstituted $C_1$-$C_8$ alkyl and aryl.

"Alkenyl" refers to a $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" refers to a $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like. A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. A carbocyclic aromatic group (aryl) or a heterocyclic aromatic group (heteroaryl) can be unsubstituted or substituted with one or more groups including, but not limited to $C_1$-$C_8$ alkyl, —O—($C_1$-$C_8$ alkyl), —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from H, $C_1$-$C_8$ alkyl and unsubstituted aryl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 6 to 14 carbon atoms.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g., the alkyl moiety, including alkanyl, alkenyl or alkynyl groups, of the heteroarylalkyl group is 1 to 6 carbon atoms and the heteroaryl moiety is 5 to 14 ring atoms, typically 1 to 3 heteroatoms selected from N, O, P, and S, with the remainder being carbon atoms. The heteroaryl moiety of the heteroarylalkyl group may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —$NR_2$, —$NR_3$, =NR, —$CX_3$, —CN, —OCN, —SCN, —N=C=O, —NCS, —NO, —$NO_2$, =$N_2$, —$N_3$, —NRC(=O)R, —C(=O)R, —C(=O)$NR_2$, —$SO_3^-$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —$PO_3H_2$, —$AsO_2H_2$, —C(=O)R, —C(=O)X, —C(=S)R, —$CO_2$R, —$CO_2^-$, —C(=S)OR, —C(=O)SR, —C(=S)SR, —C(=O)$NR_2$, —C(=S)$NR_2$, or —C(=NR)$NR_2$, where each X is independently a halogen: F, Cl, Br, or I; and each R is independently H, $C_1$-$C_{20}$ alkyl, $C_6$-$C_{20}$ aryl, $C_3$-$C_{14}$ heterocycle, a protecting group or a prodrug moiety. Alkylene, alkenylene, and alkynylene groups as described above may also be similarly substituted.

"Heteroaryl" and "heterocycle" refer to a ring system in which one or more ring atoms is a heteroatom, e.g., nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl. "$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl. A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl. A "$C_3$-$C_8$ carbocyclo" refers to a $C_3$-$C_8$ carbocycle group defined above wherein one of the carbocycle groups' hydrogen atoms is replaced with a bond.

An "arylene" is an aryl group which has two covalent bonds and can be in the ortho, meta, or para configurations as shown in the following structures:

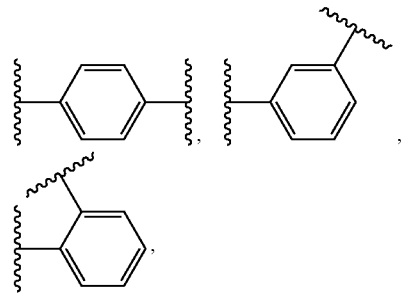

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., *McGraw-Hill Dictionary of Chemical Terms*, McGraw-Hill Book Company, New York (1984); and Eliel and Wilen, *Stereochemistry of Organic Compounds*, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

Examples of a "patient" include, but are not limited to, a human, rat, mouse, guinea pig, monkey, pig, goat, cow, horse, dog, cat, bird and fowl. In an exemplary embodiment, the patient is a human.

The phrase "pharmaceutically acceptable salt," as used herein, refers to pharmaceutically acceptable organic or inorganic salts of a compound (e.g., a Drug, Drug-Linker compound, or a Drug-Linker-Ligand compound). The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" or "solvate" refer to an association of one or more solvent molecules and a compound of the invention, e.g., an Exemplary Compound or Exemplary Conjugate. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: AE is auristatin E, Boc is N-(t-butoxycarbonyl), cit is citrulline, dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN(CH$_3$CN) is acetonitrile, MeOH is methanol, Mtr is 4-anisyldiphenylmethyl (or 4-methoxytrityl), nor is (1S,2R)-(+)-norephedrine, PAB is p-aminobenzyl, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TBTU is O-benzotriazol-1-yl-N,N,N,N-tetramethyluronium tetrafluoroborate, TFA is trifluoroacetic acid, TLC is thin layer chromatography, UV is ultraviolet, and val is valine.

The following linker abbreviations are used herein and have the indicated definitions: Val Cit or vc is a valine-citrulline, dipeptide site in protease cleavable linker; PAB is p-aminobenzylcarbamoyl; (Me)vc is N-methyl-valine citrulline, where the linker peptide bond has been modified to prevent its cleavage by cathepsin B; MC(PEG)$_6$-OH is maleimidocaproyl-polyethylene glycol; SPP is N-Succinimidyl 4-(2-pyridylthio) pentanoate; and SMCC is N-Succinimidyl 4-(N-maleimidomethyl)cyclohexane-1 carboxylate.

The terms "treat" or "treatment," unless otherwise indicated by context, refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, and ameliorating one or more symptoms associated with the disease.

In the context of an autoimmune disease, the term "treating" includes any or all of: preventing replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

The following cytotoxic drug abbreviations are used herein and have the indicated definitions: "MMAF" is N-methylvaline-valine-dolaisoleuine-dolaproine-phenylalanine (MW 731.5); "MMAZ" is N-methylvaline-valine-dolaisoleuine-dolaproine with a phenylalanine analog at the C-terminus. Z is —NR$^9$Z$^1$.

Embodiments of the Invention

Compounds and Conjugates

As noted in the Summary of the Invention, the present invention is drawn to a series of compounds and conjugates containing a drug compound (D). The drug compounds are useful as discrete entities, or can be conjugated to Ligands (L, in some embodiments, antibodies), either directly or through a Linker Unit (LU). The Linker Unit can operate to provide a suitable release of D or spacing between D and L. Additionally, some Linker Units can have multiple attached drugs (e.g., one to four attached drugs can be represented as -LU-(D)$_{1-4}$).

In one group of embodiments, the invention provides compounds having Formula I:

or a pharmaceutically acceptable salt or solvate thereof, wherein L- is a Ligand unit; p is an integer of from 1 to about 20; and D is a drug moiety having Formula D:

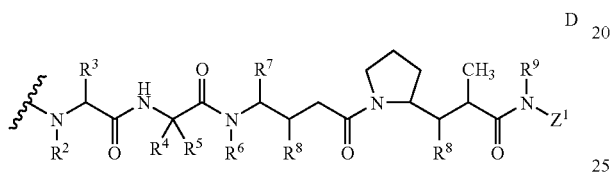

wherein: $R^2$ is selected from the group consisting of H and $C_1$-$C_8$ alkyl; $R^3$ is selected from the group consisting of H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); $R^4$ is selected from the group consisting of H, $C_1$-$C_9$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); $R^5$ is selected from the group consisting of H and methyl; or $R^4$ and $R^5$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle and n is selected from the group consisting of 2, 3, 4, 5 and 6; $R^6$ is selected from the group consisting of H and $C_1$-$C_8$ alkyl; $R^7$ is selected from the group consisting of H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); each $R^8$ is independently selected from the group consisting of H, OH, $C_1$-$C_8$ alkyl, $C_3$-$C_8$ carbocycle and O—($C_1$-$C_8$ alkyl); each $X^1$ is independently $C_1$-$C_{10}$ alkylene; and the moiety —$NR^9Z^1$ is a phenylalanine bioisostere with a modified amino acid side chain.

In one embodiment, the phenylalanine bioisostere moiety

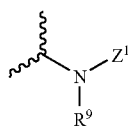

is selected from the group consisting of:

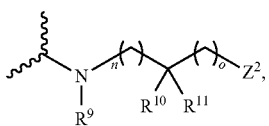

(a)

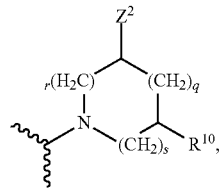

(b)

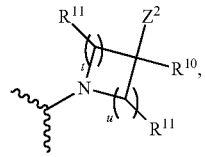

(c)

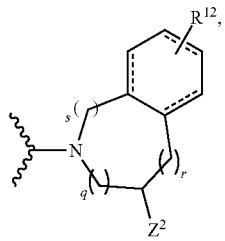

(d)

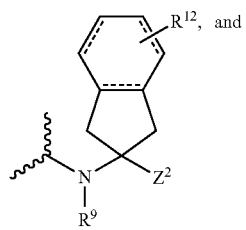

(e)

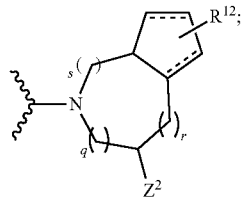

(f)

wherein === represents a single or double bond;
$R^9$ is selected from the group consisting of H and an amino protecting group;
$R^{10}$ is selected from the group consisting of H and —$(CR^{13}R^{14})_xR^{15}$;
each $R^{11}$ is independently selected from the group consisting of H, $C_1$-$C_{20}$alkyl, halogen, aryl, aryl$C_1$-$C_{20}$alkyl, $C_1$-$C_{10}$haloalkyl, $OR^{16}$ and $N(R^{16})_2$;
$R^{12}$ is selected from the group consisting of H, $C_1$-$C_{20}$alkyl, halogen, aryl, aryl$C_1$-$C_{20}$alkyl, aryl$C_2$-$C_{20}$alkenyl, aryl$C_2$-$C_{20}$alkynyl, $OR^{16}$, $N(R^{16})_2$ and —$C(O)R^{16}$;
each $R^{13}$ and $R^{14}$ is independently selected from the group consisting of H, $C_1$-$C_{20}$ alkyl, halogen, arylalkyl, $C_1$-$C_{10}$haloalkyl, $OR^{16}$, $SR^{16}$, $N(R^{16})_2$, —$OC(O)R^{16}$, —$N(R^{16})C(O)R^{16}$, —$COOR^{16}$, —$CON(R^{16})_2$, $X^1$—$SO_3H$, $X^1$—$SO_3$—$C_1$-$C_{20}$alkyl, $X^1$—$OSO_3H$, $X^1$—$OSO_3$—$C_1$-$C_{20}$alkyl, $X^1$—$SO_2$—$C_1$-$C_{20}$alkyl, $X^1$—$SO$—$C_1$-$C_{20}$ alkyl, —$OP(O)(OR^{16})_2$, —$OP(O)(NR^{16})_2$, —$OP(O)N(R^{16})_2OR^{16}$, —$OP(O)(R^{16})OR^{16}$, —$OP(O)(R^{16})N(R^{16})_2$, —$P(O)(OR^{16})_2$, —$P(O)(NR^{16})_2$, —$P(O)N(R^{16})_2OR^{16}$, $C_1$-$C_{20}$ alkyl, $C_3$-$C_8$carbocycle, aryl, $X^1$-aryl, $X^1$—$C_3$-$C_8$carbocycle, $C_3$-$C_{20}$heterocycle and $X^1$—$C_3$-$C_8$heterocycle;

or $R^{13}$ and $R^{14}$ are combined together to form a member selected from the group consisting of =O, =N—NH—$R^{17}$, =N—NH—C(O)—$R^{17}$ and a $C_3$-$C_8$ carbocycle;

each $R^{15}$ is independently selected from the group consisting of H, $C_1$-$C_{20}$alkyl, $C_3$-$C_8$ carbocycle, aryl, $X^1$-aryl, $C_1$-$C_{20}$ alkyl-$C_3$-$C_8$ carbocycle, $C_3$-$C_{20}$ heterocycle, $X^1$—$C_3$-$C_8$ heterocycle, —COOR$^{16}$, —CON(R$^{16}$)$_2$, —C(O)R$^{16}$ and $Y^1$(CR$^{13}$R$^{14}$)$_x$R$^{18}$; and the carbocycle, aryl and heterocycle portions are optionally substituted with from one to three $R^{12}$ groups.

each $R^{16}$ is independently H or $C_1$-$C_{20}$alkyl;

$R^{17}$ is selected from the group consisting of H, $C_1$-$C_{20}$alkyl, $C_3$-$C_8$carbocycle, aryl, $X^1$-aryl, $C_1$-$C_{20}$alkyl-$C_3$-$C_8$carbocycle, $C_3$-$C_8$heterocycle and $X^1$—$C_3$-$C_8$heterocycle;

each $R^{18}$ is independently selected from the group consisting of H, $C_1$-$C_{20}$alkyl, $C_3$-$C_8$carbocycle, aryl, $X^1$-aryl, $X^1$—$C_3$-$C_8$carbocycle, $C_3$-$C_{20}$heterocycle, $X^1$—$C_3$-$C_8$heterocycle, —COOR$^{16}$, —CON(R$^{16}$)$_2$ and —C(O)R$^{16}$;

$Y^1$ is O, S, NR$^{16}$, SO, SO$_2$ or Se;

each $X^1$ is independently $C_1$-$C_{10}$ alkylene;

the subscript x is an integer from 0 to 10;

the subscripts n, o, q, r, s, t and u are integers independently from 0 to 2;

$Z^2$ is COZ$^3$R$^{19}$;

$Z^3$ is O, S, NH, or NR$^{20}$, wherein $R^{20}$ is $C_1$-$C_8$ alkyl;

$R^{19}$ is selected from H, $C_1$-$C_{20}$ alkyl, aryl, $C_3$-$C_8$ heterocycle, —(X$^1$O)$_v$—R$^{22}$, or —(X$^1$O)$_v$—CH(R$^{23}$)$_2$;

v is an integer ranging from 1-1000;

$R^{22}$ is H or $C_1$-$C_8$ alkyl;

each $R^{23}$ is independently H, COOH, —(CH$_2$)$_l$—N(R$^{24}$)$_2$, —(CH$_2$)$_l$—SO$_3$H or —(CH$_2$)$_l$—SO$_3$—$C_1$-$C_8$ alkyl; and each $R^{24}$ is independently H, $C_1$-$C_8$ alkyl or —(CH$_2$)$_l$—COOH; where; l is an integer ranging from 0 to 6; with the proviso when n and o are 0, and $R^{11}$ is H, then $R^{10}$ is other than CH$_2$-aryl or CH$_2$—$C_3$-$C_8$heterocycle.

In one embodiment, $R^9$ is selected from the group consisting of H, $C_1$-$C_{20}$ alkyl, $C_3$-$C_8$ carbocyclyl, $X^1$-aryl, $X^1$—($C_3$-$C_8$-carbocyclyl) and $X^1$–$C_3$-$C_8$-heterocyclyl. In another embodiment $R^9$ is H.

In one embodiment, the phenylalanine bioisostere moiety is

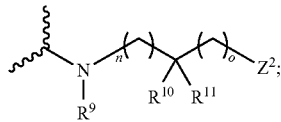

wherein $R^9$ is H; $R^{10}$ is benzyl; $R^{11}$ is H; $Z^2$ is CO$_2$H; the subscript n is an integer of from 0 to 2; and the subscript o is an integer of from 0 to 1 with the proviso that n+o is at least 1.

In one embodiment, the phenylalanine bioisostere moiety is selected from the group consisting of

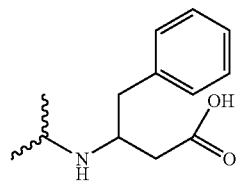

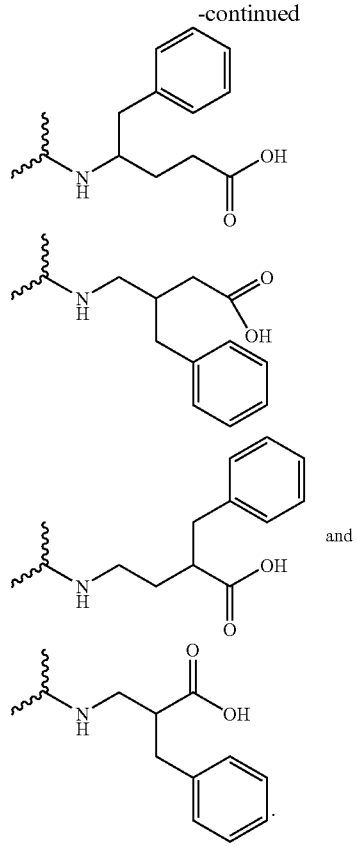

and

In one embodiment, the phenylalanine bioisostere moiety is

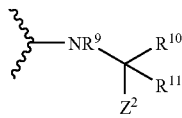

wherein $R^9$ is H or an amino protecting group; $R^{10}$ is H and —(CR$^{13}$R$^{14}$)$_x$R$^{15}$; each $R^{11}$ is independently H, $C_1$-$C_{20}$alkyl, halogen, aryl, arylC$_1$-$C_{20}$alkyl, $C_1$-$C_{10}$haloalkyl, OR$^{16}$ and N(R$^{16}$)$_2$; $R^{12}$ is H, $C_1$-$C_{20}$alkyl, halogen, aryl, arylC$_1$-$C_{20}$alkyl, arylC$_2$-$C_{20}$alkenyl, arylC$_2$-$C_{20}$alkynyl, OR$^{16}$, N(R$^{16}$)$_2$ and —C(O)R$^{16}$; each $R^{13}$ and $R^{14}$ is independently H, $C_1$-$C_{20}$ alkyl, halogen, arylalkyl, $C_1$-$C_{10}$haloalkyl, OR$^{16}$, SR$^{16}$, N(R$^{16}$)$_2$, —OC(O)R$^{16}$, —N(R$^{16}$)C(O)R$^{16}$, —COOR$^{16}$, —CON(R$^{16}$)$_2$, —X$^1$—SO$_3$H, —X$^1$—SO$_3$—$C_1$-$C_{20}$alkyl, —X$^1$—OSO$_3$H, —X$^1$—OSO$_3$—$C_1$-$C_{20}$alkyl, —X$^1$—SO$_2$—$C_1$-$C_{20}$alkyl, —X$^1$—SO—$C_1$-$C_{20}$ alkyl, —OP(O)(OR$^{16}$)$_2$, —OP(O)(NR$^{16}$)$_2$, —OP(O)N(R$^{16}$)$_2$OR$^{16}$, —OP(O)(R$^{16}$)OR$^{16}$, —OP(O)(R$^{16}$)N(R$^{16}$)$_2$, —P(O)(OR$^{16}$)$_2$, —P(O)(NR$^{16}$)$_2$, —P(O)N(R$^{16}$)$_2$OR$^{16}$, $C_1$-$C_{20}$ alkyl, $C_3$-$C_8$carbocycle, aryl, —X$^1$-aryl, —X$^1$—$C_3$-$C_8$carbocycle, $C_3$-$C_8$ heterocycle and —X$^1$—$C_3$-$C_8$ heterocycle; or $R^{13}$ and $R^{14}$ are combined together to form a member selected from the group consisting of =O, =N—NH—R$^{17}$, =N—NH—C(O)—R$^{17}$ and a $C_3$-$C_8$ carbocycle; each $R^{15}$ is independently H, $C_1$-$C_{20}$alkyl, $C_3$-$C_8$ carbocycle, aryl, —X$^1$-aryl, $C_1$-$C_{20}$ alkyl-$C_3$-$C_8$ carbocycle, $C_3$-$C_8$ heterocycle, —X$^1$—$C_3$-$C_8$heterocycle, —COOR$^{16}$, —CON(R$^{16}$)$_2$, —C(O)R$^{16}$ and —Y$^1$(CR$^{13}$R$^{14}$)$_x$R$^{18}$ wherein the carbocycle, aryl and heterocycle portions are optionally substituted with from one to three $R^{12}$ groups; each $R^{16}$ is independently H or $C_1$-$C_{20}$alkyl; $R^{17}$ is H, $C_1$-$C_{20}$alkyl, $C_3$-$C_8$carbocycle, aryl, $X^1$-aryl, $C_1$-$C_{20}$alkyl-$C_3$-$C_8$carbocycle, $C_3$-$C_8$heterocycle and $X^1$—$C_3$-$C_8$heterocycle; each $R^{18}$ is independently H, $C_1$-$C_{20}$alkyl, $C_3$-$C_8$carbocycle, aryl, $X^1$-aryl, $X^1$—$C_3$-$C_8$carbocycle, $C_3$-$C_8$ heterocycle, $X^1$—$C_3$—C heterocycle, —COOR$^{16}$, —CON(R$^{16}$)$_2$ and —C(O)R$^{16}$; $Y^1$ is O, S, NR$^{16}$, SO, SO$_2$ or Se; each $X^1$ is independently $C_1$-$C_{10}$ alkylene; the subscript x is an integer from 0 to 10; the subscripts n, o, q, r, s, t and u are integers independently from 0 to 2 with the proviso that n+o is at least 1; $Z^2$ is COZ$^3$R$^{19}$; $Z^3$ is O, S, NH, or NR$^{20}$, wherein R$^{20}$ is $C_1$-$C_8$ alkyl; R$^{19}$ is selected from H, $C_1$-$C_{20}$ alkyl, aryl, $C_3$-$C_8$ heterocycle, —(X$^1$O)$_v$—R$^{22}$, or —(X$^1$O)$_v$—CH(R$^{23}$)$_2$; v is an integer ranging from 1-1000; R$^{22}$ is H or $C_1$-$C_8$ alkyl; and each R$^{23}$ is independently H, COOH, —(CH$_2$)$_l$—N(R$^4$)$_2$, —(CH$_2$)$_l$—SO$_3$H or —(CH$_2$)$_l$—SO$_3$—$C_1$-$C_8$ alkyl; each R$^{24}$ is independently H, $C_1$-$C_8$ alkyl or —(CH$_2$)$_l$—COOH; where; l is an integer ranging from 0 to 6; with the proviso when n and o are 0, R$^{11}$ is H the R$^{10}$ is other than CH$_2$-aryl or CH$_2$—$C_3$-$C_8$heterocycle.

In one embodiment, the phenylalanine bioisostere moiety is

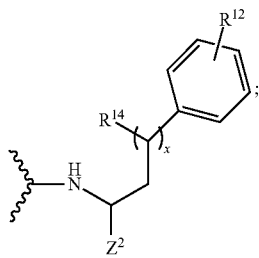

wherein $R^{12}$ and $R^{14}$ are as described above; $Z^2$ is CO$_2$H; and the subscript x is an integer of from 0 to 2.

In one embodiment, the phenylalanine bioisostere moiety is

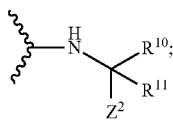

wherein $R^{10}$ is CH$_2$—$C_3$-$C_8$heterocycle or CH$_2$-aryl; $R^{11}$ is H; and $Z^2$ is as described above. In some embodiments, $R^{10}$ is selected from the group consisting of:

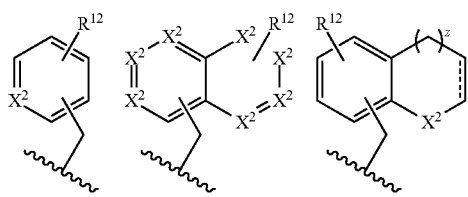

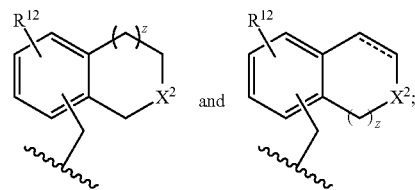

wherein $R^{12}$ is as described above; each $X^2$ is independently selected from the group consisting of N, NR$^{16}$, S, O, CR$^{16}$ and CHR$^{16}$; and the subscript z is an integer of from 0 to 2. In other embodiments, $R^{10}$ is selected from the group consisting of:

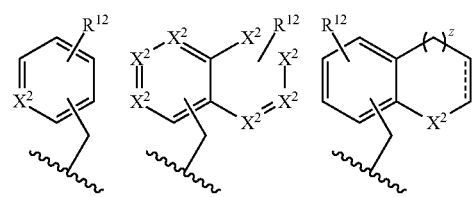

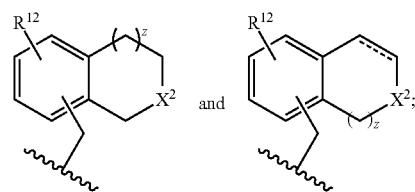

wherein $R^{12}$ is as described above; each $X^2$ is independently selected from the group consisting of N, NR$^{16}$, S, O, CR$^{16}$ and CHR$^{16}$; and the subscript z is an integer of from 0 to 2; and no more than two adjacent $X^2$ groups are other than CR$^{16}$ or CHR$^{16}$. In still other embodiments, $R^{10}$ is selected from the group consisting of:

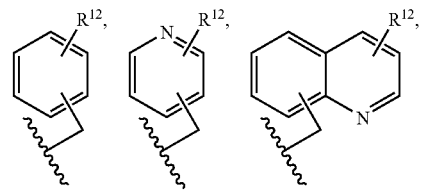

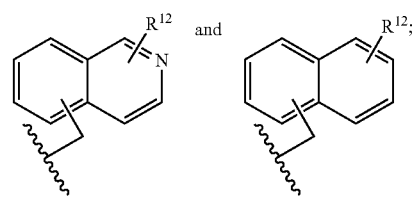

wherein $R^{12}$ is selected from the group: H, alkyl, halogen, amino, carboxy, amido, carboethoxy, formyl, phenyl, E-2-phenylethenyl, Z-2-phenylethenyl, and 2-phenylethynyl.

In one group of embodiments, the phenylalanine bioisostere moiety is selected from the group consisting of:

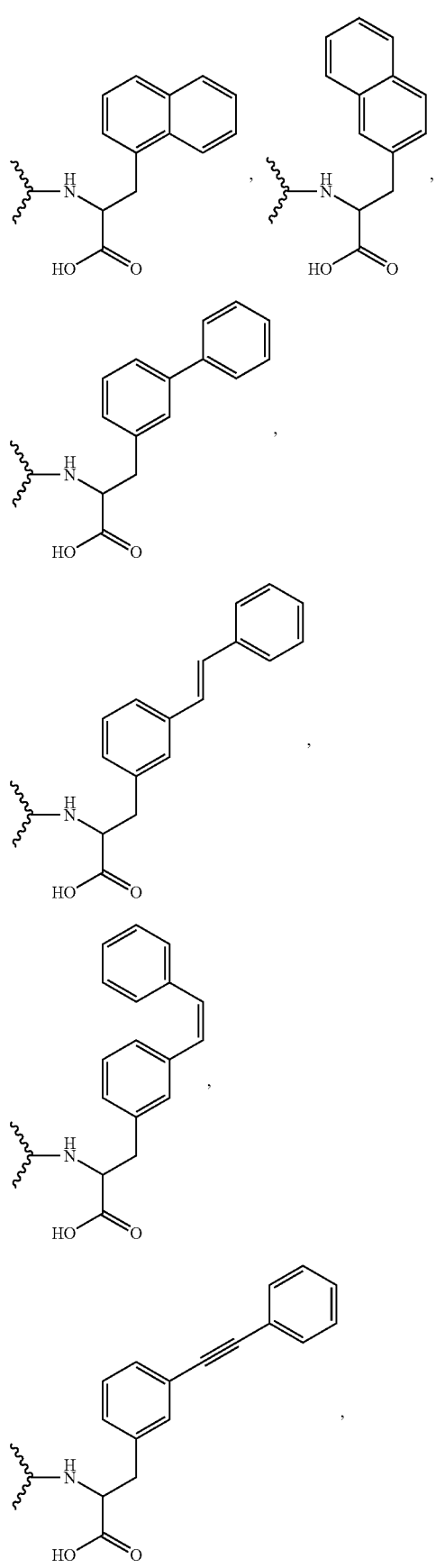
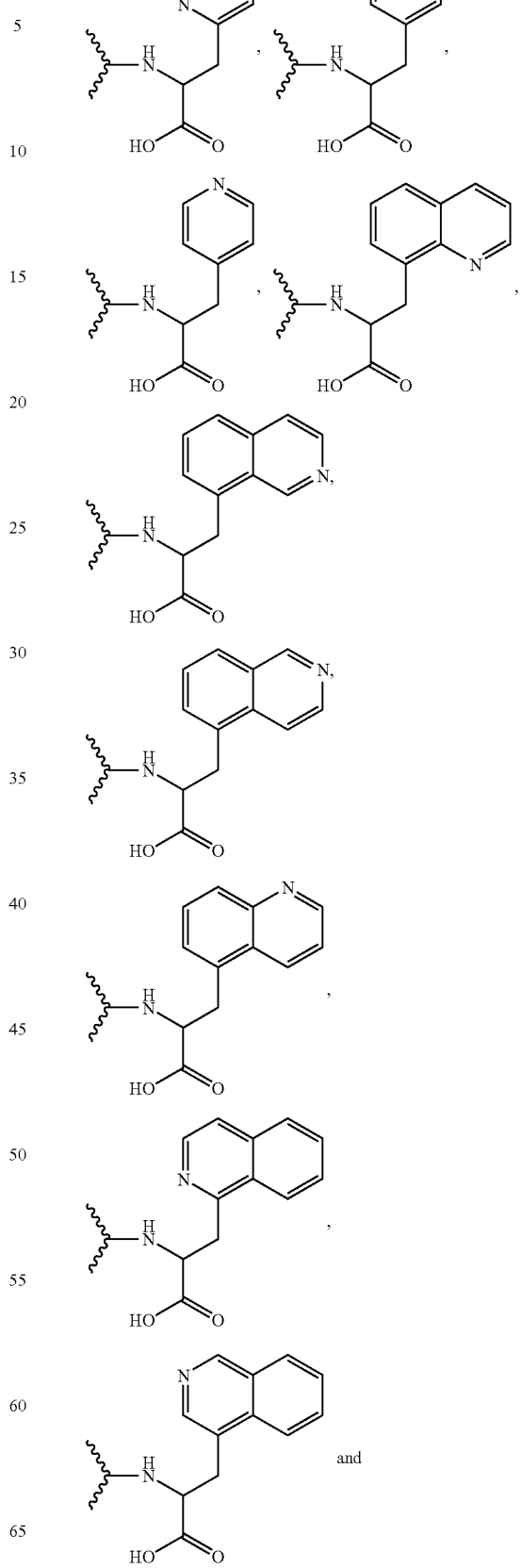
-continued

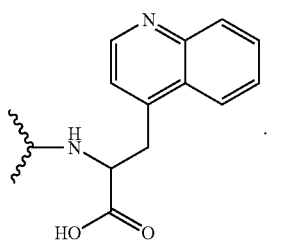
In one embodiment, the phenylalanine bioisostere moiety is selected from the group consisting of:
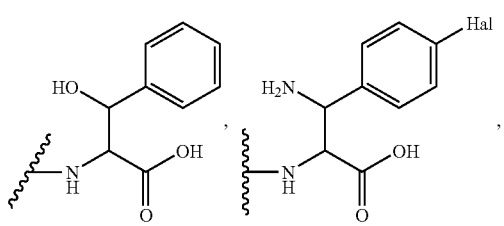
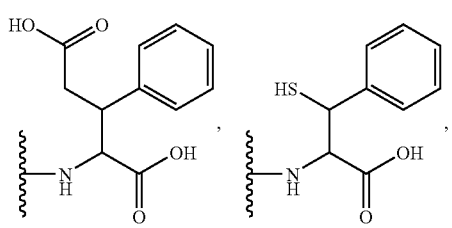
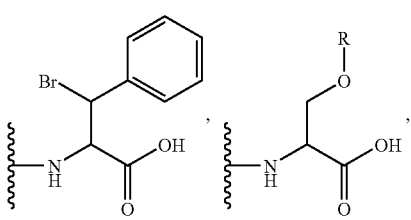
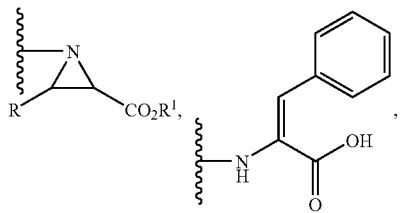
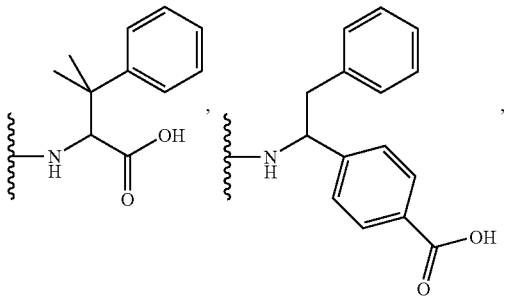
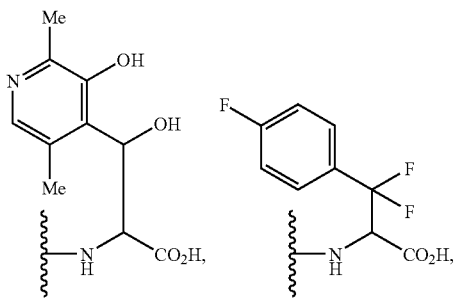
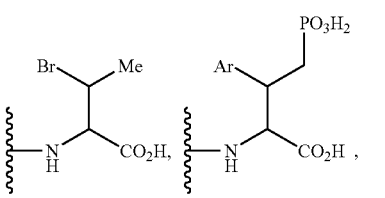
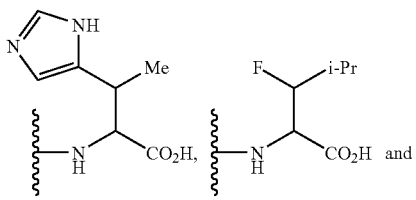
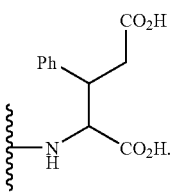
and
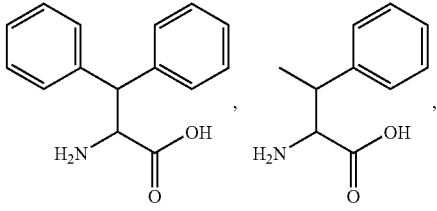
In one embodiment, the phenylalanine bioisostere moiety is the amide of an α-amino acid selected from the group consisting of:
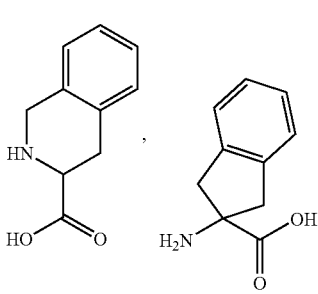

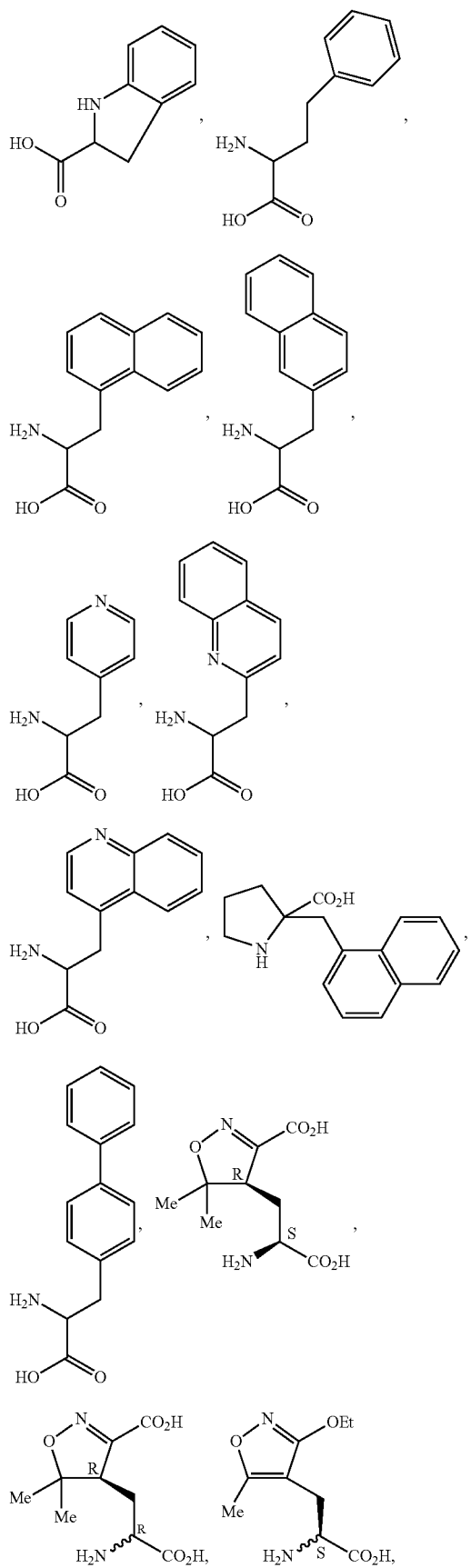
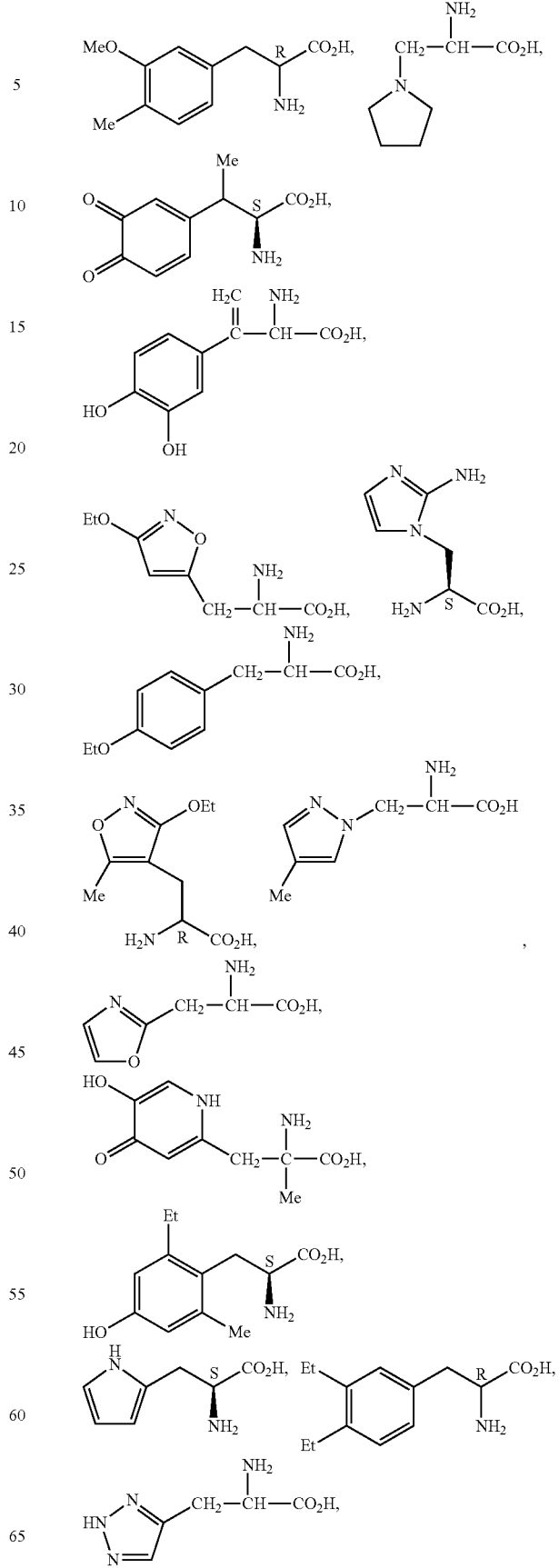

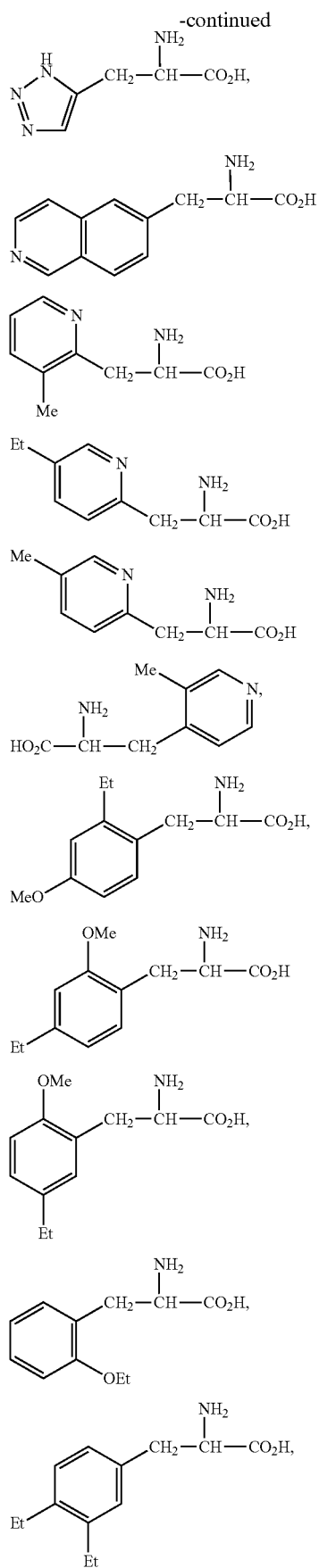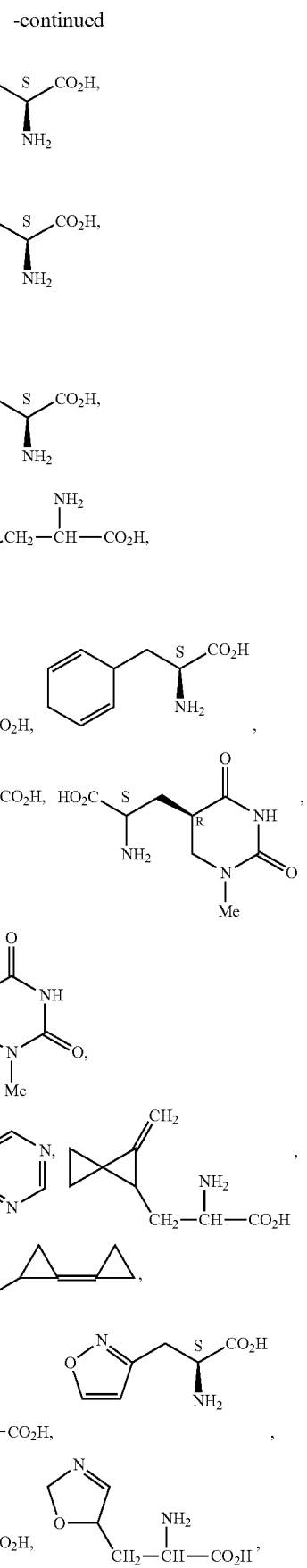

-continued
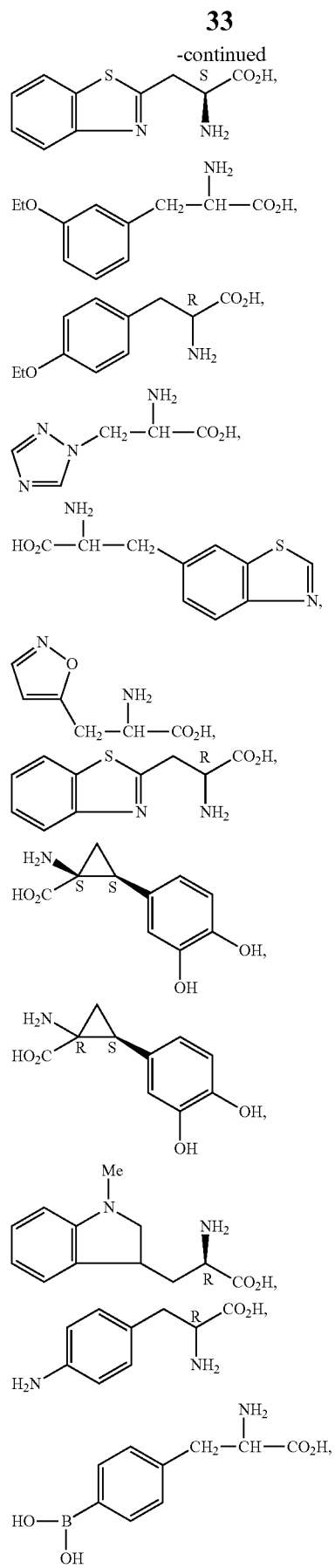
-continued
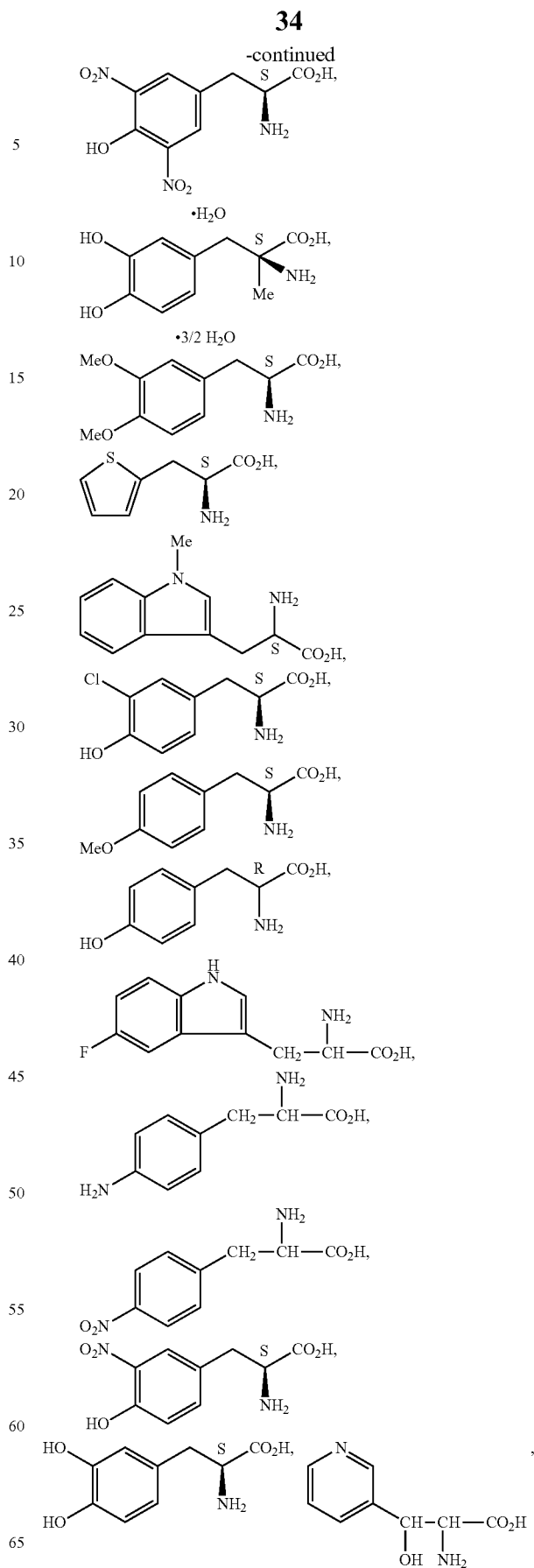

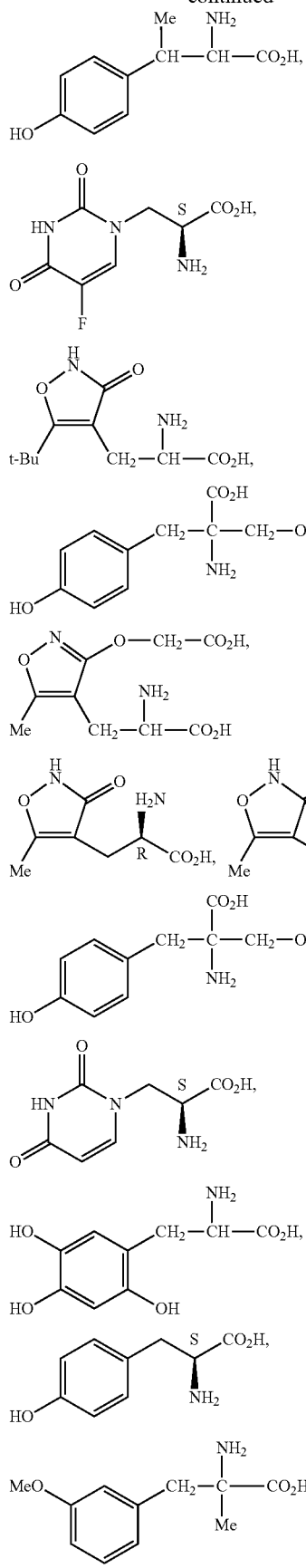
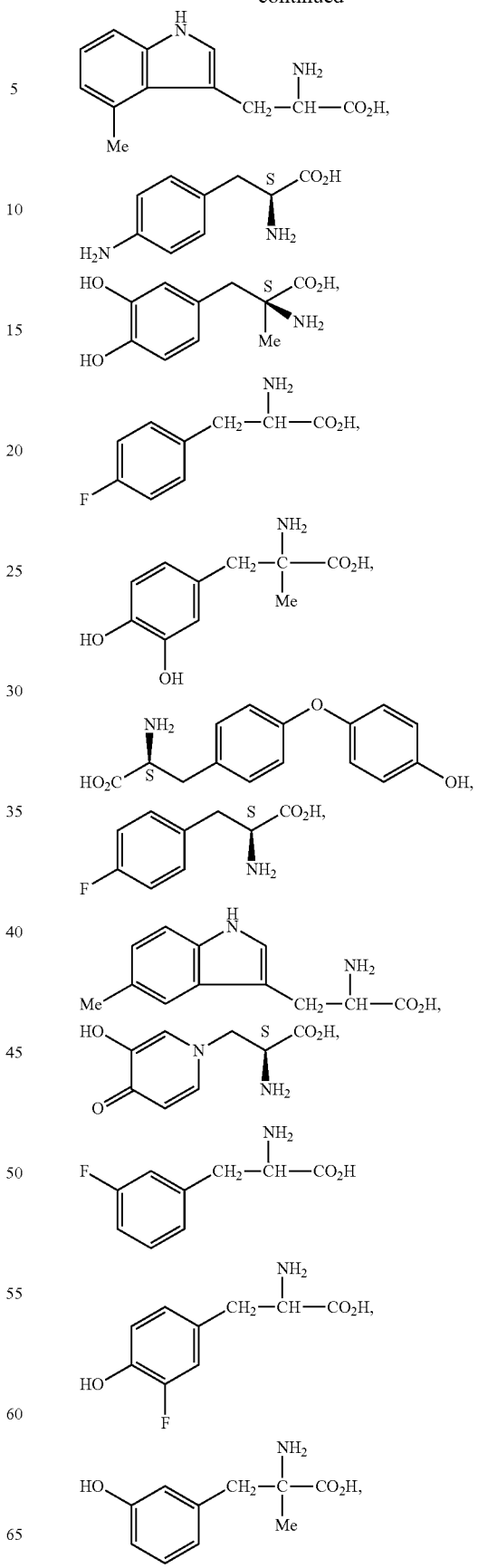

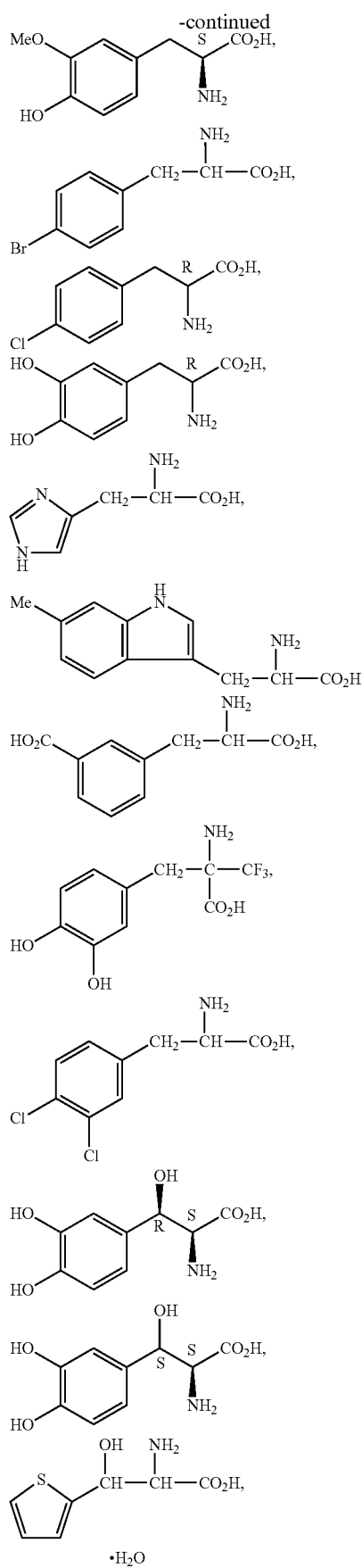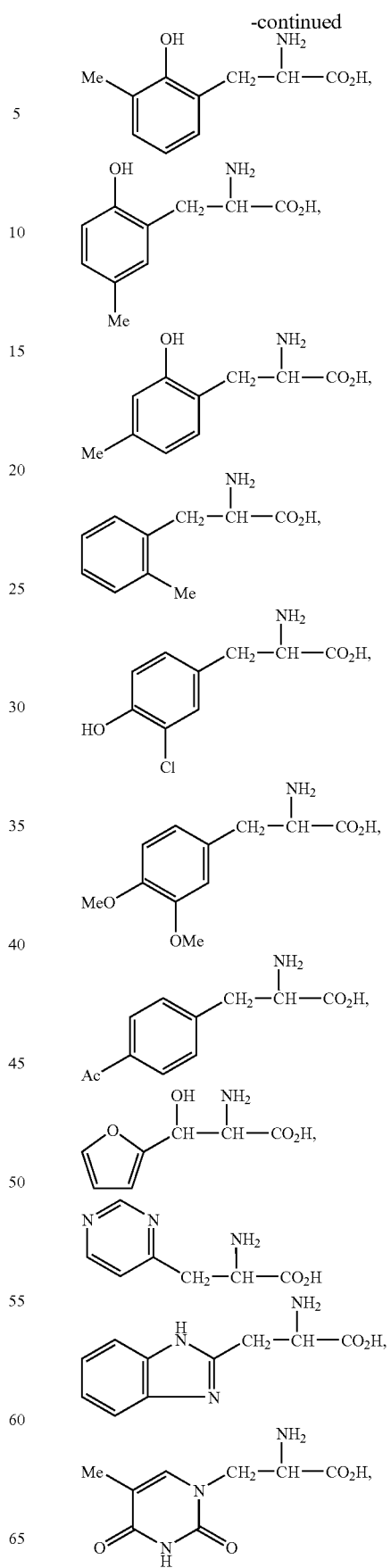

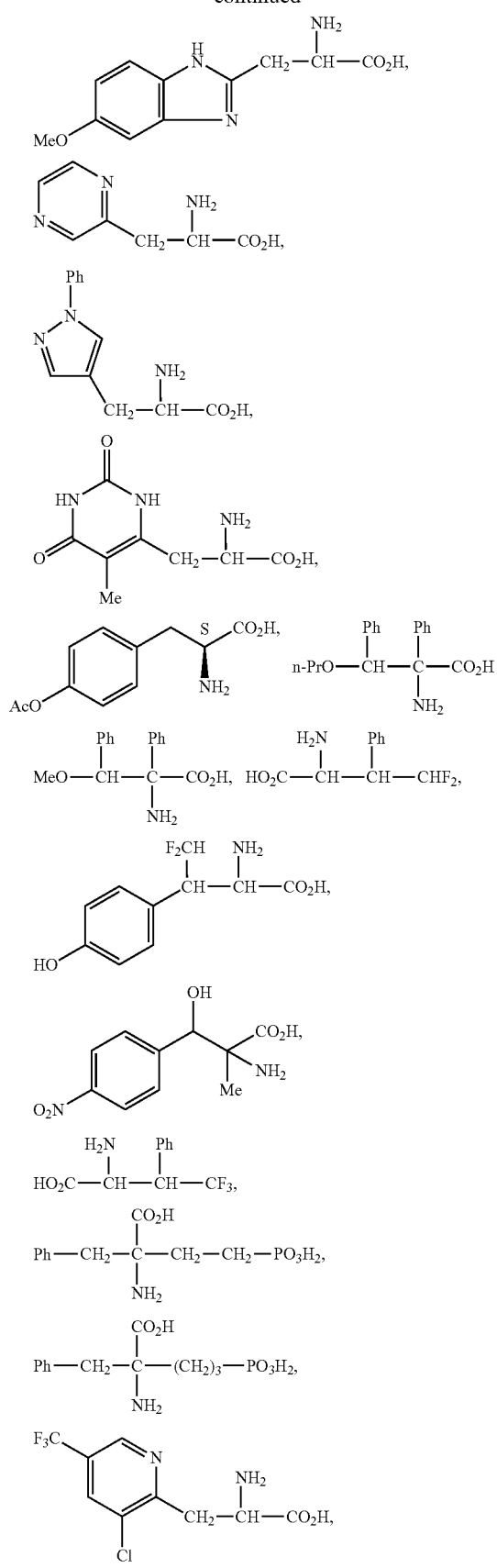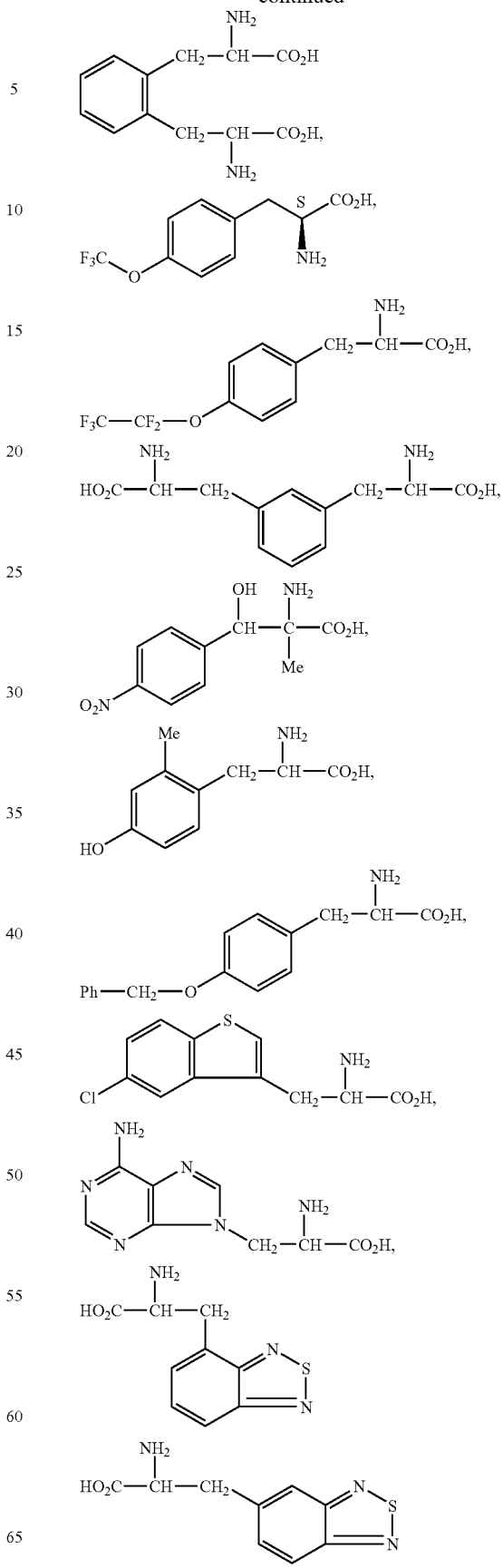

-continued
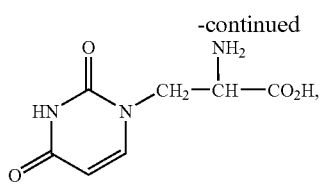
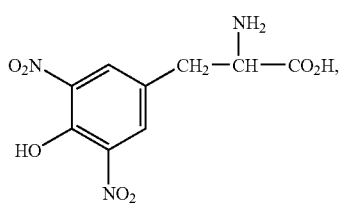
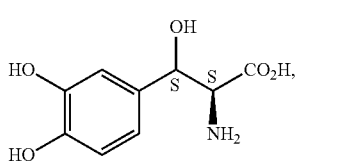
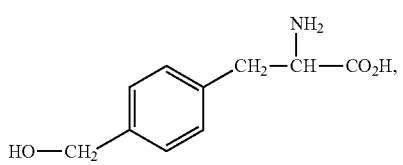
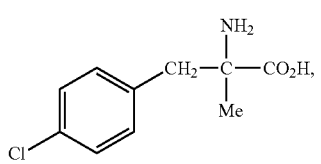
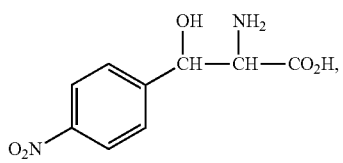
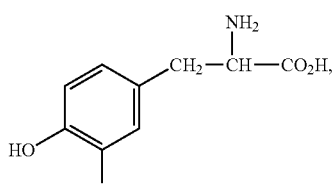
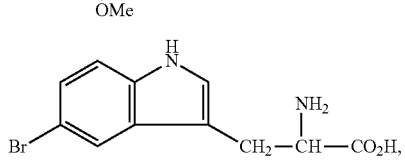
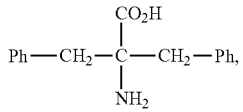
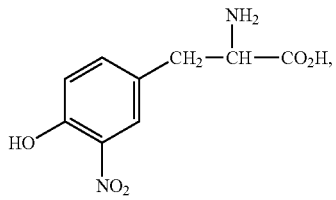
-continued
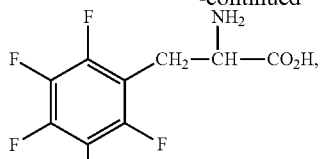
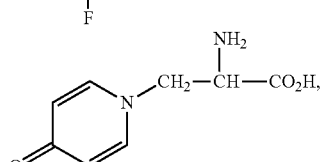
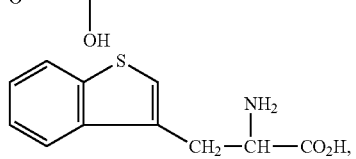
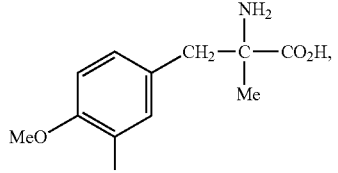
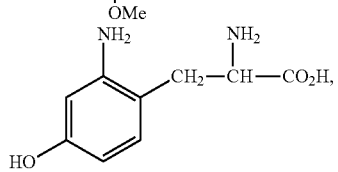
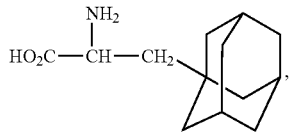
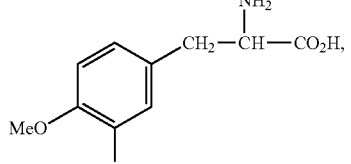
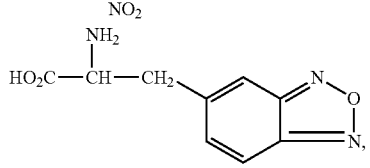
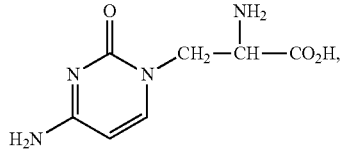
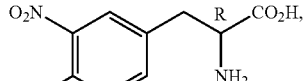
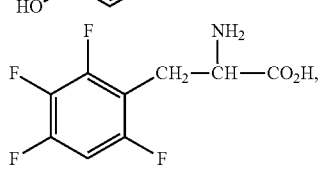

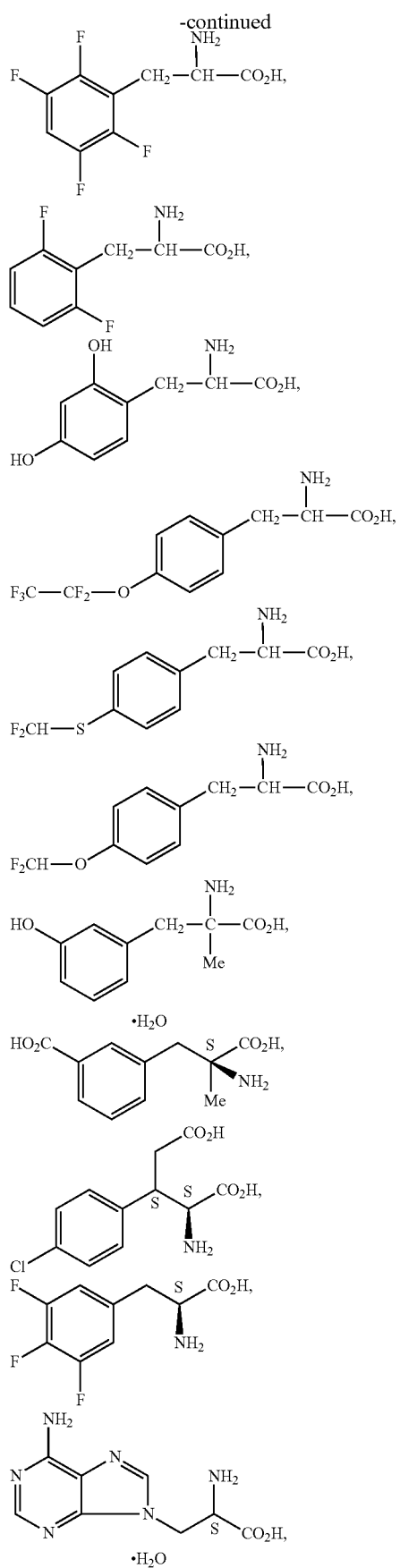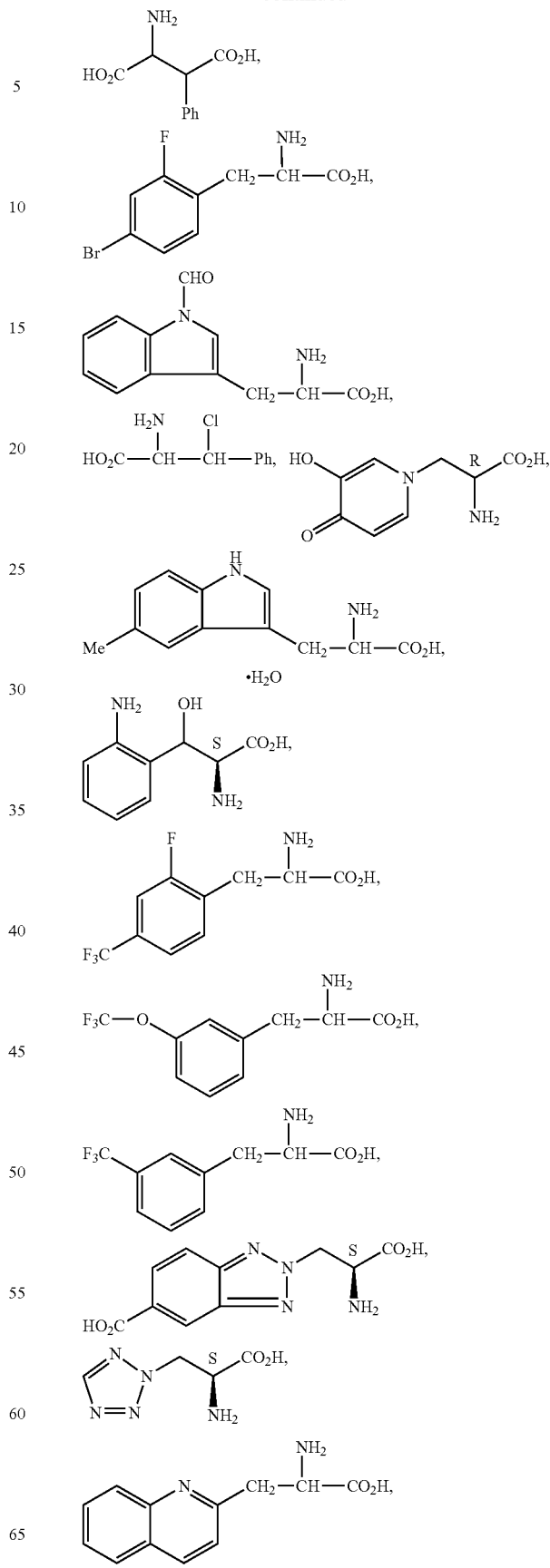

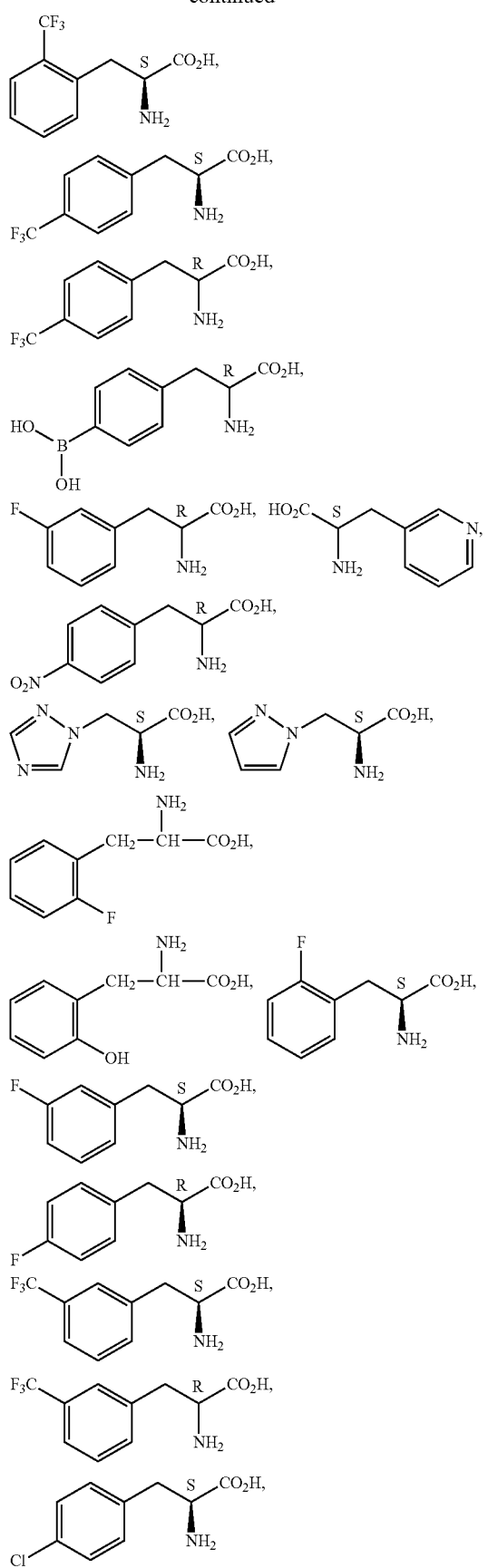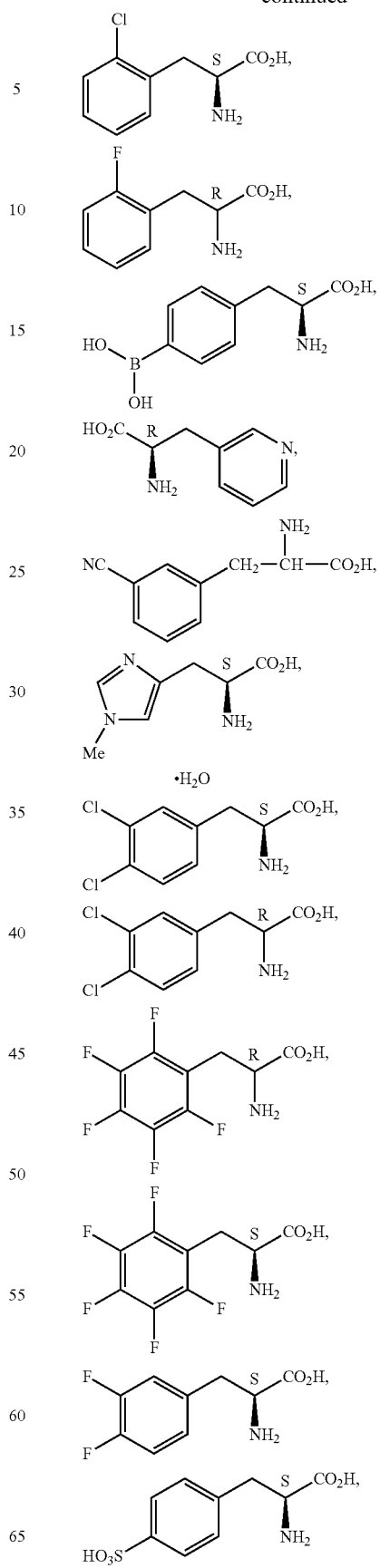

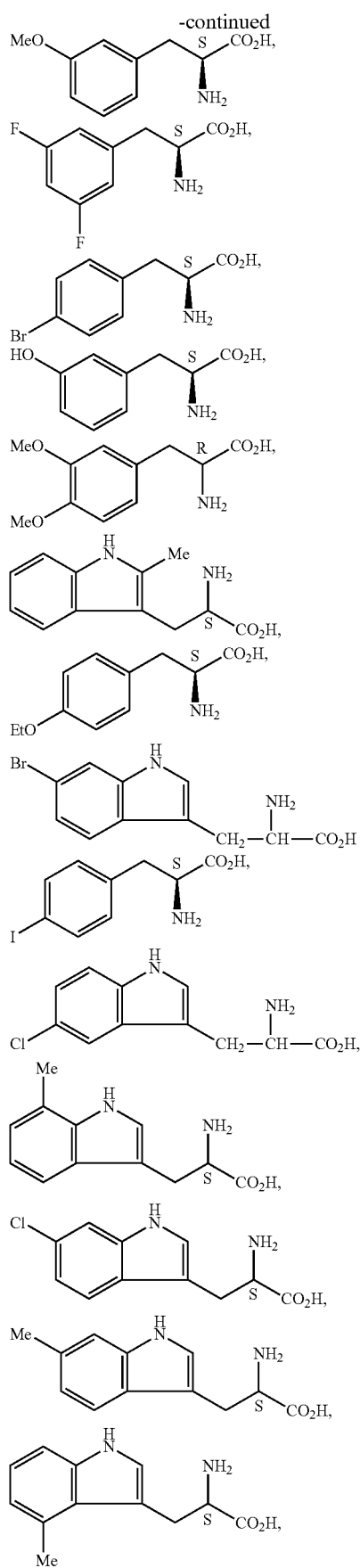
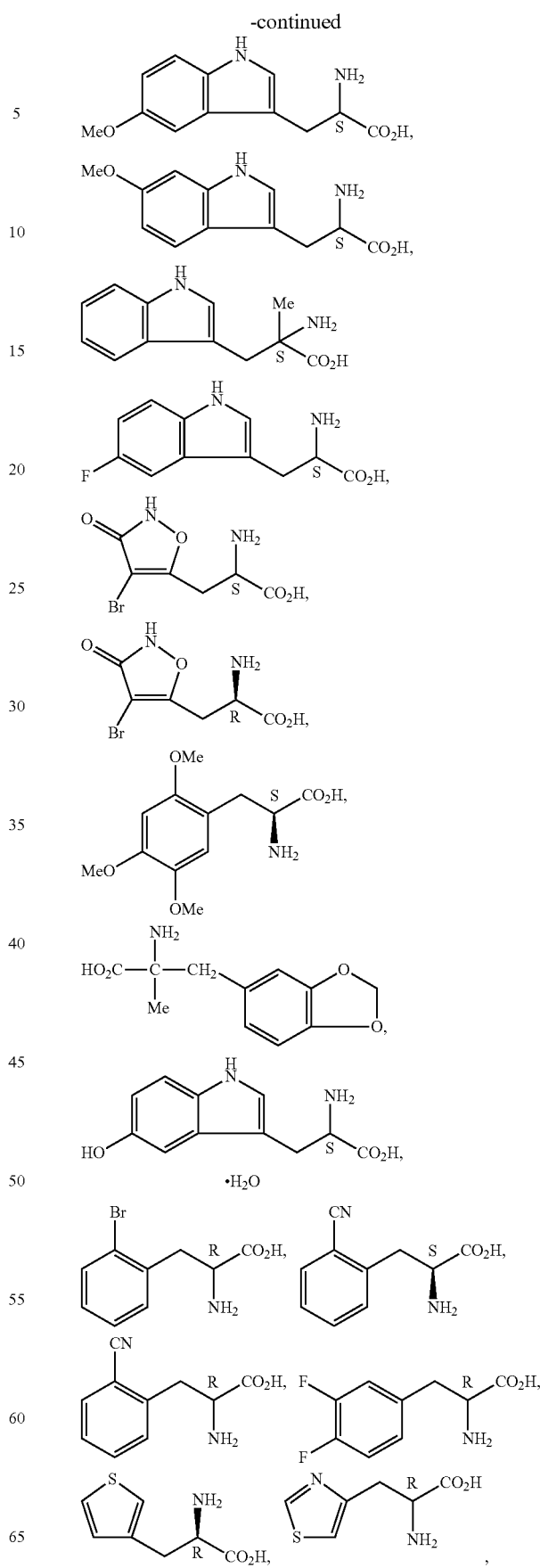

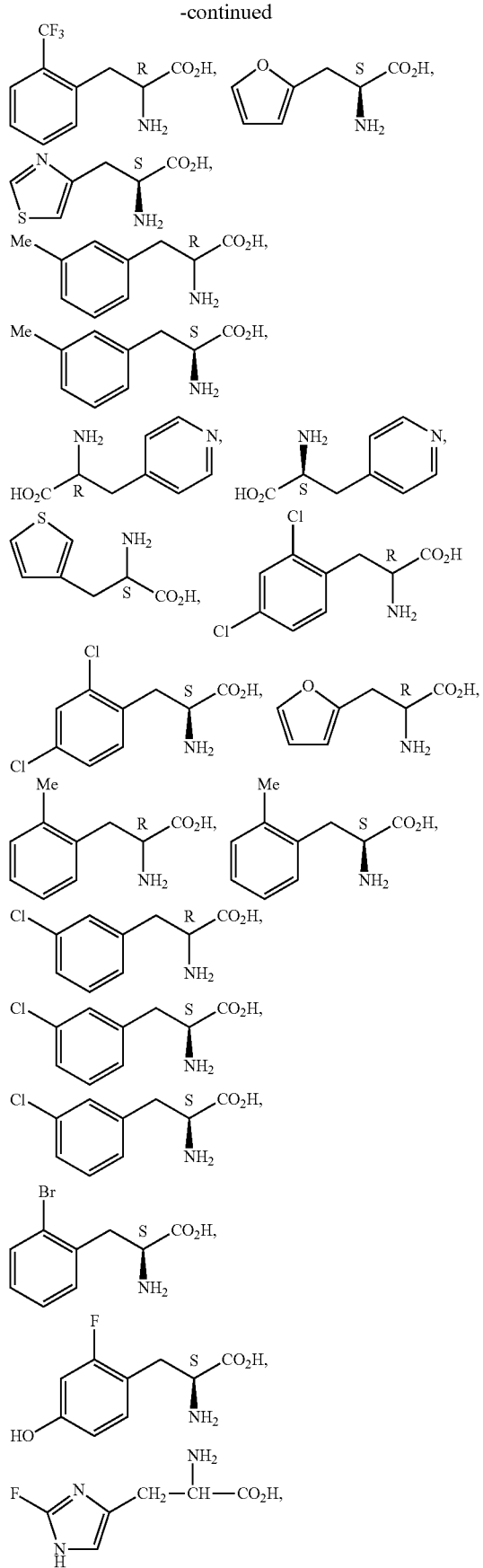
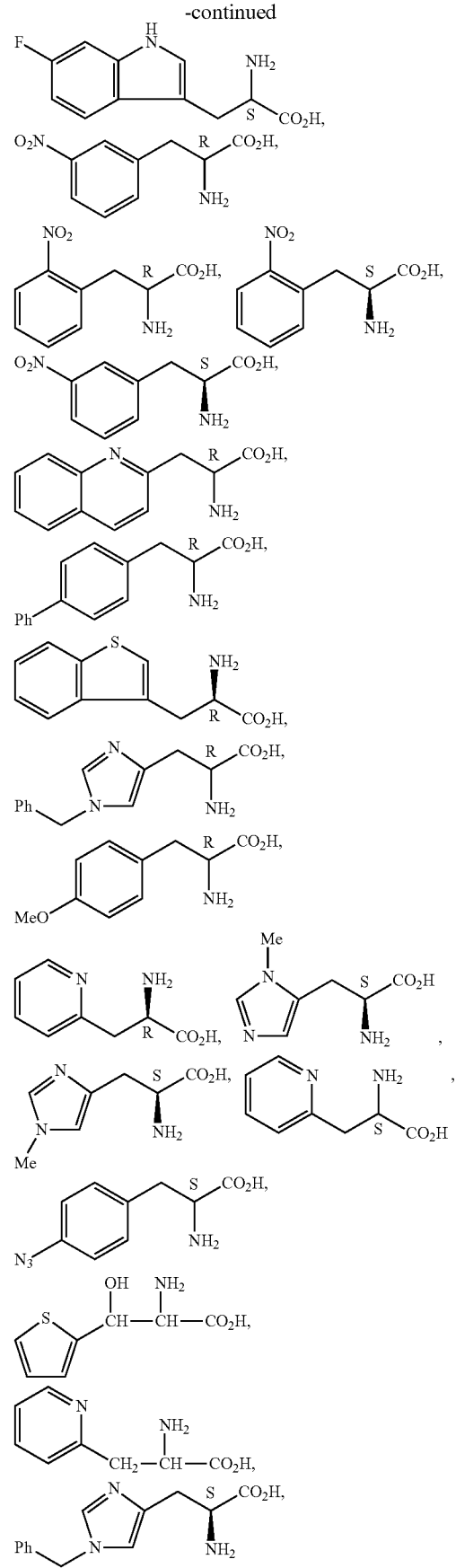

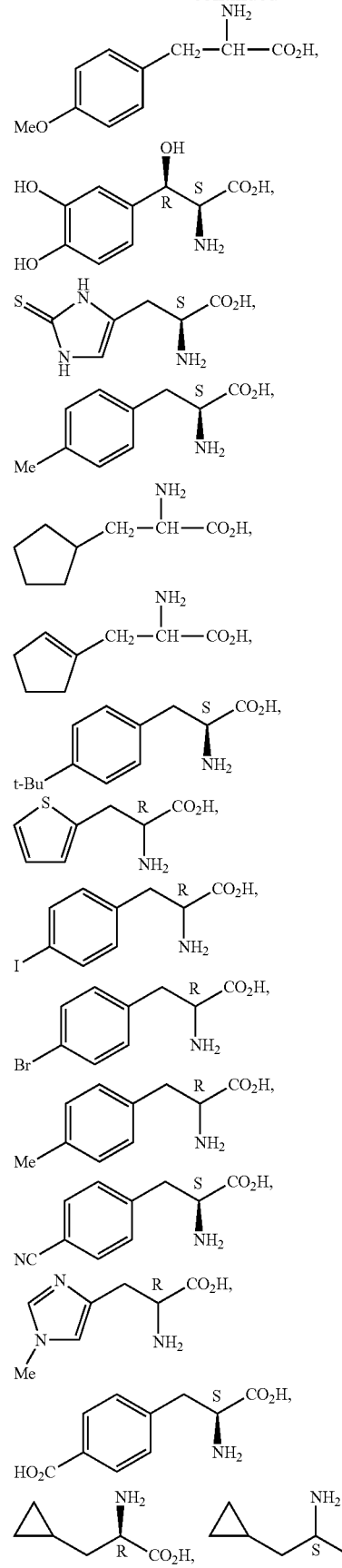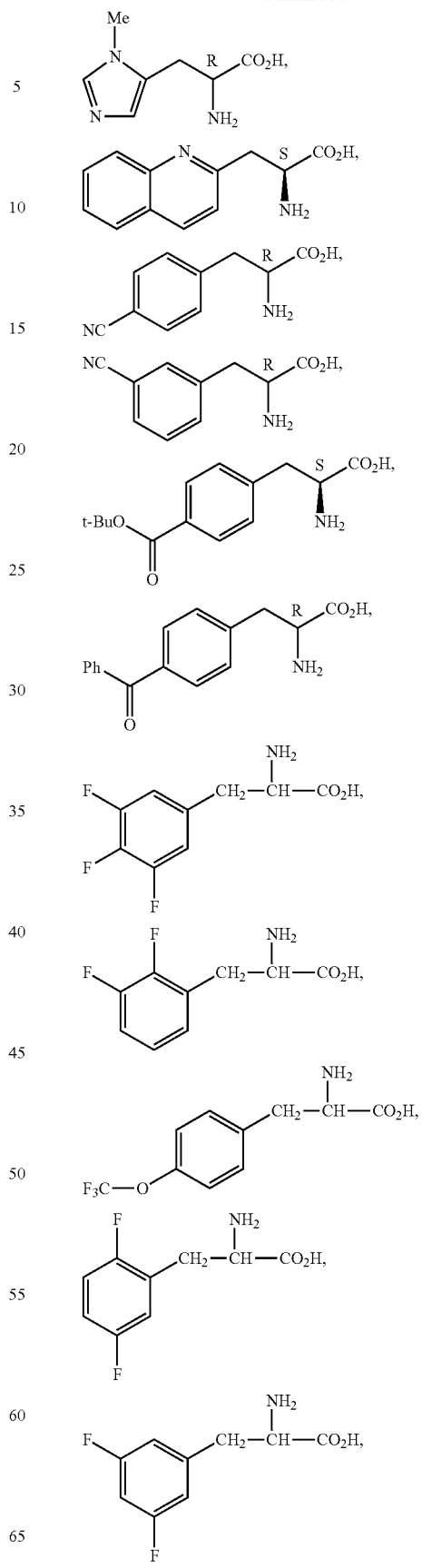

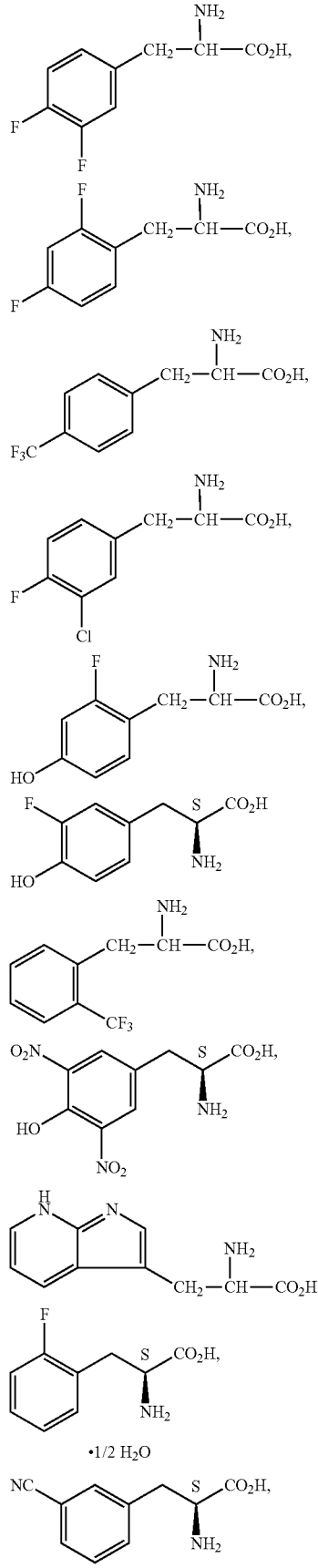
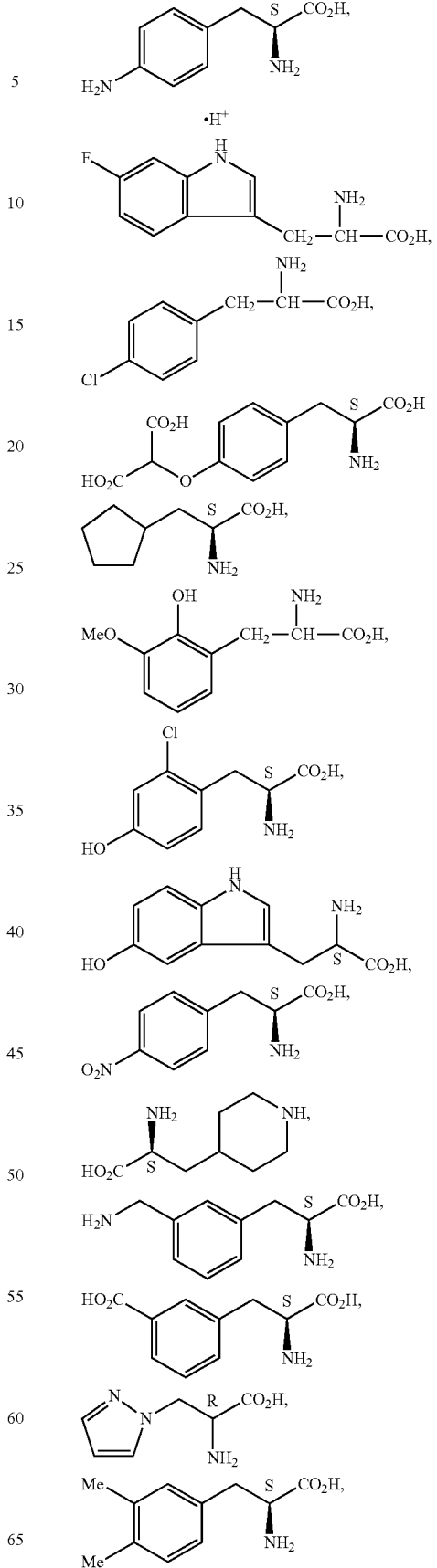

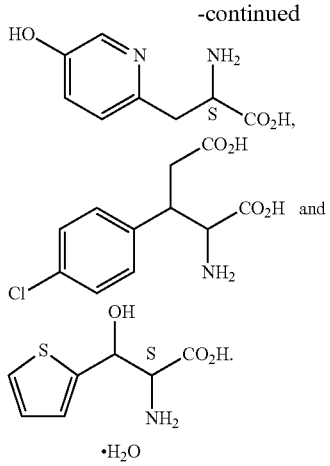

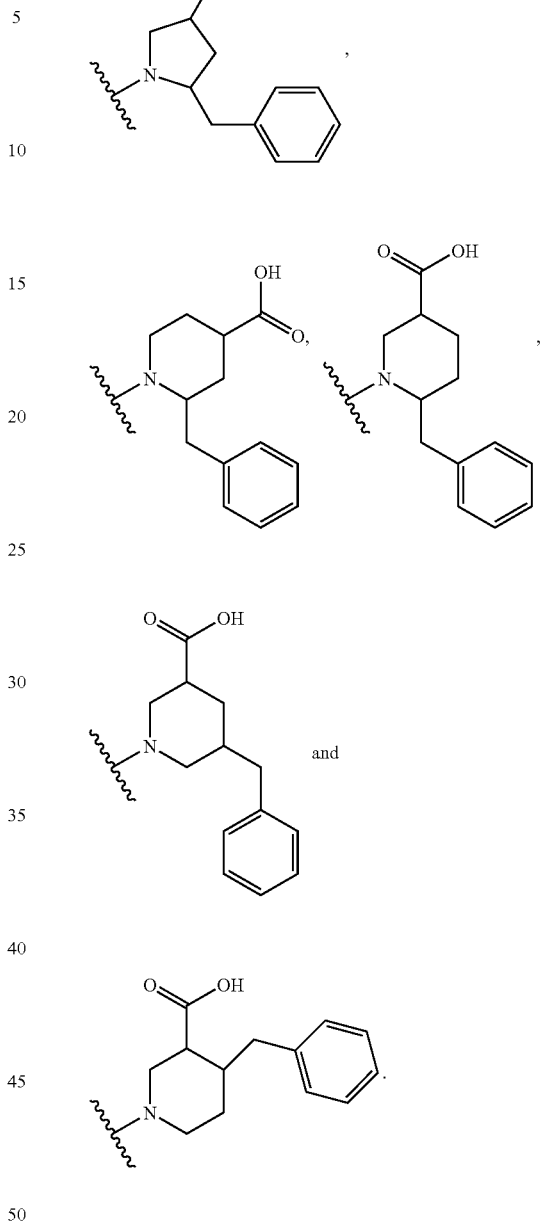

In one embodiment, the phenylalanine bioisostere moiety is the α-amino amide of an amino acid selected from the group consisting of: 4-chloro-phenylalanine, 4-fluoro-phenylalanine, 4-nitro-phenylalanine, N-α-methyl-phenylalanine, α-methyl-phenylalanine, glutamic acid, aspartic acid, tryptophan, isoleucine, leucine, methionine, tyrosine, glutamine, threonine, valine, asparagine, phenylglycine, O-benzyl-serine, O-t-butyl-serine, O-t-butyl-threonine, homophenylalanine, methionine-DL-sulfoxide, methionine-sulfone, α-aminobutyric acid, α-aminoisobutyric acid, 4-amino-1-piperidine-4-carboxylic acid, 4-amino-tetrahydropyran-4-carboxylic acid, aspartic acid, benzothiazol-2-yl-alanine, α-t-butyl-glycine, cyclohexylalanine, norleucine, norvaline, S-acetamidomethyl-penicillamine, β-3-piperidin-3-yl-alanine, piperidinyl-glycine, pyrrolidinyl-alanine, selenocysteine, tetrahydropyran-4-yl-glycine, O-benzyl-threonine, O-t-butyl-tyrosine, 3-(p-acetylphenyl)alanine, 3-phenylserine, and 1,2,3,4-tetrahydro-isoquinoline-3-carboxylic acid.

In one embodiment, the phenylalanine bioisostere moiety is

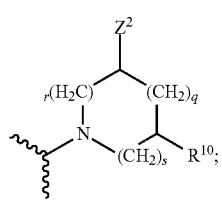

wherein $Z^2$ is $CO_2H$; $R^{10}$ is benzyl; and the subscripts q, r and s independently are integers of from 0 to 1.

In one embodiment, the phenylalanine bioisostere moiety is selected from the group consisting of:

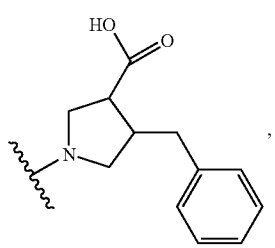

In one embodiment, the phenylalanine bioisostere moiety is

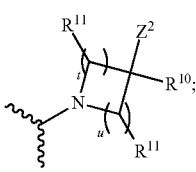

wherein $Z^2$ is $CO_2H$; $R^{10}$ is benzyl; $R^{11}$ is H; and the subscripts t and u independently are integers of from 1 to 3.

In one embodiment, the phenylalanine bioisostere moiety is selected from the group consisting of

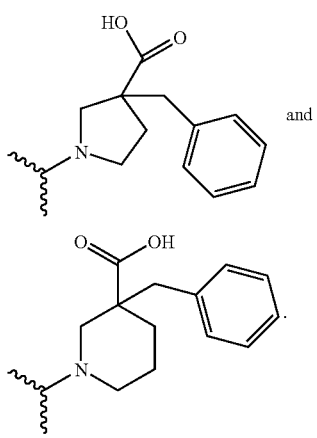

and.

In one embodiment, the phenylalanine bioisostere moiety is

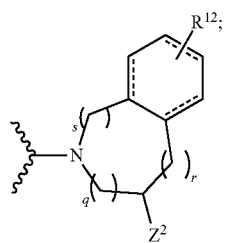

wherein $Z^2$ is $CO_2H$; $R^{12}$ is as described above; and the subscripts q, r and s independently are integers of from 1 to 3.

In one embodiment, the phenylalanine bioisostere moiety is:

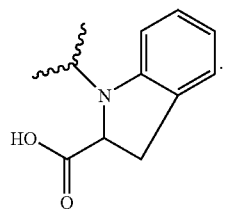 [SMILES: *N1c2ccccc2CC1C(=O)O]

In one embodiment, the phenylalanine bioisostere moiety is

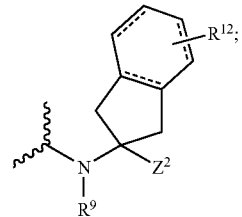

wherein $Z^2$ is $CO_2H$; $R^{10}$ is benzyl; and $R^{12}$ is as described above.

In one embodiment, the phenylalanine bioisostere moiety is

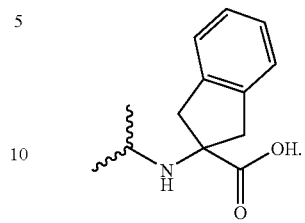

In one embodiment, the phenylalanine bioisostere moiety is

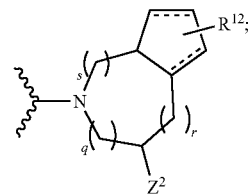

wherein $Z^2$ is $CO_2H$; $R^{12}$ is as described above; and the subscripts q, r and s independently are integers of from 1 to 3.

In one embodiment, the phenylalanine bioisostere moiety is

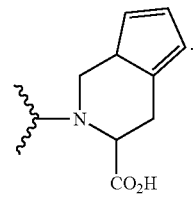

In a related aspect, the present invention provides conjugates in which the compounds further comprise a Linker unit (LU), the conjugates having the formula:

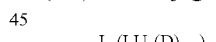

or a pharmaceutically acceptable salt or solvate thereof wherein L is a Ligand unit; -LU- is a Linker unit; and D is a Drug unit, as set forth herein.

In another related aspect, the present invention provides conjugates having the formula:

or a pharmaceutically acceptable salt or solvate thereof wherein, -LU- is a Linker unit; and D is a drug moiety having the Formula D:

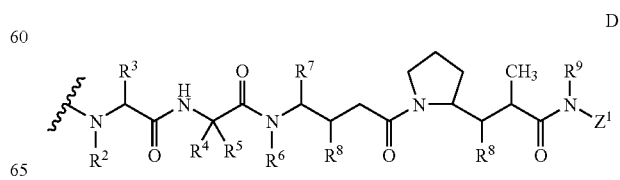

according to any of the above embodiments.

In one embodiment, Drug-Linker-Ligand Conjugates are provided that have Formula Ia:

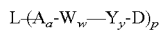
                                                                    Ia or a pharmaceutically acceptable salt or solvate thereof, wherein L- is a Ligand unit; -$A_a$-$W_w$-$Y_y$— is a Linker unit (LU), wherein -A- is a Stretcher unit, the subscript a is 0 or 1, each —W— is independently an Amino Acid unit, w is an integer ranging from 0 to 12, —Y— is a Spacer unit, and y is 0, 1 or 2; p is an integer of from 1 to about 20; and D is a Drug unit having the Formula D:

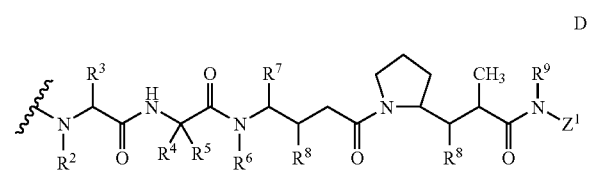

D wherein $R^2$ is selected from the group consisting of H and $C_1$-$C_8$ alkyl; $R^3$ is selected from the group consisting of H, $C_1$-$C_8$ alkyl, $C_3$-$C_8$ carbocycle, aryl, $C_1$-$C_8$ alkyl-aryl, $X^1$—($C_3$-$C_8$ carbocycle), $C_3$-$C_8$ heterocycle and $X^1$—($C_3$-$C_8$ heterocycle); $R^4$ is selected from the group consisting of H, $C_1$-$C_8$ alkyl, $C_3$-$C_8$ carbocycle, aryl, $X^1$-aryl, $C_1$-$C_8$ alkyl-($C_3$-$C_8$ carbocycle), $C_3$-$C_8$ heterocycle and $X^1$—($C_3$-$C_8$ heterocycle); $R^5$ is selected from the group consisting of H and methyl; or $R^4$ and $R^5$ jointly form a carbocyclic ring and have the formula —($CR^aR^b$)$_n$—, wherein $R^a$ and $R^b$ are independently selected from the group consisting of H, $C_1$-$C_8$ alkyl and $C_3$-$C_8$ carbocycle and n is selected from the group consisting of 2, 3, 4, 5 and 6; $R^6$ is selected from the group consisting of H and $C_1$-$C_8$ alkyl; $R^7$ is selected from the group consisting of H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle); each $R^8$ is independently selected from the group consisting of H, OH, $C_1$-$C_8$ alkyl, $C_3$-$C_8$ carbocycle and O—($C_1$-$C_8$ alkyl); each $X^1$ is independently $C_1$-$C_{10}$ alkylene; and the moiety —$NR^9Z^1$ is a phenylalanine bioisostere of any of the above embodiments.

Another aspect of the invention are the Drug Compounds having the Formula Ib. These drug compounds are those described above wherein the wavy line is replaced by a hydrogen atom. Specifically, the compounds are represented below:

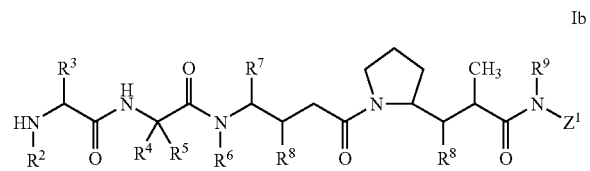

Ib or pharmaceutically acceptable salts or solvates thereof, wherein, $R^2$ is selected from H and $C_1$-$C_8$ alkyl; $R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); $R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); $R^5$ is selected from H and methyl; or $R^4$ and $R^5$ jointly form a carbocyclic ring and have the formula —($CR^aR^b$)$_n$—, wherein $R^a$ and $R^b$ are independently selected from H, $C_1$-$C_8$ alkyl and $C_3$-$C_8$ carbocycle and n is selected from 2, 3, 4, 5 and 6; $R^6$ is selected from H and $C_1$-$C_8$ alkyl; $R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); each $R^8$ is independently selected from the group consisting of H, OH, $C_1$-$C_8$ alkyl, $C_3$-$C_8$ carbocycle and O—($C_1$-$C_8$ alkyl); and the moiety —$NR^9Z^1$ is a phenylalanine bioisostere of any of the above embodiments.

In one embodiment, $R^3$, $R^4$ and $R^7$ are independently isopropyl or sec-butyl and $R^5$ is —H. In an exemplary embodiment, $R^3$ and $R^4$ are each isopropyl, $R^5$ is —H, and $R^7$ is sec-butyl.

In another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

Illustrative Compounds of Formula (Ib), each of which may be used as drug moieties (D) in an ADC, include compounds having the following structures:

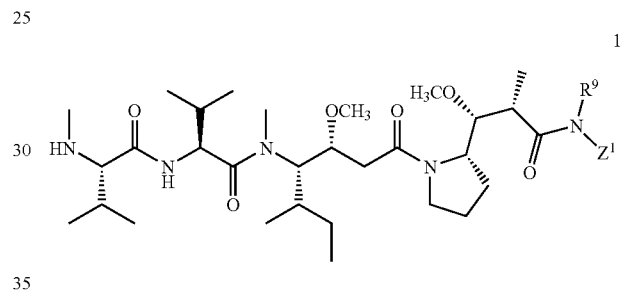

1 and pharmaceutically acceptable salts or solvates thereof.

In yet another aspect, Drug-Linker-Ligand Conjugates are provided in which the Ligand is an antibody. In this aspect, the conjugates are represented by Formula Ia':

                                                                    Formula Ia' or pharmaceutically acceptable salts or solvates thereof, wherein Ab is an antibody, A is a Stretcher unit, a is 0 or 1, each W is independently an Amino Acid unit, w is an integer ranging from 0 to 12, Y is a Spacer unit, and y is 0, 1 or 2, p is an integer of from 1 to about 20, and D is a Drug moiety of Formula D:

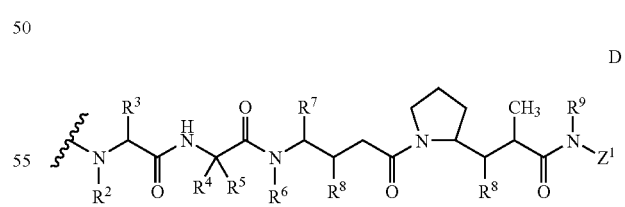

D wherein $R^2$, $R^3$, $R^4$, $R^5$, $R^6$, $R^7$, each $R^8$, and —$N(R^9)Z^1$ have the meanings provided above.

The antibody Ab can be any antibody covalently attached to one or more drug units. For example, Ab can be an antibody that specifically binds to CD20, CD30, CD33, CD40, CD70, BCMA, or Lewis Y antigen.

In one embodiment —$W_w$— is -Val-Cit-.

In another embodiment, $R^3$, $R^4$ and $R^7$ are independently isopropyl or sec-butyl and $R^5$ is —H. In an exemplary embodiment, $R^3$ and $R^4$ are each isopropyl, $R^5$ is —H, and $R^7$ is sec-butyl. In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one aspect, the antibody Ab is chimeric AC10, chimeric BR96, chimeric S2C6, chimeric 1F6, chimeric 2F2, humanized AC10, humanized BR96, humanized S2C6, humanized 1F6, M195, humanized M195 or humanized 2F2.

Exemplary embodiments of Formula Ia' have the following structures:

ments, p is from about 2 to about 6, or 2 to about 4 Drug units per Ligand unit. In some embodiments, p is about 2, about 4, about 6 or about 8 Drug units per Ligand unit The average number of Drugs units per Ligand unit in preparation of conjugation reactions may be characterized by conventional means such as mass spectroscopy, ELISA assay, and HPLC. The quantitative distribution of Ligand-Drug-Conjugates in terms of p may also be determined. In some instances, separation, purification, and characterization of homogeneous Ligand-Drug-conjugates where p is a certain value from Ligand-Drug-Conjugates with other drug loadings may be achieved by means such as reverse phase HPLC or electrophoresis.

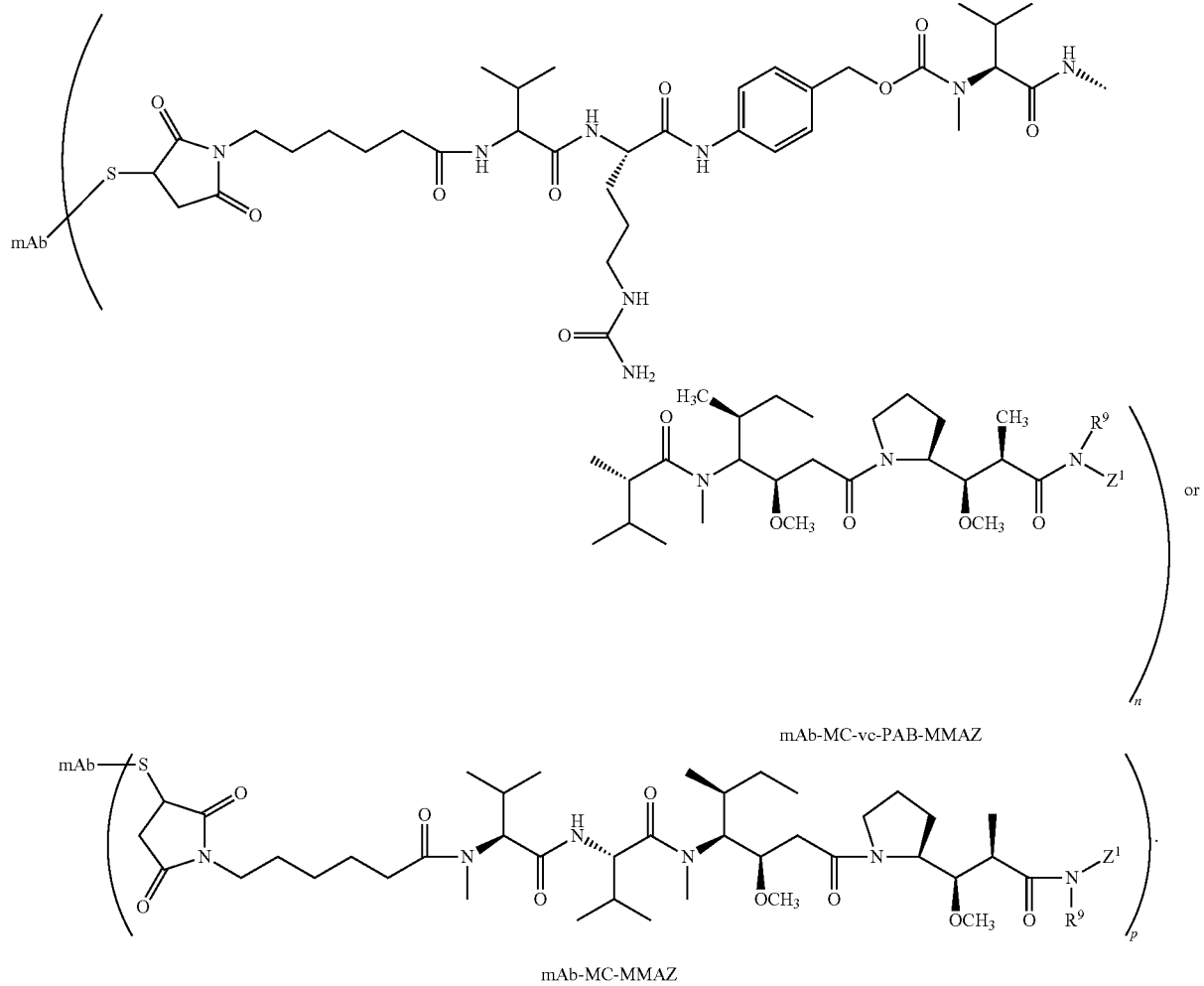

mAb-MC-vc-PAB-MMAZ

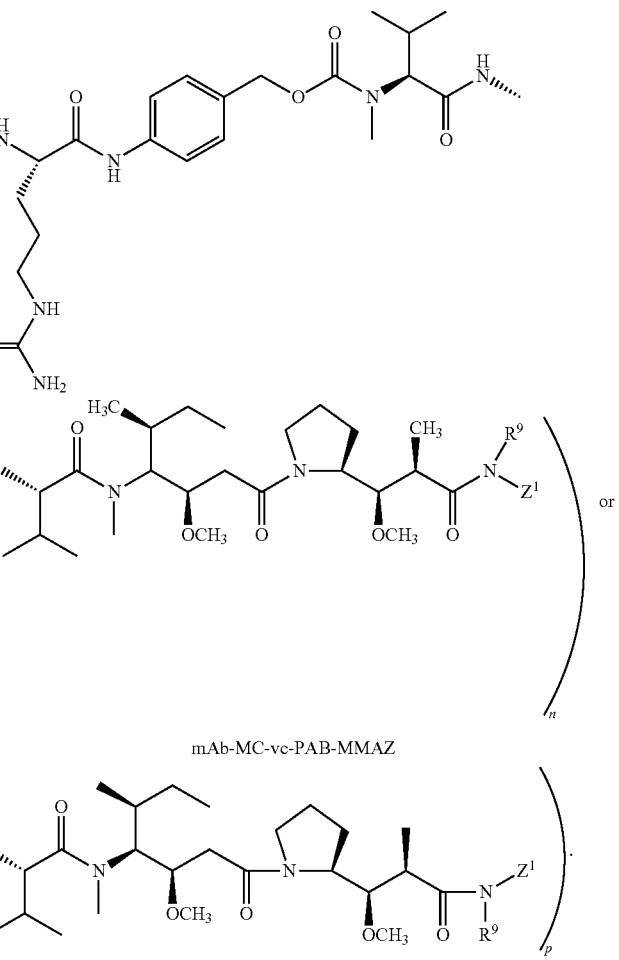

mAb-MC-MMAZ

The drug loading is represented by p, the average number of drug molecules per ligand (e.g., an antibody) (e.g., of Formula I, Ia, Ia'). Drug loading may range from 1 to 20 Drug units (D) per Ligand (e.g., Ab or mAb). The Drug unit may be conjugated directly or indirectly to the Ligand unit (e.g., via a Linker unit). Compositions of Formula Ia and Formula Ia' include collections of antibodies conjugated with a range of drugs, from 1 to 20.

In some embodiments, p is from about 1 to about 8 Drug units per Ligand unit. In some embodiments, p is from about 2 to about 8 Drug units per Ligand unit. In some embodi- Returning to Formula Ia', the conjugates comprising an antibody covalently attached to one or more Drug units (moieites): A, a, W, w, Y and y are as described above. The antibody drug conjugate compounds include pharmaceutically acceptable salts or solvates thereof.

The drug loading is represented by p, the average number of Drugs units per antibody in a molecule of Formula I. Drug loading may range from 1 to 20 drugs (D) per antibody (Ab or mAb). The Drug Unit may be conjugated directly or indirectly to the Ligand unit (e.g., via a Linker unit). Compositions of ADC of Formula Ic include collections of antibodies conjugated with a range of drugs, from 1 to 20. In some embodiments, p is from about 1 to about 8 Drug units per antibody. In some embodiments, p is from about 2 to about 8 Drug units per antibody. In some embodiments, p is from about 2 to about 6, or 2 to about 4 Drug units per antibody. In some embodiments, p is about 2, about 4, about 6 or about 8 Drug units per antibody.

The average number of drugs per antibody in preparations of ADC from conjugation reactions may be characterized by conventional means such as UV/visible spectroscopy, mass spectrometry, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached.

Typically, fewer than the theoretical maximum of drug moieties are conjugated to an antibody during a conjugation reaction. An antibody may contain, for example, many lysine residues that do not react with the drug-linker intermediate or linker reagent. Only the most reactive lysine groups may react with an amine-reactive linker reagent. Generally, antibodies do not contain many, if any, free and reactive cysteine thiol groups which may be linked to a drug moiety. Most cysteine thiol residues in the antibodies exist as disulfide bridges and must be reduced with a reducing agent such as dithiothreitol (DTT). Additionally, the antibody must be subjected to denaturing conditions to reveal reactive nucleophilic groups such as lysine or cysteine. The loading (drug/antibody ratio) of an ADC may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

Where more than one nucleophilic group reacts with a drug-linker intermediate, or linker reagent followed by drug moiety reagent, then the resulting product is a mixture of ADC compounds with a distribution of one or more drug moieties attached to an antibody. The average number of drugs per antibody may be calculated from the mixture by dual ELISA antibody assay, specific for antibody and specific for the drug. Individual ADC molecules may be identified in the mixture by mass spectroscopy, and separated by HPLC, e.g., hydrophobic interaction chromatography ("Effect of drug loading on the pharmacology, pharmacokinetics, and toxicity of an anti-CD30 antibody-drug conjugate", Hamblett, K. J., et al, Abstract No. 624, American Association for Cancer Research; Hamblett et al., 2004, Cancer Research 10:7063; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). Thus, a homogeneous ADC with a single loading value may be isolated from the conjugation mixture by electrophoresis or chromatography.

The Linker Unit (LU)

A "Linker unit" (LU) is a bifunctional compound which can be used to link a Drug unit and a Ligand unit to form Drug-Linker-Ligand Conjugates, or which are useful in the formation of immunoconjugates directed against tumor associated antigens. Such immunoconjugates allow the selective delivery of toxic drugs to tumor cells.

In one embodiment, the Linker unit of the Drug-Linker Compound and Drug-Linker-Ligand Conjugate has the formula:

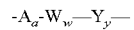

wherein -A- is a Stretcher unit; a is 0 or 1; each —W— is independently an Amino Acid unit; w is independently an integer ranging from 0 to 12; —Y— is a Spacer unit; and y is 0, 1 or 2.

In the Drug-Linker-Ligand Conjugate, the Linker is serves to attach the Drug moiety and the Ligand unit.

The Stretcher Unit

The Stretcher unit (-A-), when present, is capable of linking a Ligand unit to an amino acid unit (—W—). In this regard a Ligand (L) has a functional group that can form a bond with a functional group of a Stretcher. Useful functional groups that can be present on a ligand, either naturally or via chemical manipulation include, but are not limited to, sulfhydryl (—SH), amino, hydroxyl, carboxy, the anomeric hydroxyl group of a carbohydrate, and carboxyl. In one aspect, the Ligand functional groups are sulfhydryl and amino. Sulfhydryl groups can be generated by reduction of an intramolecular disulfide bond of a Ligand. Alternatively, sulfhydryl groups can be generated by reaction of an amino group of a lysine moiety of a Ligand using 2-iminothiolane (Traut's reagent) or another sulfhydryl generating reagent.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and IIIb, wherein L-, —W—, —Y—, -D, w and y are as defined above, and $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, and —($CH_2CH_2O$)$_r$—$CH_2$—; and r is an integer ranging from 1-10. It is to be understood from all the exemplary embodiments of Formula Ia, such as III-VI, that even where not denoted expressly, from 1 to 20 drug moieties are linked to a Ligand (p=1-20).

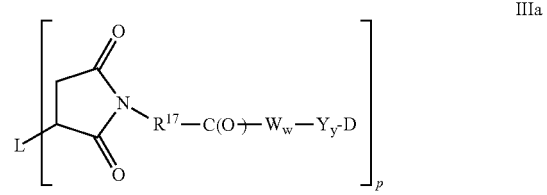

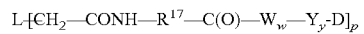

An illustrative Stretcher unit is that of Formula IIIa wherein $R^{17}$ is —($CH_2$)$_5$—:

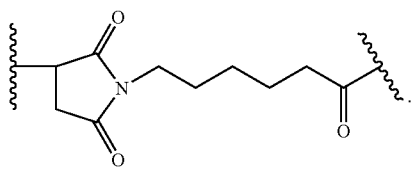 [SMILES: *C(=O)CCCCCN1C(=O)CC(*)C1=O]

Another illustrative Stretcher unit is that of Formula IIIa wherein $R^{17}$ is —(CH$_2$CH$_2$O)$_r$—CH$_2$—; and r is 2:

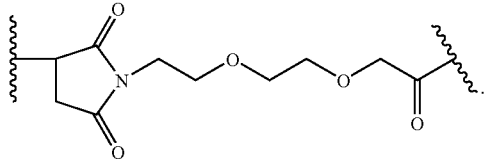 [SMILES: *C(=O)COCCOCCN1C(=O)CC(*)C1=O]

Still another illustrative Stretcher unit is that of Formula IIIb wherein $R^{17}$ is —(CH$_2$)$_5$—:

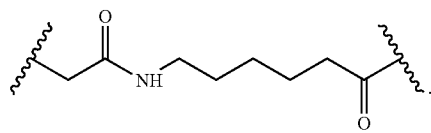 [SMILES: *CC(=O)NCCCCCC(*)=O]

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^{17}$, L-, —W—, —Y—, -D, w and y are as defined above.

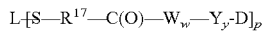

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va-Vc, wherein —$R^{17}$—, L-, —W—, —Y—, -D, w and y are as defined above;

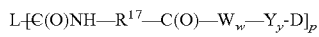    Va

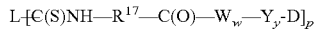    Vb

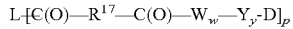    Vc

In yet another aspect, the reactive group of the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. (1991) Bioconjugate Chem 2:133-41. Representative Stretcher units of this embodiment are depicted within the square brackets of Formulas VIa, VIb, and VIc, wherein —$R^{17}$—, L-, —W—, —Y—, -D, w and y are as defined above.

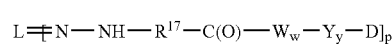    VIa

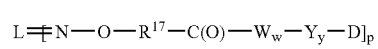    VIb

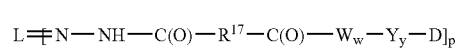    VIc

The Amino Acid Unit

The Amino Acid unit (—W—), when present, links the Stretcher unit to the Spacer unit if the Spacer unit is present, links the Stretcher unit to the Drug moiety if the Spacer unit is absent, and links the Ligand unit to the Drug unit if the Stretcher unit and Spacer unit are absent.

$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

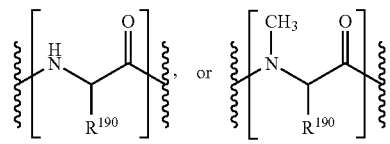

wherein $R^{190}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

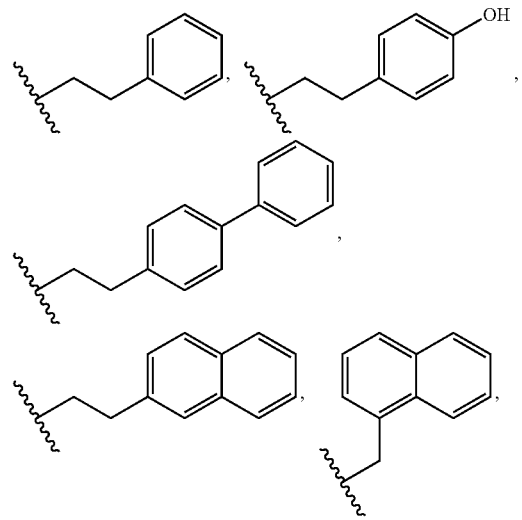

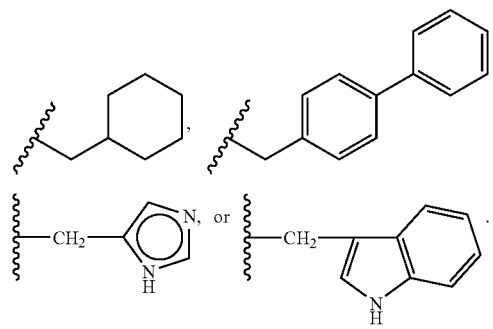

The Amino Acid unit can be enzymatically cleaved by one or more enzymes, including a tumor-associated protease, to liberate the Drug unit (-D), which in one embodiment is protonated in vivo upon release to provide a Drug (D).

Illustrative $W_w$ units are represented by formulas (VII)-(IX):

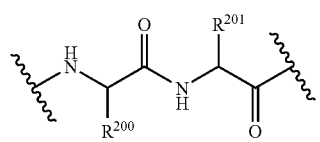

wherein $R^{200}$ and $R^{201}$ are as follows:

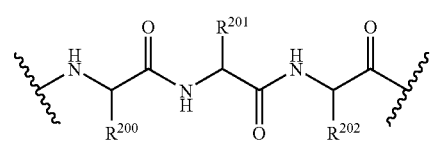

| $R^{200}$ | $R^{201}$ |
|---|---|
| benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 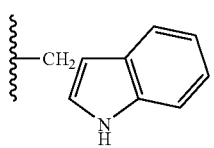 | $(CH_2)_3NHCONH_2$; |
| benzyl | methyl; and |
| benzyl | $(CH_2)_3NHC(=NH)NH_2$; | wherein $R^{200}$, $R^{201}$ and $R^{202}$ are as follows:

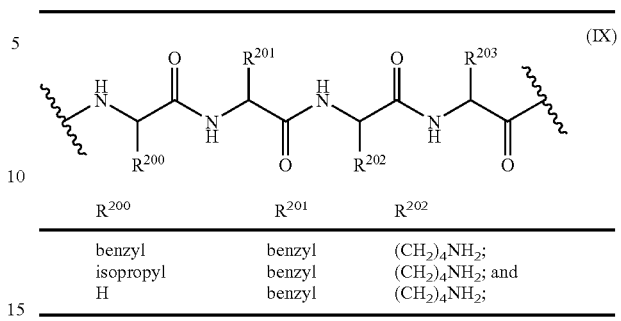

| $R^{200}$ | $R^{201}$ | $R^{202}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; | wherein $R^{200}$, $R^{201}$, $R^{202}$ and $R^{203}$ are as follows:

| $R^{200}$ | $R^{201}$ | $R^{202}$ | $R^{203}$ |
|---|---|---|---|
| H | benzyl | isobutyl | H; and |
| methyl | isobutyl | methyl | isobutyl. |

Exemplary Amino Acid units include, but are not limited to, units of formula (VII) where: $R^{200}$ is benzyl and $R^{201}$ is —$(CH_2)_4NH_2$; $R^{200}$ isopropyl and $R^{201}$ is —$(CH_2)_4NH_2$; $R^{200}$ isopropyl and $R^{201}$ is —$(CH_2)_3NHCONH_2$. Another exemplary Amino Acid unit is a unit of formula (VIII) wherein $R^{200}$ is benzyl, $R^{201}$ is benzyl, and $R^{202}$ is —$(CH_2)_4NH_2$.

Useful —$W_w$— units can be designed and optimized in their selectivity for enzymatic cleavage by a particular enzymes, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide.

When $R^{190}$, $R^{200}$, $R^{201}$, $R^{202}$ or $R^{203}$ is other than hydrogen, the carbon atom to which $R^{190}$, $R^{200}$, $R^{201}$, $R^{202}$ or $R^{203}$ is attached is chiral.

Each carbon atom to which $R^{190}$, $R^{200}$, $R^{201}$, $R^{202}$ or $R^{203}$ is attached is independently in the (S) or (R) configuration.

In one aspect of the Amino Acid unit, the Amino Acid unit is valine-citrulline. In another aspect, the Amino Acid unit is phenylalanine-lysine (i.e. fk). In yet another aspect of the Amino Acid unit, the Amino Acid unit is 5-aminovaleric acid, homophenylalanine-lysine, tetraisoquinolinecarboxylate-lysine, cyclohexylalanine-lysine, isonepecotic acid-lysine, beta-alanine-lysine, glycine-serine-valine-glutamine (SEQ ID NO:1) or isonepecotic acid.

In certain embodiments, the Amino Acid unit can comprise natural amino acids. In other embodiments, the Amino Acid unit can comprise non-natural amino acids.

The Spacer Unit

The Spacer unit (—Y—), when present, links an Amino Acid unit to the Drug moiety when an Amino Acid unit is present. Alternately, the Spacer unit links the Stretcher unit to the Drug moiety when the Amino Acid unit is absent. The Spacer unit also links the Drug moiety to the Ligand unit when both the Amino Acid unit and Stretcher unit are absent.

Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the Drug-Linker-Ligand Conjugate or the Drug-Linker Compound. Examples of a non self-immolative Spacer unit include, but are not limited to a (glycine-glycine) Spacer unit and a glycine Spacer unit (both depicted in Scheme 1) (infra). When an Exemplary Compound containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from L-$A_a$-$W_w$—. In one embodiment, an independent hydrolysis reaction takes place within the target cell, cleaving the glycine-Drug moiety bond and liberating the Drug.

Scheme 1

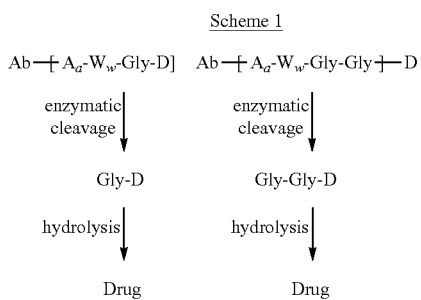

In one embodiment, a non self-immolative Spacer unit (—Y—) is -Gly-Gly-. In another embodiment, a non self-immolative the Spacer unit (—Y—) is -Gly-.

In another embodiment, —$Y_y$— is a p-aminobenzyl alcohol (PAB) unit (see Schemes 2 and 3, infra) whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

In one embodiment, a Drug-Linker Compound or a Drug-Linker Ligand Conjugate is provided in which the Spacer unit is absent (y=0), or a pharmaceutically acceptable salt or solvate thereof.

Alternatively, an Exemplary Compound containing a self-immolative Spacer unit can release -D without the need for a separate hydrolysis step. In this embodiment, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group espoused by Toki et al, 2002, *J. Org. Chem.* 67:1866-1872.

Scheme 2

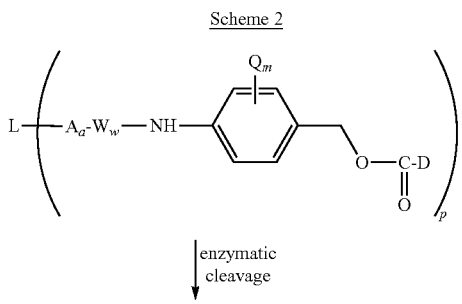

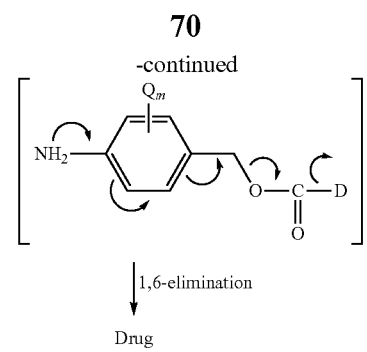

wherein Q is —$C_1$-$C_8$ alkyl, —O—($C_1$-$C_8$ alkyl), -halogen, -nitro or -cyano; m is an integer ranging from 0-4; and p is an integer of from 1 to 20.

Without being bound by any particular theory or mechanism, Scheme 3 depicts a possible mechanism of Drug release of a PAB group which is attached directly to -D via an ether or amine linkage.

Scheme 3

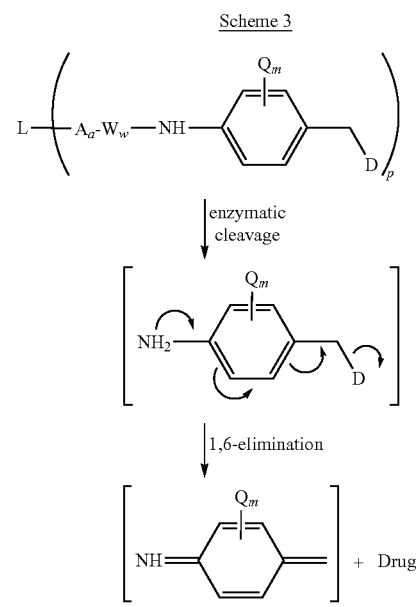

wherein Q is —$C_1$-$C_8$ alkyl, —O—($C_1$-$C_8$ alkyl), -halogen, -nitro or -cyano; m is an integer ranging from 0-4; and p is an integer of from 1 to about 20.

Other examples of self-immolative spacers include, but are not limited to, aromatic compounds that are electronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) and 2-aminophenylpropionic acid amides (see, e.g., Amsberry et al., 1990, *J. Org. Chem.* 55:5867). Elimination of amine-containing drugs that are substituted at the α-position of glycine (see, e.g., Kingsbury et al., 1984, *J. Med. Chem.* 27:1447) are also examples of self-immolative spacer useful in Exemplary Compounds.

In one embodiment, the Spacer unit is a branched bis (hydroxymethyl)styrene (BHMS) unit as depicted in Scheme 4, which can be used to incorporate and release multiple drugs.

Scheme 4

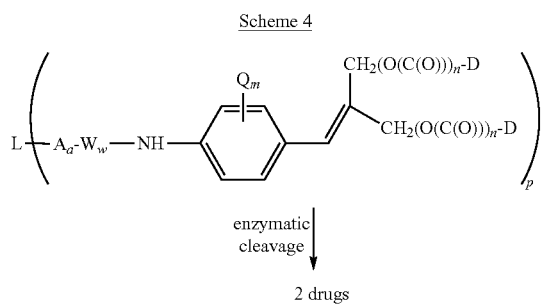

enzymatic cleavage ↓

2 drugs wherein Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to about 20.

In one embodiment, the -D moieties are the same. In yet another embodiment, the -D moieties are different.

In one aspect, Spacer units (—$Y_y$—) are represented by Formulas (X)-(XII):

X

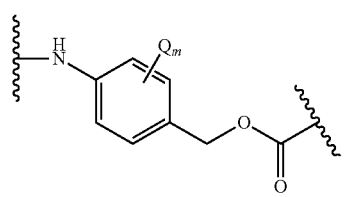

wherein Q is —$C_1$-$C_8$ alkyl, —O—($C_1$-$C_8$ alkyl), -halogen, -nitro or -cyano; and m is an integer ranging from 0-4;

XI

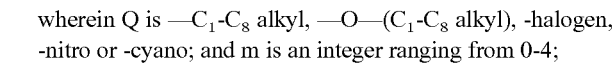

XII

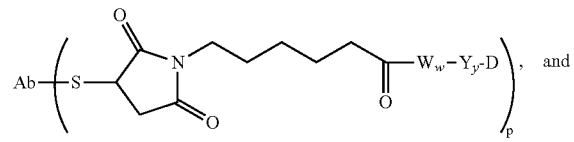

Embodiments of the Formula Ia' Antibody-Drug Conjugate compounds include:

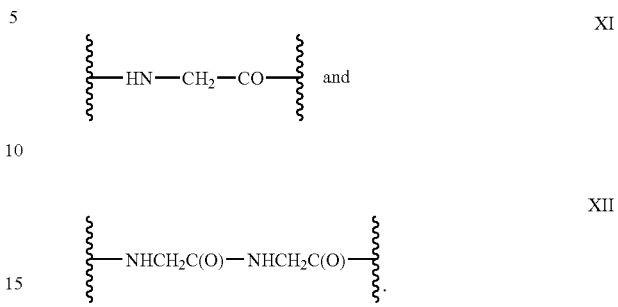

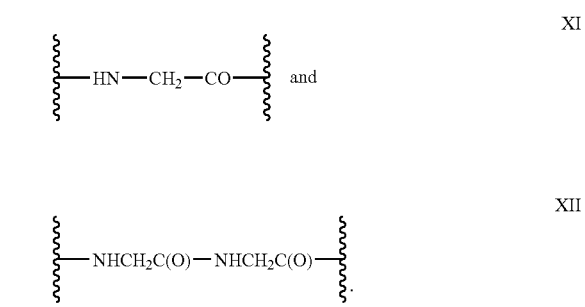

wherein w and y are each 0,

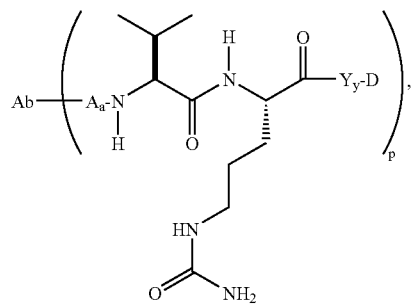

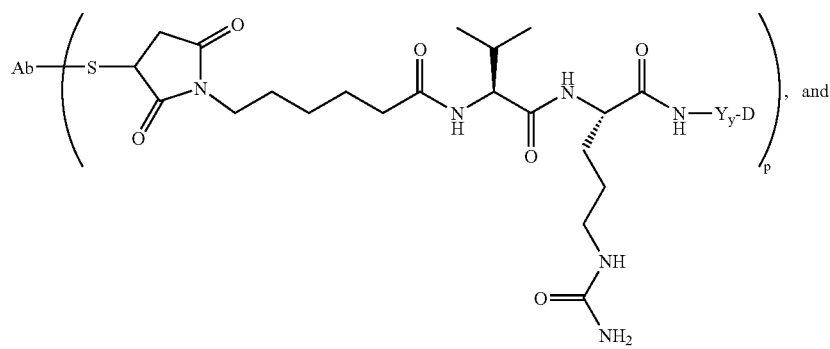

-continued

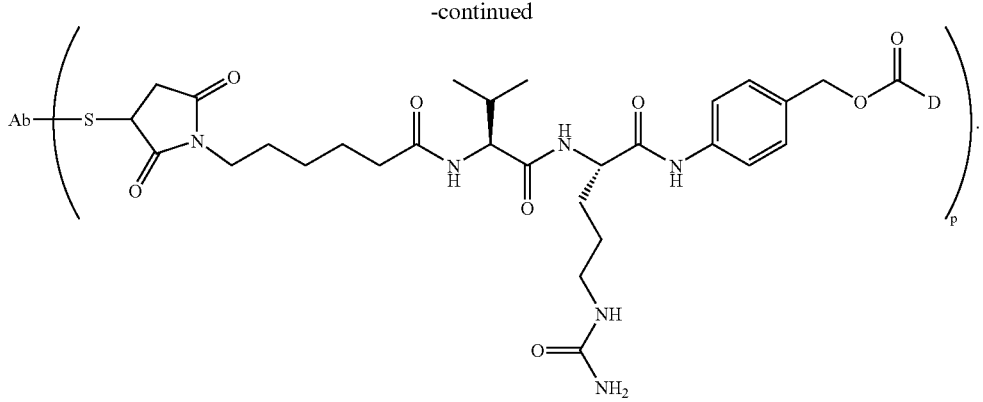

The drug moiety (D) is of the dolastatin/auristatin type (see, e.g., U.S. Pat. Nos. 5,635,483; and 5,780,588) which have been shown to interfere with microtubule dynamics, GTP hydrolysis, and nuclear and cellular division (see, Woyke et al., 2001, *Antimicrob. Agents and Chemother.* 45(12):3580-3584) and have anticancer (see, e.g., U.S. Pat. No. 5,663,149) activity. Some dolastins have antifungal activity (see, e.g., Pettit et al., 1998, *Antimicrob. Agents Chemother.* 42:2961-2965)

As noted above, D refers to a Drug Unit (moiety) having a nitrogen atom or other atom that can form a bond with the Spacer unit when y=1 or 2, with the C-terminal carboxyl group of an Amino Acid unit when y=0, with the of a Stretcher unit when w and y=0, and with the Reactive Site of a Ligand unit when a, w, and y=0. It is to be understood that the terms "Drug unit" and "Drug moiety" are synonymous and used interchangeably herein.

In one embodiment, -D is formula D:

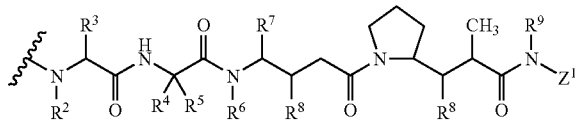

D wherein, independently at each location:
$R^2$ is selected from the group consisting of H and $C_1$-$C_8$ alkyl;
$R^3$ is selected from the group consisting of H, $C_1$-$C_8$ alkyl, $C_3$-$C_8$ carbocycle, aryl, $C_1$-$C_8$ alkyl-aryl, $X^1$—($C_3$-$C_8$ carbocycle), $C_3$-$C_8$ heterocycle and $X^1$—($C_3$-$C_8$ heterocycle);
$R^4$ is selected from the group consisting of H, $C_1$-$C_8$ alkyl, $C_3$-$C_8$ carbocycle, aryl, $X^1$-aryl, $C_1$-$C_8$ alkyl-($C_3$-$C_8$ carbocycle), $C_3$-$C_8$ heterocycle and $X^1$—($C_3$-$C_8$ heterocycle);
$R^5$ is selected from the group consisting of H and methyl;
or $R^4$ and $R^5$ jointly form a carbocyclic ring and have the formula —$(CR^aR^b)_n$— wherein $R^a$ and $R^b$ are independently selected from the group consisting of H, $C_1$-$C_8$ alkyl and $C_3$-$C_8$ carbocycle and n is selected from the group consisting of 2, 3, 4, 5 and 6;
$R^6$ is selected from the group consisting of H and $C_1$-$C_8$ alkyl;
$R^7$ is selected from the group consisting of H, $C_1$-$C_8$ alkyl, $C_3$-$C_8$ carbocycle, aryl, $X^1$-aryl, $X^1$—($C_3$-$C_8$ carbocycle), $C_3$-$C_8$ heterocycle and $X^1$—($C_3$-$C_8$ heterocycle);

each $R^8$ is independently selected from the group consisting of H, OH, $C_1$-$C_8$ alkyl, $C_3$-$C_8$ carbocycle and O—($C_1$-$C_8$ alkyl);
each $X^1$ is independently $C_1$-$C_{10}$ alkylene; and
the moiety —$NR^9Z^1$ is a phenylalanine bioisostere of any of the above embodiments.

In one embodiment, $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl.

In another embodiment, $R^2$ and $R^6$ are each methyl, and $R^9$ is H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is H, $R^7$ is sec-butyl, each occurrence of $R^8$ is —$OCH_3$, and $R^9$ is H.

Illustrative Drug units (-D) include the drug units have the following structure:

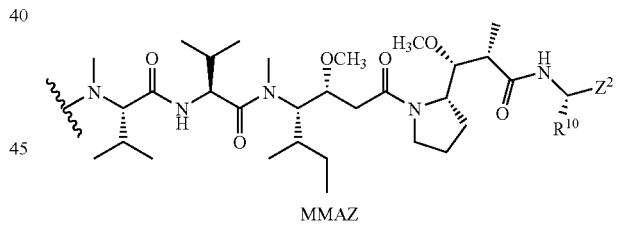

MMAZ and pharmaceutically acceptable salts or solvates thereof wherein $R^{10}$ and $Z^2$ have the meanings provided above.

In one aspect, hydrophilic groups, such as but not limited to triethylene glycol esters (TEG) can be attached to the Drug Unit. Without being bound by theory, the hydrophilic groups assist in the internalization and non-agglomeration of the Drug Unit.

The Ligand Unit (L)

The Ligand unit (L-) includes within its scope any unit of a Ligand (L) that binds or reactively associates or complexes with a receptor, antigen or other receptive moiety associated with a given target-cell population. A Ligand unit is a molecule that binds to, complexes with, or reacts with a receptor, antigen or other receptive moiety of a cell population sought to be therapeutically or otherwise biologically modified. In one aspect, the Ligand unit acts to deliver the Drug unit to the particular target cell population with which the Ligand unit interacts. Such Ligands include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A Ligand unit can form a bond to a Stretcher unit, an Amino Acid unit, a Spacer Unit, or a Drug Unit. A Ligand unit can form a bond to a Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These heteroatoms can be present on the Ligand in the Ligand's natural state, for example a naturally-occurring antibody, or can be introduced into the Ligand via chemical modification.

In one embodiment, a Ligand has a sulfhydryl group and the Ligand bonds to the Linker unit via the sulfhydryl group's sulfur atom.

In another embodiment, the Ligand has lysine residues that can react with activated esters (such esters include, but are not limited to, N-hydroxysuccinimde, pentafluorophenyl, and p-nitrophenyl esters) of the Linker and thus form an amide bond consisting of the nitrogen atom of the Ligand and the C=O group of the Linker.

In yet another aspect, the Ligand has one or more lysine residues that can be chemically modified to introduce one or more sulfhydryl groups. The Ligand unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the Ligand can have one or more carbohydrate groups that can be chemically modified to have one or more sulfhydryl groups. The Ligand unit bonds to the Linker unit, such as the Stretcher Unit, via the sulfhydryl group's sulfur atom.

In yet another embodiment, the Ligand can have one or more carbohydrate groups that can be oxidized to provide an aldehyde (—CHO) group (see, e.g., Laguzza, et al., 1989, *J. Med. Chem.* 32(3):548-55). The corresponding aldehyde can form a bond with a Reactive Site on a Stretcher. Reactive sites on a Stretcher that can react with a carbonyl group on a Ligand include, but are not limited to, hydrazine and hydroxylamine. Other protocols for the modification of proteins for the attachment or association of Drug Units are described in Coligan et al., *Current Protocols in Protein Science*, vol. 2, John Wiley & Sons (2002) (incorporated herein by reference).

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al., 1983, *Proc. Natl. Acad. Sci. USA*. 80:7308-7312; Kozbor et al., 1983, *Immunology Today* 4:72-79; and Olsson et al., 1982, *Meth. Enzymol.* 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, tribodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. No. 4,816,567; and U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, *Int. Rev. Immunol.* 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, *Biotechnology* 12:899-903). Human antibodies can also be produced using various techniques known in the art, including phage display libraries (see, e.g., Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics*, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment or prevention of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, RITUXAN® (rituximab; Genentech) which is a chimeric anti-CD20 monoclonal antibody for the treatment of patients with non-Hodgkin's lymphoma; OVAREX which is a murine antibody for the treatment of ovarian cancer; PANOREX (Glaxo Wellcome, NC) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART MI195 (Protein Design Labs, Inc., CA) and SGN-33 (Seattle Genetics, Inc., WA) which is a humanized anti-CD33 IgG antibody for the treatment of acute myeloid leukemia (AML); LYMPHOCIDE (Immunomedics, Inc., NJ) which is a humanized anti-CD22 IgG antibody for the treatment of non-Hodgkin's lymphoma; SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; AVASTIN (Genentech, Inc., CA) which is an anti-VEGF humanized antibody for the treatment of lung and colorectal cancers; EPRATUZAMAB (Immunomedics, Inc., NJ and Amgen, CA) which is an anti-CD22 antibody for the treatment of non-Hodgkin's lymphoma; and CEACIDE (Immunomedics, NJ) which is a humanized anti-CEA antibody for the treatment of colorectal cancer.

Other antibodies useful in the treatment of cancer include, but are not limited to, antibodies against the following antigens (where exemplary cancers that can be treated with the antibody are in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, *Science* 261:212-215), BR64 (Trail et al., 1997, *Cancer Research* 57:100-105), mAbs against the CD40 antigen, such as S2C6 mAb (Francisco et al., 2000, *Cancer Res.* 60:3225-3231), mAbs against the CD70 antigen, such as 1F6 mAb, humanized 1F6 mAb, 2F2 mAb and humanized 2F2 mAb (see, e.g., International Published Application No. WO 04/073656 and U.S. Published Application No. 2006-0083736) and mAbs against the CD30 antigen, such as AC10 (Bowen et al., 1993, *J. Immunol.* 151:5896-5906; Wahl et al., 2002 *Cancer Res.* 62(13):3736-42) and MDX-060. Many other internalizing antibodies that bind to tumor associated antigens can be used and have been reviewed (see, e.g., Franke et al., 2000, *Cancer Biother. Radiopharm.* 15, 459-76; Murray, 2000, *Semin Oncol.* 27:64-70; Breitling and Dubel, *Recombinant Antibodies*, John Wiley, and Sons, New York, 1998).

In another specific embodiment, antibodies for the treatment or prevention of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques. In another embodiment, useful antibodies are immunospecific for the treatment of autoimmune diseases include, but are not limited to, anti-nuclear antibody; anti-ds DNA; Anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL-70 antibody; anti-Jo antibody; anti-U₁RNP antibody; anti-La/SSB antibody; anti-SSA; anti-SSB antibody; anti-perital cells antibody; anti-histones antibody; anti-RNP antibody; C-ANCA antibody; P-ANCA antibody; anti-centromere antibody; Anti-Fibrillarin antibody and anti-GBM antibody.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the Ligand unit binds to an activated lymphocyte that is associated with an autoimmune disease.

In another specific embodiment, useful Ligands immunospecific for a viral or a microbial antigen are monoclonal antibodies. The antibodies may be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment or prevention of viral or microbial infection in accordance with the methods disclosed herein. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc, CA) which is a humanized IgG₁ antibody useful for the treatment of cytomegalovirus (CMV); and anti-LPS antibodies.

Other antibodies useful in the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudoinonas aeraginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasnia* spp., *Rickettsia prowazeki, Rickettsia tsutsugumushi*, and *Chlamydia* spp.); pathogenic fungi (*Coccidioides immitis, Aspergillus fumigatus, Candida albicans, Blastomyces dermatitidis, Cryptococcus neoformans,* and *Histoplasma capsulatum*); protozoa (*Entomoeba histolytica, Toxoplasma gondii, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

In an exemplary embodiment, the Ligand-Linker-Drug Conjugate has Formula IIIa, where the Ligand is an antibody Ab that binds at least one of CD20, CD30, CD33, CD40, CD70, BCMA, and Lewis Y antigen, w=0, y=0, and D has Formula Ib. Exemplary Conjugates of Formula IIIa include those in which $R^{17}$ is —$(CH_2)_5$—. Also included are such Conjugates of Formula IIIa containing about 2 to about 8, or about 2 to about 6 Drug moieties D per Ligand unit (that is, Conjugates of Formula Ia wherein p is a value in the range about 2-8, for example about 2-6). Conjugates containing combinations of the structural features noted in this paragraph are also contemplated as within the scope of the compounds of the invention.

In another embodiment, the Ligand-Linker-Drug Conjugate has Formula IIIa, where Ligand is an Antibody Ab that binds one of CD20, CD30, CD33, CD40, CD70, BCMA, and Lewis Y antigen, w=1, y=0, and D has Formula Ib. Included are such Conjugates of Formula IIIa in which $R^{17}$ is —$(CH_2)_5$—. Also included are such Conjugates of Formula IIIa containing about 2 to about 8, or about 2 to about 6 Drug moieties D per Ligand unit (that is, Conjugates of Formula Ia wherein p is a value in the range of about 2-8, or about 2-6). Conjugates containing combinations of the structural features noted in this paragraph are also exemplary.

In another embodiment, the Ligand-Linker-Drug Conjugate has Formula IIIa, where the Ligand is an Antibody Ab that binds one of CD20, CD30, CD33, CD40, CD70, BCMA, and Lewis Y antigen, w=1, y=1, and D has Formula Ib. Included are Conjugates of Formula IIIa in which $R^{17}$ is —$(CH_2)_5$—. Conjugates containing combinations of the structural features noted in this paragraph are also contemplated within the scope of the compounds of the invention.

Production of Recombinant Antibodies

Antibodies of the invention can be produced using any method known in the art to be useful for the synthesis of antibodies, in particular, by chemical synthesis or by recombinant expression.

Recombinant expression of antibodies, or fragment, derivative or analog thereof, requires construction of a nucleic acid that encodes the antibody. If the nucleotide sequence of the antibody is known, a nucleic acid encoding the antibody may be assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides, e.g., by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by, e.g., PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing a non-human animal, or suitable animal model such as a rabbit or mouse, to generate polyclonal antibodies or, more preferably, by generating monoclonal antibodies, e.g., as described by Kohler and Milstein (1975, *Nature* 256: 495-497) or as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody can be obtained by screening Fab expression libraries (e.g., as described in Huse et al., 1989, *Science* 246:1275-1281) for clones of Fab fragments that bind the specific antigen or by screening antibody libraries (see, e.g., Clackson et al., 1991, *Nature* 352:624; Hane et al., 1997, *Proc. Natl. Acad. Sci. USA* 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; WO 89/01036; and U.S. Pat. No. 5,122,464). Vectors containing the complete light or heavy chain that allow for the expression of a complete antibody molecule are available. The nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis and in vitro site directed mutagenesis (Hutchinson et al., 1978, *J. Biol. Chem.* 253:6551).

In addition, techniques developed for the production of "chimeric antibodies" (see, e.g., Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, *Science* 242:1038-1041).

Antibody fragments that recognize specific epitopes can be generated by known techniques. For example, such fragments include F(ab')$_2$ fragments, Fab fragments, Fv fragments, diabodies, triabodies, tetrabodies, single chain antibodies, scFv, scFv-Fc and the like.

Once a nucleic acid sequence encoding an antibody has been obtained, the vector for the production of the antibody can be produced by recombinant DNA technology using techniques well known in the art. Methods that are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, *Molecular Cloning, A Laboratory Manual*, 2$^{nd}$ Ed., Cold Spring Harbor Laboratory, Cold Spring Harbor, N.Y.; 2001; *Molecular Cloning, A Laboratory Manual*, 3$^{rd}$ ed., Cold Spring Harbor Publish., Cold Spring Harbor, N.Y.) and Ausubel et al., eds., in *Current Protocols in Molecular Biology series of laboratory technique manuals*, 1987-1999, *Current Protocols,*© 1994-199 John Wiley and Sons, Inc.).

An expression vector comprising the nucleotide sequence of an antibody or the nucleotide sequence of an antibody can be transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

The host cells used to express the recombinant antibody can be either bacterial cells such as *Escherichia coli* or eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 198, *Gene* 45:101; Cockett et al., 1990, *BioTechnology* 8:2).

A variety of host-expression vector systems can be utilized to express the immunoglobulin antibodies. Such host-expression systems represent vehicles by which the coding sequences of the antibody can be produced and subsequently purified, but also represent cells that can, when transformed or transfected with the appropriate nucleotide coding sequences, express an antibody immunoglobulin molecule in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces Pichia*) transformed with recombinant yeast expression vectors containing immunoglobulin coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing immunoglobulin coding sequences; or mammalian cell systems (e.g., COS, CHO, BH, 293, 293T, or 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX Vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) or the analogous virus from *Drosophila Melanogaster* can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (e.g., see Logan & Shenk, 1984, *Proc. Natl. Acad. Sci. USA* 81:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.* 153:51-544). In some embodiments, antibodies can be expressed using the CHEF system. (See, e.g., U.S. Pat. No. 5,888,809; the disclosure of which is incorporated by reference herein.)

In addition, a host cell strain can be chosen to modulate the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO (e.g., DG44), VERY, BH, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is typically used. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody. Such engineered cell lines can be particularly useful in screening and evaluation of tumor antigens that interact directly or indirectly with the antibody.

A number of selection systems can be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:817) genes can be employed in tk−, hgprt− or aprt-cells, respectively. Also, antimetabolite resistance can be used as the basis of selection for the following genes: DHFR, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (*Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (supra; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1).

The expression levels of an antibody can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (see, e.g., Crouse et al., 1983, *Mol. Cell. Biol.* 3:257).

The host cell can be co-transfected with two expression vectors, the first vector encoding a heavy chain derived polypeptide and the second vector encoding a light chain derived polypeptide. The two vectors can contain identical selectable markers that enable equal expression of heavy and light chain polypeptides. Alternatively, a single vector can be used to encode both heavy and light chain polypeptides. In such situations, the light chain is typically placed before the heavy chain to avoid an excess of toxic free heavy chain (see, e.g., Proudfoot, 1986, *Nature* 322:52; Kohler, 1980, *Proc. Natl. Acad. Sci. USA* 77:2197). The coding sequences for the heavy and light chains can comprise cDNA or genomic DNA.

Once the antibody has been recombinantly expressed, it can be purified using any method known in the art for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

In yet another exemplary embodiment, the antibody is a monoclonal antibody.

Production of Antibodies

The production of antibodies will be illustrated with reference to anti-CD30 antibodies but it will be apparent for those skilled in the art that antibodies to other targets (such as members of the TNF receptor family) can be produced and modified in a similar manner. The use of CD30 for the production of antibodies is exemplary only and not intended to be limiting.

The CD30 antigen to be used for production of antibodies may be, e.g., a soluble form of the extracellular domain of CD30 or a portion thereof, containing the desired epitope. Alternatively, cells expressing CD30 at their cell surface (e.g., L540 (Hodgkin's lymphoma derived cell line with a T cell phenotype) and L428 (Hodgkin's lymphoma derived cell line with a B cell phenotype)) can be used to generate antibodies. Other forms of CD30 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Typically, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., 1975, *Nature* 256:495, or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (see, e.g., Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (see, e.g., Kozbor, 1984, *J. Immunol.* 133:3001; and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., 1980, *Anal. Biochem.* 107:220.

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, *Curr. Opinion in Immunol.* 5:256-262 and Plückthun, 1992, *Immunol. Revs.* 130:151-188.

In a further embodiment, monoclonal antibodies or antibody fragments can be isolated from antibody phage libraries generated using the techniques described in McCafferty et al., 1990, *Nature* 348:552-554. Clackson et al., 1991, *Nature,* 352:624-628 and Marks et al., 1991, *J. Mol. Biol.* 222:581-597 describe the isolation of murine and human antibodies, respectively, using phage libraries. Subsequent publications describe the production of high affinity (nM range) human antibodies by chain shuffling (Marks et al., 1992, *Bio/Technology,* 10:779-783), as well as combinatorial infection and in vivo recombination as a strategy for constructing very large phage libraries (see, e.g., Waterhouse et al., 1993, *Nuc. Acids. Res.,* 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (see, e.g., U.S. Pat. No. 4,816,567; and Morrison et al., 1984, *Proc. Natl. Acad. Sci. USA* 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

A humanized antibody may have one or more amino acid residues introduced into it from a source which is non-human. These non-human amino acid residues are often referred to as "import" residues, which are typically taken from an "import" variable domain. Humanization can be essentially performed following the method of Winter and co-workers (see, e.g., Jones et al., 1986, *Nature* 321:522-525; Riechmann et al., 1988, *Nature* 332:323-327; Verhoeyen et al., 1988, *Science* 239:1534-1536), by substituting hypervariable region sequences for the corresponding sequences of a human antibody. Accordingly, such "humanized" antibodies are chimeric antibodies (see, e.g., U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., 1993, *J. Immunol.* 151:2296; Chothia et al., 1987, *J. Mol. Biol.* 196:901). Another method uses a particular framework region derived from the consensus sequence of all human antibodies of a particular subgroup of light or heavy chains. The same framework may be used for several different humanized antibodies (see, e.g., Carter et al., 1992, *Proc. Natl. Acad. Sci. USA,* 89:4285; Presta et al., 1993, *J. Immunol.* 151:2623).

In another embodiment, the antibodies may be humanized with retention of high affinity for the antigen and other favorable biological properties. Humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of the humanized antibody are contemplated. For example, the humanized antibody may be an antibody fragment, such as a Fab fragments, F(ab')$_2$ fragments, Fv fragments, diabodies, triabodies, tetrabodies, single chain antibodies, scFv, scFv-Fc and the like. Alternatively, the humanized antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., 1993, *Proc. Natl. Acad. Sci. USA,* 90:2551; Jakobovits et al., 1993, *Nature* 362:255-258; Bruggermann et al., 1993, *Year in Immuno.* 7:33; and U.S. Pat. Nos. 5,591,669, 5,589,369 and 5,545,807.

Alternatively, phage display technology (see, e.g., McCafferty et al., 1990, *Nature* 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson and Chiswell, 1993, *Current Opinion in Structural Biology* 3:564-571. Several sources of V-gene segments can be used for phage display. Clackson et al., 1991, *Nature* 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., 1991, *J. Mol. Biol.* 222:581-597), or Griffith et al., 1993, *EMBO J.* 12:725-734. See also U.S. Pat. Nos. 5,565,332 and 5,573,905. As discussed above, human antibodies may also be generated by in vitro activated B cells (see, e.g., U.S. Pat. Nos. 5,567,610 and 5,229,275). Human anti-CD30 antibodies are described in U.S. Patent Application Publication No. 2004-0006215.

(v) Antibody Fragments

Various techniques have been developed for the production of antibody fragments. Traditionally, these fragments were derived via proteolytic digestion of intact antibodies (see, e.g., Morimoto et al., 1992, *Journal of Biochemical and Biophysical Methods* 24:107-117; and Brennan et al., 1985, *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (see, e.g., Carter et al., 1992, *Bio/Technology* 10: 163-167). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of a target protein. Alternatively, an antibody arm may be combined with an arm which binds to a Fc receptors for IgG (FcγR), such as FcγRI (CD64), FcγRII (CD32) and FcγRIII (CD16) so as to focus cellular defense mechanisms to the target-expressing cell. Bispecific antibodies may also be used to localize cytotoxic agents to cells which express the target.

Traditional production of full length bispecific antibodies is based on the coexpression of two immunoglobulin heavy chain-light chain pairs, where the two chains have different specificities (see, e.g., Millstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J. 10:3655-3659. According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology 121:210.

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have also been described in the literature. For example, bispecific antibodies can be prepared using chemical linkage. Brennan et al., 1985, Science, 229: 81 describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., 1992, J. Exp. Med. 175: 217-225 describe the production of a fully humanized bispecific antibody $F(ab')_2$ molecule. Each Fab' fragment was separately secreted from E. coli and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., 1992, J. Immunol. 148(5):1547-1553. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., 1993, Proc. Natl. Acad. Sci. USA 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., 1994, J. Immunol. 152:5368.

Antibodies with more than two valencies are contemplated. For example, trispecific antibodies can be prepared. Tutt et al. J. Immunol. 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are favored locations for mutagenesis is called "alanine scanning mutagenesis" as described by Cunningham and Wells, 1989, *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues can be divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., 1992, *J. Exp Med.* 176:1191-1195 and Shopes, 1992, *J. Immunol.* 148: 2918-2922. Homodimeric antibodies with enhanced anti-tumor activity may also be prepared using heterobifunctional cross-linkers as described in Wolff et al., 1993, *Cancer Research* 53:2560-2565. Alternatively, an antibody can be engineered which has dual Fc regions and may thereby have enhanced complement lysis and ADCC capabilities. See Stevenson et al., 1989, *Anti-Cancer Drug Design* 3:219-230.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(viii) Glycosylation Variants

Antibodies in the ADC of the invention may be glycosylated at conserved positions in their constant regions (see, e.g., Jefferis and Lund, 1997, *Chem. Immunol.* 65:111-128; Wright and Morrison, 1997, *TibTECH* 15:26-32). The oligosaccharide side chains of the immunoglobulins affect the protein's function (see, e.g., Boyd et al., 1996, *Mol. Immunol.* 32:1311-1318; Wittwe and Howard, 1990, *Biochem.* 29:4175-4180), and the intramolecular interaction between portions of the glycoprotein which can affect the conformation and presented three-dimensional surface of the glycoprotein (Hefferis and Lund, supra; Wyss and Wagner, 1996, *Current Opin. Biotech.* 7:409-416). Oligosaccharides may also serve to target a given glycoprotein to certain molecules based upon specific recognition structures. For example, it has been reported that in agalactosylated IgG, the oligosaccharide moiety 'flips' out of the inter-$C_H2$ space and terminal N-acetylglucosamine residues become available to bind mannose binding protein (Malhotra et al., 1995, *Nature Med.* 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., 1996, *Mol. Immunol.* 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, *Nature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., 1997, *J. Biol. Chem.* 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261; and 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

Screening for Ligand-Linker-Drug Conjugates

Transgenic animals and cell lines are particularly useful in screening Drug-Linker-Ligand conjugates (e.g., antibody drug conjugates (ADC)) for prophylactic or therapeutic treatments of diseases or disorders involving overexpression of a target protein (e.g., CD20, CD30, CD33, CD40, CD70, BCMA, and Lewis Y). The screening of Drug-Linker-Ligand conjugates as ADCs is exemplified herein;

Transgenic animals and cell lines are particularly useful in screening antibody drug conjugates (ADC). Screening for a useful ADC may involve administering candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. Candidate ADC may be screened serially and individually, or in parallel under medium or high-throughput screening format. The rate at which ADC may be screened for utility for prophylactic or therapeutic treatments of diseases or disorders is limited only by the rate of synthesis or screening methodology, including detecting/measuring/analysis of data.

One embodiment is a screening method comprising (a) transplanting cells from a stable renal cell cancer cell line into a non-human animal, (b) administering an ADC drug candidate to the non-human animal and (c) determining the ability of the candidate to inhibit the formation of tumors from the transplanted cell line.

Another embodiment is a screening method comprising (a) contacting cells from a stable Hodgkin's disease cell line with an ADC drug candidate and (b) evaluating the ability of the ADC candidate to block ligand activation of CD40.

Another embodiment is a screening method comprising (a) contacting cells from a stable Hodgkin's disease cell line with an ADC drug candidate and (b) evaluating the ability of the ADC candidate to induce cell death. In one embodiment the ability of the ADC candidate to induce apoptosis is evaluated.

One embodiment is a screening method comprising (a) transplanting cells from a stable cancer cell line into a non-human animal, (b) administering an ADC drug candidate to the non-human animal and (c) determining the ability of the candidate to inhibit the formation of tumors from the transplanted cell line.

Another embodiment is a screening method comprising (a) contacting cells from a stable cancer cell line with an ADC drug candidate and (b) evaluating the ability of the ADC candidate to induce cell death. In one embodiment the ability of the ADC candidate to induce apoptosis is evaluated.

In one embodiment, candidate ADC are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with co-factors that would enhance the efficacy of the compound. If cell lines derived from the subject transgenic animals are used to screen for compounds useful in treating various disorders, the test compounds are added to the cell culture medium at an appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, provided herein are assays for identifying Drug-Linker-Ligand conjugates (such as ADCs) which specifically target and bind a target protein, the presence of which is correlated with abnormal cellular function, and in the pathogenesis of cellular proliferation and/or differentiation that is causally related to the development of tumors.

To identify growth inhibitory compounds that specifically target an antigen of interest, one may screen for compounds which inhibit the growth of cancer cells overexpressing antigen of interest derived from transgenic animals, the assay described in U.S. Pat. No. 5,677,171 can be performed. According to this assay, cancer cells overexpressing the antigen of interest are grown in a 1:1 mixture of F12 and DMEM medium supplemented with 10% fetal bovine serum, glutamine and penicillin streptomycin. The cells are plated at 20,000 cells in a 35 mm cell culture dish (2 mls/35 mm dish) and the test compound is added at various concentrations. After six days, the number of cells, compared to untreated cells is counted using an electronic COULTER™ cell counter. Those compounds which inhibit cell growth by about 20-100% or about 50-100% may be selected as growth inhibitory compounds.

To select for compounds which induce cell death, loss of membrane integrity as indicated by, e.g., PI, trypan blue or 7AAD uptake may be assessed relative to control. The PI uptake assay uses cells isolated from the tumor tissue of interest of a transgenic animal. According to this assay, the cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. The cells are seeded at a density of $3 \times 10^6$ per dish in 100×20 mm dishes and allowed to attach overnight. The medium is then removed and replaced with fresh medium alone or medium containing various concentrations of the compound. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those compounds which induce statistically significant levels of cell death as determined by PI uptake may be selected as cell death-inducing compounds.

In order to select for compounds which induce apoptosis, an annexin binding assay using cells established from the tumor tissue of interest of the transgenic animal is performed. The cells are cultured and seeded in dishes as discussed in the preceding paragraph. The medium is then removed and replaced with fresh medium alone or medium containing 10 µg/ml of the antibody drug conjugate (ADC). Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g., annexin V-FITC) (1 µg/ml). Samples may be analyzed using a FACSCAN™ flow cytometer and FACSCONVERT™ CellQuest software (Becton Dickinson). Those compounds which induce statistically significant levels of annexin binding relative to control are selected as apoptosis-inducing compounds.

In Vitro Cell Proliferation Assays

Generally, the cytotoxic or cytostatic activity of a Drug-Linker-Ligand conjugate, such as an antibody drug conjugate (ADC), is measured by: exposing mammalian cells having receptor proteins to the antibody of the conjugate in a cell culture medium; culturing the cells for a period from about 6 hours to about 5 days; and measuring cell viability. Cell-based in vitro assays are used to measure viability (proliferation), cytotoxicity, and induction of apoptosis (caspase activation) of a Drug-Linker-Ligand conjugate. The screening of Drug-Linker-Ligand conjugates as ADCs is exemplified herein.

The in vitro potency of antibody drug conjugates is measured by a cell proliferation assay (see Examples). The Cell-Titer-Glo® Luminescent Cell Viability Assay is a commercially available (Promega Corp., Madison, Wis.), homogeneous assay method based on the recombinant expression of *Coleoptera* luciferase (U.S. Pat. Nos. 5,583, 024; 5,674,713 and 5,700,670). This cell proliferation assay determines the number of viable cells in culture based on quantitation of the ATP present, an indicator of metabolically active cells (Crouch et al., 1993, *J. Immunol. Meth.* 160:81-88, U.S. Pat. No. 6,602,677). The CellTiter-Glo® Assay is conducted in 96 well format, making it amenable to automated high-throughput screening (HTS) (Cree et al. (1995) *AntiCancer Drugs* 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e., 3 hours, show the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g., 96 or 384 well format. Data can be recorded by luminometer or CCD camera imaging device. The luminescence output is presented as relative light units (RLU), measured over time.

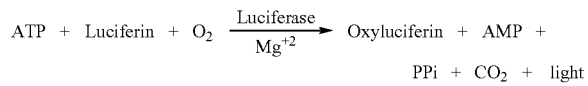

The anti-proliferative effects of antibody drug conjugates can be measured by the cell proliferation, in vitro cell killing assay above against different breast tumor cell lines.

In Vivo Plasma Clearance and Stability

Pharmacokinetic plasma clearance and stability of Drug-Linker-Ligand conjugates, such as ADCs, can be investigated in rats and cynomolgus monkeys over time. The screening of Drug-Linker-Ligand conjugates as ADCs is exemplified herein.

Rodent Toxicity

Antibody drug conjugates and an ADC-minus control, "Vehicle", are evaluated in an acute toxicity rat model. Toxicity of ADC is investigated by treatment of male and female Sprague-Dawley rats with the ADC and subsequent inspection and analysis of the effects on various organs. Gross observations include changes in body weights and signs of lesions and bleeding. Clinical pathology parameters (serum chemistry and hematology), histopathology, and necropsy are conducted on dosed animals. It is considered that weight loss, or weight change relative to animals dosed only with Vehicle, in animals after dosing with ADC is a gross and general indicator of systemic or localized toxicity.

Hepatotoxicity is measured by elevated liver enzymes, increased numbers of mitotic and apoptotic figures and hepatocyte necrosis. Hematolymphoid toxicity is observed by depletion of leukocytes, primarily granuloctyes (neutrophils), and/or platelets, and lymphoid organ involvement, i.e. atrophy or apoptotic activity. Toxicity is also noted by gastrointestinal tract lesions such as increased numbers of mitotic and apoptotic figures and degenerative enterocolitis.

Enzymes indicative of liver injury that are studied include:
AST (aspartate aminotransferase)
  Localization: cytoplasmic; liver, heart, skeletal muscle, kidney
  Liver:Plasma ratio of 7000:1
  T1/2: 17 hrs
ALT (alanine aminotransferase)
  Localization: cytoplasmic; liver, kidney, heart, skeletal muscle
  Liver:Plasma ratio of 3000:1
  T1/2: 42 hrs; diurnal variation
GGT (g-glutamyl transferase)
  Localization: plasma membrane of cells with high secretory or absorptive capacity; liver, kidney, intestine
Poor predictor of liver injury; commonly elevated in bile duct disorders Cynomolgus Monkey Toxicity/Safety Similar to the rat toxicity/safety study, cynomolgus monkeys are treated with ADC followed by liver enzyme measurements, and inspection and analysis of the effects on various organs. Gross observations include changes in body weights and signs of lesions and bleeding. Clinical pathology parameters (serum chemistry and hematology), histopathology, and necropsy are conducted on dosed animals.

Synthesis of the Compounds

The Exemplary Compounds and Exemplary Conjugates can be made using the synthetic procedures outlined below in Schemes 5-16. As described in more detail below, the Exemplary Compounds or Exemplary Conjugates can be conveniently prepared using a Linker having a reactive site for binding to the Drug and Ligand. In one aspect, a Linker has a reactive site which has an electrophilic group that is reactive to a nucleophilic group present on a Ligand, such as but not limited to an antibody. Useful nucleophilic groups on an antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide and haloacetamide groups. The electrophilic group provides a convenient site for antibody attachment.

In another embodiment, a Linker has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Carboxylic acid functional groups and chloroformate functional groups are also useful reactive sites for a Linker because they can react with secondary amino groups of a Drug to form an amide linkage. Also useful as a reactive site is a carbonate functional group on a Linker, such as but not limited to p-nitrophenyl carbonate, which can react with an amino group of a Drug, such as but not limited to N-methyl valine, to form a carbamate linkage. Typically, peptide-based Drugs can be prepared by forming a peptide bond between two or more amino acids and/or peptide fragments. Such peptide bonds can be prepared, for example, according to the liquid phase synthesis method (see Schröder and Lübke, "The Peptides", volume 1, pp 76-136, 1965, Academic Press) that is well known in the field of peptide chemistry.

The synthesis of an illustrative Stretcher having an electrophilic maleimide group is illustrated below in Schemes 8-9. General synthetic methods useful for the synthesis of a Linker are described in Scheme 10. Scheme 11 shows the construction of a Linker unit having a val-cit group, an electrophilic maleimide group and a PAB self-immolative Spacer group. Scheme 12 depicts the synthesis of a Linker having a phe-lys group, an electrophilic maleimide group, with and without the PAB self-immolative Spacer group. Scheme 13 presents a general outline for the synthesis of a Drug-Linker Compound, while Scheme 14 presents an alternate route for preparing a Drug-Linker Compound. Scheme 15 depicts the synthesis of a branched linker containing a BHMS group. Scheme 16 outlines the attachment of an antibody to a Drug-Linker Compound to form a Drug-Linker-Antibody Conjugate, and Scheme 14 illustrates the synthesis of Drug-Linker-Antibody Conjugates having, for example but not limited to, 2 or 4 drugs per Antibody.

As described in more detail below, the Exemplary Conjugates are conveniently prepared using a Linker having two or more Reactive Sites for binding to the Drug and a Ligand. In one aspect, a Linker has a Reactive site which has an electrophilic group that is reactive to a nucleophilic group present on a Ligand, such as an antibody. Useful nucleophilic groups on an antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide and haloacetamide groups. The electrophilic group provides a convenient site for antibody attachment.

In another embodiment, a Linker has a Reactive site which has a nucleophilic group that is reactive to an electrophilic group present on a Ligand, such as an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

In yet another embodiment a Drug containing aromatic arsine oxide can directly bind to a Ligand unit containing proximal dithiols to form stable arsine-dithiol cyclic structures.

Drug Moiety Synthesis

Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

The auristatin/dolastatin drug moieties may be prepared according to the general methods of: U.S. Pat. No. 5,635,483; U.S. Pat. No. 5,780,588; Pettit et al., 1989, *J. Am. Chem. Soc.* 111:5463-5465; Pettit et al., 1998, *Anti-Cancer Drug Design* 13:243-277; and Pettit et al., 1996, *J. Chem. Soc. Perkin Trans.* 15:859-863.

In one embodiment, a Drug is prepared by combining about a stoichiometric equivalent of a dipeptide and a tripeptide, preferably in a one-pot reaction under suitable condensation conditions. This approach is illustrated in Schemes 5-7, below.

Scheme 5 illustrates the synthesis of an N-terminal tripeptide unit F which is a useful intermediate for the synthesis of the drug compounds of Formula Ib.

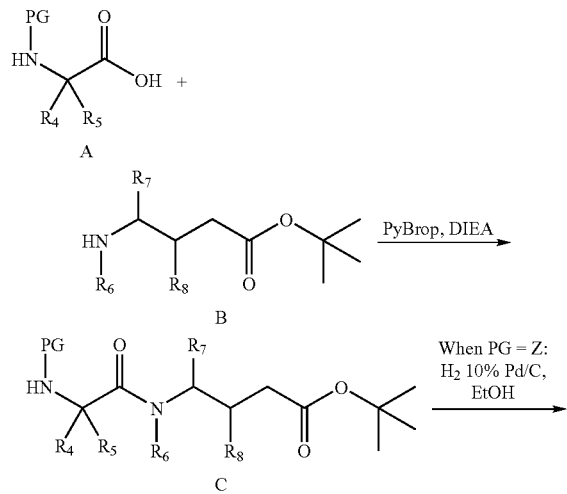

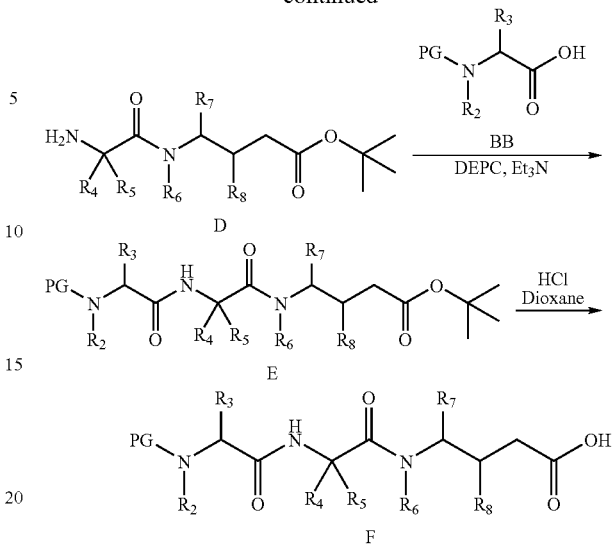

As illustrated in Scheme 5, a protected amino acid A (where PG represents an amine protecting group, $R^4$ is selected from hydrogen, $C_1$-$C_8$ alkyl, $C_3$-$C_8$ carbocycle, —O—($C_1$-$C_8$ alkyl), -aryl, $X^1$-aryl, $X^1$—($C_3$-$C_8$ carbocycle), $C_3$-$C_8$ heterocycle, $X^1$—($C_3$-$C_8$ heterocycle) and $R^5$ is selected from H and methyl; or $R^4$ and $R^5$ join, have the formula —$(CR^aR^b)_n$— wherein $R^a$ and $R^b$ are independently selected from hydrogen, $C_1$-$C_8$ alkyl and $C_3$-$C_8$ carbocycle and n is selected from 2, 3, 4, 5 and 6, and form a ring with the carbon atom to which they are attached) is coupled to t-butyl ester B (where $R^6$ is selected from —H and —$C_1$-$C_8$ alkyl; and $R^7$ is selected from hydrogen, $C_1$-$C_8$ alkyl, $C_3$-$C_8$ carbocycle, —O—($C_1$-$C_8$ alkyl), aryl, $X^1$-aryl, $X^1$—($C_3$-$C_8$ carbocycle), $C_3$-$C_8$ heterocycle and $X^1$—($C_3$-$C_8$ heterocycle)) under suitable coupling conditions, e.g., in the presence of PyBrop and diisopropylethylamine, or using DCC (see, for example, Miyazaki et. al., 1995, *Chem. Pharm. Bull.* 43(10): 1706-1718).

Suitable protecting groups PG, and suitable synthetic methods to protect an amino group with a protecting group are well known in the art. See, e.g., Greene and Wuts, *Protective Groups in Organic Synthesis, 2nd Edition,* 1991, John Wiley & Sons. Exemplary protected amino acids A are PG-e and, particularly, PG-Val, while other suitable protected amino acids include, without limitation: PG-cyclohexylglycine, PG-cyclohexylalanine, PG-aminocyclopropane-1-carboxylic acid, PG-aminoisobutyric acid, PG-phenylalanine, PG-phenylglycine, and PG-tert-butylglycine. Z is an exemplary protecting group. Fmoc is another exemplary protecting group. An exemplary t-butyl ester B is dolaisoleuine t-butyl ester.

The dipeptide C can be purified, e.g., using chromatography, and subsequently deprotected, e.g., using H2 and 10% Pd—C in ethanol when PG is benzyloxycarbonyl, or using diethylamine for removal of an Fmoc protecting group. The resulting amine D readily forms a peptide bond with an amino acid BB (wherein $R^1$ is selected from —H, —$C_1$-$C_8$ alkyl and —$C_3$-$C_8$ carbocycle; and $R^2$ is selected from —H and —$C_1$-$C_8$ alkyl; or $R^1$ and $R^2$ join, have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the nitrogen atom to which they are attached; and $R^3$ is selected from hydrogen, $C_1$-$C_8$ alkyl, $C_3$-$C_8$ carbocycle, —O—($C_1$-$C_8$ alkyl), aryl, $X^1$-aryl, $X^1$—($C_3$-$C_8$ carbocycle), $C_3$-$C_8$ heterocycle and $X^1$—($C_3$-$C_8$ heterocycle)). N,N-Dialkyl amino acids are exemplary amino acids for BB, such as commercially available N,N-dimethyl valine. Other N,N-dialkyl amino acids can be prepared by reductive bis-alkylation using known procedures (see, e.g., Bowman et al., 1950, *J. Chem. Soc.* 1342-1340). Fmoc-Me-L-Val and Fmoc-Me-L-glycine are two exemplary amino acids BB useful for the synthesis of N-monoalkyl derivatives. The amine D and the amino acid BB react to provide the tripeptide E using coupling reagent DEPC with triethylamine as the base. The C-terminus protecting group of E is subsequently deprotected using HCl to provide the tripeptide compound of formula F.

Illustrative DEPC coupling methodology and the PyBrop coupling methodology shown in Scheme 5 are outlined below in General Procedure A and General Procedure B, respectively. Illustrative methodology for the deprotection of a CBZ-protected amine via catalytic hydrogenation is outlined below in General Procedure C.

General Procedure A: Peptide Synthesis Using DEPC.

The N-protected or N,N-disubstituted amino acid or peptide D (1.0 eq.) and an amine BB (1.1 eq.) are diluted with an aprotic organic solvent, such as dichloromethane (0.1 to 0.5 M). An organic base such as triethylamine or diisopropylethylamine (1.5 eq.) is then added, followed by DEPC (1.1 eq.). The resulting solution is stirred, preferably under argon, for up to 12 hours while being monitored by HPLC or TLC. The solvent is removed in vacuo at room temperature, and the crude product is purified using, for example, HPLC or flash column chromatography (silica gel column). Relevant fractions are combined and concentrated in vacuo to afford tripeptide E which is dried under vacuum overnight.

General Procedure B: Peptide Synthesis Using PyBrop.

The amino acid B (1.0 eq.), optionally having a carboxyl protecting group, is diluted with an aprotic organic solvent such as dichloromethane or DME to provide a solution of a concentration between 0.5 and 1.0 mM, then diisopropylethylamine (1.5 eq.) is added. Fmoc- or CBZ-protected amino acid A (1.1 eq.) is added as a solid in one portion, then PyBrop (1.2 eq.) is added to the resulting mixture. The reaction is monitored by TLC or HPLC, followed by a workup procedure similar to that described in General Procedure A.

General Procedure C: Z-Removal Via Catalytic Hydrogenation.

CBZ-protected amino acid or peptide C is diluted with ethanol to provide a solution of a concentration between 0.5 and 1.0 mM in a suitable vessel, such as a thick-walled round bottom flask. 10% palladium on carbon is added (5-10% w/w) and the reaction mixture is placed under a hydrogen atmosphere. Reaction progress is monitored using HPLC and is generally complete within 1-2 h. The reaction mixture is filtered through a pre-washed pad of celite and the celite is again washed with a polar organic solvent, such as methanol after filtration. The eluent solution is concentrated in vacuo to afford a residue which is diluted with an organic solvent, preferably toluene. The organic solvent is then removed in vacuo to afford the deprotected amine C.

Scheme 6 shows a method useful for making a C-terminal dipeptide of formula K and a method for coupling the dipeptide of formula K with the tripeptide of formula F to make drug compounds of Formula Ib. This method is applicable for the phenylalanine replacement moieties H having acid labile carboxyl protecting group, preferably dimethoxybenzyl group.

Scheme 6

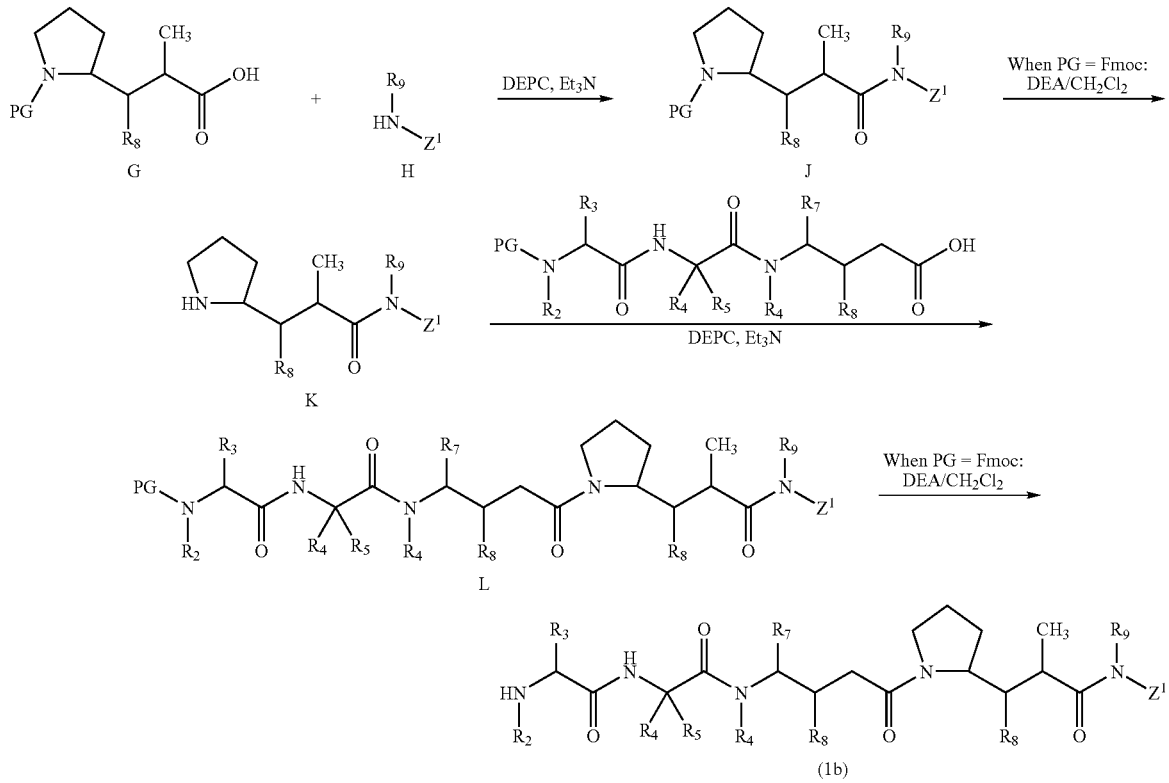

The dipeptide K can be readily prepared by condensation of the N-protected modified amino acid PG-Dolaproine (G) with an amine of formula H using condensing agents well known for peptide chemistry, such as, for example, DEPC in the presence of triethylamine, as shown in Schemes 5 and 6. Suitable N-protected groups for Dolaproine include, but are not limited to, an Fmoc-protecting group.

The dipeptide of formula K can then be coupled with a tripeptide of formula F using General Procedure D to make the Fmoc-protected drug compounds of formula L which can be subsequently deprotected using General Procedure E in order to provide the drug compounds of formula (Ib).

General Procedure D: Drug Synthesis.

A mixture of dipeptide K (1.0 eq.) and tripeptide F (1 eq.) is diluted with an aprotic organic solvent, such as dichloromethane, to form a 0.1M solution, then a strong acid, such as trifluoroacetic acid (½ v/v) is added and the resulting mixture is stirred under a nitrogen atmosphere for two hours at 0° C. The reaction can be monitored using TLC or, preferably, HPLC. The solvent is removed in vacuo and the resulting residue is azeotropically dried twice, preferably using toluene. The resulting residue is dried under high vacuum for 12 h and then diluted with and aprotic organic solvent, such as dichloromethane. An organic base such as triethylamine or diisopropylethylamine (1.5 eq.) is then added, followed by either PyBrop (1.2 eq.) or DEPC (1.2 eq.) depending on the chemical functionality on the residue. The reaction mixture is monitored by either TLC or HPLC and upon completion, the reaction is subjected to a workup procedure similar or identical to that described in General Procedure A.

General Procedure E: Fmoc-Removal Using Diethylamine.

An Fmoc-protected Drug L is diluted with an aprotic organic solvent such as dichloromethane and to the resulting solution is added diethylamine (½ v/v). Reaction progress is monitored by TLC or HPLC and is typically complete within 2 h. The reaction mixture is concentrated in vacuo and the resulting residue is azeotropically dried, preferably using toluene, then dried under high vacuum to afford Drug Ib having a deprotected amino group. Thus, the above method is useful for making Drugs that can be used in the present invention.

Alternatively Drug Compounds can be conveniently prepared by solid phase peptide synthesis using standard Fmoc chemistry well known in the art (see, e.g., Novabiochem® catalogue 2006/2007, Synthesis Notes) as shown in Scheme 6a (infra). Fmoc-protected amino acids can be prepared from unprotected amino acids using, for example, Fmoc-OSu via well established procedures (see, e.g., Greene and Wuts, *Protective Groups in Organic Synthesis*, 2nd Edition, 1991, John Wiley & Sons, p. 506).

Scheme 6a. Solid Phase Synthesis Route

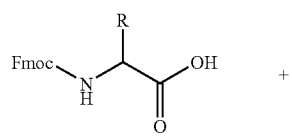

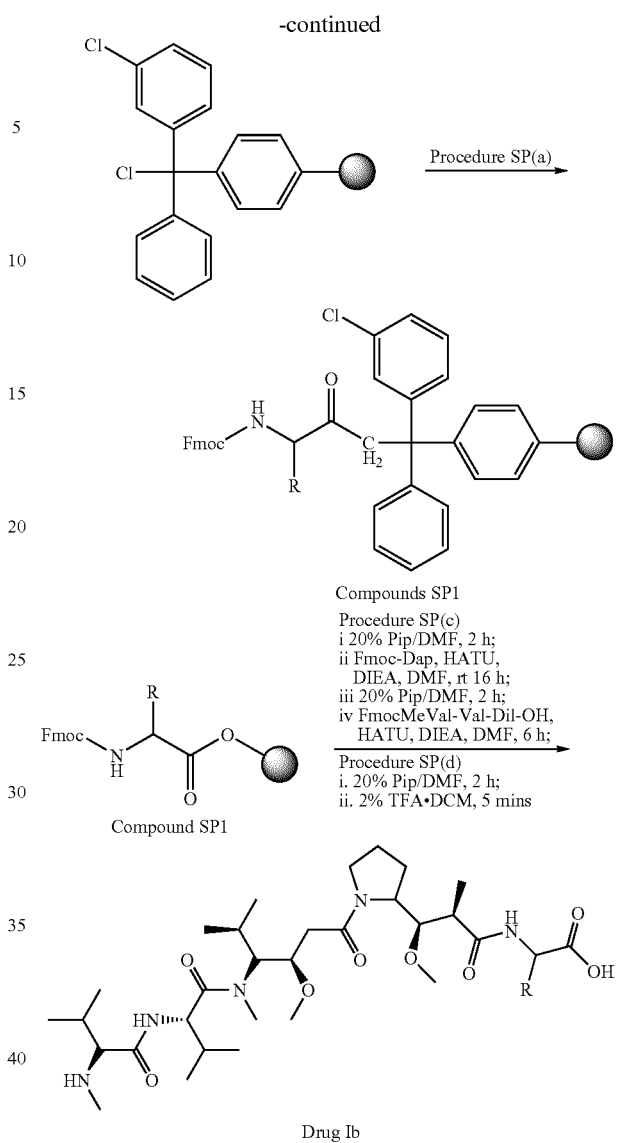

Amino acids not commercially available pre-loaded on an appropriate acid labile resin, preferably 2-chlorotrityl resin, can be loaded onto 2-chlorotrityl chloride resin as described in General Procedure SP(a). Loading can be determined by spectrophotometric Fmoc-quantitation assay. Loading levels (mmol/g) of commercially available pre-loaded amino acids on chlorotrityl resin can be determined as described in General Procedure SP(b). Peptides can then be assembled on the resin loaded with the first amino acid by coupling Fmoc-Dolaproine using appropriate coupling agent, preferably HATU/DIEA, followed by Fmoc deprotection and subsequent coupling of Fmoc-MeVal-Val-Dil tripeptide. Solid phase coupling routine is well established in the art and is described in General Procedure SP(c). Final deprotection of peptides and cleavage off resin can be readily performed following General Procedure SP(d).

General Procedure SP(a). Resin Loading

Fmoc-amino acid (0.84 µmmol) is suspended in anhydrous $CH_2Cl_2$ (4 mL) and DIEA (585 µL, 3.36 mmol, 4 equiv). The resulting mixture is added to a 10-mL syringe containing 2-Chlorotryityl chloride resin (500 mg, 0.70 mmol, 1.4 mmol/g). Mixture is agitated for 6 hours at room temperature.

Then the resin is filtered, washed with DCM/MeOH/DIEA (17:2:1; 4×5 mL), MeOH (1×5 mL), DCM (4×5 mL), DMF (4×5 mL), DCM (2×5 mL), ethyl ether (4×5 mL), and is dried in vacuo for 2 h. The resin is then left under vacuum overnight to produce resin SP1.

Loading is determined by Fmoc-quantitation. A known quantity (4.4 mg) SP1 resin is weighed into a 10-mL volumetric flask. To the flask is transferred 20% piperidine/DMF (2 mL). The mixture is allowed to cleave for 1 h, with occasional agitation by hand. To flask is transferred DMF (8 mL) to bring the total volume to 10 mL. A blank solution is prepared with 10 mL, 20% piperidine/DMF in a 10-mL volumetric flask. The spectrophotometer is zeroed with the blank solution. The absorbance is measured at 301 nm and the loading level is given by:

Loading (mmol/g)=$A_{301}$×10 mL/7800×wt whereby $A_{301}$ is the absorbance at 301 nm, 7800 is the extinction coefficient of the piperidine-fluorenone adduct, and wt is the weight of resin used in milligrams. Fmoc quantitation is generally performed in duplicate.

General Procedure SP(b). Fmoc Quantitation of Commercially Available Pre-Loaded Resins Fmoc-Cl (259 mg, 1 mmol) is dissolved in anhydrous $CH_2Cl_2$ (2 mL) to make a 0.5M working solution. This solution is transferred to a 3-mL plastic syringe containing Aminoacid-2-Chlorotrityl resin (0.86 mmol/g, 0.0215 mmol). The mixture is agitated for 2 h. The resin is then filtered and washed with DMF (2×5 mL), $CH_2Cl_2$ (2×5 mL), ethyl ether (2×5 mL), and dried in-vacuo for 2 h. The resin is subjected to Kaiser amine test. Upon negative results (free amine fully protected) the Fmoc quantitation to obtain loading level is performed as shown in General Procedure SP(a).

General Procedure SP(c). Solid Phase Peptide Coupling Using HATU.

A 20% piperidine in DMF solution (5 μL) is added to the syringe containing SP1 resin, and the mixture is agitated for 2 h. The resin is then filtered, washed with DMF (4×5 mL), DCM (4×5 mL), DMF (4×5 mL), DCM (4×5 mL), ethyl ether (4×5 μL), and is dried in-vacuo for 2 h.

Fmoc-Dap (278 mg, 0.680 mmol) and HATU (259 mg, 0.680 mmol, 2 equiv.) are suspended in anhydrous DMF (5 mL) and DIEA (237 μL, 1.36 mmol, 4 equiv.). The resulting mixture is transferred to the 10-mL plastic syringe containing H-Aminoacid-2-Chlorotrityl Resin (555.6 mg, 0.340 mmol). The mixture is agitated overnight, at room temperature. Reaction completion is determined by Kaiser amine test and LCMS analysis of material cleaved off a small amount of resin (using 2% TFA/$CH_2Cl_2$). The resin is then filtered, washed with DMF (4×5 mL), DCM (4×5 mL), DMF (4×5 mL), DCM (4×5 mL), ethyl ether (4×5 mL), and is dried in vacuo for 2 h.

A 20% piperidine in DMF solution (5 mL) is added to the syringe containing Fmoc-Dap-Aminoacid-2-Chlorotrityl Resin, and the mixture is agitated for 2 h. The resin is filtered, washed with DMF (4×5 mL), DCM (4×5 mL), DMF (4×5 mL), DCM (4×5 mL), ethyl ether (4×5 mL), and is dried in vacuo for 2 h.

Fmoc-MeVal-Val-Dil-OH (510 mg, 0.680 mmol, 2 equiv.) and HATU (259 mg, 0.680 mmol, 2 equiv.) are suspended in anhydrous DMF (5-mL) and DIEA (237 μL, 1.70 mmol, 5 equiv.). The resulting mixture is transferred to the 10-mL plastic syringe containing H-Dap-Aminoacid-2-Chlorotrityl resin. The mixture is agitated for 6 h. Reaction completion is determined by LCMS analysis of material cleaved off a small amount of resin (using 2% TFA/$CH_2Cl_2$). The resin is then filtered, washed with DMF (4×5 mL), DCM (4×5 mL), DMF (4×5 mL), DCM (4×5 mL), ethyl ether (4×5 mL), and is dried in vacuo for 2 h.

General Procedure SP(d). Final Deprotection and Cleavage Off Resin.

A 20% piperidine in DMF solution (5 mL) is added to the syringe containing Fmoc-MeVal-Val-Dil-Dap-Aminoacid-2-Chlorotrityl resin, and the mixture is agitated for 2 h. The resin is filtered, washed with DMF (4×5 mL), DCM (4×5 mL), DMF (4×5 mL), DCM (4×5 mL), ethyl ether (4×5 mL), and is dried in vacuo for 2 h. Further drying can be achieved if necessary by leaving resin overnight under vacuum.

A 2% TFA/$CH_2Cl_2$ (5 mL) solution is transferred to a 10-mL plastic syringe containing MeVal-Val-Dil-Dap-Aminoacid-2-Chlorotrityl resin and mixture is agitated, at room temperature, for 5 minutes. Filtrate is collected in a 100 mL round-bottom flask. The process is repeated three times. Filtrate is evaporated to leave white solid. Peptides Ib can be isolated by preparative HPLC.

Drug-Linker Synthesis

To prepare a Drug-Linker Compound of the present invention, the Drug is reacted with a reactive site on the Linker. In general, the Linker can have the structure:

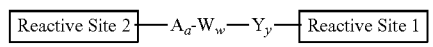

when both a Spacer unit (—Y—) and a Stretcher unit (-A-) are present. Alternately, the Linker can have the structure:

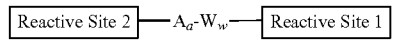

when the Spacer unit (—Y—) is absent.

The Linker can also have the structure:

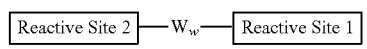

when both the Stretcher unit (-A-) and the Spacer unit (—Y—) are absent.

The Linker can also have the structure:

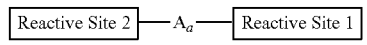

when both the Amino Acid unit (W) and the Spacer Unit (Y) are absent.

In general, a suitable Linker has an Amino Acid unit linked to an optional Stretcher Unit and an optional Spacer Unit. Reactive Site 1 is present at the terminus of the Spacer and Reactive site 2 is present at the terminus of the Stretcher. If a Spacer unit is not present, then Reactive site 1 is present at the C-terminus of the Amino Acid unit.

In an exemplary embodiment, Reactive Site No. 1 is reactive to a nitrogen atom of the Drug, and Reactive Site No. 2 is reactive to a sulfhydryl group on the Ligand. Reactive Sites 1 and 2 can be reactive to different functional groups.

In another exemplary embodiment, Reactive Site No. 2 is reactive to amino groups on lysines on the Ligand.

In one aspect of the invention, Reactive Site No. 1 is

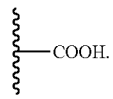

In another aspect, Reactive Site No. 1 is

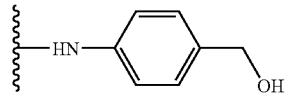 [SMILES: *Nc1ccc(CO)cc1]

In still another aspect, Reactive Site No. 1 is a p-nitrophenyl carbonate having the formula

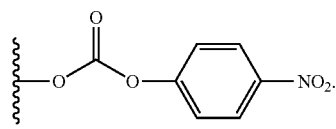 [SMILES: *OC(=O)Oc1ccc([N+](=O)[O-])cc1]

In one aspect of, Reactive Site No. 2 is a thiol-accepting group. Suitable thiol-accepting groups include haloacetamide groups having the formula

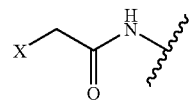

wherein X represents a leaving group, preferably O-mesyl, O-tosyl, —Cl, —Br, or —I; or a maleimide group having the formula

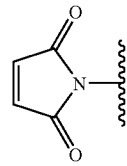 [SMILES: *N1C(=O)C=CC1=O]

Useful Linkers can be obtained via commercial sources, such as Molecular Biosciences Inc. (Boulder, Colo.), or prepared as summarized in Schemes 8-10 below.

Scheme 8

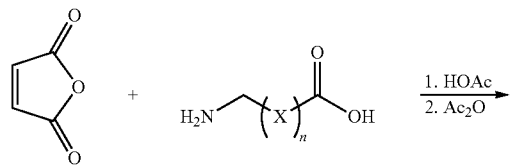

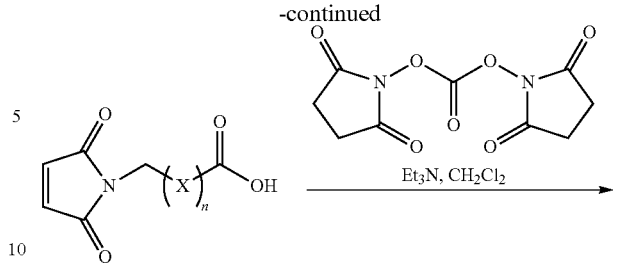

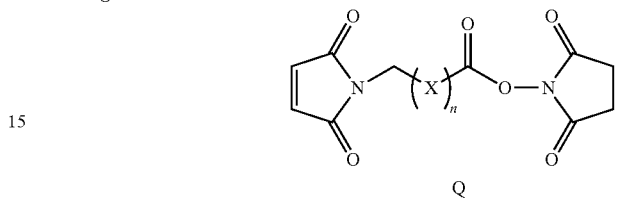

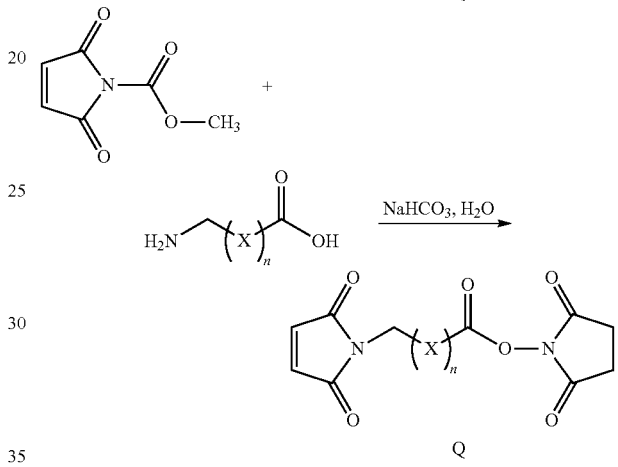

wherein X is —CH$_2$— or —CH$_2$OCH$_2$—; and n is an integer ranging either from 0-10 when X is —CH$_2$—; or 1-10 when X is —CH$_2$OCH$_2$—.

The method shown in Scheme 9 combines maleimide with a glycol under Mitsunobu conditions to make a polyethylene glycol maleimide Stretcher (see, e.g., example, Walker, 1995, *J. Org. Chem.* 60, 5352-5), followed by installation of a p-nitrophenyl carbonate Reactive Site group.

Scheme 9

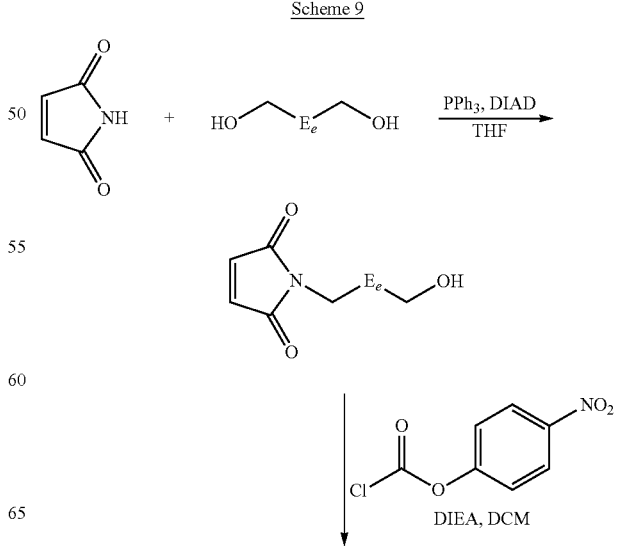

-continued

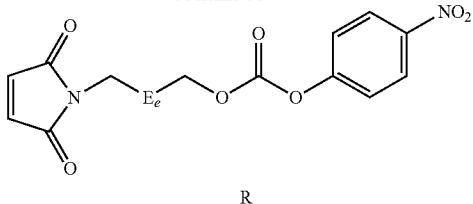

wherein E is —CH$_2$— or —CH$_2$OCH$_2$—; and e is an integer ranging from 0-8;

Alternatively, PEG-maleimide and PEG-haloacetamide stretchers can be prepared as described by Frisch et al., 1996, *Bioconjugate Chem.* 7:180-186.

Scheme 10 illustrates a general synthesis of an illustrative Linker unit containing a maleimide Stretcher group and optionally a p-aminobenzyl ether self-immolative Spacer.

Stretchers of formula (IIIa) can be introduced into a Linker by reacting the following intermediates with the N-terminus of an Amino Acid unit as depicted in Schemes 11 and 12:

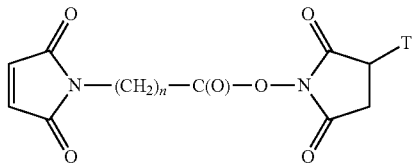

where n is an integer ranging from 1-10 and T is —H or —SO$_3$Na;

Scheme 10

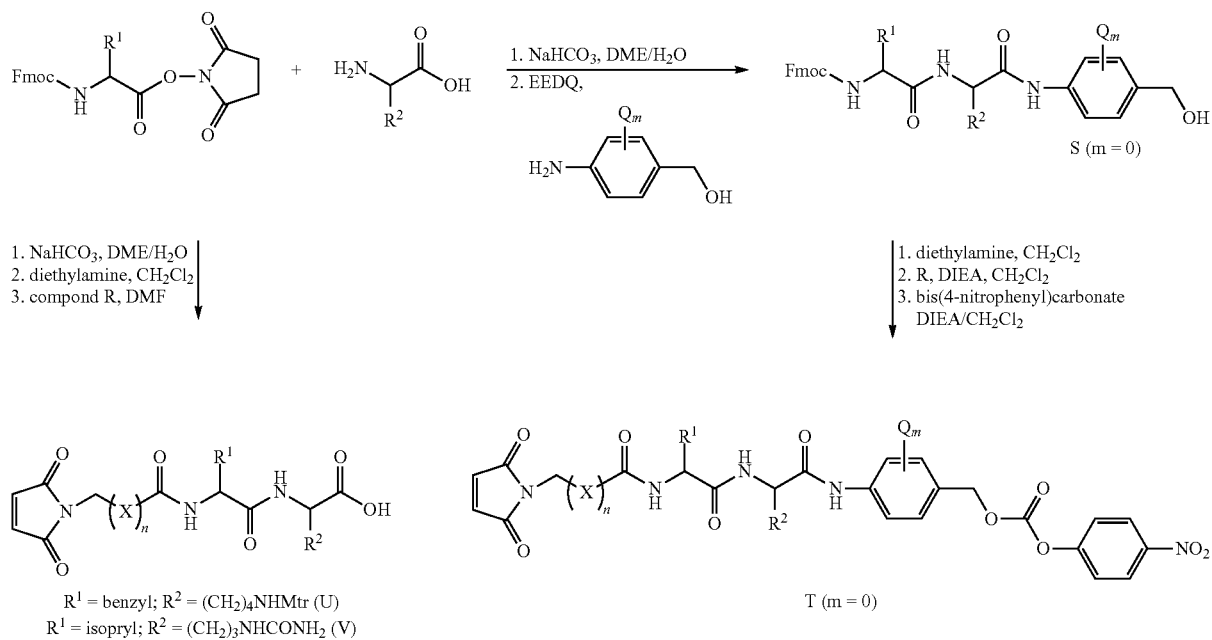

$R^1$ = benzyl; $R^2$ = (CH$_2$)$_4$NHMtr (U)
$R^1$ = isopryl; $R^2$ = (CH$_2$)$_3$NHCONH$_2$ (V)

T (m = 0)

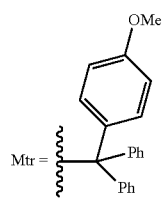

wherein Q is —C$_1$-C$_8$ alkyl, —O—(C$_1$-C$_8$ alkyl), -halogen, -nitro or -cyano; m is an integer ranging from 0-4; and n is an integer ranging from 0-10.

Useful Stretchers may be incorporated into a Linker using the commercially available intermediates from Molecular Biosciences (Boulder, Colo.) described below by utilizing known techniques of organic synthesis.

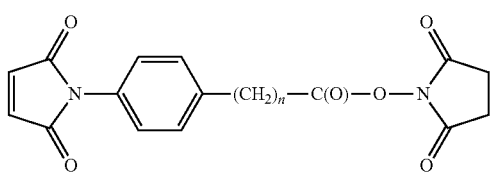

where n is an integer ranging from 0-3;

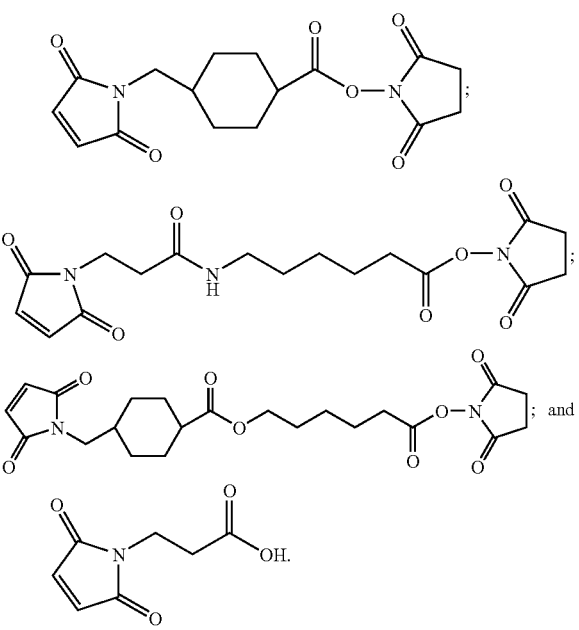

Stretcher units of formula (IIIb) can be introduced into a Linker by reacting the following intermediates with the N-terminus of an Amino Acid unit:

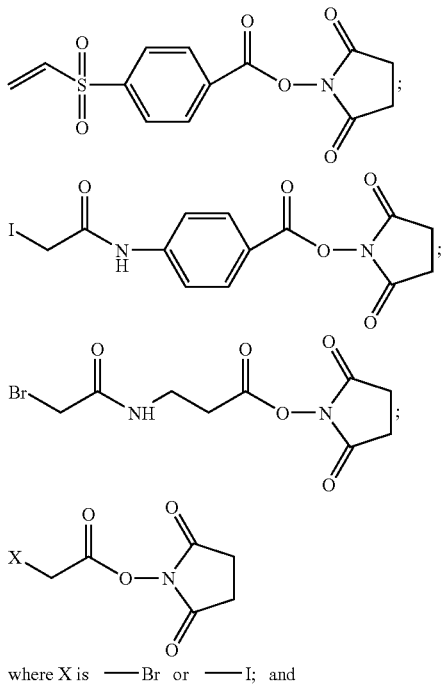

where X is —Br or —I; and

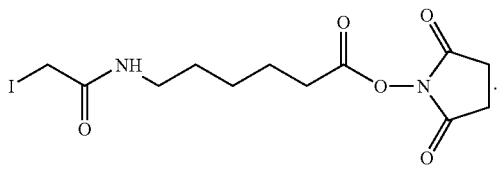

Stretcher units of formula (IV) can be introduced into a Linker by reacting the following intermediates with the N-terminus of an Amino Acid unit:

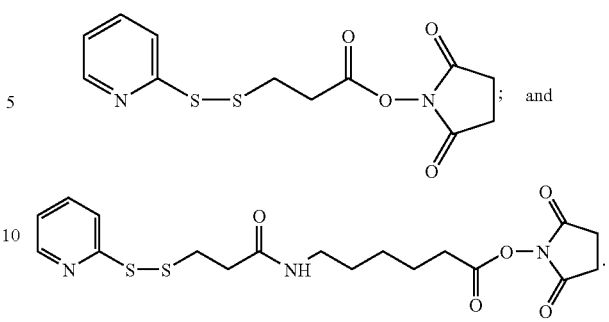

Stretcher units of formula (Va) can be introduced into a Linker by reacting the following intermediates with the N-terminus of an Amino Acid unit:

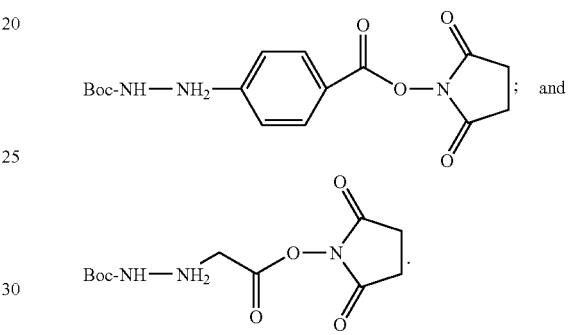

Other useful Stretchers may be synthesized according to known procedures. Aminooxy Stretchers of the formula shown below can be prepared by treating alkyl halides with N-Boc-hydroxylamine according to procedures described in Jones et al., 2000, *Tetrahedron Letters* 41(10):1531-1533; and Gilon et al., 1967, *Tetrahedron* 23(11):4441-4447.

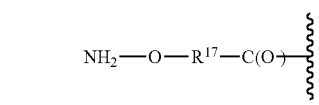

wherein —$R^{17}$— is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —($CH_2CH_2O$)$_r$—, —($CH_2CH_2O$)$_r$—$CH_2$—; and r is an integer ranging from 1-10;

Isothiocyanate Stretchers of the formula shown below may be prepared from isothiocyanatocarboxylic acid chlorides as described in *Angew. Chem.*, 87(14):517 (1975).

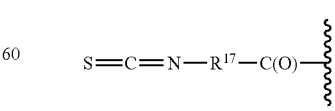

wherein —$R^{17}$— is as described herein.

Scheme 11 shows a method for obtaining of a val-cit dipeptide Linker having a maleimide Stretcher and optionally a p-aminobenzyl self-immolative Spacer.

Scheme 11

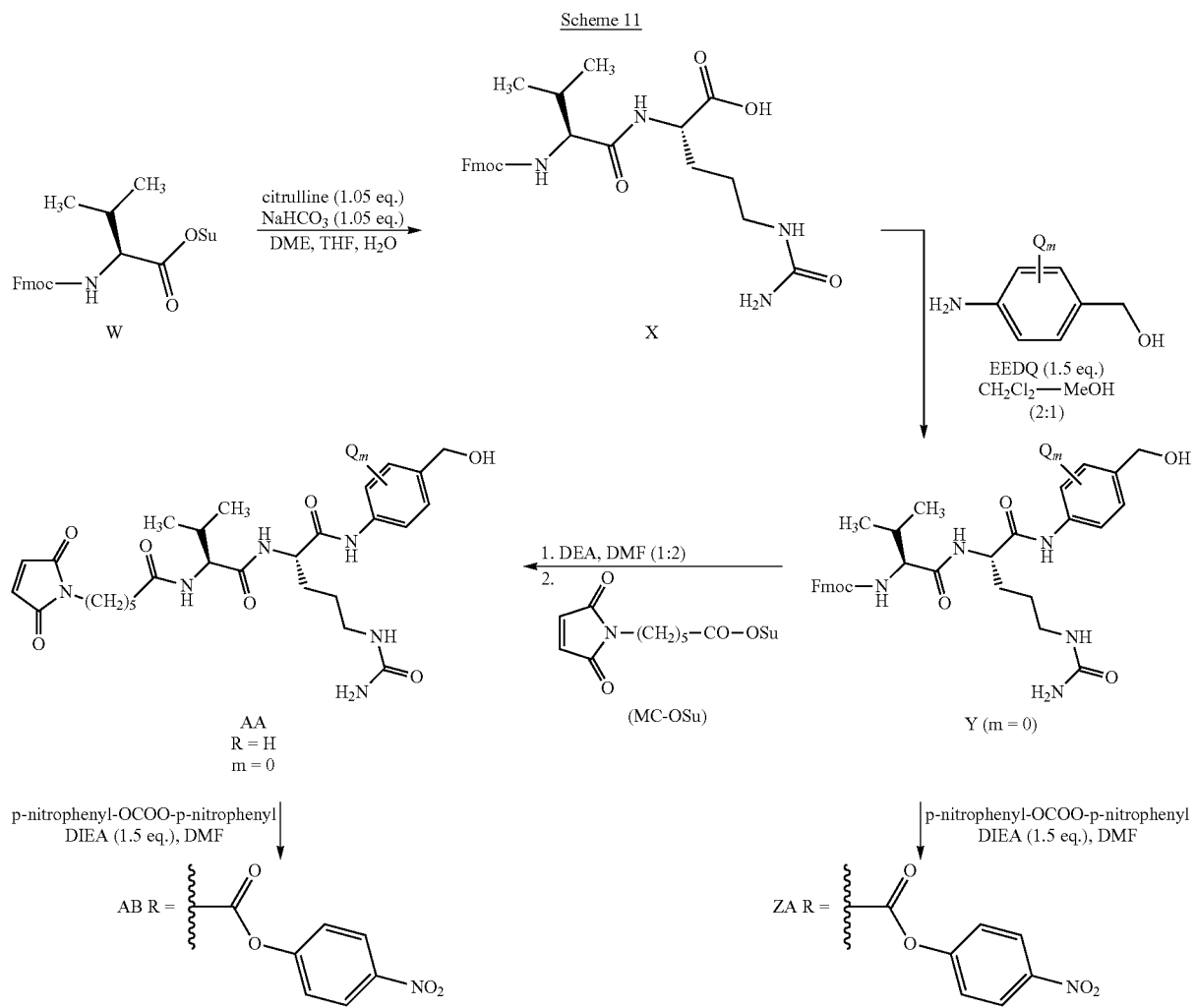

wherein Q is —$C_1$-$C_8$ alkyl, —O—($C_1$-$C_8$ alkyl), -halogen, -nitro or -cyano; and m is an integer ranging from 0-4.

Scheme 12 illustrates the synthesis of a phe-lys(Mtr) dipeptide Linker unit having a maleimide Stretcher unit and a p-aminobenzyl self-immolative Spacer unit. Starting material AD (lys(Mtr)) is commercially available (Bachem, Torrance, Calif.) or can be prepared according to Dubowchik, et al., 1997 *Tetrahedron Letters* 38:5257-60.

Scheme 12

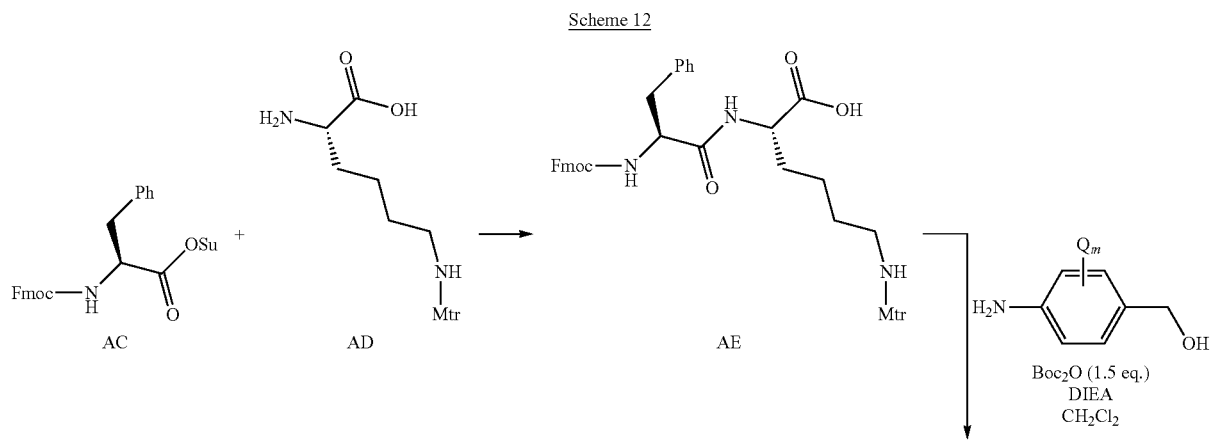

-continued

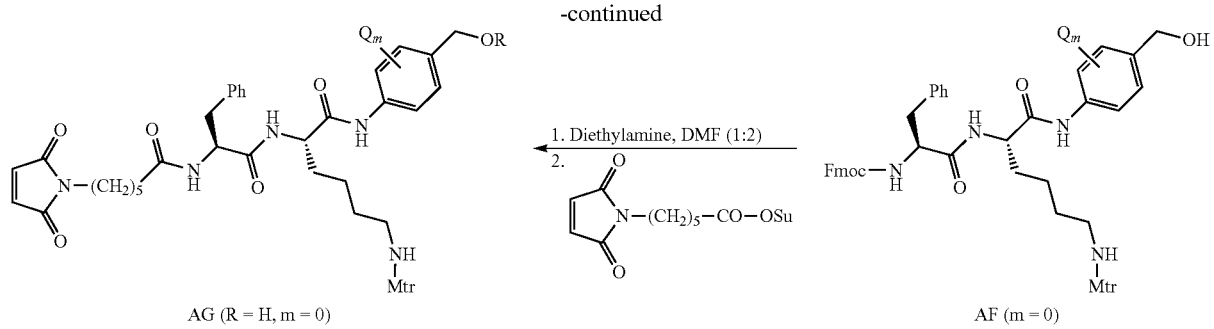

AG (R = H, m = 0)

AF (m = 0)

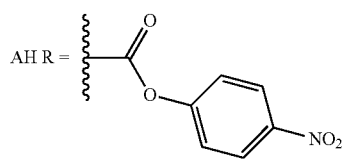

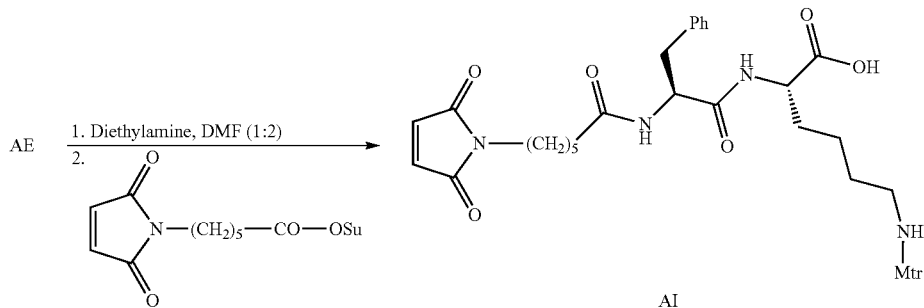

AI wherein Q is —$C_1$-$C_8$ alkyl, —O—($C_1$-$C_8$ alkyl), -halogen, -nitro or -cyano; and m is an integer ranging from 0-4.

As shown in Scheme 13, a Linker can be reacted with an amino group of a Drug Compound of Formula (Ib) to form a Drug-Linker Compound that contains an amide or carbamate group, linking the Drug unit to the Linker unit. When Reactive Site No. 1 is a carboxylic acid group, as in Linker AJ, the coupling reaction can be performed using HATU or PyBrop and an appropriate amine base, resulting in a Drug-Linker Compound AK, containing an amide bond between the Drug unit and the Linker unit. When Reactive Site No. 1 is a carbonate, as in Linker AL, the Linker can be coupled to the Drug using HOBt in a mixture of DMF/pyridine to provide a Drug-Linker Compound AM, containing a carbamate bond between the Drug unit and the Linker unit.

Alternately, when Reactive Site No. 1 is a good leaving group, such as in Linker AN, the Linker can be coupled with an amine group of a Drug via a nucleophilic substitution process to provide a Drug-Linker Compound having an amine linkage (AO) between the Drug unit and the Linker unit.

Illustrative methods useful for linking a Drug to a Ligand to form a Drug-Linker Compound are depicted in Scheme 13 and are outlined in General Procedures G-H.

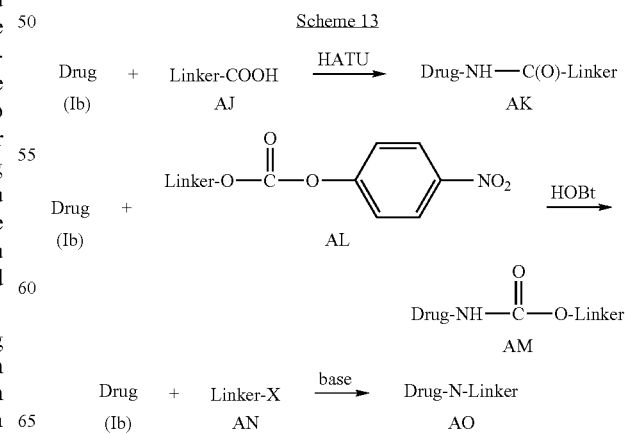

General Procedure G: Amide Formation Using HATU.

A Drug (Ib) (1.0 eq.) and an N-protected Linker containing a carboxylic acid Reactive site (1.0 eq.) are diluted with a suitable organic solvent, such as dichloromethane, and the resulting solution is treated with HATU (1.5 eq.) and an organic base, preferably pyridine (1.5 eq.). The reaction mixture is allowed to stir under an inert atmosphere, preferably argon, for 6 hours, during which time the reaction mixture is monitored using HPLC. The reaction mixture is concentrated and the resulting residue is purified using HPLC to yield the amide of formula AK.

Procedure H: Carbamate Formation Using HOBt.

A mixture of a Linker AL having a p-nitrophenyl carbonate Reactive site (1.1 eq.) and Drug (Ib) (1.0 eq.) are diluted with an aprotic organic solvent, such as DMF, to provide a solution having a concentration of 50-100 mM, and the resulting solution is treated with HOBt (0.2 eq.) and placed under an inert atmosphere, preferably argon. The reaction mixture is allowed to stir for 15 min, then an organic base, such as pyridine (¼ v/v), is added and the reaction progress is monitored using HPLC. The Linker is typically consumed within 16 h. The reaction mixture is then concentrated in vacuo and the resulting residue is purified using, for example, HPLC to yield the carbamate AM.

General Procedure S: Amide bond formation between the Linker and the Drug

A Linker containing carboxylic acid (30 mg), and anhydrous DMF (10 μl) are placed under an inert atmosphere, preferably argon, and cooled on dry ice for about 5 min. To this mixture oxalyl chloride (1 mL) was added dropwise by syringe. Typically, after few minutes, the mixture is allowed to warm up to room temperature and left for 30 min with occasional manual stirring. Volatiles are removed under reduced pressure. The residue is re-suspended in anhydrous CH₂Cl₂ (1 mL) and the solvent is removed in vacuo. The residue is dried at vacuum pump overnight to produce Linker AN.

The acylchloride AN is suspended in anhydrous CH₂Cl₂ (3 mL). A Drug Ib (0.006 mmol) and N,N-diisopropylethylamine (4 μl, ~4 eq.) are suspended in anhydrous CH₂Cl₂ (100 μl) and the mixtures is cooled on the ice bath typically for about 10 min. To this mixture, 150 μl of the acylchloride in CH₂Cl₂ (~1.1 eq.) are added via syringe. After 15 min on ice, reaction mixture is allowed to warm up to room temperature and stirring continued for about 2 more hours. Reaction progress can be monitored by RP-HPLC. Solvent then is removed in vacuo. The residue is suspended in DMSO (0.5 mL). Water (100 μl) was added and after 0.5 h the mixture is purified, for example, using preparative HPLC to yield Drug-Linker AO.

General Procedure T: N-Hydroxysuccinimide Ester Linker-Drug Preparation

Scheme 13a depictures example of preparation Linker-Drug Compounds AA2 containing N-hydroxysuccinimide esters via amide bond formation between a Drug unit and a Linker. This procedure is particularly useful for Drug units that do not contain free carboxylic group, or for Drugs that have carboxylic group protected as acid labile esters, preferably a dimethoxybenzyl ester.

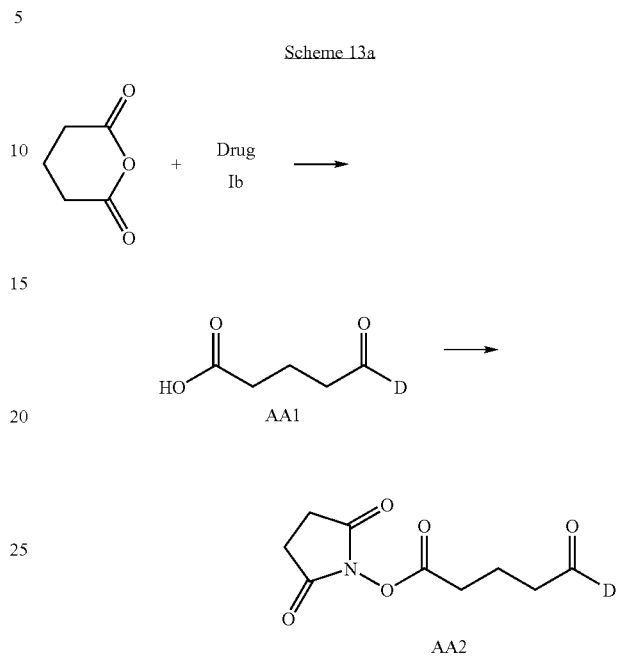

Scheme 13a

Drug (Ib) (1.0 eq.) and a suitable cyclic anhydride, preferably glutaric anhydride (1.0 eq.), are diluted with a suitable organic solvent, such as dichloromethane, and the resulting solution is treated with an organic base, preferably DIEA (3 eq.). The reaction mixture is allowed to stir under an inert atmosphere, preferably argon, for 24 h, during which time the reaction mixture is monitored using HPLC. The reaction product AA1 is isolated using flash chromatography on silica gel. Vacuum dried material AA1 and N,N'-disuccinimidyl carbonate (3 eq.) are diluted with a suitable organic solvent, such as dichloromethane, and the resulting solution is treated with an organic base, preferably DIEA (3 eq.). The reaction mixture is allowed to stir under an inert atmosphere, preferably argon, for 24 h, during which time the reaction mixture is monitored using HPLC. The reaction product AA2 is isolated using flash chromatography on silica gel. If necessary, the acid protecting group of the Drug-Linker AA2 can now be removed by the appropriate treatment, preferably with 1% TFA in dichloromethane for dimethoxybenzyl ester.

An alternate method of preparing Drug-Linker Compounds is outlined in Scheme 14. Using the method of Scheme 14, the Drug is attached to a partial Linker unit (ZA, for example), which does not have a Stretcher unit attached. This provides intermediate AP, which has an Amino Acid unit having an Fmoc-protected N-terminus. The Fmoc group is then removed and the resulting amine intermediate AQ is then attached to a Stretcher unit via a coupling reaction catalyzed using PyBrop or DEPC. The construction of Drug-Linker Compounds containing either a bromoacetamide Stretcher AR or a PEG maleimide Stretcher AS is illustrated in Scheme 14.

Scheme 14
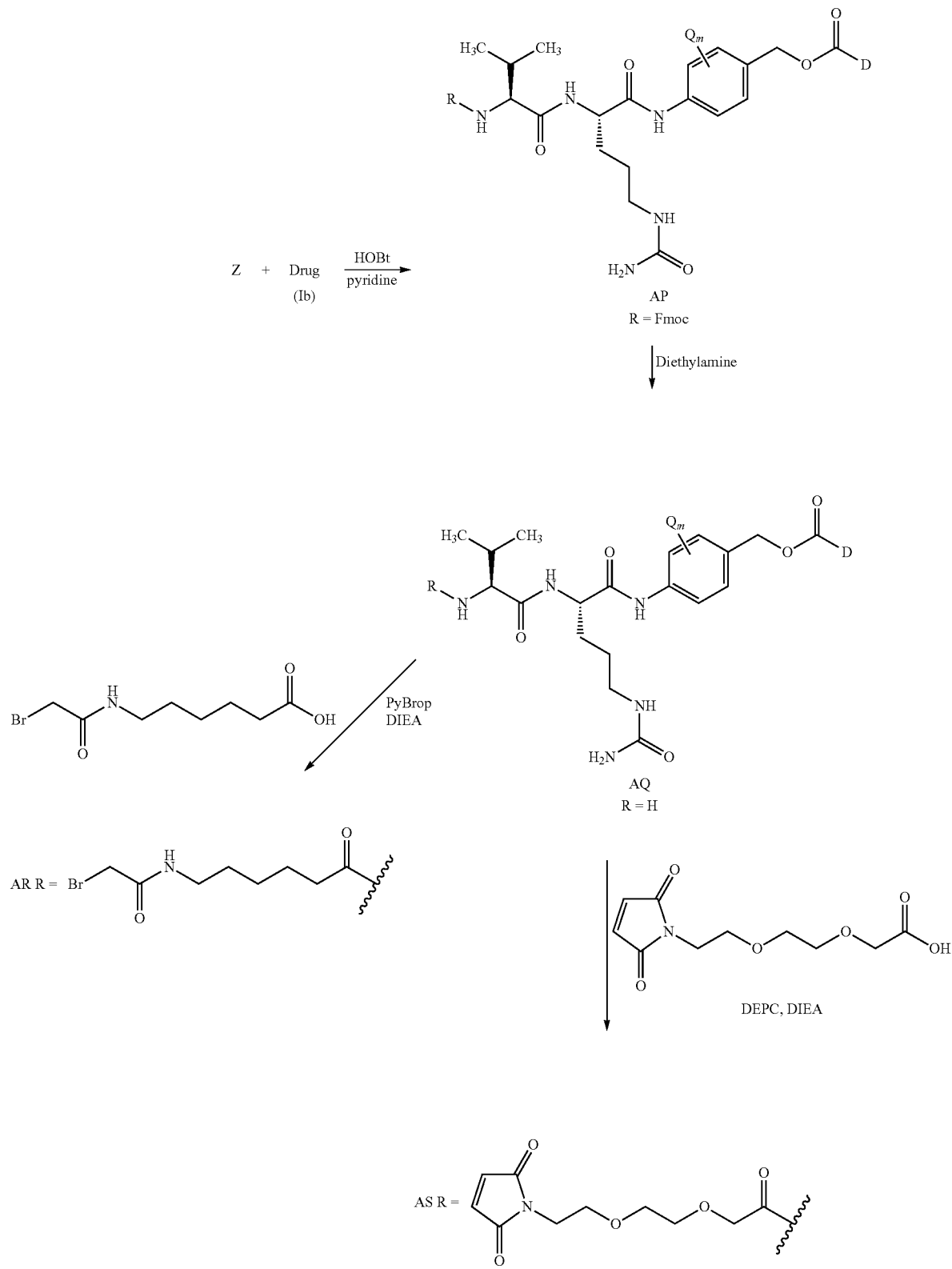
wherein Q is —$C_1$-$C_8$ alkyl, —O—($C_1$-$C_8$ alkyl), -halogen, -nitro or -cyano; and m is an integer ranging from 0-4.

Application of this general strategy for preparation of lysines reactive N-hydroxysuccinimide ester Linker-Drug is depicted in Scheme 14a.

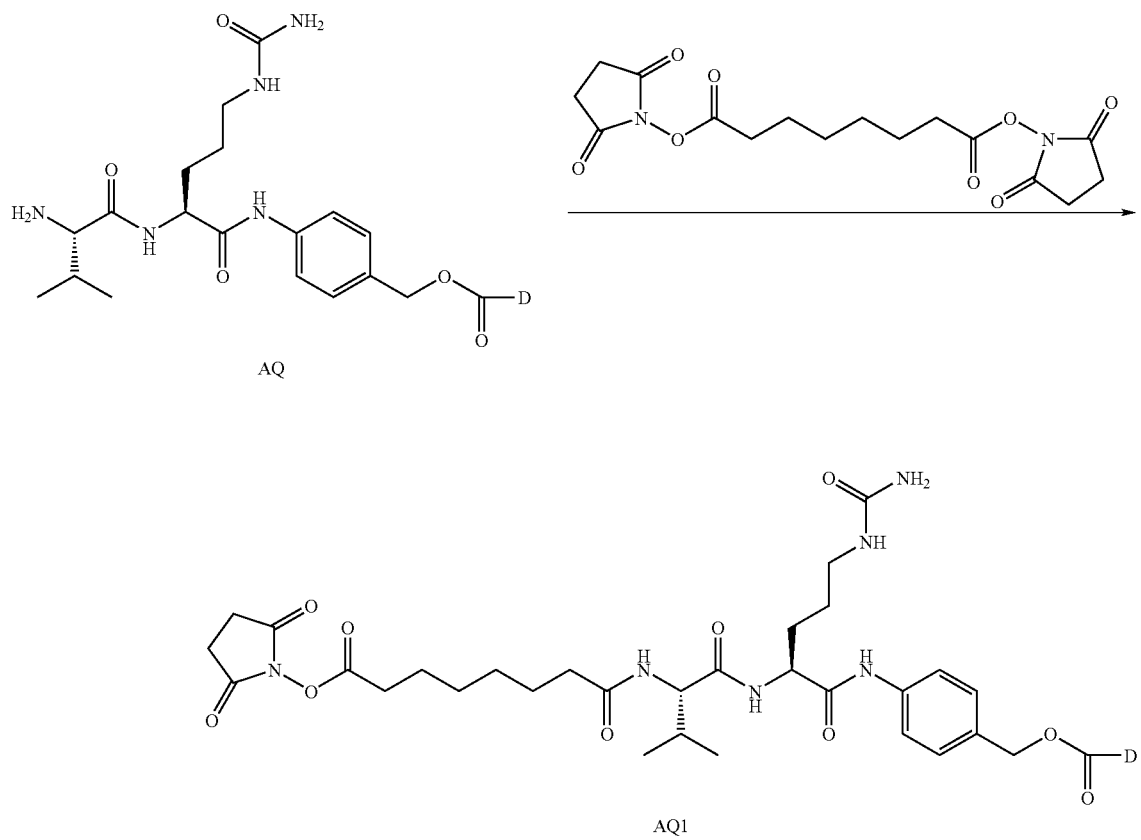

General Procedure U

Alternative Method of N-Hydroxysuccinimide Ester Linker-Drug Preparation

The intermediate AQ (1 eq.) is suspended in pyridine, and this mixture is added dropwise to the suspension of disuccinimidyl suberate (5 eq) in pyridine. The reaction mixture is then allowed to stir under an inert atmosphere, preferably argon, for about 4 h, during which time the reaction progress is monitored using HPLC. Pyridine is then removed in vacuo, the residue is suspended in a suitable organic solvent, such as dichloromethane, and the Drug-Linker AQ1 is isolated using flash chromatography on silica gel. If necessary, the carboxyl protecting group of the Drug can now be removed by the appropriate treatment, preferably with 1% TFA in dichloromethane for dimethoxybenzyl ester.

Methodology useful for the preparation of a Linker unit containing a branched spacer is shown in Scheme 15.

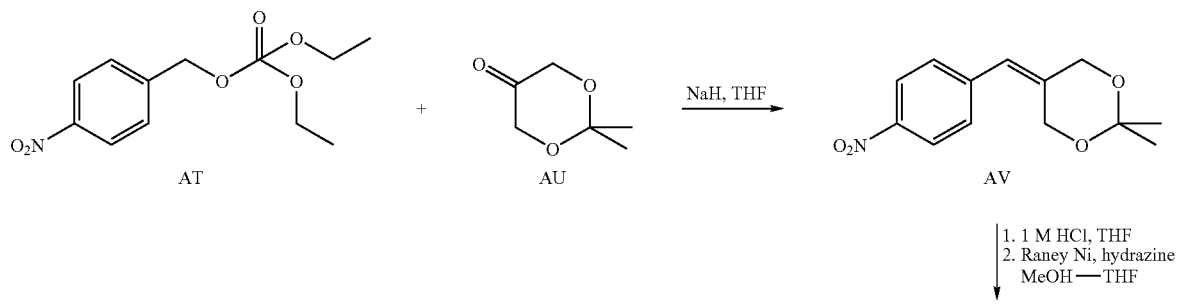

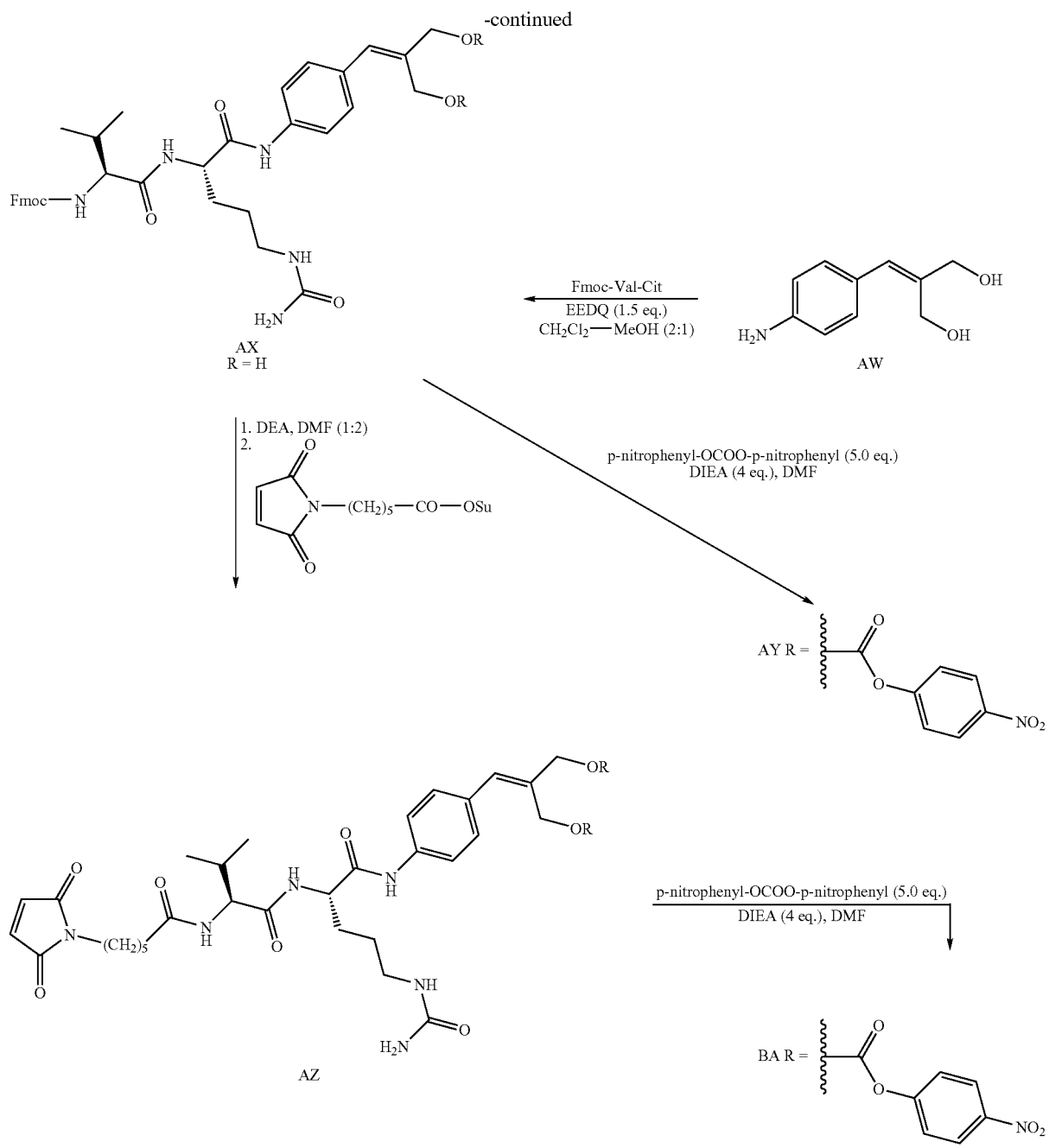

Scheme 15 illustrates the synthesis of a val-cit dipeptide linker having a maleimide Stretcher unit and a bis(4-hydroxymethyl)styrene (BHMS) unit. The synthesis of the BHMS intermediate (AW) has been improved from previous procedures (see, e.g., International Publication No. WO 98/13059 to Firestone et al., and Crozet et al., 1985, *Tetrahedron Lett.* 26:5133-5134) and utilizes as starting materials, commercially available diethyl (4-nitrobenzyl)phosphonate (AT) and commercially available 2,2-dimethyl-1,3-dioxan-5-one (AU). Linkers AY and BA can be prepared from intermediate AW using the methodology described in Scheme 9.

Dentritic Linkers

The linker may be a dendritic type linker for covalent attachment of more than one drug moiety through a branching, multifunctional linker moiety to a Ligand, such as but not limited to an antibody (see, e.g., Sun et al., 2002, *Bioorganic & Medicinal Chemistry Letters* 12:2213-2215; Sun et al., 2003, *Bioorganic & Medicinal Chemistry* 11:1761-1768). Dendritic linkers can increase the molar ratio of drug to antibody, i.e. loading, which is related to the potency of the Drug-Linker-Ligand Conjugate. Thus, where a cysteine engineered antibody bears only one reactive cytsteine thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

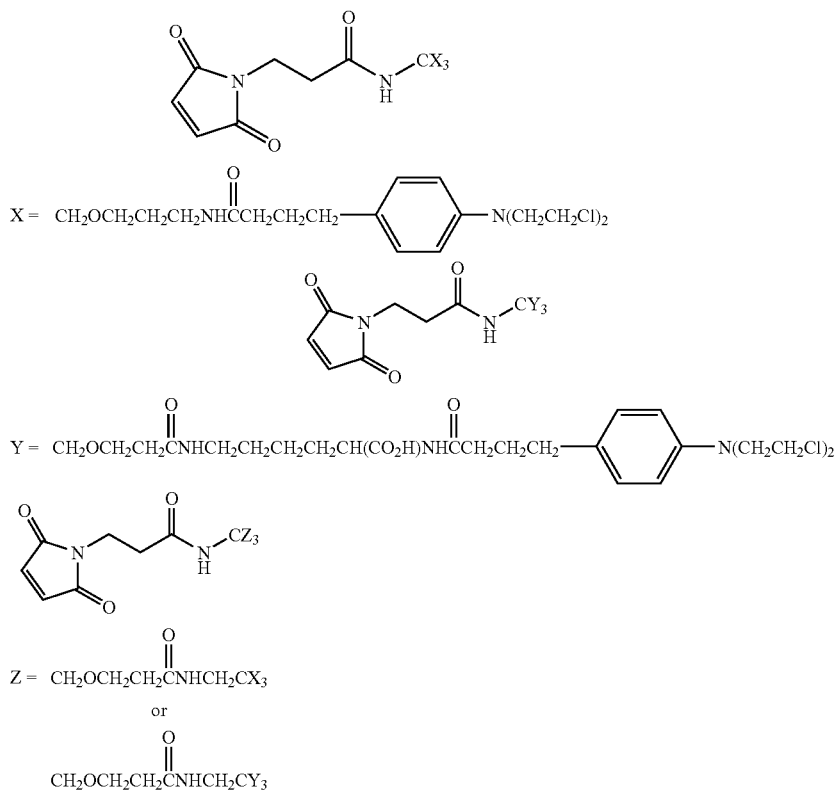

Conjugation of Drug Moieties to Antibodies

Scheme 16 illustrates methodology useful for making Drug-Linker-Ligand conjugates having about 2 to about 4 drugs per antibody. An antibody is treated with a reducing agent, such as dithiothreitol (DTT) to reduce some or all of the cysteine disulfide residues to form highly nucleophilic cysteine thiol groups (—CH$_2$SH). The partially reduced antibody thus reacts with drug-linker compounds, or linker reagents, with electrophilic functional groups such as maleimide or α-halo carbonyl, according to the conjugation method at page 766 of Klussman et al., 2004, *Bioconjugate Chemistry* 15(4):765-773.

Scheme 16

For example, an antibody, e.g., AC10, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody is dissolved in PBS and is chilled on ice. The drug linker, e.g., MC-val-cit-PAB-MMAZ in DMSO, dissolved in acetonitrile and water at known concentration, is added to the chilled reduced antibody in PBS. After about one hour, an excess of maleimide is added to quench the reaction and cap any unreacted antibody thiol groups. The reaction mixture is concentrated by centrifugal ultrafiltration and the ADC, e.g., AC10-MC-vc-PAB-MMAZ, is purified and desalted by elution through G25 resin in PBS, filtered through 0.2 μm filters under sterile conditions, and frozen for storage.

A variety of antibody drug conjugates (ADC) can be prepared, with a variety of linkers, and the drug moieties, MMAZ following the protocols of the Examples, and characterized by HPLC and drug loading assay.

Compositions and Methods of Administration

In other embodiments, described is a composition including an effective amount of an Exemplary Compound and/or Exemplary Conjugate and a pharmaceutically acceptable carrier or vehicle. For convenience, the Drug units and Drug-Linker Compounds can be referred to as Exemplary Compounds, while Drug-Ligand Conjugates and Drug-Linker-Ligand Conjugates can be referred to as Exemplary Conjugates. The compositions are suitable for veterinary or human administration.

The present compositions can be in any form that allows for the composition to be administered to a patient. For example, the composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In one aspect, the compositions are administered parenterally. In yet another aspect, the Exemplary Compounds and/or the Exemplary Conjugates or compositions are administered intravenously.

Pharmaceutical compositions can be formulated so as to allow an Exemplary Compound and/or Exemplary Conjugate to be bioavailable upon administration of the composition to a patient. Compositions can take the form of one or more dosage units, where for example, a tablet can be a single dosage unit, and a container of an Exemplary Compound and/or Exemplary Conjugate in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Exemplary Compound or Exemplary Conjugate, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the Exemplary Compound and/or Exemplary Conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of an Exemplary Compound and/or Exemplary Conjugate such that a suitable dosage will be obtained. Typically, this amount is at least about 0.01% of an Exemplary Compound and/or Exemplary Conjugate by weight of the composition. When intended for oral administration, this amount can be varied to range from about 0.1% to about 80% by weight of the composition. In one aspect, oral compositions can comprise from about 4% to about 50% of the Exemplary Compound and/or Exemplary Conjugate by weight of the composition. In yet another aspect, present compositions are prepared so that a parenteral dosage unit contains from about 0.01% to about 2% by weight of the Exemplary Compound and/or Exemplary Conjugate.

For intravenous administration, the composition can comprise from about 0.01 to about 100 mg of an Exemplary Compound and/or Exemplary Conjugate per kg of the animal's body weight. In one aspect, the composition can include from about 1 to about 100 mg of an Exemplary Compound and/or Exemplary Conjugate per kg of the animal's body weight. In another aspect, the amount administered will be in the range from about 0.1 to about 25 mg/kg of body weight of the Exemplary Compound and/or Exemplary Conjugate.

Generally, the dosage of an Exemplary Compound and/or Exemplary Conjugate administered to a patient is typically about 0.01 mg/kg to about 2000 mg/kg of the animal's body weight. In one aspect, the dosage administered to a patient is between about 0.01 mg/kg to about 10 mg/kg of the animal's body weight, in another aspect, the dosage administered to a patient is between about 0.1 mg/kg and about 250 mg/kg of the animal's body weight, in yet another aspect, the dosage administered to a patient is between about 0.1 mg/kg and about 20 mg/kg of the animal's body weight, in yet another aspect the dosage administered is between about 0.1 mg/kg to about 10 mg/kg of the animal's body weight, and in yet another aspect, the dosage administered is between about 1 mg/kg to about 10 mg/kg of the animal's body weight.

The Exemplary Compounds and/or Exemplary Conjugate or compositions can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer an Exemplary Compound and/or Exemplary Conjugate or composition. In certain embodiments, more than one Exemplary Compound and/or Exemplary Conjugate or composition is administered to a patient.

In specific embodiments, it can be desirable to administer one or more Exemplary Compounds and/or Exemplary Conjugate or compositions locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more Exemplary Compounds and/or Exemplary Conjugate or compositions into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In yet another embodiment, the Exemplary Compounds and/or Exemplary Conjugate or compositions can be delivered in a controlled release system, such as but not limited to, a pump or various polymeric materials can be used. In yet another embodiment, a controlled-release system can be placed in proximity of the target of the Exemplary Compounds and/or Exemplary Conjugate or compositions, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which an Exemplary Compound and/or Exemplary Conjugate is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the Exemplary Compound and/or Exemplary Conjugate or compositions and pharmaceutically acceptable carriers are sterile. Water is an exemplary carrier when the Exemplary Compounds and/or Exemplary Conjugates are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

In an embodiment, the Exemplary Compounds and/or Exemplary Conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where an Exemplary Compound and/or Exemplary Conjugate is to be administered by infusion, it can be dispensed, for example, with an infusion bottle containing sterile pharmaceutical grade water or saline. Where the Exemplary Compound and/or Exemplary Conjugate is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The compositions can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of an Exemplary Compound and/or Exemplary Conjugate of from about 0.05% to about 50% w/v (weight per unit volume of composition), in another aspect, from 0.1% to 10% w/v.

The composition can be intended for rectal administration, in the form, e.g., of a suppository which will melt in the rectum and release the Exemplary Compound and/or Exemplary Conjugate.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients.

Whether in solid, liquid or gaseous form, the present compositions can include a pharmacological agent used in the treatment of cancer, an autoimmune disease or an infectious disease.

Therapeutics Uses of the Exemplary Conjugates

The Exemplary Compounds and/or Exemplary Conjugates are useful for treating cancer, an autoimmune disease or an infectious disease in a patient.

Treatment of Cancer

The Exemplary Compounds and/or Exemplary Conjugates are useful for inhibiting the multiplication of a tumor cell or cancer cell, causing apoptosis in a tumor or cancer cell, or for treating cancer in a patient. The Exemplary Compounds and/or Exemplary Conjugates can be used accordingly in a variety of settings for the treatment of animal cancers. The Drug-Linker-Ligand Conjugates can be used to deliver a Drug or Drug unit to a tumor cell or cancer cell. Without being bound by theory, in one embodiment, the Ligand unit of an Exemplary Conjugate binds to or associates with a cancer-cell or a tumor-cell-associated antigen, and the Exemplary Conjugate can be taken up (internalized) inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the Linker unit are hydrolytically cleaved by one or more tumor-cell or cancer-cell-associated proteases, resulting in release of a Drug or a Drug-Linker Compound. The released Drug or Drug-Linker Compound is then free to migrate within the cell and induce cytotoxic or cytostatic activities. The Drug-Linker-Ligand conjugate also can be cleaved by intracellular protease to release the Drug moiety, the Drug-Linker compound, and/or an active fragment of the Drug-Linker-Ligand conjugate (e.g., cystyl-Linker-Drug). In an alternative embodiment, the Drug or Drug unit is cleaved from the Exemplary Conjugate outside the tumor cell or cancer cell, and the Drug or Drug-Linker Compound subsequently penetrates the cell. In an alternative embodiment, the Drug or Drug unit is cleaved from the Exemplary Conjugate outside the tumor cell or cancer cell, and the Drug or Drug-Linker Compound subsequently penetrates the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, Exemplary Conjugates having a BR96 Ligand unit can be useful for treating antigen positive carcinomas including those of the lung, breast, colon, ovaries, and pancreas. Exemplary Conjugates having an anti-CD30 or an anti-CD40 Ligand unit can be useful for treating hematologic malignancies.

Other particular types of cancers that can be treated with Exemplary Conjugates include, but are not limited to, those disclosed in Table 1:

TABLE 1

Solid tumors, including but not limited to:

fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma blood-borne cancers, including but not limited to:

acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma acute and chronic leukemias:

lymphoblastic, myelogenous, lymphocytic, myelocytic leukemias

Lymphomas:

Hodgkin's disease, non-Hodgkin's Lymphoma, Multiple myeloma, Waldenström's macroglobulinemia, Heavy chain disease, Polycythemia vera The Exemplary Conjugates provide conjugation-specific tumor or cancer targeting, thus reducing general toxicity of these compounds. The Linker units stabilize the Exemplary Conjugates in blood, yet are cleavable by tumor-specific proteases within the cell, liberating a Drug.

Multi-Modality Therapy for Cancer

Cancers, including, but not limited to, a tumor, metastasis, or other disease or disorder characterized by uncontrolled cell growth, can be treated or prevented by administration of an Exemplary Conjugate and/or an Exemplary Compound.

In other embodiments, methods for treating or preventing cancer are provided, including administering to a patient in need thereof an effective amount of an Exemplary Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Exemplary Conjugates can be administered to a patient that has also undergone surgery as treatment for the cancer.

In some embodiment, the patient is also receives an additional treatment, such as radiation therapy. In a specific embodiment, the Exemplary Conjugate is administered concurrently with the chemotherapeutic agent or with radiation therapy. In another specific embodiment, the chemotherapeutic agent or radiation therapy is administered prior or subsequent to administration of an Exemplary Conjugates, in one aspect at least an hour, five hours, 12 hours, a day, a week, a month, in further aspects several months (e.g., up to three months), prior or subsequent to administration of an Exemplary Conjugate.

A chemotherapeutic agent can be administered over a series of sessions. Any one or a combination of the chemotherapeutic agents listed in Table 4 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with an Exemplary Compound and/or Exemplary Conjugate are provided as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Exemplary Compounds and/or Exemplary Conjugates can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of an Exemplary Compound and/or Exemplary Conjugate with or without accompanying high dose radiation therapy, and the stem cell graft is infused back into the animal. Supportive care is then provided while bone marrow function is restored and the animal recovers.

Multi-Drug Therapy for Cancer

Methods for treating cancer include administering to a patient in need thereof an effective amount of an Exemplary Conjugate and another therapeutic agent that is an anti-cancer agent. An "anti-cancer agent" or a "chemotherapeutic agent" is a chemical compound useful in the treatment of cancer.

Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel.

Examples of chemotherapeutic agents include alkylating agents such as thiotepa and CYTOXAN® cyclosphosphamide; alkyl sulfonates such as busulfan, improsulfan, pipo-sulfan and treosulfan; aziridines such as benzodopa, carboquone, meturedopa, and uredopa; ethylenimines and methylamelamines including altretamine, triethylen-emelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, crisnatol; and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas such as carmustine (BCNU), chlorozotocin, fotemustine, lomustine, nimustine, and ranimustine; triazines, such as dacarbazine; bisphosphonates, such as clodronate; antibiotics such as the enediyne antibiotics (e.g., calicheamicin, especially calicheamicin gamma1I and calicheamicin omega1I (see, e.g., Agnew, 1994, Chem Intl. Ed. Engl. 33:183-186) and anthracyclines such as annamycin, AD 32, alcarubicin, daunorubicin, dexrazoxane, DX-52-1, epirubicin, GPX-100, idarubicin, pirarubicin, zorubicin, mitoxantrone, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 or B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), EICAR, esorubicin, marcellomycin, mitomycins such as mitomycin C, mycophenolic acid, nogalamycin, olivomycins, peplomycin, potfiromycin, puromycin, quelamycin, ribavirin, rodorubicin, streptonigrin, streptozocin, tiazofurin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, cytoarabinoside, dideoxyuridine, doxifluridine, enocitabine, floxuridine and fludarabine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate, anti-metabolites such as 5-fluorouracil (5-FU) and its prodrugs such as UFT, S-1 and capecitabine, and thymidylate synthase inhibitors and glycinamide ribonucleotide formyl-transferase inhibitors such as raltitrexed (TOMUDEX™, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; defereoxamine; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinblastine; vindesine; vinorelbine; vinca alkaloid; vinorelbine (NAVELBINE®); novantrone; edatrexate; daunomycin; aminopterin; xeloda; ibandronate; topoisomerase inhibitor RPS 2000; difluoromethylornithine (DMFO); MDR inhibitors such as verapamil; retinoids such as retinoic acid; cell cycle inhibitors, such as staurosporine; Lovastatin; REVLIMID (lenalidomide); THALAMID (thalidomide); VELADE (bortezomib); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, megestrol, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide (e.g., leuprolide acetate), and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Also included in this definition are Vitamin D3 analogs, such as EB 1089, CB 1093 and KH 1060; and Photodynamic therapies, such as vertoporfin (BPD-MA), phthalocyanine, photosensitizer Pc4, demethoxy-hypocrellin A and 2BA-2-DMHA.

Treatment of Autoimmune Diseases

The Exemplary Conjugates are useful for killing or inhibiting the replication of a cell that produces an autoimmune disease or for treating an autoimmune disease. The Exemplary Conjugates can be used accordingly in a variety of settings for the treatment of an autoimmune disease in a patient. The Drug-Linker-Ligand Conjugates can be used to deliver a Drug to a target cell. Without being bound by theory, in one embodiment, the Drug-Linker-Ligand Conjugate associates with an antigen on the surface of a target cell, and the Exemplary Conjugate is then taken up inside a target-cell through receptor-mediated endocytosis. Once inside the cell, one or more specific peptide sequences within the Linker unit are enzymatically or hydrolytically cleaved, resulting in release of a Drug. The released Drug is then free to migrate in the cytosol and induce cytotoxic or cytostatic activities. The Drug-Linker-Ligand conjugate also can be cleaved by intracellular protease to release the Drug moiety, the Drug-Linker compound, and/or an active fragment of the Drug-Linker-Ligand conjugate (e.g., cystyl-Linker-Drug). In an alternative embodiment, the Drug is cleaved from the Exemplary Conjugate outside the target cell, and the Drug subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand binds to activated lymphocytes that are associated with the autoimmune disease state.

In a further embodiment, the Exemplary Conjugates kill or inhibit the multiplication of cells that produce an autoimmune antibody associated with a particular autoimmune disease.

Particular types of autoimmune diseases that can be treated with the Exemplary Conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjogren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 3.

TABLE 3

Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma, Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, Wegener's Granulomatosis Multi-Drug Therapy of Autoimmune Diseases Methods for treating an autoimmune disease are also disclosed including administering to a patient in need thereof an effective amount of an Exemplary Conjugate and another therapeutic agent known for the treatment of an autoimmune disease. In one embodiment, the anti-autoimmune disease agent includes, but is not limited to, agents listed in Table 4.

TABLE 4 cyclosporine, cyclosporine A, mycophenylate mofetil, sirolimus, tacrolimus, enanercept, prednisone, azathioprine, methotrexate, cyclophosphamide, prednisone, aminocaproic acid, chloroquine, hydroxychloroquine, hydrocortisone, dexamethasone, chlorambucil, DHEA, danazol, bromocriptine, meloxicam, infliximab Treatment of Infectious Diseases The Exemplary Conjugates are useful for killing or inhibiting the multiplication of a cell that produces an infectious disease or for treating an infectious disease. The Exemplary Conjugates can be used accordingly in a variety of settings for the treatment of an infectious disease in a patient. The Drug-Linker-Ligand Conjugates can be used to deliver a Drug to a target cell. In one embodiment, the Ligand unit binds to the infectious disease cell.

In one embodiment, the Conjugates kill or inhibit the multiplication of cells that produce a particular infectious disease.

Particular types of infectious diseases that can be treated with the Exemplary Conjugates include, but are not limited to, those disclosed in Table 5.

TABLE 5

Bacterial Diseases:

Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococca, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, Salmonella, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, Chlamydia, Chlamydial Pneumonia, Trachoma, Inclusion Conjunctivitis
Systemic Fungal Diseases:

Histoplamosis, Coccidiodomycosis, Blastomycosis, Sporotrichosis, Cryptococcsis, Systemic Candidiasis, Aspergillosis, Mucormycosis, Mycetoma, Chromomycosis
Rickettsial Diseases:

Typhus, Rocky Mountain Spotted Fever, Ehrlichiosis, Eastern Tick-Borne Rickettsioses, Rickettsialpox, Q Fever, Bartonellosis
Parasitic Diseases:

Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease
Viral Diseases:

Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic TABLE 5-continued keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, Smallpox Multi-Drug Therapy of Infectious Diseases Methods for treating an infectious disease are disclosed including administering to a patient in need thereof an Exemplary Conjugate and another therapeutic agent that is an anti-infectious disease agent. In one embodiment, the anti-infectious disease agent is, but not limited to, agents listed in Table 6.

TABLE 6

β-Lactam Antibiotics:

Penicillin G, Penicillin V, Cloxacilliin, Dicloxacillin, Methicillin, Nafcillin, Oxacillin, Ampicillin, Amoxicillin, Bacampicillin, Azlocillin, Carbenicillin, Mezlocillin, Piperacillin, Ticarcillin
Aminoglycosides:

Amikacin, Gentamicin, Kanamycin, Neomycin, Netilmicin, Streptomycin, Tobramycin
Macrolides:

Azithromycin, Clarithromycin
Erythromycin, Lincomycin, Clindamycin
Tetracyclines:

Demeclocycline, Doxycycline, Minocycline, Oxytetracycline, Tetracycline
Quinolones:

Cinoxacin, Nalidixic Acid
Fluoroquinolones:

Ciprofloxacin, Enoxacin, Grepafloxacin, Levofloxacin, Lomefloxacin, Norfloxacin, Ofloxacin, Sparfloxacin, Trovafloxicin
Polypeptides:

Bacitracin, Colistin, Polymyxin B
Sulfonamides:

Sulfisoxazole, Sulfamethoxazole, Sulfadiazine, Sulfamethizole, Sulfacetamide
Miscellaneous Antibacterial Agents:

Trimethoprim, Sulfamethazole, Chloramphenicol, Vancomycin, Metronidazole, Quinupristin, Dalfopristin, Rifampin, Spectinomycin, Nitrofurantoin
Antiviral Agents:
General Antiviral Agents:

Idoxuradine, Vidarabine, Trifluridine, Acyclovir, Famcicyclovir, Pencicyclovir, Valacyclovir, Gancicyclovir, Foscarnet, Ribavirin, Amantadine, Rimantadine, Cidofovir, Antisense Oligonucleotides, Immunoglobulins, Inteferons
Drugs for HIV infection:

Tenofovir, Emtricitabine, Zidovudine, Didanosine, Zalcitabine, Stavudine, Lamivudine, Nevirapine, Delavirdine, Saquinavir, Ritonavir, Indinavir, Nelfinavir

EXAMPLES

Example 1

Preparation of Compound AB

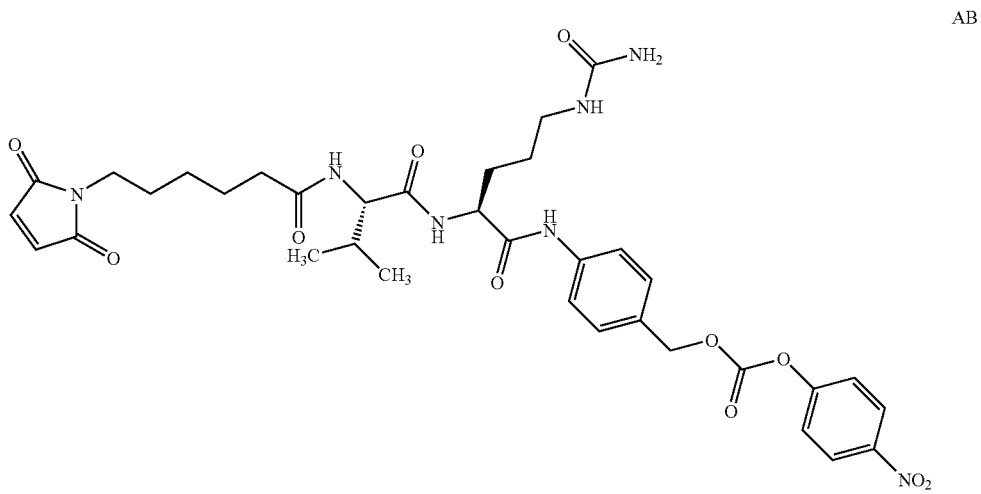 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

Fmoc-val-cit-PAB-OH (14.61 g, 24.3 mmol, 1.0 eq.; see, e.g., U.S. Pat. No. 6,214,345 to Firestone et al.) was diluted with DMF (120 mL, 0.2 M) and to this solution was added a diethylamine (60 mL). The reaction was monitored by HPLC and found to be complete in 2 h. The reaction mixture was concentrated and the resulting residue was precipitated using ethyl acetate (ca. 100 mL) under sonication over for 10 min. Ether (200 mL) was added and the precipitate was further sonicated for 5 min. The solution was allowed to stand for 30 min. without stirring and was then filtered and dried under high vacuum to provide Val-cit-PAB-OH, which was used in the next step without further purification. Yield: 8.84 g (96%). Val-cit-PAB-OH (8.0 g, 21 mmol) was diluted with DMF (110 mL) and the resulting solution was treated with MC-OSu (Willner et al., 1993, *Bioconjugate Chem.* 4:521; 6.5 g, 21 mmol, 1.0 eq.). The reaction was complete according to HPLC after 2 h. The reaction mixture was concentrated and the resulting oil was precipitated using ethyl acetate (50 mL). After sonicating for 15 min, ether (400 mL) was added and the mixture was sonicated further until all large particles were broken up. The solution was then filtered and the solid dried to provide an off-white solid intermediate. Yield: 11.63 g (96%); ES-MS m/z 757.9 [M–H]

The off-white solid intermediate (8.0 g, 14.0 mmol) was diluted with DMF (120 mL, 0.12 M) and to the resulting solution was added bis(4-nitrophenyl)carbonate (8.5 g, 28.0 mmol, 2.0 eq.) and DIEA (3.66 mL, 21.0 mmol, 1.5 eq.). The reaction was complete in 1 h according to HPLC. The reaction mixture was concentrated to provide an oil that is precipitated with EtOAc, and then triturated with EtOAc (ca. 25 mL). The solute was further precipitated with ether (ca. 200 mL) and triturated for 15 min. The solid was filtered and dried under high vacuum to provide Compound AB which is 93% pure according to HPLC and used in the next step without further purification. Yield: 9.7 g (94%).

Example 2

Preparation of Compounds MMAZ by Solid Phase Synthesis

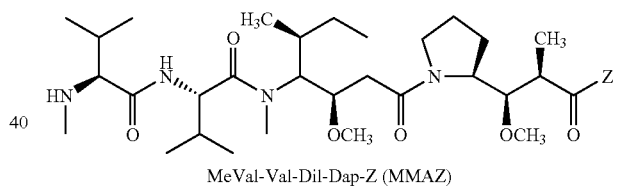

MeVal-Val-Dil-Dap-Z (MMAZ)

Fmoc-Aminoacid-2-Chlorotrityl Resins (SP1) were prepared according to general Procedure SP(a). The following examples illustrate the preparation of certain resins.

Fmoc-2-chloro-Phe-2-Chlorotrityl Resin (SP1-z)

Fmoc-2-chloro-L-phenylalanine (354 mg, 0.84 mmol) was dissolved in anhydrous $CH_2Cl_2$ (4-mL) and DIEA (585 μL, 3.36 mmol, 4 equiv). The resulting solution was added to a 10-mL syringe containing 2-Chlorotrityl chloride resin (500 mg, 0.70 mmol, 1.4 mmol/g). The mixture was agitated for 6 hours at room temperature. The resin was filtered, washed with DCM/MeOH/DIEA (17:2:1; 4×5 mL), MeOH (1×5 mL), DCM (4×5 mL), DMF (4×5 mL), DCM (2×5 mL) and ethyl ether (4×5 mL), and was dried in-vacuo for 2 h. The resin was then left under vacuum overnight. Loading was determined by Fmoc-quantitation. A known quantity (4.4 mg) 2-Chloro-Phe-2-Chlorotrityl resin was weighed into a 10-mL volumetric flask. To the flask was transferred 20% piperidine/DMF (2-mL). The mixture was allowed to cleave for 1 h, with occasional agitation by hand. To the flask was transferred DMF (8-mL) to bring the total volume to 10-mL. A blank solution was prepared with 10-mL of 20% piperidine/DMF in a 10-mL volumetric flask. The spectrophotometer was zeroed with the blank solution. The absorbance was measured at 301 nm and the loading level was given by:

Loading (mmol/g)=$A_{301}$×10 mL/7800×wt $A_{301}$ is the absorbance at 301 nm; 7800 is the extinction coefficient of the piperidine-fluorenone adduct, and wt is the weight of resin used in milligrams. Fmoc quantitation is generally performed in duplicate. Loading level of the Fmoc-2-Chloro-Phe-2-Chlorotrityl resin was determined as 0.612 mmol/g.

Fmoc-Me-Phe-2-Chlorotrityl Resin (SP1-b)

Fmoc-Me-L-phenylalanine (337 mg, 0.84 mmol) was loaded onto 2-Chlorotrityl Chloride resin as described in General Procedure SP(a). The loading level of the Fmoc-Me-L-Phe-2-Chlorotrityl resin was determined to be 0.4908 mmol/g.

Fmoc-Tic-2-Chlorotrityl Resin (SP1-c)

Fmoc-Tic-OH (335 mg, 0.84 mmol) was loaded onto 2-Chlorotrityl Chloride resin as described in General Procedure SP(a). The loading level of the Fmoc-Tic-2-Chlorotrityl resin was determined to be 0.638 mmol/g.

Fmoc-L-β-homophe-2-Chlorotrityl Resin (SP1-d)

Fmoc-L-β-homophenylalanine (337 mg, 0.84 mmol) was loaded onto 2-Chlorotrityl Chloride resin as described in General Procedure SP(a). The loading level of the Fmoc-L-β-homophe-2-chlorotrityl resin was determined to be 0.579 mmol/g.

Boc-p-Amino-Phe(Fmoc)-2-Chlorotrityl Resin (SP1-e)

Boc-p-Amino-Phe(Fmoc)-OH (704 mg, 0.70 mmol) was loaded onto 2-Chlorotrityl Chloride resin as described in General Procedure SP(a). The loading level of the Boc-p-Amino-Phe(Fmoc)-2-chlorotrityl resin was determined as 0.650 mmol/g.

Fmoc-3-cyclohexyl-L-Ala-2-Chlorotrityl Resin (SP1-f)

Fmoc-3-cyclohexyl-L-alanine (550 mg, 0.70 mmol) was loaded onto 2-Chlorotrityl Chloride resin as described in General Procedure SP(a). The loading level of the Fmoc-3-cyclohexyl-L-Ala-2-chlorotrityl resin was determined to be 0.660 mmol/g.

Fmoc-L-4-Thiazolylalanine-2-Chlorotrityl Resin (SP1-g)

Fmoc-L-4-Thiazolylalanine (552 mg, 0.70 mmol) was loaded onto 2-Chlorotrityl Chloride resin as described in General Procedure SP(a). The loading level of the Fmoc-L-4-Thiazolylalanine-2-Chlorotrityl resin was determined to be 0.790 mmol/g.

Fmoc-3-(3-pyridyl)-L-Ala-2-Chlorotrityl Resin (SP1-h)

Fmoc-3-(3-pyridyl)-L-Alanine (543 mg, 0.70 mmol) was loaded onto 2-Chlorotrityl Chloride resin as described in General Procedure SP(a). Loading level of the Fmoc-3-(3-pyridyl)-L-Ala-2-Chlorotrityl resin was determined to be 0.790 mmol/g.

Fmoc quantitation of commercially available pre-loaded resins was performed according to General Procedure SP(b)

H-Leu-2-Chlorotrityl Resin (SP1-i)

Fmoc-Cl (259 mg, 1 mmol) was dissolved in anhydrous $CH_2Cl_2$ (2-mL) to make a 0.5M working solution. The solution was transferred to a 3-mL plastic syringe containing H-Leu-2-Chlorotrityl resin (25 mg, 0.86 mmol/g, 0.0215 mmol). The mixture was agitated for 2 hours. The resin was filtered and washed with DMF (2×5 mL), $CH_2Cl_2$ (2×5 mL), and ethyl ether (2×5 mL), and dried in-vacuo for 2 hours. The resin was tested by the Kaiser amine test. Upon negative results (free amine fully protected), Fmoc quantitation was performed to obtain the loading level, as described in General Procedure SP(a). The loading level of the H-Leu-2-Chlorotrityl resin was determined to be 0.85 mmol/g.

H-Met-2-Chlorotrityl Resin (SP1-j)

H-Met-2-Chlorotrityl resin (25 mg, 0.64 mmol/g, 0.016 mmol) was acylated with excess Fmoc-Cl (259 mg, 1 mmol), as described in General Procedure SP(b). The loading level of the H-Met-2-Chlorotrityl resin was determined to be 0.27 mmol/g.

H-Trp(Boc)-2-Chlorotrityl Resin (SP1-k)

H-Trp(Boc)-2-Chlorotrityl Resin (25 mg, 0.74 mmol/g, 0.033 mmol) was acylated with excess Fmoc-Cl (259 mg, 1 mmol), as described in General Procedure SP(b). The loading level of the H-Trp(Boc)-2-Chlorotrityl resin was determined to be 0.70 mmol/g.

H-Glu(OtBu)-2-Chlorotrityl Resin (SP1-l)

H-Glu(OtBu)-2-Chlorotrityl resin (25 mg, 0.90 mmol/g, 0.022 mmol) was acylated with excess Fmoc-Cl (259 mg, 1 mmol), as described in General Procedure SP(b). The loading level of the H-Glu(OtBu)-2-Chlorotrityl resin was determined to be 0.88 mmol/g.

MeVal-Val-Dil-Dap-2-Chloro-Phe-2-Chlorotrityl Resin

MeVal-Val-Dil-Dap-2-Chloro-Phe-2-Chlorotrityl Resin was prepared following General Procedure SP(c). Briefly, a 20% piperidine in DMF solution (5-mL) was added to the syringe containing Fmoc-2-Chloro-Phe-2-Chlorotrityl Resin, and the mixture was agitated for 2 hours. The resin was filtered, washed with DMF (4×5 mL), DCM (4×5 mL), DMF (4×5 mL), DCM (4×5 mL) and ethyl ether (4×5 mL), and was dried in-vacuo for 2 h.

Fmoc-Dap (278 mg, 0.680 mmol) and HATU (259 mg, 0.680 mmol, 2 equiv.) were dissolved in anhydrous DMF (5-mL) and DIEA (237 µL, 1.36 mmol, 4 equiv.). The resulting solution was transferred to the 10-mL plastic syringe containing H-2-Chloro-Phe-2-Chlorotrityl Resin (555.6 mg, 0.340 mmol). The mixture was agitated overnight at room temperature. Reaction completion was determined by the Kaiser amine test and LCMS analysis of material cleaved off a small amount of resin (using 2% TFA/$CH_2Cl_2$). The resin was filtered, washed with DMF (4×5 mL), DCM (4×5 mL), DMF (4×5 mL), DCM (4×5 mL) and ethyl ether (4×5 mL), and was dried in-vacuo for 2 hours.

A 20% piperidine in DMF solution (5-mL) was added to the syringe containing Fmoc-Dap-2-Chloro-Phe-2-Chlorotrityl Resin, and the mixture was agitated for 2 hours. The resin was filtered, washed with DMF (4×5 mL), DCM (4×5 mL), DMF (4×5 mL), DCM (4×5 mL) and ethyl ether (4×5 mL), and was dried in-vacuo for 2 hours.

Fmoc-MeVal-Val-Dil-OH (510 mg, 0.680 mmol, 2 equiv.) and HATU (259 mg, 0.680 mmol, 2 equiv.) were dissolved in anhydrous DMF (5-mL) and DIEA (237 µL, 1.70 mmol, 5 equiv.). The resulting solution was transferred to the 10-mL plastic syringe containing H-Dap-2-Chloro-Phe-2-Chlorotrityl resin. The mixture was agitated for 6 hours. Reaction completion was determined by LCMS analysis of material cleaved off a small amount of resin (using 2% TFA/CH$_2$Cl$_2$). The resin was filtered, washed with DMF (4×5 mL), DCM (4×5 mL), DMF (4×5 mL), DCM (4×5 mL) and ethyl ether (4×5 mL), and was dried in-vacuo for 2 hours.

MeVal-Val-Dil-Dap-2-Chloro-Phe-OH(SP2-a)

MeVal-Val-Dil-Dap-2-Chloro-Phe was prepared following General Procedure SP(d). Briefly, a 20% piperidine in DMF solution (5-mL) was added to the syringe containing Fmoc-MeVal-Val-Dil-Dap-2-Chloro-Phe-2-Chlorotrityl resin, and the mixture was agitated for 2 hours. The resin was filtered, washed with DMF (4×5 mL), DCM (4×5 mL), DMF (4×5 mL), DCM (4×5 mL) and ethyl ether (4×5 mL), and was dried in-vacuo for 2 hours. Further drying was achieved by leaving resin overnight under vacuum.

A 2% TFA/CH$_2$Cl$_2$ (5 mL) solution was transferred to a 10-mL plastic syringe containing MeVal-Val-Dil-Dap-2-Chloro-Phe-2-Chlorotrityl resin and the mixture was agitated at room temperature for 5 minutes. The filtrate was collected in a 100 mL round-bottom flask. The process was repeated three times. The filtrate was evaporated to leave a white solid. Preparative HPLC purification provided 200 mg (67% TFA salt) of white solid. Reversed-phase HPLC analysis: 96% at 6.72 mins. LC-MS m/z (ES$^+$) calculated for C$_{39}$H$_{64}$ClN$_5$O$_8$, 765.44. found 767.063 (M+H)$^+$.

Fmoc-MeVal-Val-Dil-Dap-Me-Phe-2-Chlorotrityl Resin

Fmoc-Dap-OH and Fmoc-MeVal-Val-Dil-OH were coupled, respectively, onto H-Me-L-Phe-2-Chlorotrityl resin as described in General Procedure SP(c).

MeVal-Val-Dil-Dap-Me-Phe-OH(SP2-b)

MeVal-Val-Dil-Dap-Me-Phe-OH was cleaved off the resin as described in General Procedure SP(d). The filtrate was evaporated to leave a white solid. Preparative HPLC purification provided 62.3 mg (26% TFA salt) of white solid. Reversed-phase HPLC analysis: 98% at 6.88 mins. LC-MS m/z (ES$^+$) calculated for C$_{40}$H$_{67}$N$_5$O$_8$, 745.5. found 746.908 (M+H)$^+$.

Fmoc-MeVal-Val-Dil-Dap-Tic-2-Chlorotrityl Resin

Fmoc-Dap-OH and Fmoc-MeVal-Val-Dil-OH were coupled, respectively, onto H-Tic-2-Chlorotrityl resin as described in General Procedure SP(c).

MeVal-Val-Dil-Dap-Tic-OH(SP2-c)

MeVal-Val-Dil-Dap-Tic-OH was cleaved off the resin as shown General Procedure SP(d). The filtrate was evaporated to leave white solid. Preparative HPLC purification provided 178.40 mg (55% TFA salt) of white solid. Reversed-phase HPLC analysis: 98% at 6.74 mins. LC-MS m/z (ES$^+$) calculated for C$_{40}$H$_{65}$N$_5$O$_8$, 743.48. found, 744.839 (M+H)$^+$.

Fmoc-MeVal-Val-Dil-Dap-L-β-homophe-2-Chlorotrityl Resin

Fmoc-Dap-OH and Fmoc-MeVal-Val-Dil-OH were coupled, respectively, onto H-L-β-homophe-2-Chlorotrityl Resin as described in General Procedure SP(c).

MeVal-Val-Dil-Dap-L-β-homophe-OH(SP2-d)

MeVal-Val-Dil-Dap-L-β-homophe-OH was cleaved off the resin as described in General Procedure SP(d). The filtrate was evaporated to leave white solid. Preparative HPLC purification provided 282.9 mg (99% TFA salt) of white solid. Reversed-phase HPLC analysis: 98% at 6.65 mins. LC-MS m/z (ES$^+$) calculated for C$_{40}$H$_{67}$N$_5$O$_8$ 745.5. found, 746.869 (M+H)$^+$.

Fmoc-MeVal-Val-Dil-Dap-Boc-p-Amino-Phe-2-Chlorotrityl Resin

Fmoc-Dap-OH and Fmoc-MeVal-Val-Dil-OH were coupled, respectively, onto Boc-p-Amino-Phe-2-Chlorotrityl resin as described in General Procedure SP(c).

MeVal-Val-Dil-Dap-Boc-p-Amino-Phe-OH(SP2-e)

MeVal-Val-Dil-Dap-Boc-p-Amino-Phe-OH was cleaved off the resin as described in General Procedure SP(d). The filtrate was evaporated to leave white solid. Preparative HPLC purification provided 210.6 mg (48% TFA salt) of white solid. Reversed-phase HPLC analysis: 98% at 6.9 mins. LC-MS m/z (ES$^+$) calculated for C$_{44}$H$_{74}$N$_6$O$_{10}$, 846.55. found, 847.459 (M+H)$^+$.

Fmoc-MeVal-Val-Dil-Dap-3-cyclohexyl-L-Ala-2-Chlorotrityl Resin

Fmoc-Dap-OH and Fmoc-MeVal-Val-Dil-OH were coupled, respectively, onto H-3-Cyclohexyl-L-Ala-2-Chlorotrityl resin as described in General Procedure SP(c).

MeVal-Val-Dil-Dap-3-cyclohexyl-L-Ala-OH(SP2-f)

MeVal-Val-Dil-Dap-3-cyclohexyl-L-Ala-OH was cleaved off the resin as described in General Procedure SP(d). The filtrate was evaporated to leave a white solid. Preparative HPLC purification provided 343.4 mg (99% TFA salt) of white solid. Reversed-phase HPLC analysis: 98% at 6.87 mins. LC-MS m/z (ES$^+$) calculated for C$_{39}$H$_{71}$N$_5$O$_8$, 737.53. found, 738.974 (M+H)$^+$.

Fmoc-MeVal-Val-Dil-Dap-L-4-Thiazolylalanine-2-Chlorotrityl Resin

Fmoc-Dap-OH and Fmoc-MeVal-Val-Dil-OH were coupled, respectively, onto H-L-4-Thiazolylalanine-2-Chlorotrityl resin as described in General Procedure SP(c).

MeVal-Val-Dil-Dap-L-4-Thiazolylalanine (SP2-g)

MeVal-Val-Dil-Dap-L-4-Thiazolylalanine was cleaved off the resin as described in General Procedure SP(d). The filtrate was evaporated to leave a white solid. Preparative HPLC purification provided 357 mg (87% TFA salt) of a white solid. Reversed-phase HPLC analysis: 98% at 6.23 mins. LC-MS m/z (ES$^+$) calculated for $C_{39}H_{62}N_6O_8S$, 738.43. found, 739.889 (M+H)$^+$.

Fmoc-MeVal-Val-Dil-Dap-3-(3-pyridyl)-L-Ala-2-Chlorotrityl Resin

Fmoc-Dap-OH and Fmoc-MeVal-Val-Dil-OH were coupled, respectively, onto H-3-(3-pyridyl)-L-Ala-2-Chlorotrityl resin as described in General Procedure SP(c).

MeVal-Val-Dil-Dap-3-(3-pyridyl)-L-Ala-OH(SP2-h)

MeVal-Val-Dil-Dap-3-(3-pyridyl)-L-Ala-OH was cleaved off the resin as described in General Procedure SP(d). The filtrate was evaporated to leave a white solid. Preparative HPLC purification provided 388.6 mg (94% TFA salt) of a white solid. Reversed-phase HPLC analysis: 98% at 6.13 mins. LC-MS m/z (ES$^+$) calculated for $C_{38}H_{64}N_6O_8$, 732.48. found, 733.842 (M+H)$^+$.

Fmoc-MeVal-Val-Dil-Dap-Leu-2-Chlorotrityl Resin

Fmoc-Dap-OH and Fmoc-MeVal-Val-Dil-OH were coupled, respectively, onto H-Leu-2-Chlorotrityl resin as described in General Procedure SP(c).

MeVal-Val-Dil-Dap-Leu-OH(SP2-i)

MeVal-Val-Dil-Dap-Leu-OH was cleaved off the resin as described in General Procedure SP(d). The filtrate was evaporated to leave a white solid. Preparative HPLC purification provided 217.4 mg (62% TFA salt) of a white solid. Reversed-phase HPLC analysis: 98% at 6.43 mins. LC-MS m/z (ES$^+$) calculated for $C_{36}H_{67}N_6O_8$, 697.5. found 698.999 (M+H)$^+$.

Fmoc-MeVal-Val-Dil-Dap-Met-2-Chlorotrityl Resin

Fmoc-Dap-OH and Fmoc-MeVal-Val-Dil-OH were coupled, respectively, onto H-Met-2-Chlorotrityl resin as described in General Procedure SP(c).

MeVal-Val-Dil-Dap-Met-OH(SP2-j)

MeVal-Val-Dil-Dap-Met-OH was cleaved off the resin as shown General Procedure SP(d). The filtrate was evaporated to leave a white solid. Preparative HPLC purification provided 90.7 mg (82% TFA salt) of a white solid. Reversed-phase HPLC analysis: 98% at 6.39 mins. LC-MS m/z (ES$^+$) calculated for $C_{35}H_{65}N_5O_8S$, 715.46. found 716.399 (M+H)$^+$.

Fmoc-MeVal-Val-Dil-Dap-Trp(Boc)-2-Chlorotrityl Resin

Fmoc-Dap-OH and Fmoc-MeVal-Val-Dil-OH were coupled, respectively, onto H-Trp-(Boc)-2-Chlorotrityl resin as described in General Procedure SP(c).

MeVal-Val-Dil-Dap-Trp(Boc)-OH(SP2-k)

MeVal-Val-Dil-Dap-Trp(Boc)-OH was cleaved off the resin as described in General Procedure SP(d). The filtrate was evaporated to leave a white solid. Preparative HPLC purification provided 151.7 mg (42% TFA salt) of a white solid. Reversed-phase HPLC analysis: 98% at 7.39 mins. LC-MS m/z (ES$^+$) calculated for $C_{46}H_{74}N_6O_{10}$, 870.55. found 871.645 (M+H)$^+$.

Fmoc-MeVal-Val-Dil-Dap-Glu(OtBu)-2-Chlorotrityl Resin

Fmoc-Dap-OH and Fmoc-MeVal-Val-Dil-OH were coupled, respectively, onto H-Glu(OtBu)-2-Chlorotrityl resin as described in General Procedure SP(c).

MeVal-Val-Dil-Dap-Glu(OtBu)-OH(SP2-l)

MeVal-Val-Dil-Dap-Glu(OtBu)-OH was cleaved off the resin as described in General Procedure SP(d). The filtrate was evaporated to leave a white solid. Preparative HPLC purification provided 219.4 mg (55% TFA salt) of white solid. Reversed-phase HPLC analysis: 98% at 6.67 mins. LC-MS m/z (ES$^+$) calculated for $C_{39}H_{71}N_5O_{10}$, 769.52. found 770.989 (M+H)$^+$.

Example 3

Preparation of MC-Val-Cit-PAB-MMAZ

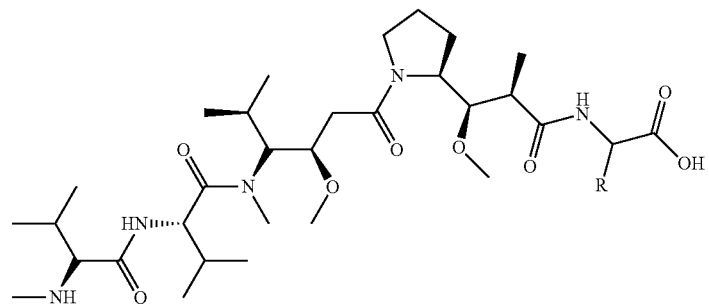

Compounds SP2

Linker AB, HOBt, DIEA, pyridine, DMF, rt, 16 h

-continued

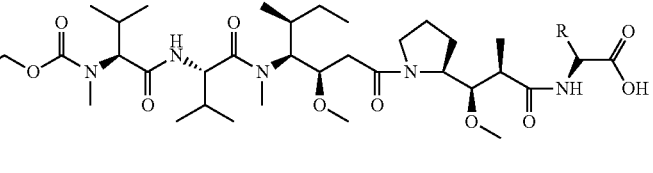
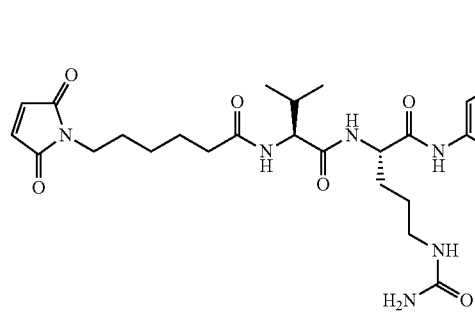

Compounds SP3

Maleimidocaproyl-Val-Cit-PAB-MeVal-Val-Dil-
Dap-2-Chloro-Phe-OH(SP3-a)

Maleimidocaproyl-Val-Cit-PAB-OCOpNP was attached to MeVal-Val-Dil-Dap-2-Chloro-Phe-OH as described in General Procedure H. Preparative HPLC purification provided 13.50 mg (14%) of white solid. Reversed-phase HPLC analysis: 96% at 7.23 mins. LC-MS m/z (ES$^+$) calculated for $C_{68}H_{102}ClN_{11}O_{16}$, 1363.72. found 1364.766 (M+H)$^+$.

Maleimidocaproyl-Val-Cit-PAB-MeVal-Val-Dil-
Dap-Me-Phe-OH(SP3-b)

Maleimidocaproyl-Val-Cit-PAB-OCOpNP was attached to MeVal-Val-Dil-Dap-Me-Phe-OH as described in General Procedure H. Preparative HPLC purification provided 17.1 mg (13%) of white solid. Reversed-phase HPLC analysis: 96% at 7.24 mins. LC-MS m/z (ES$^+$) calculated for $C_{69}H_{105}N_{11}O_{16}$, 1343.77. found, m/z 1344.835 (M+H)$^+$.

Maleimidocaproyl-Val-Cit-PAB-MeVal-Val-Dil-
Dap-Tic-OH(SP3-c)

Maleimidocaproyl-Val-Cit-PAB-OCOpNP was attached to MeVal-Val-Dil-Dap-Tic-OH as described in General Procedure H. Preparative HPLC purification provided 2.7 mg (2%) of white solid. Reversed-phase HPLC analysis: 95% at 7.21 mins. LC-MS m/z (ES$^+$) calculated for $C_{69}H_{103}N_{11}O_{16}$, 1341.76. found, m/z 1342.844 (M+H)$^+$.

Maleimidocaproyl-Val-Cit-PAB-MeVal-Val-Dil-
Dap-L-β-homophe-OH(SP3-d)

Maleimidocaproyl-Val-Cit-PAB-OCOpNP was attached to MeVal-Val-Dil-Dap-L-β-homophe-OH as described in General Procedure H. Preparative HPLC purification provided 3.1 mg (1.5%) of white solid. Reversed-phase HPLC analysis: 95% at 7.26 mins. LC-MS m/z (ES$^+$) calculated for $C_{69}H_{105}N_{11}O_{16}$, 1343.77. found, m/z 1344.788 (M+H)$^+$.

Maleimidocaproyl-Val-Cit-PAB-MeVal-Val-Dil-
Dap-p-Amino-Phe-OH(SP3-e)

Maleimidocaproyl-Val-Cit-PAB-OCOpNP was attached to MeVal-Val-Dil-Dap-Boc-p-Amino-Phe-OH as described in General Procedure H. Preparative HPLC purification provided 4.4 mg (2.5%) of white solid. Reversed-phase HPLC analysis: 95% at 7.54 min. LCMS calculated for $C_{73}H_{112}N_{12}O_{18}$ (MH)+ 1444.82. found, m/z 1445.972. A 50% solution of TFA/CH$_2$Cl$_2$ (1 mL) was transferred to Maleimidocaproyl-Val-Cit-PABC-MeVal-Val-Dil-Dap-Boc-p-Amino-Phe-OH (3.0 mg, 0.00263 mmol). Deprotection of Boc group was complete after 3 hours. The solvent was removed to leave a white solid. Preparative HPLC purification provided 2.3 mg (82%) of white solid. Reversed-phase HPLC analysis: 96% at 7.54 mins. LC-MS m/z (ES$^+$) calculated for $C_{68}H_{104}N_{12}O_{16}$, 1344.77. found, 1345.539 (M+H)$^+$.

Maleimidocaproyl-Val-Cit-PAB-MeVal-Val-Dil-
Dap-3-cyclohexyl-L-Ala-OH(SP3-f)

Maleimidocaproyl-Val-Cit-PAB-OCOpNP was attached to MeVal-Val-Dil-Dap-3-cyclohexyl-L-Ala-OH as described in General Procedure H. Preparative HPLC purification provided 1.5 mg (1%) of white solid. Reversed-phase HPLC analysis: 95% at 7.28 mins. LC-MS m/z (ES$^+$) calculated for $C_{68}H_{109}N_{11}O_{16}$, 1336.66. found, 1337.166 (M+H)$^+$.

Maleimidocaproyl-Val-Cit-PAB-MeVal-Val-Dil-
Dap-L-4-Thiazolylalanine (SP3-g)

Maleimidocaproyl-Val-Cit-PAB-OCOpNP was attached to MeVal-Val-Dil-Dap-L-4-Thiazolyalanine as described in General Procedure H. Preparative HPLC purification provided 0.5 mg (0.2%) of white solid. Reversed-phase HPLC analysis: 96% at 6.91 mins. LC-MS m/z (ES$^+$) calculated for $C_{65}H_{109}N_{12}O_6S$, 1336.71. found, 1337.867 (M+H)$^+$.

Maleimidocaproyl-Val-Cit-PAB-MeVal-Val-Dil-
Dap-pyridyl)-L-Ala-OH(SP3-h)

Maleimidocaproyl-Val-Cit-PAB-OCOpNP was attached to MeVal-Val-Dil-Dap-3-(3-pyridyl)-L-Ala-OH as described in General Procedure H. Preparative HPLC purification provided 4.4 mg (1.6%) of white solid. Reversed-phase HPLC analysis: 98% at 6.94 mins. LC-MS m/z (ES$^+$) calculated for $C_{67}H_{102}N_{12}O_{16}$, 1330.75. found, 1331.682 (M+H)$^+$.

Maleimidocaproyl-Val-Cit-PAB-MeVal-Val-Dil-
Dap-Leu-OH(SP3-i)

Maleimidocaproyl-Val-Cit-PAB-OCOpNP was attached to MeVal-Val-Dil-Dap-Leu-OH as described in General Procedure H. Preparative HPLC purification provided 10.3 mg (4.1%) of white solid. Reversed-phase HPLC analysis: 98% at 7.16 mins. LC-MS m/z (ES$^+$) calculated for $C_{65}H_{105}N_{11}O_{16}$, 1295.77. found, 1296.524 (M+H)$^+$.

Maleimidocaproyl-Val-Cit-PAB-MeVal-Val-Dil-
Dap-Met-OH(SP3-j)

Maleimidocaproyl-Val-Cit-PAB-OCOpNP was attached to MeVal-Val-Dil-Dap-Met-OH as described in General Procedure H. Preparative HPLC purification provided 7.2 mg (6%) of white solid. Reversed-phase HPLC analysis: 98% at 7.06 mins. LC-MS m/z (ES⁺) calculated for $C_{64}H_{103}N_{11}O_{16}S$, 1313.73. found 1314.729 (M+H)⁺.

Maleimidocaproyl-Val-Cit-PAB-MeVal-Val-Dil-Dap-Trp(Boc)-OH(SP3-k)

Maleimidocaproyl-Val-Cit-PAB-OCOpNP was attached to MeVal-Val-Dil-Dap-Trp(Boc)-OH as described in General Procedure H. Preparative HPLC purification provided 7.4 mg (12%) of white solid. Reversed-phase HPLC analysis: 98% at 7.62 mins. LC-MS m/z (ES⁺) calculated for $C_{75}H_{112}N_{12}O_{18}$, 1468.82. found 1469.471 (M+H)⁺.

Maleimidocaproyl-Val-Cit-PAB-MeVal-Val-Dil-Dap-Glu(OtBu)-OH(SP3-l)

Maleimidocaproyl-Val-Cit-PAB-OCOpNP was attached to MeVal-Val-Dil-Dap-Glu(OtBu)-OH as described in General Procedure H. Preparative HPLC purification provided 2.9 mg (1.6%) of white solid. Reversed-phase HPLC analysis: 95% at 7.47 mins. LC-MS m/z (ES⁺) calculated for $C_{68}H_{109}N_{11}O_{18}$, 1367.8. found 1368.452 (M+H)⁺.

Example 4

Solution Phase Preparation of MMAZ (1)

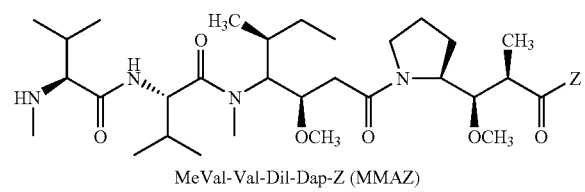

MeVal-Val-Dil-Dap-Z (MMAZ)

The synthesis of MMAZ is described in Schemes 5 and 6. Fmoc-protected amino acids can be prepared from unprotected amino acids using, for example, Fmoc-OSu via well established procedures (see, e.g., Greene and Wuts, *Protective Groups in Organic Synthesis*, 2nd Edition, 1991, John Wiley & Sons, p. 506).

Preparation of Fmoc-Dolaproine (Fmoc-Dap)

Boc-Dolaproine (58.8 g, 0.205 mol) was suspended in 4 N HCl in 1,4-dioxane (256 mL, 1.02 mol, Aldrich). After stirring for 1.5 hours, TLC analysis indicated the reaction was complete (10% MeOH/CH₂Cl₂) and the mixture was concentrated to near-dryness. Additional 1,4-dioxane was charged (50 mL) and the mixture was concentrated to dryness and dried under vacuum overnight. The resulting white solid was dissolved in H₂O (400 mL) and transferred to a 3-L, three-neck, round-bottom flask with a mechanical stirrer and temperature probe. N,N-diisopropylethylamine (214.3 mL, 1.23 mol, Acros) was added over one minute, causing an exotherm from 20.5 to 28.2° C. (internal). The mixture was cooled in an ice bath and 1,4-dioxane was added (400 mL). A solution of Fmoc-OSu (89.90 g, 0.267 mol, Advanced ChemTech) in 1,4-dioxane (400 mL) was added from an addition funnel over 15 minutes, maintaining the reaction temperature below 9° C. The mixture was allowed to warm to room temperature and stirred for 19 hours, after which the mixture was concentrated by rotary evaporation to an aqueous slurry (390 g). The suspension was diluted with H₂O (750 mL) and Et₂O (750 mL). The layers were separated, keeping any solids with the organic layer. The aqueous layer was acidified using conc. HCl (30 mL) and extracted with EtOAc (3×500 mL). The combined extracts were dried over MgSO₄, filtered and concentrated. The Et₂O extract was extracted once with sat. NaHCO₃ (200 mL), keeping any solids with the aqueous layer. The aqueous suspension was acidified using conc. HCl (50 mL) and extracted with Et₂O (50 mL), keeping any solids with the organic layer. The organic layer was filtered and concentrated. The two products were combined and purified by flash chromatography on silica gel eluting with CH₂Cl₂ (3.5 L), then 3% MeOH/CH₂Cl₂ (9 L) to give 68.23 g of Fmoc-dolaproine as a white foam (81%, 97.5% purity by HPLC (AUC)).

Preparation of Fmoc-Dap-Z

The salt and/or protected form of the phenylalanine bioisostere (3 mmol), N-Boc-Dolaproine (668 mg, 1 eq.), DEPC (820 μL, 1.5 eq.), and DIEA (1.2 mL) is diluted with dichloromethane (3 mL). After 2 hours (h) at room temperature (about 28 degrees Celsius), the reaction mixture is diluted with dichloromethane (20 mL), washed successively with saturated aqueous (aq.) NaHCO₃ (2×10 mL) and saturated aq. NaCl (2×10 mL). The organic layer is separated and concentrated. The resulting residue is re-suspended in ethyl acetate and is purified via flash chromatography in ethyl acetate. The relevant fractions are combined and concentrated to provide the dipeptide. Protecting groups are cleaved by methods known to those of skill in the art Alternative Preparation of Fmoc-Dap-Z Carboxy group protected Aminoacid Z (48.3 mmol) is suspended in anhydrous DMF (105 mL, Acros) for 5 minutes and Fmoc-Dap (19.80 g, 48.3 mmol) is added. The mixture is cooled in an ice bath and TBTU (17.08 g, 53.20 mmol, Matrix Innovations) is added. N,N-diisopropylethylamine (25.3 mL, 145.0 mmol, Acros) is added via syringe over 3 min. After 1 hour, the ice bath is removed and the mixture is allowed to warm over 30 min. The mixture is poured into water (1 L) and extracted with ethyl acetate (300 mL). After separation, the aqueous layer is re-extracted with ethyl acetate (2×150 mL). The combined organic layers are washed with brine (150 mL), dried (MgSO₄) and filtered (filter paper) to remove the insolubles (inorganics and some dibenzofulvene). After concentration, the residue is adsorbed on silica (41 g) and purified by chromatography (22 cm×8 cm column; 65% Heptane/EtOAc (2.5 L); 33% Heptane/EtOAc (3.8 L), to give product.

Preparation of Dap-Z

A 1-L round bottom flask is charged with Fmoc-Dap-Z, CH₂Cl₂ (122 mL) and diethylamine (61 mL, Acros). The solution is stirred at room temperature and the completion monitored by HPLC. After 7 hours, the mixture is concentrated (bath temp. <30° C.). The residue is suspended in CH₂Cl₂ (300 mL) and concentrated. This is repeated twice. To the residue is added MeOH (20 mL) and CH₂Cl₂ (300 mL), and the solution is concentrated. The residue is suspended in CH₂Cl₂ (100 mL) and toluene (400 mL), concentrated, and the residue left under vacuum overnight to give product.

Preparation of Fmoc-Meval-Val-Dil-Dap-Z

The tripeptide Fmoc-Meval-val-dil-O-t-Bu (prepared as described in WO 02/088172, entitled "*Pentapeptide Compounds and Uses Related Thereto*"; 0.73 mmol) is treated with TFA (3 mL) and dichloromethane (3 mL) for 2 hours at room temperature. The mixture is concentrated to dryness. The residue is co-evaporated with toluene (3×20 mL) and dried in vacuum overnight. The residue is diluted with dichloromethane (5 mL) and added to the deprotected dipeptide (287 mg, 0.73 mmol), followed by DIEA (550 μL, 4 eq.) and DEPC (201 μL, 1.1 eq.). After 2 hours at room temperature the reaction mixture is diluted with ethyl acetate (50 mL), washed successively with 10% aq. citric acid (2×20 mL), saturated aq. NaHCO₃ (2×10 mL) and saturated aq. NaCl (10 mL). The organic layer is separated and concentrated. The resulting residue is re-suspended in ethyl acetate and is purified via flash chromatography in ethyl acetate. The relevant fractions are combined and concentrated to provide Fmoc-Meval-val-dil-dap-Z.

Alternative Preparation of Fmoc-MeVal-Val-Dil-Dap-Z

Crude Dap-Z (39.1 mmol) is suspended in anhydrous DMF (135 mL, Acros) for 5 minutes and Fmoc-MeVal-Val-Dil-OH (24.94 g, 39.1 mmol, see Example 2 for preparation) is added. The mixture is cooled in an ice bath and TBTU (13.81 g, 43.0

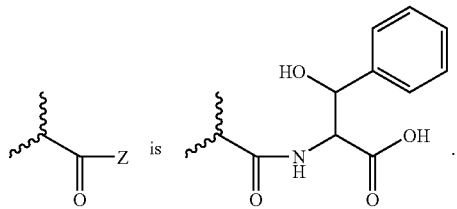

3-Phenylserine is available from Aldrich.
Synthesis of DimethylValine-Val-Dil-Dap-Phenylserine

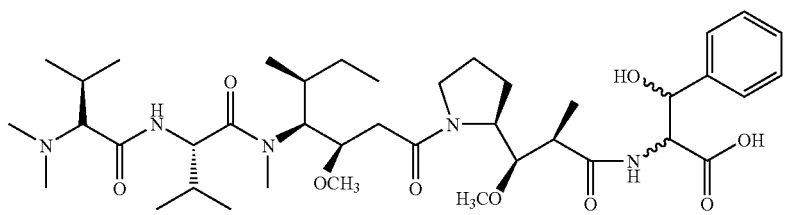

mmol, Matrix Innovations) is added. N,N-Diisopropylethylamine (20.5 mL, 117.3 mmol, Acros) is added via syringe over 2 minutes. After 1 hour, the ice bath is removed and the mixture is allowed to warm over 30 min. The mixture is poured into water (1.5 L) and diluted with ethyl acetate (480 mL). After standing for 15 minutes, the layers were separated and the aqueous layer is extracted with ethyl acetate (300 mL). The combined organic layers are washed with brine (200 mL), dried (MgSO4) and filtered (filter paper) to remove insolubles (inorganics and some dibenzofulvene). After concentration, the residue (49 g) is scraped from the flask and adsorbed on silica (49 g) and purified by chromatography (15 cm×10 cm dia column; 2:1 EtOAc/Heptane (3 L), EtOAc (5 L); 250 mL fractions) to give Fmoc-MeVal-Val-Dil-Dap-Z.

Preparation of Meval-Val-Dil-Dap-Z

The product (0.2 mmol) is diluted with dichloromethane (3 mL), diethylamine (1 mL). The reaction mixture is stirred overnight at room temperature. Solvents are removed to provide an oil that is purified by flash silica gel chromatography in a step gradient 0-10% MeOH in dichloromethane to provide Compound 1.

Using the above procedure, the compounds of the following formula are prepared:

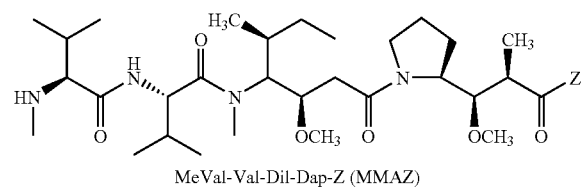

MeVal-Val-Dil-Dap-Z (MMAZ)

Example 5

Synthesis of MMAZ Compounds

This synthesis describes the preparation of MMAZ compounds wherein

To a suspension of Fmoc-Dap (1.2 g, 2.93 mmoles) in anhydrous CH₂Cl₂ (10 mL) was added N,N'-disuccinimidyl carbonate (901 mg, 1.2 eq) followed by DIEA (1.28 mL, 2.5 eq). The reaction mixture was allowed to stir at room temperature overnight. Additional amounts of N,N'-disuccinimidyl carbonate (901 mg, 1.2 eq) followed by DIEA (1.28 mL, 2.5 eq) were charged and stirring was continued for 18 h more. The reaction mixture was diluted with EtOAc; organic layer was washed with 0.1 M aq. HCl twice, then dried over MgSO₄, filtered and concentrated in vacuo. Silica gel column chromatography in a step gradient of MeOH from 0 to 5% in CH₂Cl₂ afforded 1.12 g (75% yield) Fmoc-Dap-OSu as off-white foam.

Fmoc-Dap-OSu (0.615 g, 1.21 mmol) was suspended in dry DMSO (6 mL). D,L-threo-3-phenyl serine (0.2 g, 1.1 mmol) was added, and the reaction mixture was stirred overnight at room temperature. Mixture was directly loaded on prep RP-HPLC and the product was isolated in a linear gradient of MeCN from 10 to 90% in aqueous 0.1% TFA. Obtained Fmoc-Dap-Phenylserine, 280 mg (44% yield), was suspended in dry CH₂Cl₂ (2 mL) and treated with dimethyl amine (2 mL) for 4 hours at room temperature. Volatiles were removed under reduced pressure. Residue was co-evaporated with Et₃N/CH₂Cl₂ 3 times to remove as much diethylamine as possible, then dried in vacuo overnight. Residue was extensively triturated with ether to remove DBF. Dap-Phenylserine was dried and used without further purification.

DimethylVal-Val-Dil-COOH (130 mg, 0.3 mmol, 1 eq), N-hydroxysuccinimide (39 mg, 0.3 mmol, 1 eq) and DCC (93 mg, 1.5 eq) were suspended in dry CH₂Cl₂ (1.5 mL). To this, DMAP (1 mg, cat.) was added and the reaction mixture was stirred at room temperature overnight. Precipitate was filtered off. Thus prepared DimethylVal-Val-Dil-OSu was suspended in CH₂Cl₂ (2 mL) and the mixture was added to Dap-Phenylserine, followed by DMSO (4 mL) and DIEA (100 uL). Reaction was allowed to stir at room temperature overnight. Precipitate was filtered off. CH₂Cl₂ was replaced by DMSO and the product was isolated by preparative RP-HPLC (linear gradient of MeCN, 10 to 90% in aq. 0.005% TFA) as two diastereomers. Isomer A: 84 mg, white foam. LC-MS m/z (ES⁺) 762.67 (M+H)⁺ at 10.58 min. Isomer B: 62 mg white solid. LC-MS m/z (ES⁺) 762.54 (M+H)⁺ at 10.67 min.

Synthesis of N-MethylValine-Val-Dil-Dap-Phenylserine

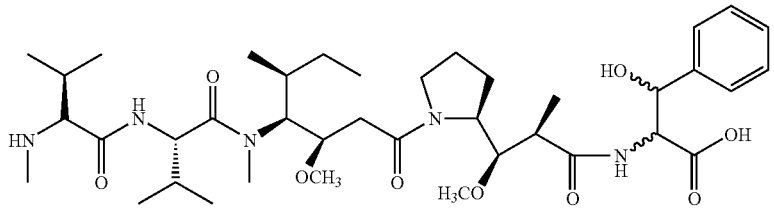

MeVal-Val-Dil-Dap-Phenylserine can be prepared as described above using Fmoc-MeVal-Val-Dil tripeptide. Fmoc can be later cleaved off the final drug according to General Procedure E.

Appropriately protected 3-phenylserine can be subjected to oxidizing conditions, e.g., pyridinium chlorochromate (PCC)/pyridine (see, e.g., *Synthesis*, 1982, 245, 881, review), in order to provide the corresponding ketone. The ketone can be further converted to various hydrazones (hydrazones, acyl hydrazones, semicarbazones, thiosemicarbazones, etc.) as described, for example, by Kaneko et al. *Bioconjugate Chemistry*, 1991, 2(3), 133-141. Alternatively hydroxyl group of amino- and carboxylate-protected 3-phenylserine can be readily condensed with various acids using DCC/DMAP chemistry to provide esters (Larock, R. C., Comprehensive Organic Transformations, Wiley-VCH, 1999, p. 1937).

Methylphosphonate ester of 3-phenylserine can be generated by reacting methylphosphonic diimidazolide (from commercially available methylphosphonic dichloride, Aldrich) with protected 3-phenylserine followed by aqueous hydrolysis.

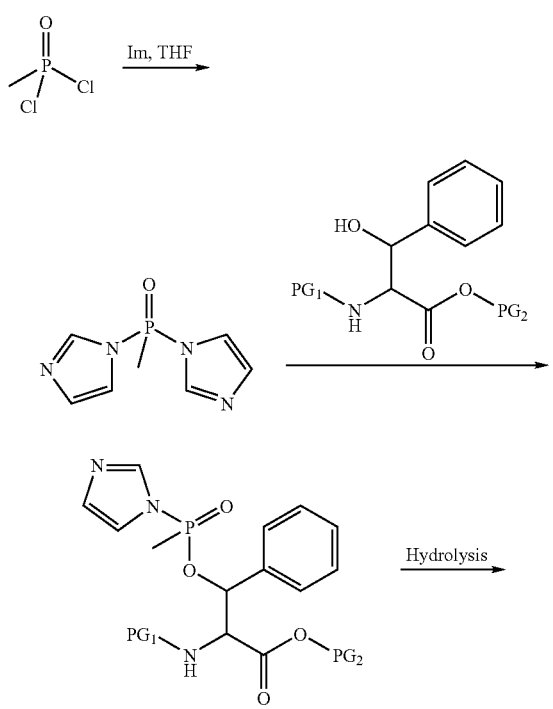

-continued

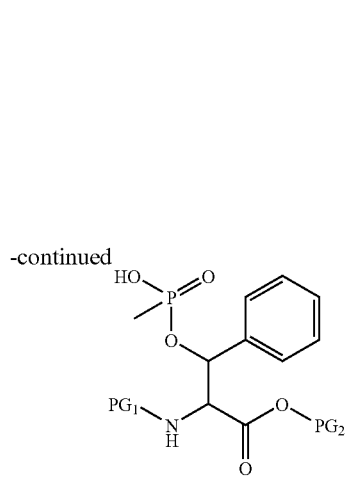

3-Phenylserine phosphate ester can be generated by similar procedure from phosphorus oxychloride (Aldrich). Chemistries similar to the described above can be used for the preparation of various derivatives of serine and threonine.

MMAZ is prepared by using the above phenylalanine analog and conjugating with Fmoc-Meval-val-dil-O-t-Bu following the procedure of Example 4.

Example 6

Synthesis of MMAZ Compounds

This synthesis describes the preparation of MMAZ compounds wherein

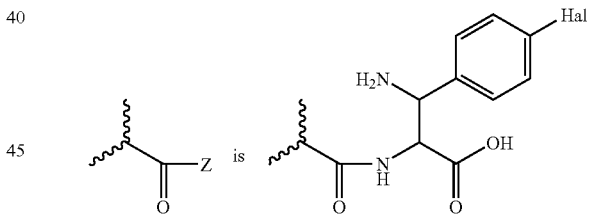

Enantiomerically pure diamino acids shown below wherein Hal is a halogen can be conveniently prepared as described in Zhou et al. 1999, *Tetrahedron: Asymmetry* 10(5): 855-862.

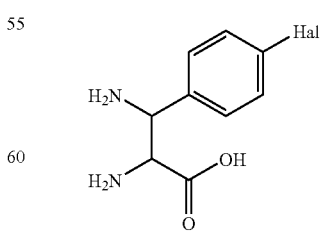

MMAZ is prepared by using the above phenylalanine analog and conjugating with Fmoc-Meval-val-dil-O-t-Bu following the procedure of Example 4.

Example 7

Synthesis of MMAZ Compounds

This synthesis describes the preparation of MMAZ compounds wherein:

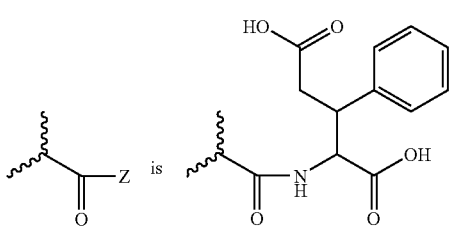

3-Aryl-glutamic acid and other 3-substituted pyroglutamic and glutamic acids can be prepared as described in *Tetrahedron* 9(2):217-229 (2002), or *Journal of Organic Chemistry* 66(4):1339-1350 (2001).

MMAZ is prepared by using the above phenylalanine analog and conjugating with Fmoc-Meval-val-dil-O-t-Bu following the procedure of Example 4.

Example 8

Synthesis of MMAZ Compounds

This synthesis describes the preparation of MMAZ compounds wherein:

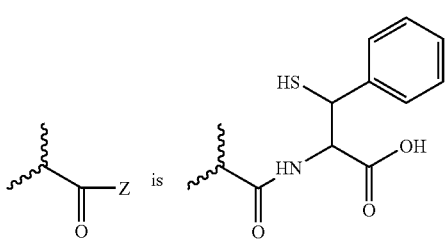

3-Phenylcysteine can be prepared as described in Lago et al., 1992, *Journal of Organic Chemistry* 57(12):3493-6.

MMAZ is prepared by using the above phenylalanine analog and conjugating with Fmoc-Meval-val-dil-O-t-Bu following the procedure of Example 4.

Example 9

Synthesis of MMAZ Compounds

This synthesis describes the preparation of MMAZ compounds wherein:

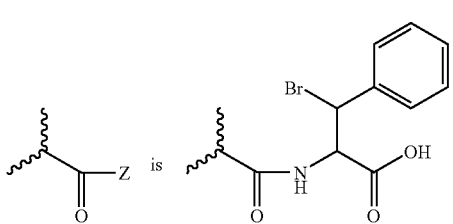

2-Bromo-phenylalanine can be synthesized as described in Righi et al., 1996, *Tetrahedron Letters* 37(38):6893-6896.

MMAZ is prepared by using the above phenylalanine analog and conjugating with Fmoc-Meval-val-dil-O-t-Bu following the procedure of Example 4.

Example 10

Synthesis of MMAZ Compounds

This synthesis describes the preparation of MMAZ compounds wherein:

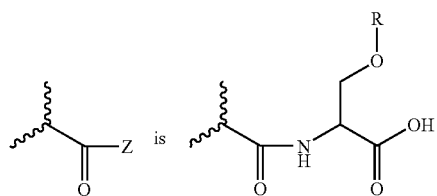

Beta-alkoxy-amino acids above, where R=alkyl, cyclohexyl, phenyl, benzyl, etc., can be synthesized as described in *Bulletin of the Chemical Society of Japan*, 1982, 55(9):3049-50.

MMAZ is prepared by using the above phenylalanine analog and conjugating with Fmoc-Meval-val-dil-O-t-Bu following the procedure of Example 4.

Example 11

Synthesis of MMAZ Compounds

This synthesis describes the preparation of MMAZ compounds wherein:

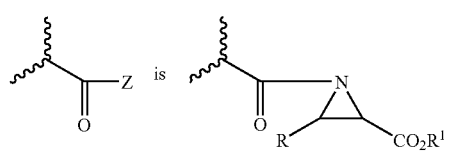

Azi

The phenylalanine analogs are synthesized as described below. Aziridines (Azi) (infra), wherein Z=PhCH$_2$O$_2$C; R=H or Me, and R$^1$=PhCH$_2$ or Me, were cleaved by alcohols, R$^2$OH, wherein R$^2$=Me, Me$_2$CH, EtCHMe, Me$_3$C, cyclohexyl, PhCH$_2$, Ph, or the like, in the presence of BF$_3$.Et$_2$O to afford optically pure serine and threonine derivatives R$_2$OCHRCH(NHZ)CO$_2$R$^1$. The latter were deprotected by hydrogenolysis and saponification to give the corresponding R$_2$OCHRCH(NH$_2$)CO$_2$H.

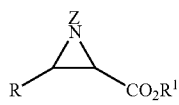

MMAZ is prepared by using the above phenylalanine analog and conjugating with Fmoc-Meval-val-dil-O-t-Bu following the procedure of Example 4.

Example 12

Synthesis of MMAZ Compounds

This synthesis describes the preparation of MMAZ compounds wherein:

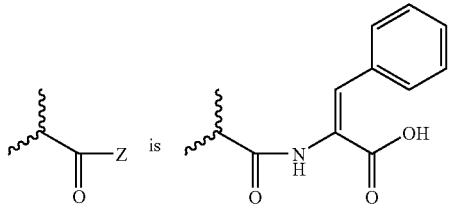

Dehydrophenylalanine and other dehydro amino acids are synthesized as described in Mathur et al., 2004, *Biopolymers* 76(2):150-161.

MMAZ is prepared by using the above phenylalanine analog and conjugating with Fmoc-Meval-val-dil-O-t-Bu following the procedure of Example 4.

Example 11

Synthesis of MMAZ Compounds

This synthesis describes the preparation of MMAZ compounds wherein:

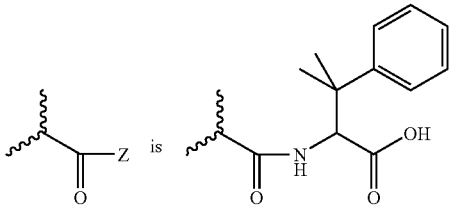

β,β-dimethyl-phenylalanine and β,β-dimethyl-tyrosine can be synthesized as described by Jonsson and Mikiver, 1976, *Acta Pharmaceutica Suecica* 13(1):75-8. Refluxing $PhCMe_2CH(CN)CO_2Et$ with $N_2H_4$ in MeOH gives 93% of the hydrazide with a pyrazolidine side product in 3.5% yield. Sequential diazotization, Curtius degradation, and hydrolysis give 74% $PhCMe_2CH(NH_2)CO_2H$. β,β-Dimethyltyrosine can be similarly prepared.

MMAZ is prepared by using the above phenylalanine analog and conjugating with Fmoc-Meval-val-dil-O-t-Bu following the procedure of Example 4.

Example 14

Synthesis of MMAZ Compounds

This synthesis describes the preparation of MMAZ compounds wherein:

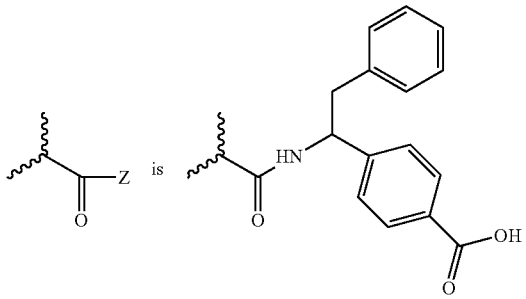

4-(1-amino-2-phenylethyl)-benzoic acid can be prepared as described in *Journal of Medicinal Chemistry* 38(10):1600-7 (1995).

MMAZ is prepared by using the above phenylalanine analog and conjugating with Fmoc-Meval-val-dil-O-t-Bu following the procedure of Example 4.

Example 15

Synthesis of MMAZ Compounds

This synthesis describes the preparation of MMAZ compounds wherein:

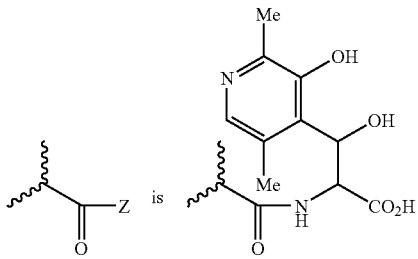

The phenylalanine analogs are synthesized following the procedures described in Toth et al., 2004, *Journal of the American Chemical Society* 126(34): 10538-10539.

MMAZ is prepared by using the above phenylalanine analog and conjugating with Fmoc-Meval-val-dil-O-t-Bu following the procedure of Example 4.

Example 16

Synthesis of MMAZ Compounds

This synthesis describes the preparation of MMAZ compounds wherein:

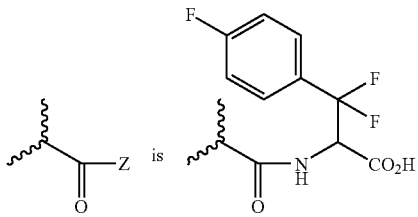

β,β-Difluoro analogs of α-oxo-β-phenylpropionic acid and phenylalanine are synthesized as shown below following the procedures described in Schlosser et al., 2004, *Tetrahe-* dron 60(35):7731-7742 and Roff et al., 2004, *Journal of the American Chemical Society* 126(13):4098-4099. A simple three-step procedure converts the readily accessible (2-bromo-1,1-difluoroethyl)arenes into α-aryl-α,α-difluoro-acetaldehydes. Subsequent hydrocyanation, hydrolysis, oxidation and further hydrolysis afforded β-aryl-β,β-difluoro-α-oxopropionic acids. Reductive amination transforms the oxo acids into a separable mixture of α-hydroxy acids and racemic β,β-difluoro-β-phenylalanine derivatives. Enantiomerically pure β,β-difluorophenylalanine is obtained when α,α-difluoro-α-phenylacetaldehyde is condensed with homochiral 1-phenylethylamine, hydrogen cyanide is add to the resulting imine, the diastereomeric mixture thus produced is hydrolyzed to the carboxamides which is separable by fractional crystallization or chromatography.

Example 17

Synthesis of MMAZ Compounds

This synthesis describes the preparation of MMAZ compounds wherein:

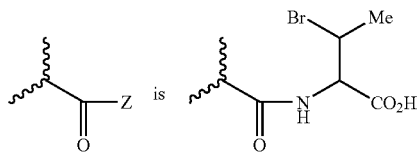

A series of diastereoisomers ((2R,3S)-, (2S,3R)-, (2S,3S)- and (2R,3R)) of β-methyl-β-arylalanine analogs can be prepared in enantiomerically pure form using a combination of chemo- and biocatalysis. Starting from Me L-threoninate, a range of β,β-disubstituted didehydroamino acids are obtained as their (Z)-isomers. Asymmetric hydrogenation, using either [Rh(R,R)-Et-DuPhos(COD)]$BF_4$ or [Rh(S,S)-Et-DuPhos(COD)]$BF_4$ as a catalyst, followed by hydrolysis yielded the (2R,3S)- and (2S,3R) isomers, respectively. Subsequent enzymic stereoinversion of the (2R,3S) isomer with D-amino acid oxidase and stereoinversion of the (2S,3R) isomer with L-amino acid oxidase in combination with $NH_3 \cdot BH_3$ yields the remaining (2S,3S)- and (2R,3R) isomers, respectively.

Example 18

Synthesis of MMAZ Compounds

This synthesis describes the preparation of MMAZ compounds wherein:

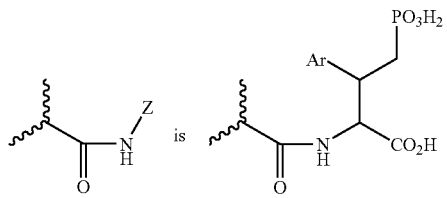

Synthesis of 2-Amino-4-phosphonobutanoic acids
2-Amino-4-phosphonobutanoic Acids above, where Ar=phenyl, 3-pyridyl and 2-thienyl, are synthesized as described in Ruiz et al., 2003, *Journal of Organic Chemistry* 68(20):7634-7645.

MMAZ is prepared by using the above phenylalanine analog and conjugating with Fmoc-Meval-val-dil-O-t-Bu following the procedure of Example 4.

Example 19

Synthesis of MMAZ of the Formula Above Wherein

Conjugate additions of lithiated bislactim ethers derived from cyclo[Gly-Val] and cyclo[Ala-Val] to α-, β-, or α,β-substituted vinylphosphonates allow direct and stereoselective access to a variety of 3- or 4-monosubstituted and 2,3-, 2,4-, or 3,4-disubstituted 2-amino-4-phosphonobutanoic acids (AP4 derivs.) in enantiomerically pure form. The relative stereochemistry can be assigned by x-ray diffraction analysis or NMR study of 1,2-oxaphosphorinane derivs. Competitive eight-membered "compact" and "relaxed" transition-state structures are invoked to rationalize the stereochemical outcome of the conjugate additions.

Example 20

Synthesis of MMAZ Compounds

This synthesis describes the preparation of MMAZ compounds wherein:

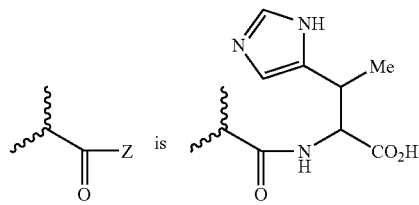

Synthesis of beta-substituted histidines is described in Wang et al., 2000, *Tetrahedron Letters* 41(9):1307-1310.

MMAZ is prepared by using the above phenylalanine analog and conjugating with Fmoc-Meval-val-dil-O-t-Bu following the procedure of Example 4.

Example 21

Synthesis of MMAZ Compounds

This synthesis describes the preparation of MMAZ compounds wherein:

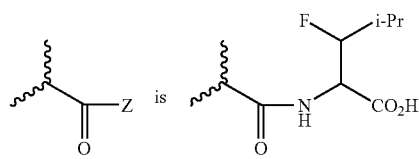

Beta-fluoro amino acids are synthesized as described in Davis et al., 1999, *Journal of Organic Chemistry* 64(18): 6931-6934.

MMAZ is prepared by using the above phenylalanine analog and conjugating with Fmoc-Meval-val-dil-O-t-Bu following the procedure of Example 4.

Example 22

Synthesis of MMAZ Compounds

This synthesis describes the preparation of MMAZ compounds wherein:

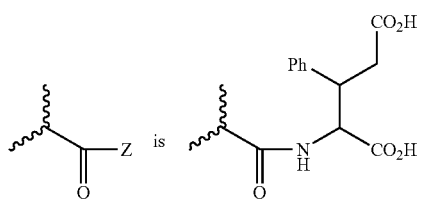

Beta-substituted glutamic acids, like the one above, can be prepared as described in Ezquerra et al., 1999, *Journal of Organic Chemistry* 64(18):6554-6565. The reaction of lithium enolates of achiral N-protected glycine esters with chiral alkoxyalkenylcarbene complexes of chromium provide the corresponding Michael adducts with either high anti or syn selectivity depending on the nature of the nitrogen protecting group, and high diastereofacial selectivity when carbene complexes containing the (−)-8-phenylmenthyloxy group are employed. Subsequent oxidation of the metal-carbene moiety followed by deprotection of the amine group and hydrolysis of both carboxylic esters affords enantiomerically enriched 3-substituted glutamic acids of natural as well as unnatural stereochemistry. For example, carbene complex can be reacted with glycine lithium enolate to give the Michael addition adduct, which can be oxidized to give a protected glutamate without any loss of stereochem. Glutamate is deprotected in two steps to give (2R,3S)-3-(3-furyl)glutamic acid hydrochloride salt. Alternatively, when the deprotection step is performed previous to the oxidation, cyclic aminocarbene complexes are formed, which will lead to optically active 3-substituted pyroglutamic acids.

MMAZ is prepared by using the above phenylalanine analog and conjugating with Fmoc-Meval-val-dil-O-t-Bu following the procedure of Example 3.

Example 23

Synthesis of Other MMAZ Compounds

MMAZ compounds can also be prepared using the following commercially available phenylalanine analogs either as their protected or unprotected amino acids incorporated in solution or solid phase synthesis as described above:

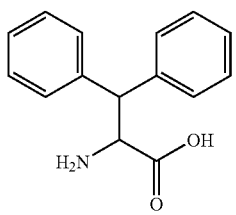 [SMILES: NC(C(=O)O)C(c1ccccc1)c1ccccc1]

(commercially available from Tyger Scientific, Inc. Ewing, N.J.);

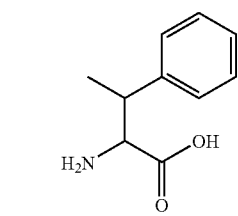

(commercially available from Acros Organics);

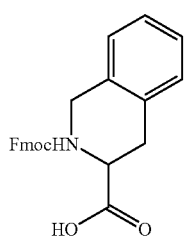

(commercially available from Advanced ChemTech);

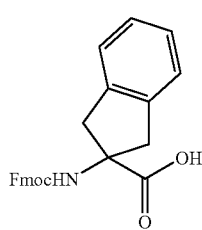

(commercially available from Acros);

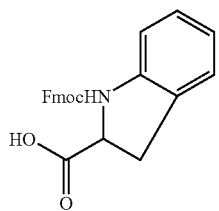

(commercially available from Advanced ChemTech);

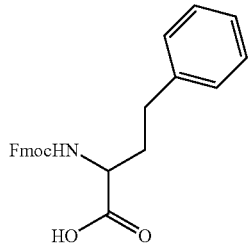

(commercially available from Advanced ChemTech);

165
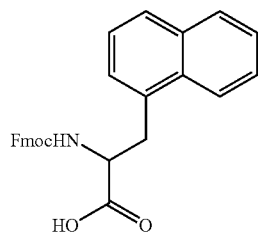
(commercially available from Pharmacore Products);
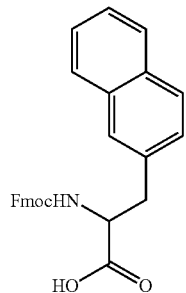
(commercially available from Fluka);
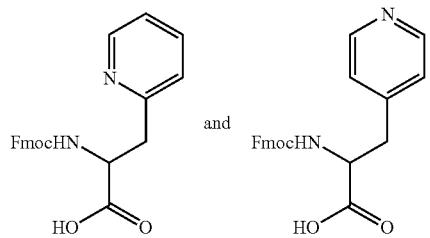
(commercially available from Peptech);
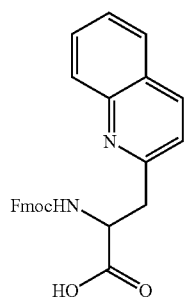
(commercially available from Bachem);
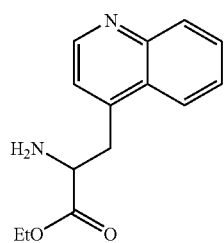 [SMILES: CCOC(=O)C(N)Cc1ccnc2ccccc12]
(commercially available from ChemStep);
166
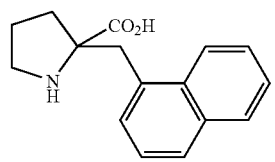 [SMILES: O=C(O)C1(Cc2cccc3ccccc23)CCCN1]
(commercially available from Chem IMPX);
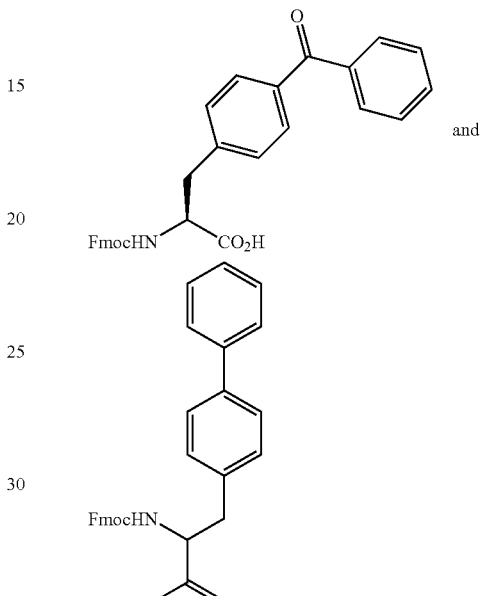
and
(commercially available from Advanced ChemTech);
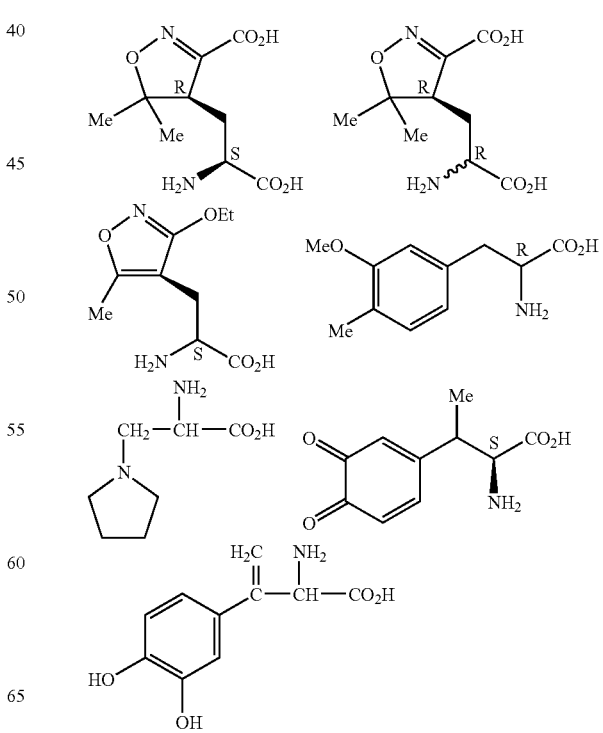

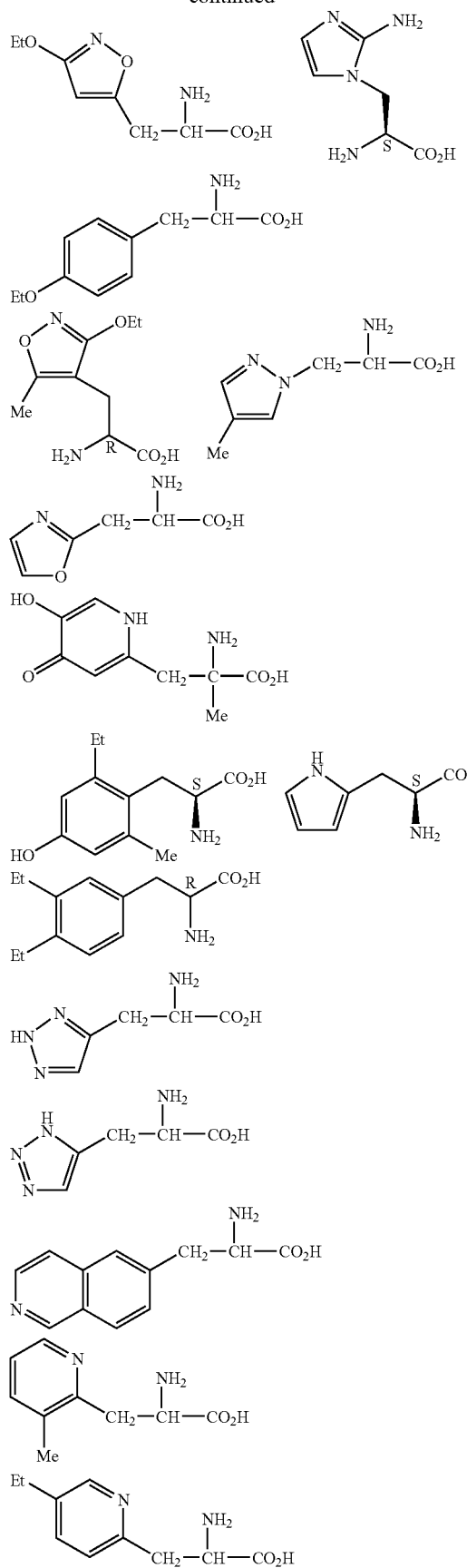
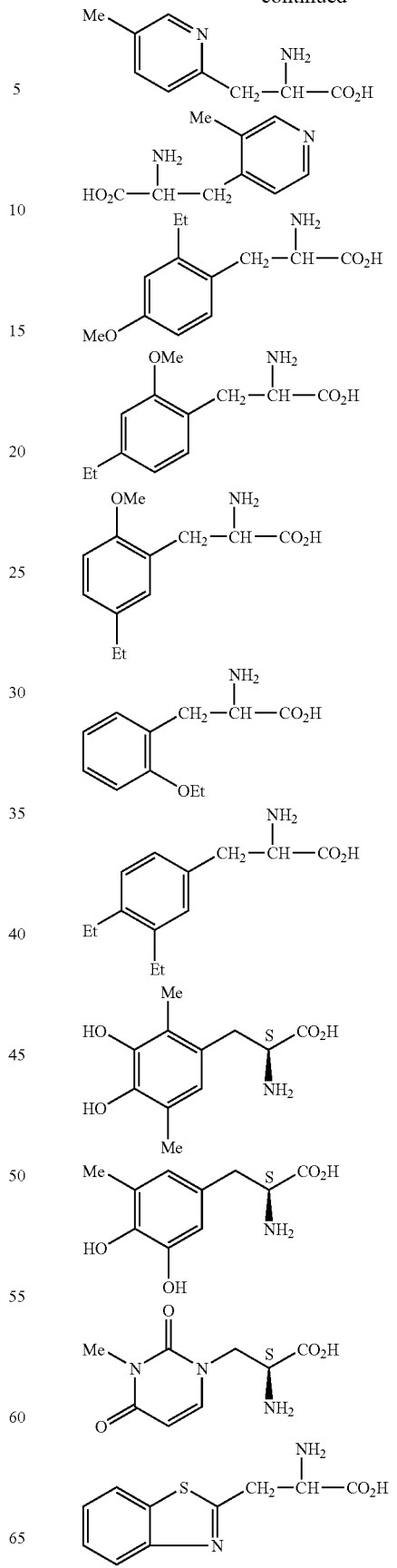

-continued
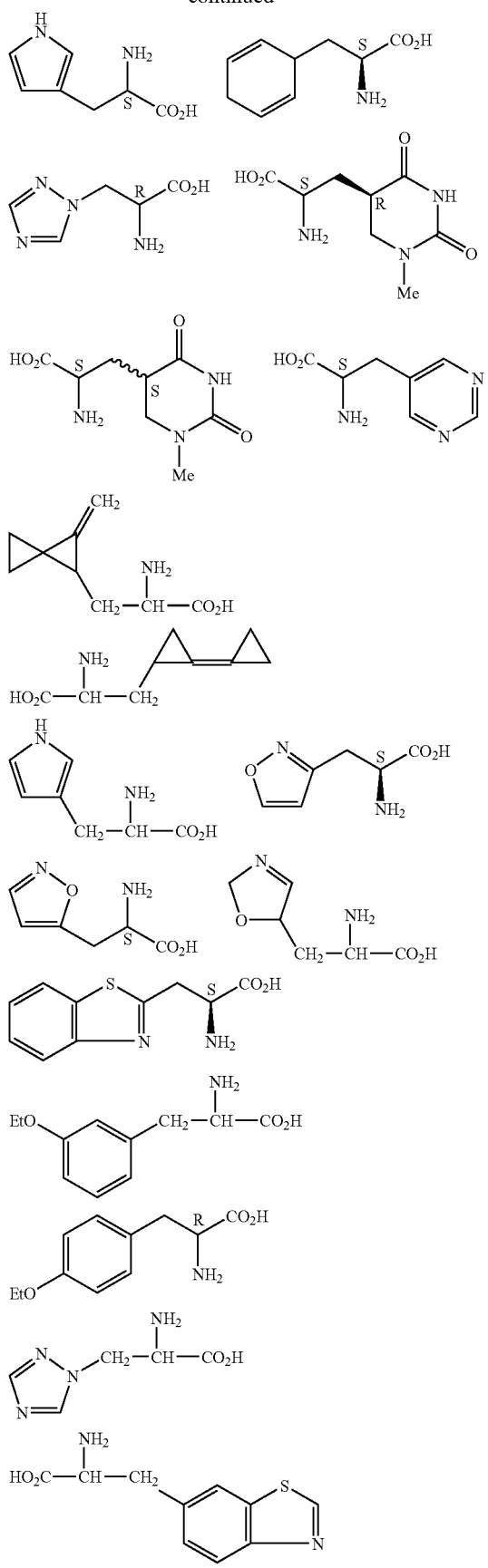
-continued
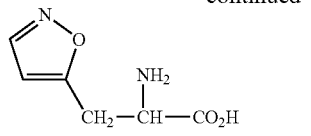
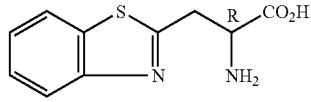 [SMILES: NC(Cc1nc2ccccc2s1)C(=O)O]
(commercially available from Chemstep);
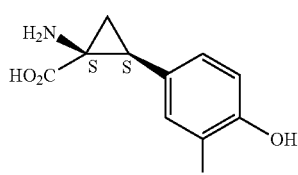
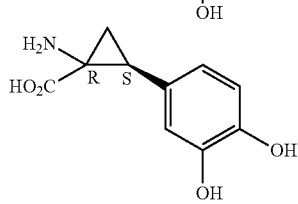
(commercially available from Aldrich);
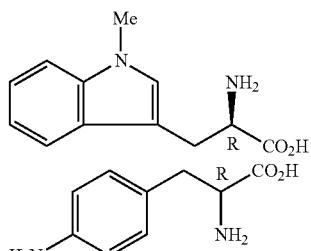
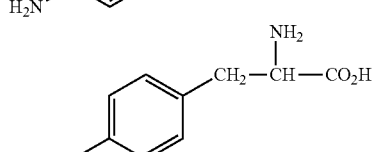
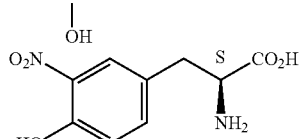
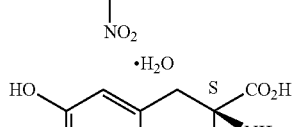
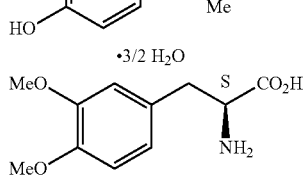

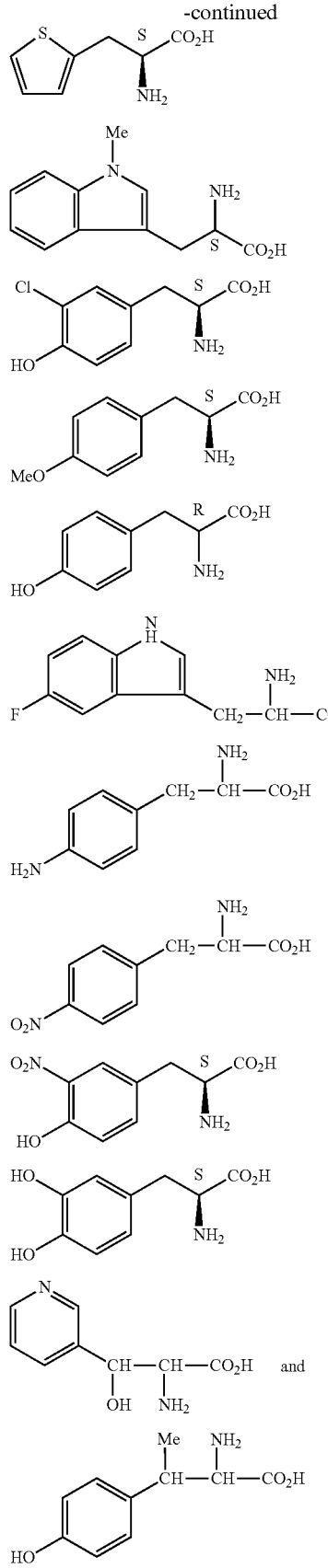
(commercially available from Sigma);
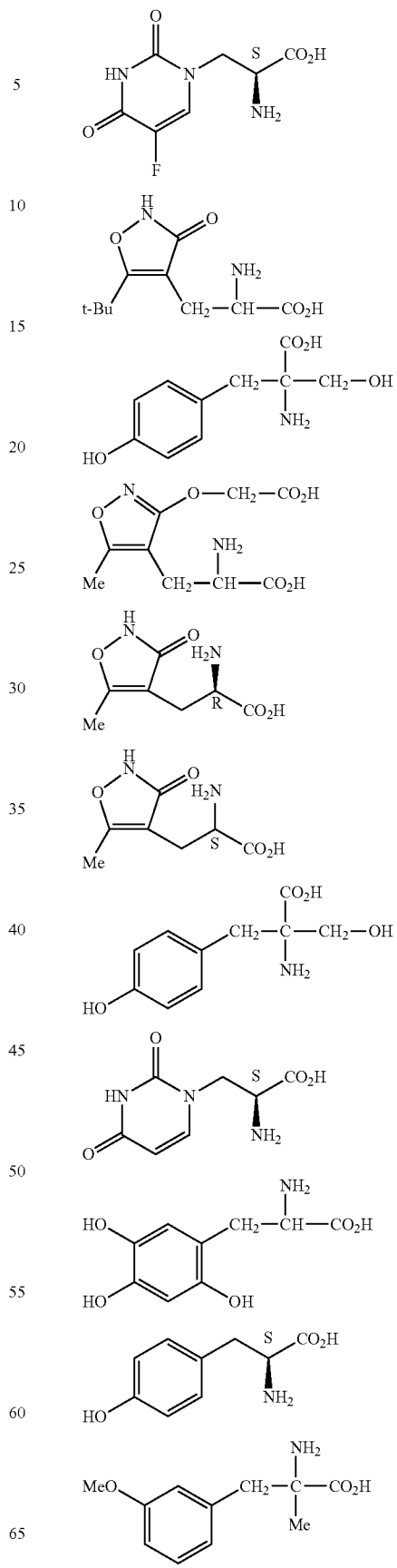

-continued
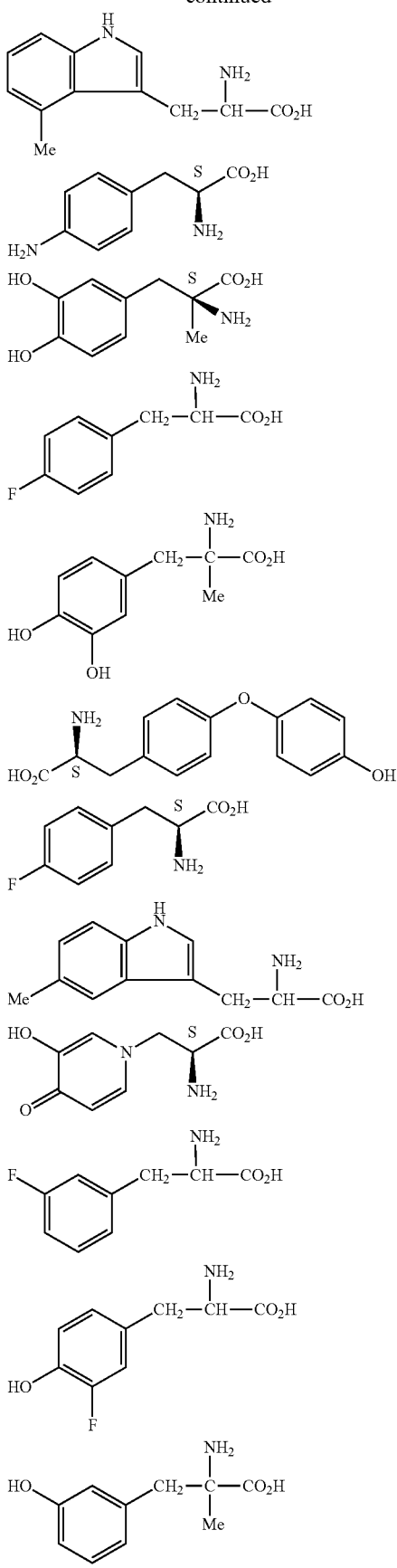
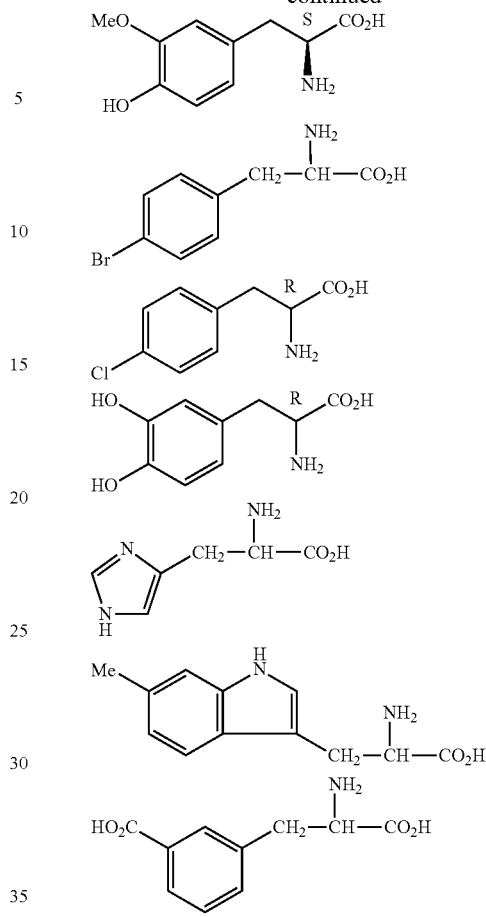
(commercially available from Apollo Scientific Ltd.);
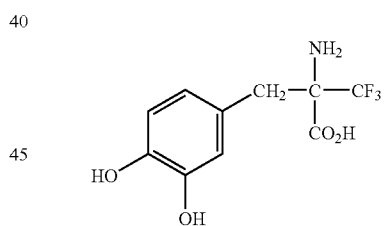
(commercially available from DSL Chemicals (Shanghai) Co., Ltd.);
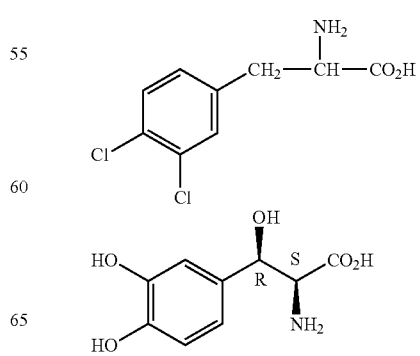

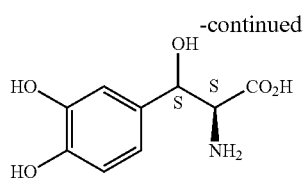
(commercially available from Salor);
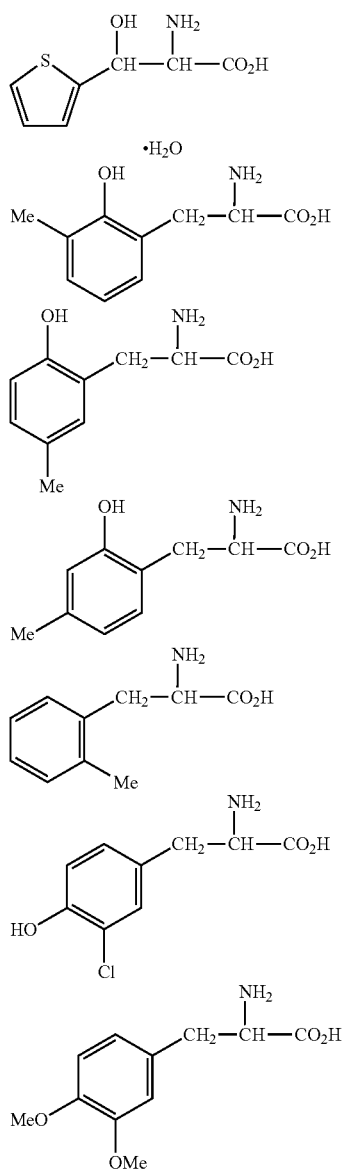
(commercially available from Synchem OHG);
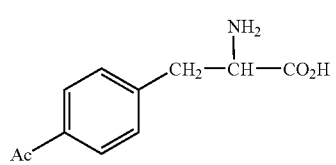 [SMILES: CC(=O)c1ccc(CC(N)C(=O)O)cc1]
(commercially available from Sequoia Research Products Ltd.);
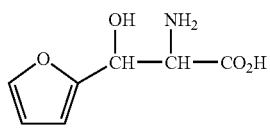 [SMILES: NC(C(=O)O)C(O)c1ccco1]
(commercially available from MicroChemistry Building Blocks);
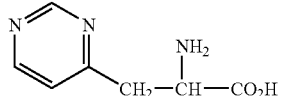
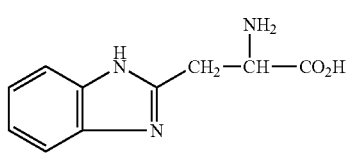
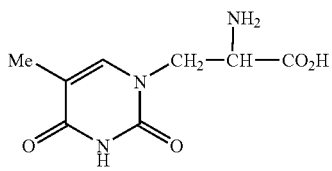
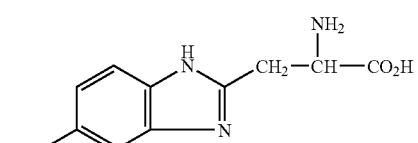
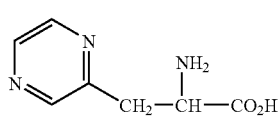
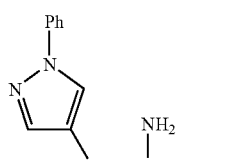
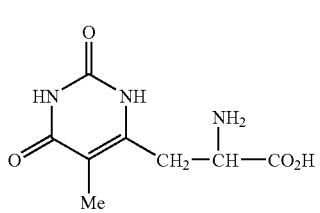
(commercially available from Lancanster);
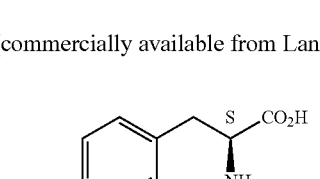
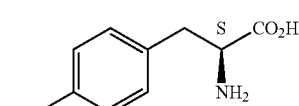
(commercially available from Ambinter, Paris, France);

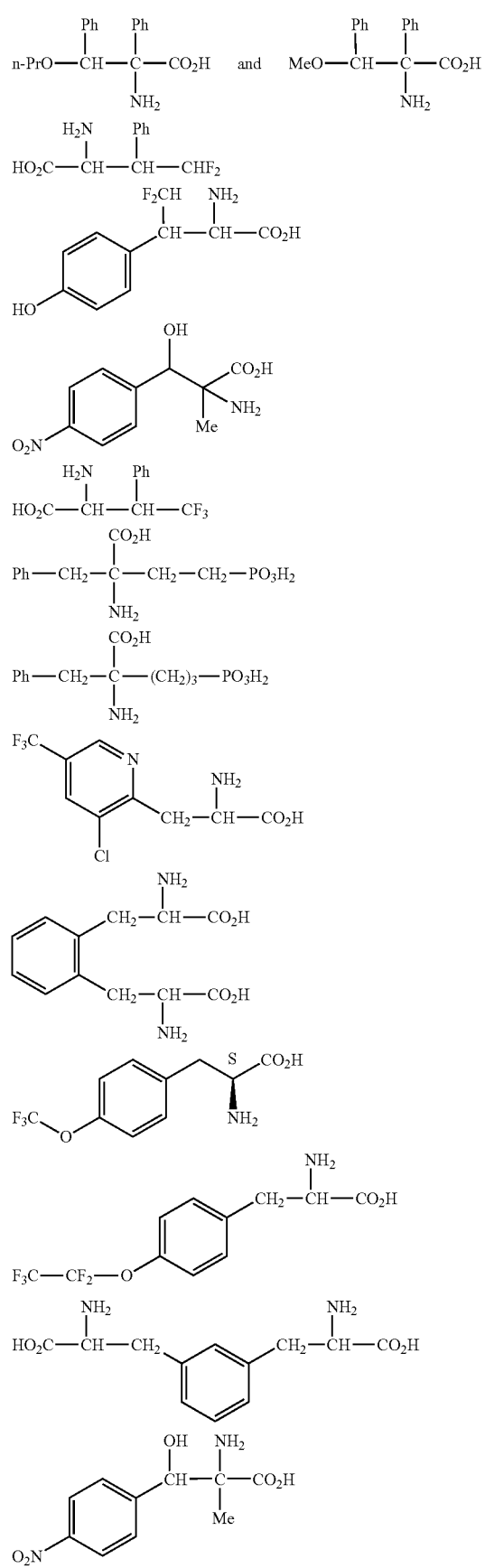
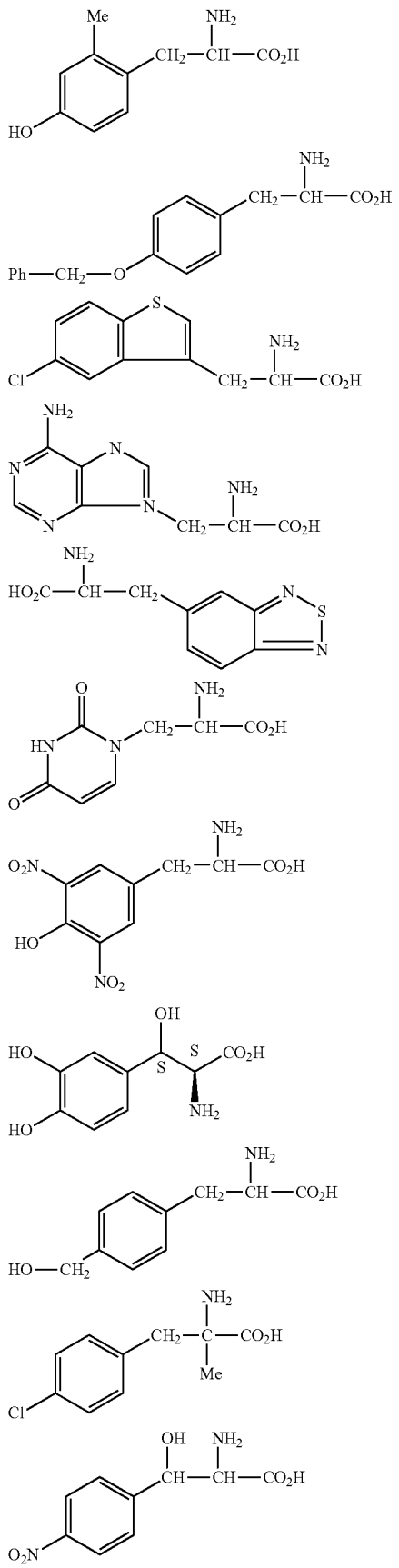

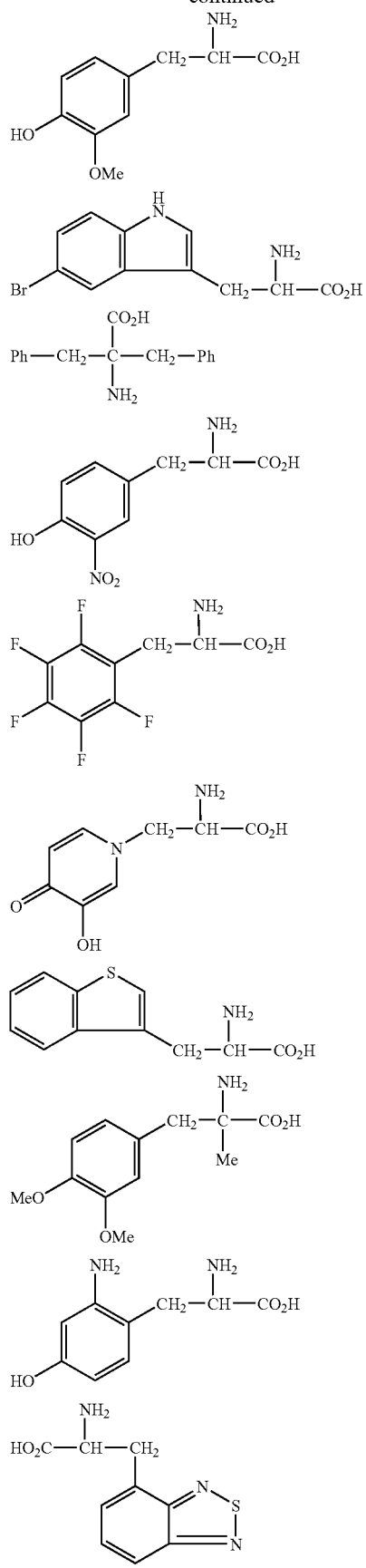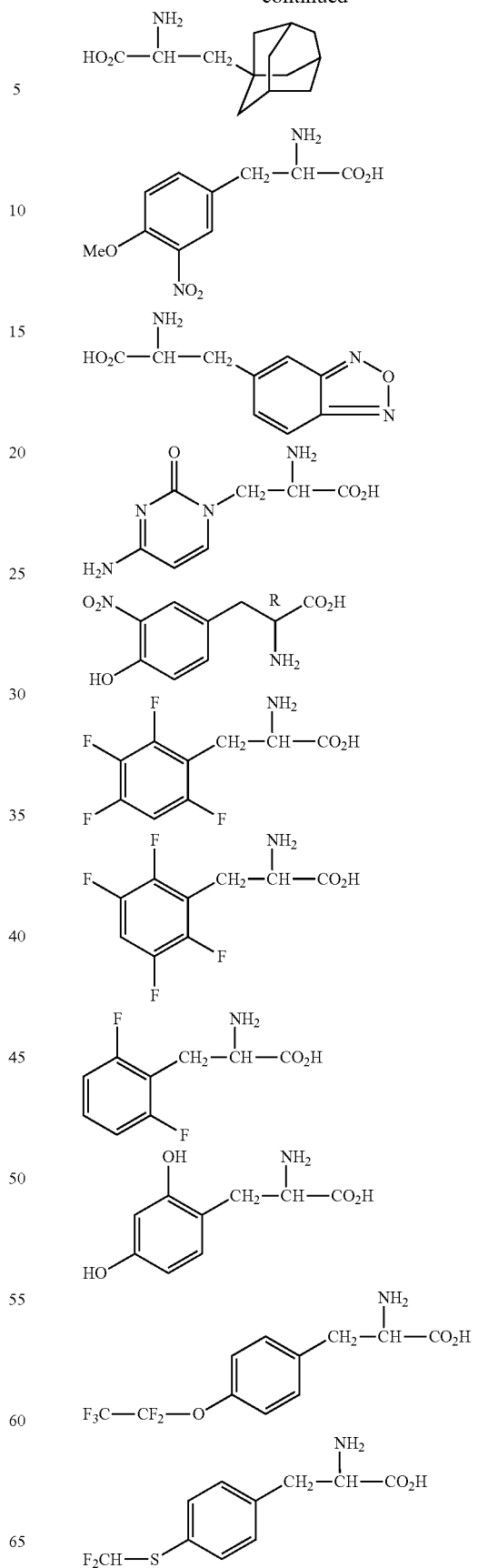

-continued
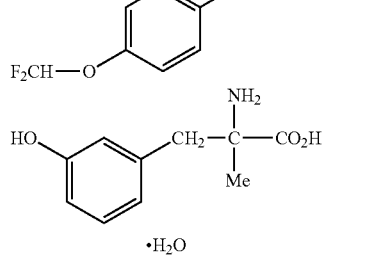
(commercially available from Biomol Research Labs);
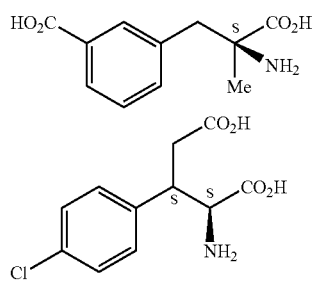
(commercially available from AstaTech);
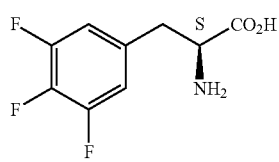
(commercially available from ChemBridge Screening Library);
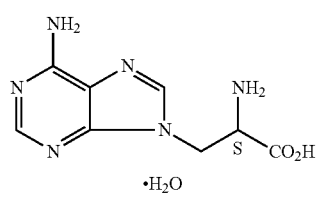
(commercially available from LaboTest);
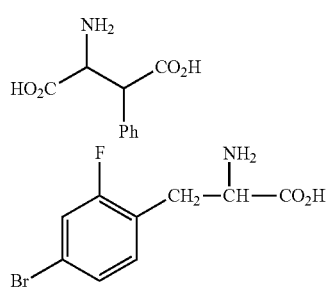
-continued
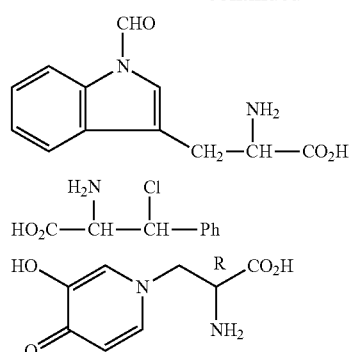
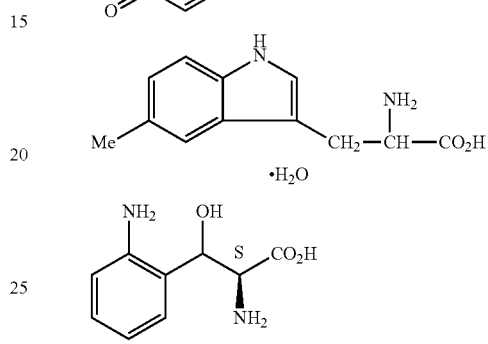
(commercially available from JRD Fluorochemicals);
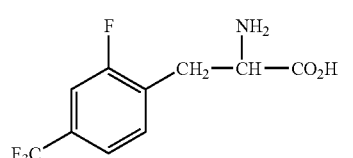
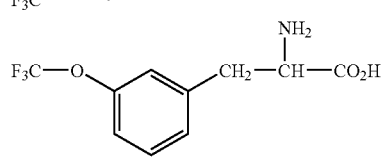
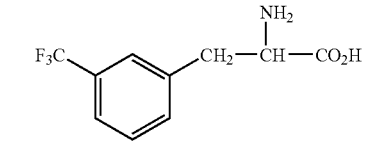
(commercially available from Fluka);
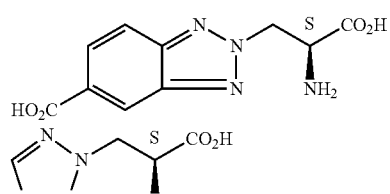
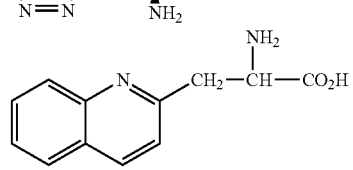

-continued
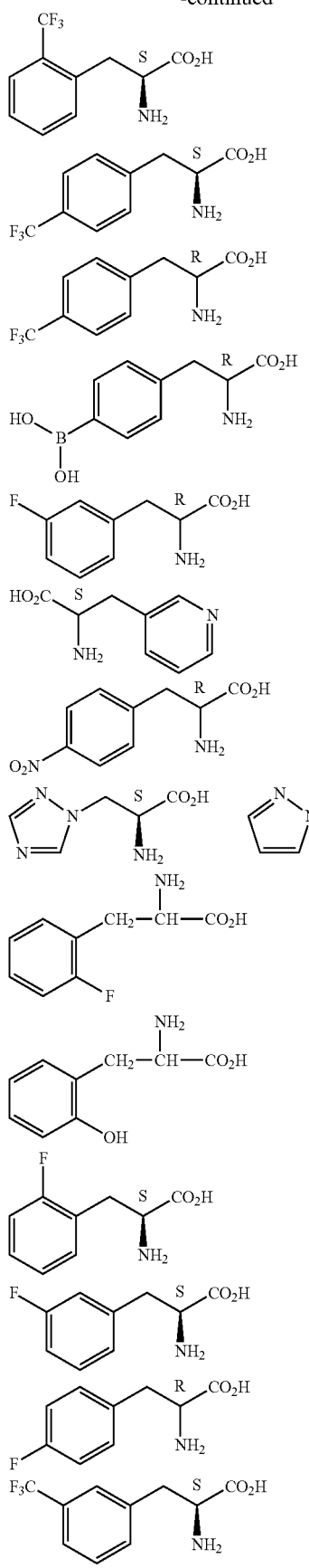
-continued
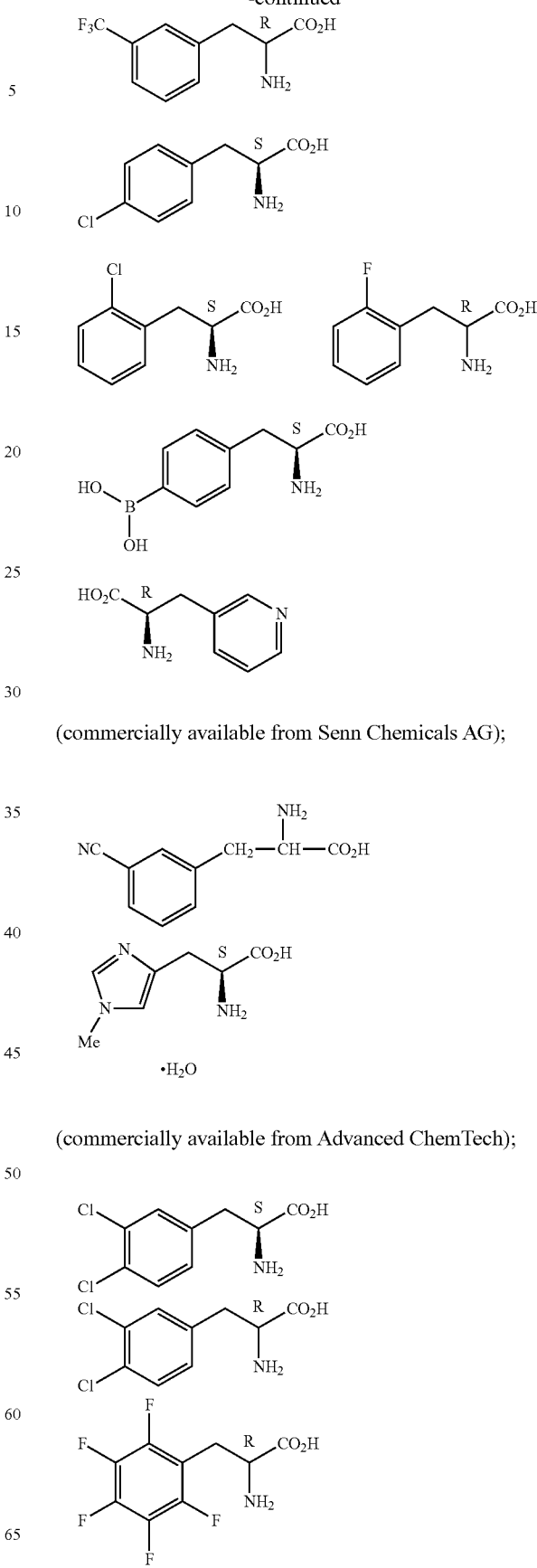
(commercially available from Senn Chemicals AG);
(commercially available from Advanced ChemTech);

-continued
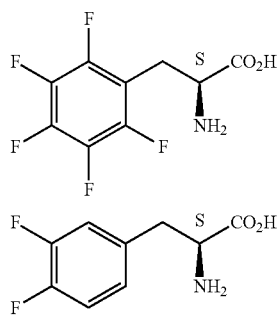
(commercially available from Tyger Scientific);
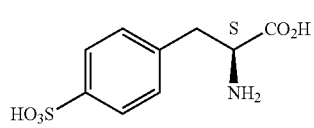
(commercially available from AMRI Fine Chemicals);
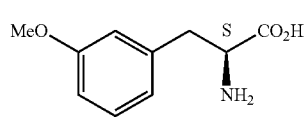
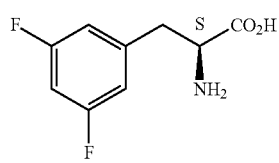
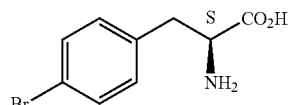
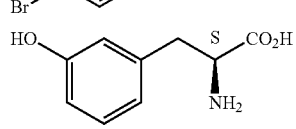
(commercially available from Synthetech);
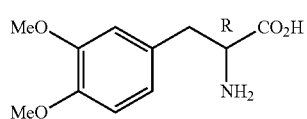
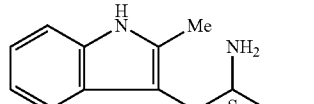
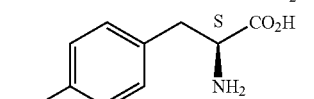
(commercially available from Apin Chemicals);
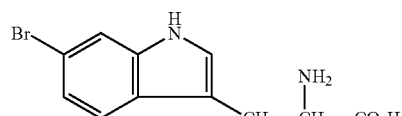
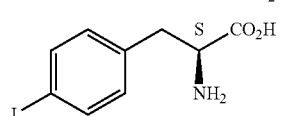
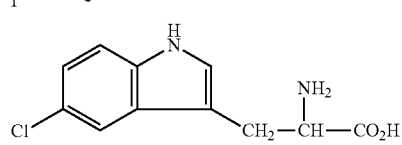
(commercially available from BioCatalytics, Inc.);
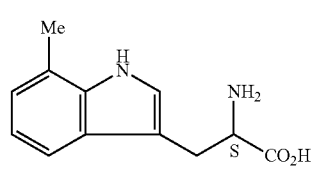
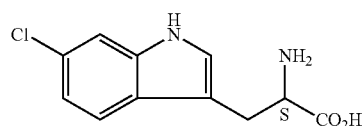
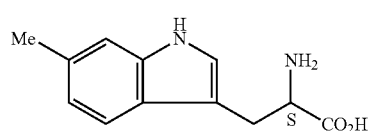
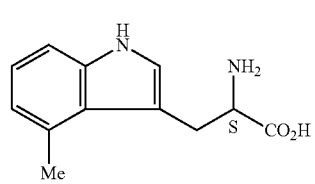
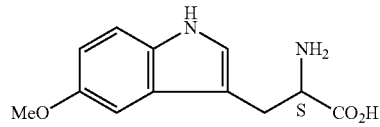
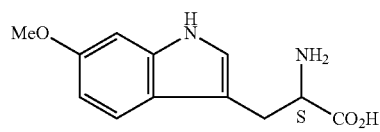
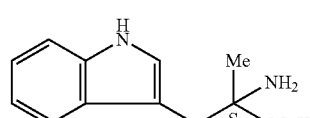
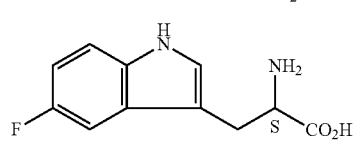
(commercially available from AG Scientific);

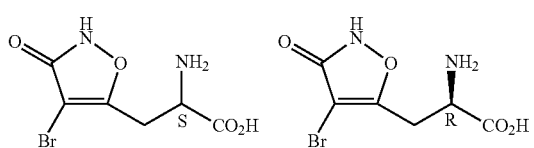
(commercially available from Synthelec);
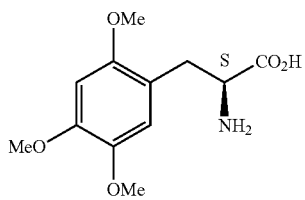
(commercially available from TimTec Stock Library);
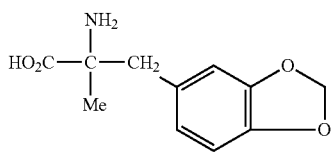
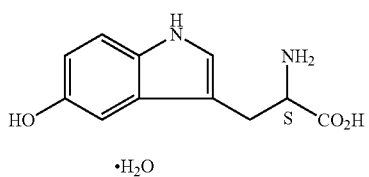
·H₂O
(commercially available from CSPS);
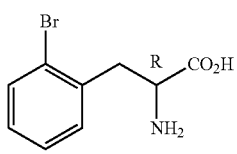 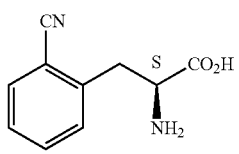
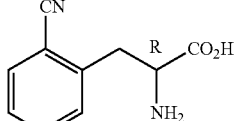
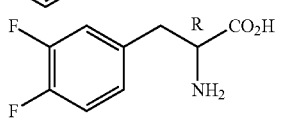
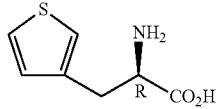
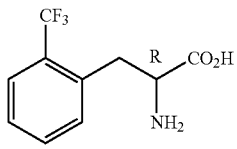 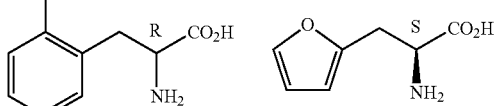
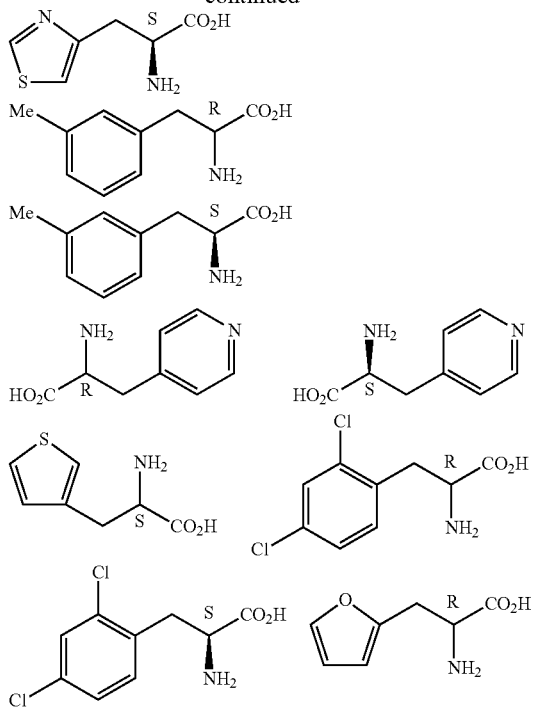
(commercially available from Qventas);
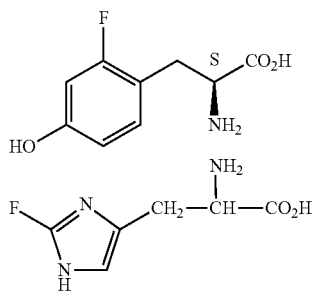

-continued
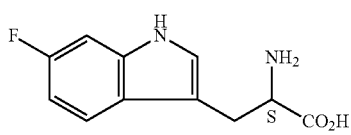
(commercially available from Encyclopedia of Amino Acid Analogs and Chiral Building Blocks);
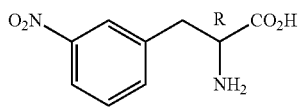
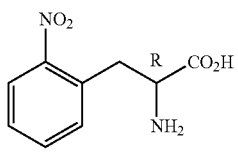
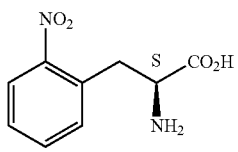
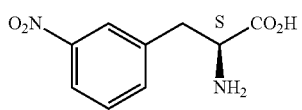
(commercially available from Bachem);
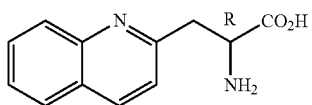
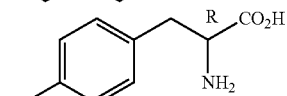
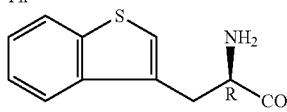
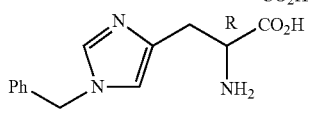
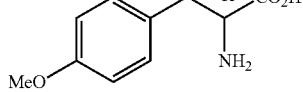
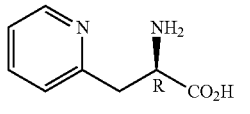
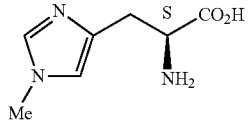
-continued
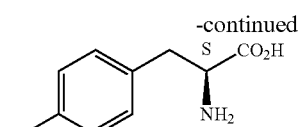
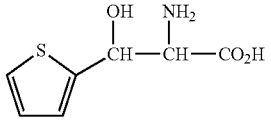
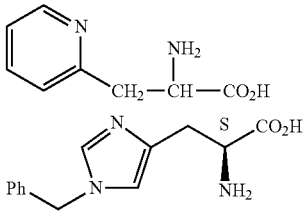
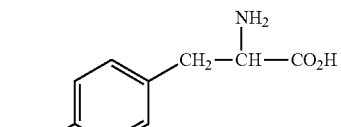
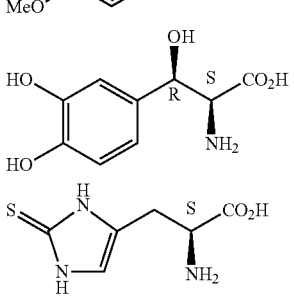
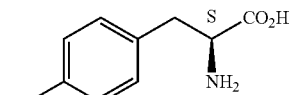
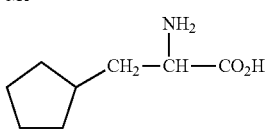
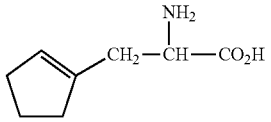
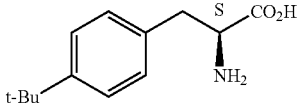
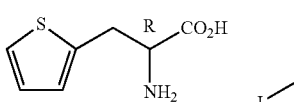
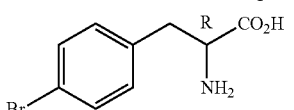
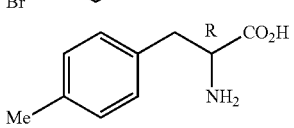

191
-continued
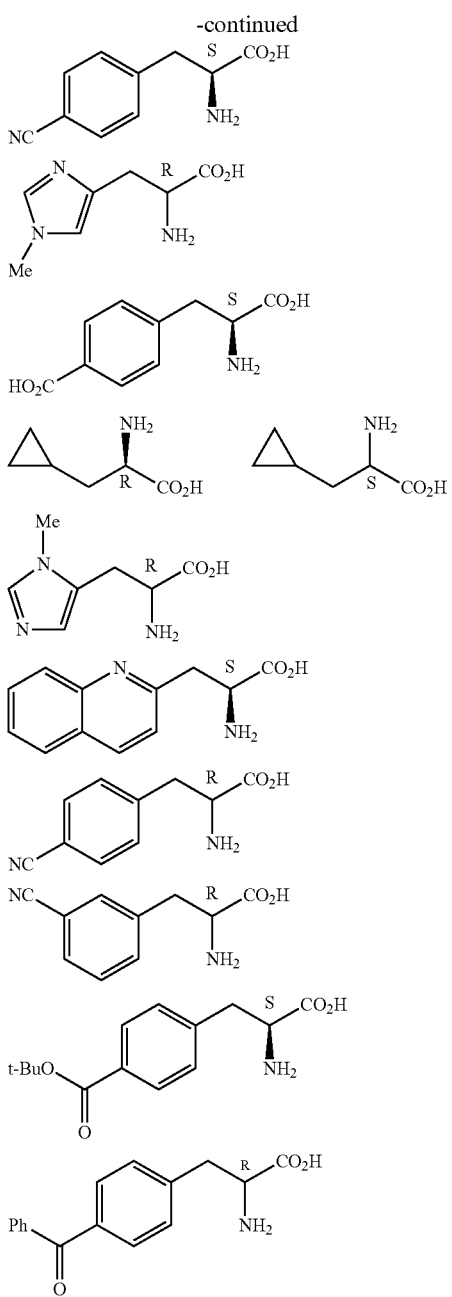
(commercially available from Matrix Scientific);
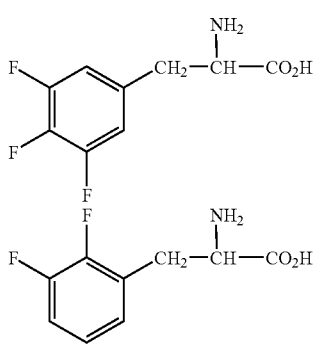
192
-continued
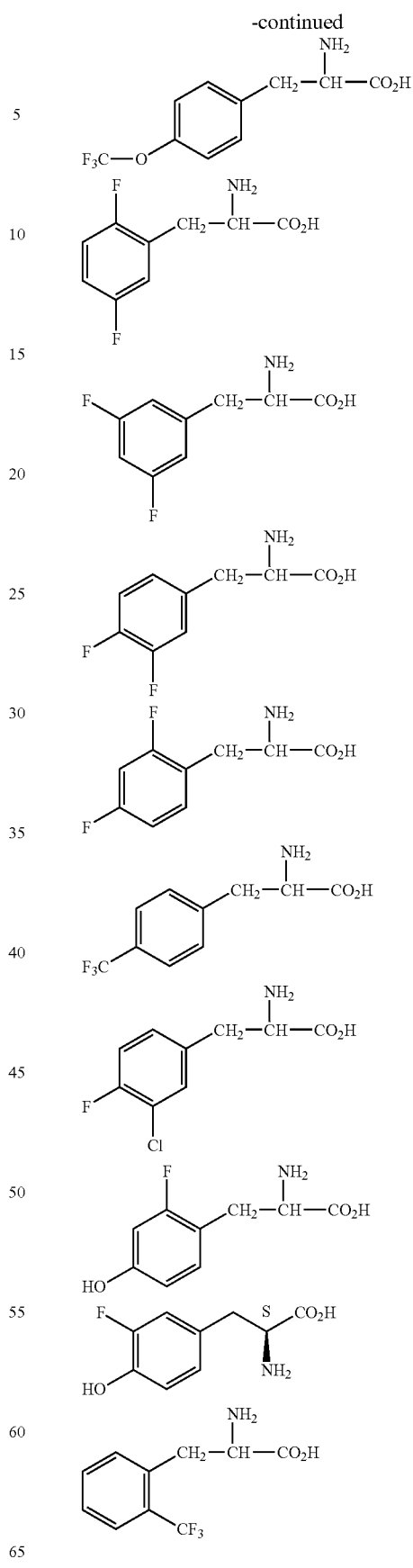
(commercially available from TCI America);

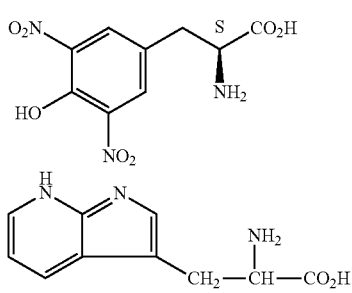

(commercially available from Acros);

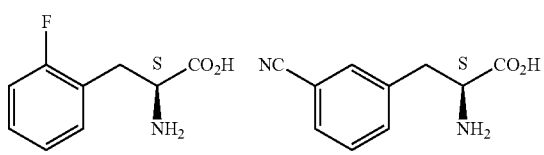

•1/2 H₂O (commercially available from Organics);

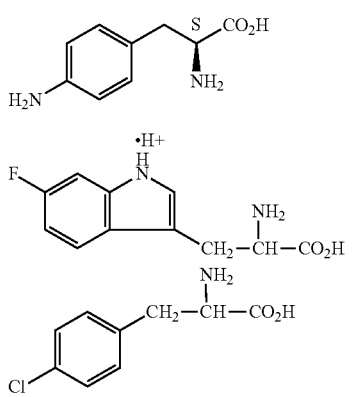

(commercially available from ChemPacific);

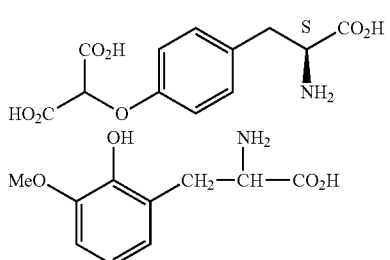

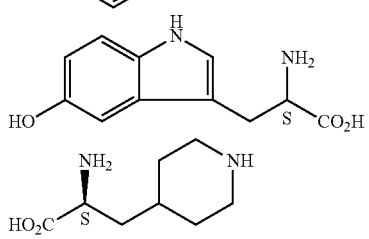

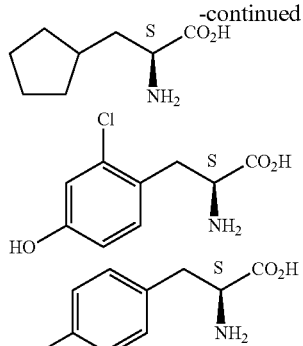

(commercially available from Rare Chemicals GmbH);

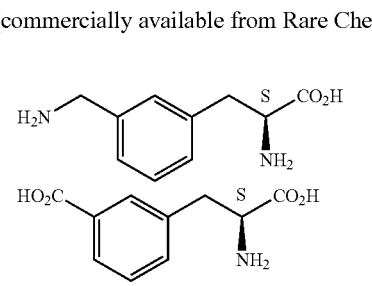

(commercially available from AstaTech);

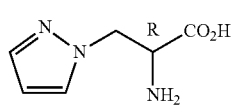

(commercially available from Austin);

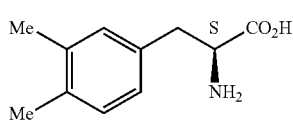

(commercially available from Advanced Asymmetrics, Inc.);

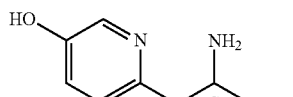

(commercially available from Tocris Cookson Inc.);

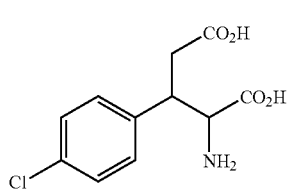 [SMILES: NC(C(=O)O)C(CC(=O)O)c1ccc(Cl)cc1]

(commercially available from Chem Service, Inc.); and

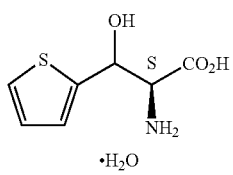

·H₂O (commercially available from Synchem OHG, Germany).

Example 24

Synthesis of MMAZ Compounds

MMAZ Compounds can also be prepared using the following commercially available phenylalanine analogs either as their protected or unprotected amino acids incorporated in solution or solid phase synthesis as described above: 4-chloro-phenylalanine, 4-fluoro-phenylalanine, 4-nitro-phenylalanine, N-α-methyl-phenylalanine, α-methyl-phenylalanine, glutamic acid, aspartic acid, tryptophane, isoleucine, leucine, methionine, tyrosine, glutamine, threonine, valine, asparagine, phenylglycine, O-benzyl-serine, O-t-butyl-serine, O-t-butyl-threonine, homophenylalanine, methionine-DL-sulfoxide, methionine-sulfone, α-aminobutyric acid, α-aminoisobutyric acid, 4-amino-1-piperidine-4-carboxylic acid, 4-amino-tetrahydropyran-4-carboxylic acid, aspartic acid, benzothiazol-2-yl-alanine, α-t-butyl-glycine, cyclohexylalanine, norleucine, norvaline, S-acetamidomethyl-penicillamine, β-3-piperidin-3-yl-alanine, piperidinyl-glycine, pyrrolidinyl-alanine, selenocysteine, tetrahydropyran-4-yl-glycine, O-benzyl-threonine, O-t-butyl-tyrosine, 3-(p-acetylphenyl)alanine, 3-phenylserine, and 1,2,3,4-tetrahydro-isoquinoline-3-carboxylic acid.

Example 25

Synthesis of MC-MMAZ

Maleimidocaproyl-MeVal-Val-Dil-Dap-Z can be prepared following General Procedure S.

Briefly, maleimidocaproic acid (30 mg, Molecular Biosciences) and anhydrous DMF (10 μl) in 10 mL glass flask under Ar (balloon) are cooled on dry ice for 5 min. To this mixture oxalyl chloride (1 mL) is added with a syringe. (A vigorous reaction and pressure increase occurred.) After 5 min, the mixture is allowed to warm up to room temperature and left for 30 min with occasional manual stirring. Volatiles are removed on Rotavap, residue is co-evaporated with anhydrous $CH_2Cl_2$ (1 mL) and dried at vacuum pump overnight. Product is initially generated as white solid, progressively turning into off-white to brownish solid. $^1$H-NMR in $CDCl_3$: 1.26-1.32 (2H, m), 1.51-1.59 (2H, m), 1.63-1.70 (2H, m), 2.82 (2H, t), 3.46 (2H, t), 6.70 (2H, s) ppm. Hydrolyzed material can be detected by triplet at 2.35 ppm. Product is used if the integral of the triplet at 2.42 ppm does not exceed 20% of the triplet at 3.46 ppm.

Maleimidocaproyl chloride can be prepared as described above and dissolved in anhydrous $CH_2Cl_2$ (3 mL).

MMAZ (1 eq.) and diisopropylethylamine (~4 eq.) are dissolved in anhydrous $CH_2Cl_2$ in a glass flask equipped with magnetic stir bar and rubber cap. The reaction mixture is cooled on the ice bath for 10 min and maleimidocaproyl chloride solution (~1.1 eq.) is added via syringe. After 15 min on ice, the reaction mixture is allowed to warm up to room temperature and stirring is continued for 2 more hours. Solvent is then removed in vacuo. The residue is suspended in DMSO (0.5 mL). Water (100 μl) is then added and after 0.5 h mixture is loaded on preparative HPLC column for separation: $C_{12}$ Phenomenex Synergi MAX-RP column, 4μ, 250×10 mm, 80 Å. Monitoring is performed at 215 nm. Product containing fractions are concentrated on Rotavap, co-evaporated with acetonitrile (2×5 mL), then with mixture of $CH_2Cl_2$ and hexane to provide final material.

Example 26

Synthesis of an Analog of MC-MMAZ

The synthesis of an analog of MC-MMAZ is shown below.

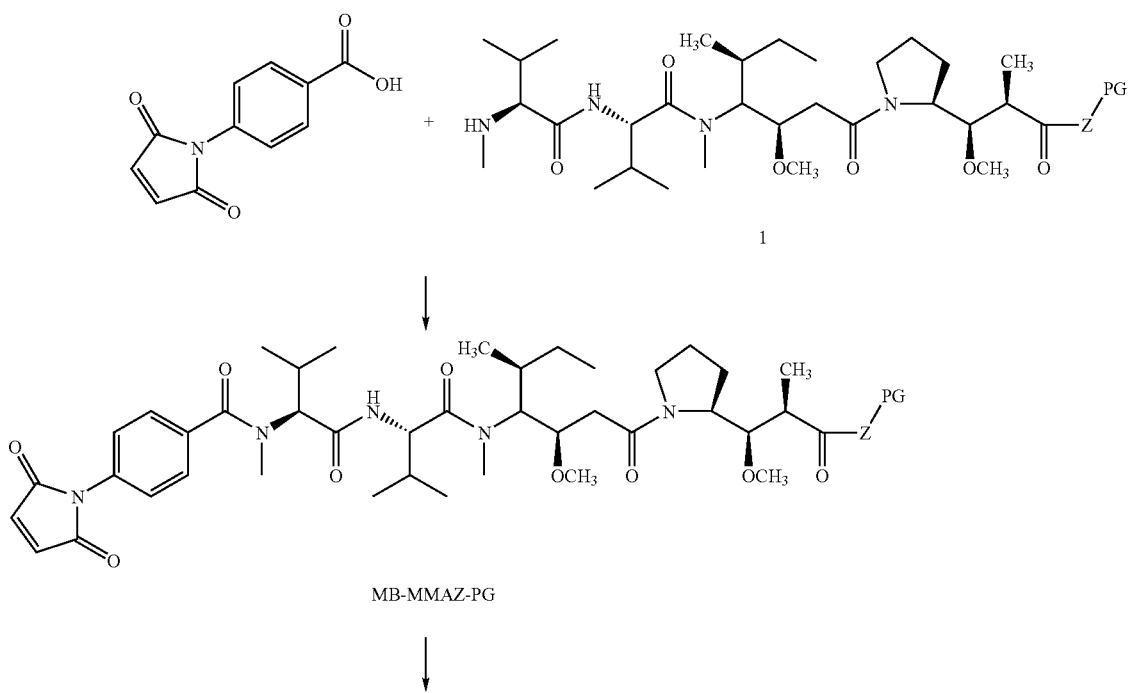

MB-MMAZ-PG

-continued

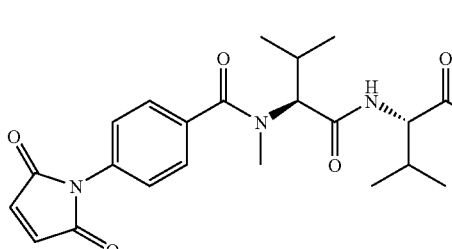

MB-MMAZ

MeVal-Val-Dil-Dap-Z-PG (compound 1, 0.044 mmol) is suspended in DMF (0.250 mL). 4-(2,5-Dioxo-2,5-dihydro-pyrrol-1-yl)-benzoic acid (11 mg, 0.049 mmol) and HATU (17 mg, 0.044 mmol) are added followed by DIEA (0.031 mL, 0.17 mmol). This reaction mixture is allowed to stir for 2.0 hr. HPLC analysis indicates complete consumption of starting compound 1. The product is isolated via preparatory RP-HPLC, using a Phenomenex $C_{12}$ Synergi Max-RP 80 Å Column (250×21.20 mm). The eluent is a linear gradient of 10% to 80% MeCN/0.05% TFA (aq) over 8 minutes, then isocratic 80% MeCN/0.05% TFA (aq) for an additional 12 minutes. MB-MeVal-Val-Dil-Dap-Z-PG (0.0385 mmol) is suspended in $CH_2Cl_2$ (1 mL) and TFA (1 mL). The mixture is stirred for 2 hr, and then volatile organics are evaporated under reduced pressure. Product (MB-MeVal-Val-Dil-Dap-Z) is purified by preparatory RP-HPLC, using a Phenomenex $C_{12}$ Synergi Max-RP 80 Å Column (250×21.20 mm). The eluent is a linear gradient of 10% to 80% MeCN/0.05% TFA (aq) over 8 minutes, then isocratic 80% MeCN/0.05% TFA (aq) for an additional 12 minutes.

Example 27

Preparation of MC-val-cit-PAB-MMAZ (9)

Compound 8 (32 µmol) is suspended in methylene chloride (6 mL) followed by the addition of TFA (3 mL). The resulting solution is allowed to stand for 2 hours. The reaction mixture is concentrated in vacuo and purified by prep-HPLC ($C_{12}$-RP column, 5µ, 100 Å, linear gradient of MeCN in water (containing 0.1% TFA) 10 to 100% in 40 min followed by 20 min at 100%, at a flow rate of 25 mL/min). The desired fractions are concentrated to provide maleimidocaproyl-valine-citrulline-p-hydroxymethylaminobenzene-MMAZ (MC-val-cit-PAB-MMAZ) 9.

Example 28

Preparation of AC10-MC-MMAZ by Conjugation of Antibody and MC-MMAZ

Antibody (e.g., AC10 or 1F6), dissolved in 500 mM sodium borate and 500 mM sodium chloride at pH 8.0, is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentra-

9

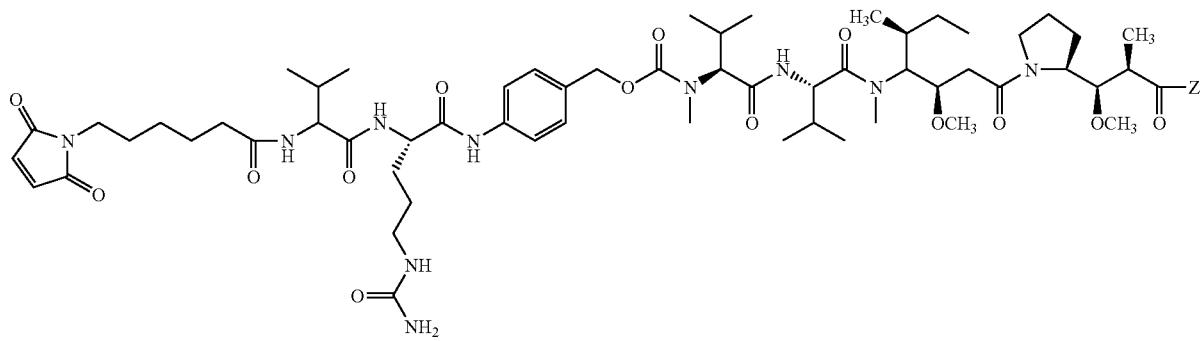

Compound 1 (0.11 mmol), Compound AB (85 mg, 0.12 mmol, 1.1 eq.), and HOBt (2.8 mg, 21 µmol, 0.2 eq.) are taken up in dry DMF (1.5 mL) and pyridine (0.3 mL) while under argon. After 30 h, the reaction is found to be essentially complete by HPLC. The mixture is evaporated, taken up in a minimal amount of DMSO and purified by prep-HPLC ($C_{12}$-RP column, 5µ, 100 Å, linear gradient of MeCN in water (containing 0.1% TFA) 10 to 100% in 40 min followed by 20 min at 100%, at a flow rate of 25 mL/min) to provide Compound 9.

tion by reaction with DTNB (Aldrich, Milwaukee, Wis.) and determination of the absorbance at 412 nm. The reduced antibody dissolved in PBS is chilled on ice.

The drug linker reagent, maleimidocaproyl-monomethyl auristatin Z, i.e. MC-MMAZ, dissolved in DMSO, is diluted in acetonitrile and water at known concentration, and added to the chilled reduced antibody in PBS. After about one hour, an excess of maleimide is added to quench the reaction and cap any unreacted antibody thiol groups. The reaction mixture is concentrated by centrifugal ultrafiltration and antibody-MC-

Example 29

Preparation of Antibody-MC-val-cit-PAB-MMAZ by Conjugation of Antibody and MC-val-cit-PAB-MMAZ (SP3, 9)

Antibody-MC-val-cit-PAB-MMAZ (e.g., AC10-MC-val-cit-PAB-MMAZ or 1F6-MC-val-cit-PAB-MMAZ) is prepared by conjugation of the antibody and MC-val-cit-PAB-MMAZ (9, SP3) following the procedure of Example 28.

Example 30

Preparation of MC-MeVal-Cit-PAB-MMAZ

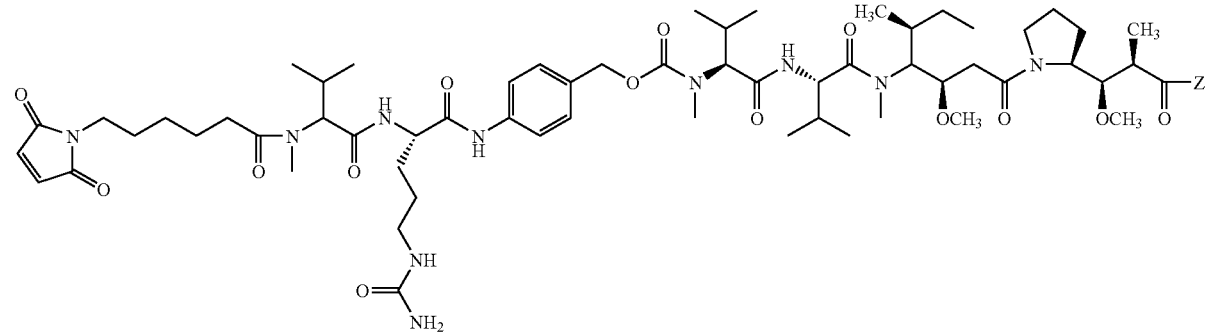

To a room temperature suspension of Fmoc-MeVal-OH (3.03 g, 8.57 mmol) and N,N'-disuccimidyl carbonate (3.29 g, 12.86 mmol) in $CH_2Cl_2$ (80 mL) is added DIEA (4.48 mL, 25.71 mmol). This reaction mixture is allowed to stir for 3 hr, and then poured into a separation funnel where the organic mixture is extracted with 0.1 M HCl (aq). The crude organic residue is concentrated under reduced pressure, and the product is isolated by flash column chromatography on silica gel using a 20-100% ethyl acetate/hexanes linear gradient (e.g., a total of 2.18 g of pure Fmoc-MeVal-OSu (4.80 mmoles, 56% yield) can be recovered).

To a room temperature suspension of Fmoc-MeVal-OSu (2.18 g, 4.84 mmol) in DME (13 mL) and THF (6.5 mL) is added a solution of L-citrulline (0.85 g, 4.84 mmol) and $NaHCO_3$ (0.41 g, 4.84 mmol) in $H_2O$ (13 mL). The suspension is allowed to stir at room temperature for 16 hr, then it is extracted into tert-BuOH/$CHCl_3$/$H_2O$ and acidified to pH=2-3 with 1 M HCl. The organic phase is separated, dried and concentrated under reduced pressure. The residue is triturated with diethyl ether resulting Fmoc-MeVal-Cit-COOH (e.g., 2.01 g) which is used without further purification.

The crude Fmoc-MeVal-Cit-COOH is suspended in 2:1 $CH_2Cl_2$/MeOH (100 mL), and to it is added p-aminobenzyl alcohol (0.97 g, 7.9 mmol) and EEDQ (1.95 g, 7.9 mmol). This suspension is allowed to stir for 125 hr, then the volatile organics are removed under reduced pressure, and the residue is purified by flash column chromatography on silica gel using a 10% MeOH/$CH_2Cl_2$. Pure Fmoc-MeVal-Cit-PAB-OH (e.g., 0.55 g, 0.896 mmol, 18.5% yield) is recovered.

To a suspension of Fmoc-MeVal-Cit-PAB-OH (0.55 g, 0.896 mmol) in $CH_2Cl_2$ (40 mL) is added STRATOSPHERES™ (piperizine-resin-bound) (>5 mmol/g, 150 mg). After being stirred at room temperature for 16 hr the mixture is filtered through celite (pre-washed with MeOH), and concentrated under reduced pressure. The residue is triturated with diethyl ether and hexanes. The resulting solid material, MeVal-Cit-PAB-OH, is suspended in $CH_2Cl_2$ (20 mL), and to it is added MC-OSu (0.28 g, 0.896 mmol), DIEA (0.17 mL, 0.99 mmol), and DMF (15 mL). This suspension is stirred for 16 hr. If HPLC analysis of the reaction mixture indicates an incomplete reaction, the suspension is concentrated under reduced pressure to a volume of 6 mL, then a 10% $NaHCO_3$ (aq) solution is added and the suspension stirred for an additional 16 hr. The solvent is removed under reduced pressure, and the residue is purified by flash column chromatography on silica gel using a 0-10% MeOH/$CH_2Cl_2$ gradient, resulting in MC-MeVal-Cit-PAB-OH (e.g., 42 mg (0.072 mmol, 8% yield)).

To a suspension of MC-MeVal-Cit-PAB-OH (2.37 g, 4.04 mmol) and bis(nitrophenyl)carbonate (2.59 g, 8.52 mmol) in $CH_2Cl_2$ (10 mL) is added DIEA (1.06 mL, 6.06 mmol). This suspension is stirred for 5.5 hr, concentrated under reduced pressure and purified by trituration with diethyl ether. MC-MeVal-Cit-PAB-OCO-pNP (147 mg, 0.196 mmol) is suspended in a 1:5 pyridine/DMF solution (3 mL), and to it is added HOBt (5 mg, 0.039 mmol), DIEA (0.17 mL, 0.978 mmol) and MMAZ (0.205 mmol). This reaction mixture is stirred for 16 hr at room temperature, and then purified by preparatory RP-HPLC (x3), using a Phenomenex $C_{12}$ Synergi Max-RP 80 Å Column (250×21.20 mm). The eluent is a linear gradient of 10% to 90% MeCN/0.05% TFA (aq) over 30 minutes, then isocratic 90% MeCN/0.05% TFA (aq) for an additional 20 minutes. MC-MeVal-Cit-PAB-MMAZ is obtained.

Example 31

Preparation of Succinimide Ester of suberyl-Val-Cit-PAB-MMAZ

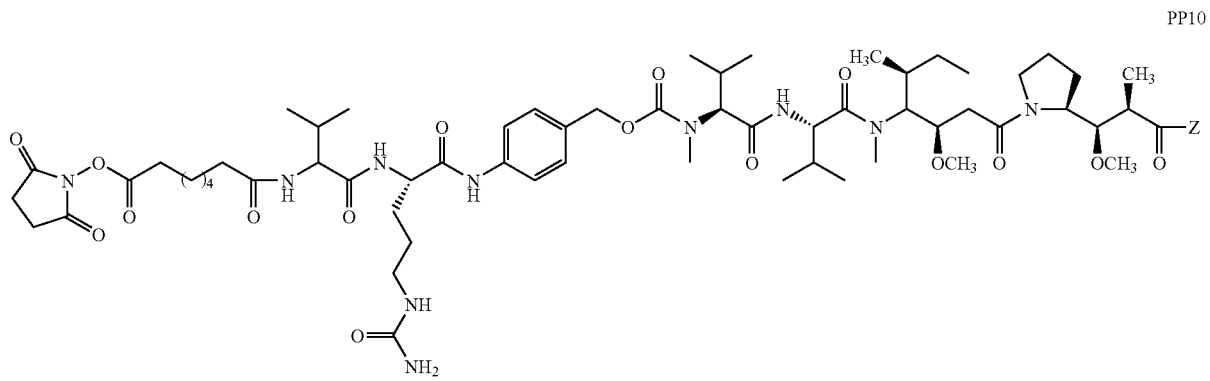

PP10

Compound 1 (0.38 mmol), Fmoc-Val-Cit-PAB-pNP (436 mg, 0.57 mmol, 1.5 eq.) were suspended in anhydrous pyridine, 5 mL. HOBt (10 mg, 0.076 mmol, 0.2 eq.) is added followed by DIEA (199 µl, 1.14 mmol, 3 eq.). The reaction mixture is sonicated for 10 min, and then stirred overnight at room temperature. Pyridine is removed under reduced pressure, and the residue is re-suspended in $CH_2Cl_2$. The mixture is separated by silica gel flash chromatography in a step gradient of MeOH, from 0 to 10%, in $CH_2Cl_2$. The product containing fractions are collected, concentrated and dried in vacuum overnight to give Fmoc-Val-Cit-PAB-MMAZ.

Fmoc-Val-Cit-PAB-MMAZ is suspended in $CH_2Cl_2$ (2 mL) diethylamine (2 mL) and DMF (2 mL). The mixture is stirred for 2 hrs at room temperature. The solvent is removed under reduced pressure. The residue is co-evaporated with pyridine (2 mL), then with toluene (2×5 mL), and dried in vacuum. Val-Cit-PAB-MMAZ is obtained.

All Val-Cit-PAB-MMAZ prepared from Fmoc-Val-Cit-PAB-MMAZ is suspended in pyridine (2 mL), and added to a solution of disuccinimidyl suberate (74 mg, 0.2 mmol, 4 eq.), in pyridine (1 mL). The reaction mixture is stirred at room temperature. After 3 hrs ether (20 mL) is added. The precipitate is collected and washed with additional amount of ether. The reddish solid is suspended in 30% MeOH/$CH_2Cl_2$ and filtered through a pad of silica gel with 30% MeOH/$CH_2Cl_2$ as an eluent.

Example 32

Determination of Cytotoxicity of Selected Compounds

The cytotoxic activity of MMAZ and antibody-drug conjugates is evaluated on the CD70+ positive cell lines, for example, Caki-1, renal cell carcinoma; L428, Hodgkin's disease; U251, glioblastoma. To evaluate the cytotoxicity of compounds, cells can be seeded at approximately 5-10,000 per well in 150 µl of culture medium, then treated with graded doses of compounds in quadruplicates at the initiation of assay. Cytotoxicity assays are usually carried out for 96 hours after addition of test compounds. Fifty µl of resazurin dye may be added to each well during the last 4 to 6 hours of the incubation to assess viable cells at the end of culture. Dye reduction can be determined by fluorescence spectrometry using the excitation and emission wavelengths of 535 nm and 590 nm, respectively. For analysis, the extent of resazurin reduction by the treated cells can be compared to that of the untreated control cells.

Example 33

General In Vitro Cytotoxicity Determination

To evaluate the cytotoxicity of conjugates, cells are seeded at approximately 5-10,000 per well in 150 µl of culture medium and then treated with graded doses of conjugates in quadruplicates at the initiation of assay. Cytotoxicity assays are carried out for 96 hours after addition of test compounds. Fifty µl of the resazurin dye is added to each well during the last 4 to 6 hours of the incubation to assess viable cells at the end of culture. Dye reduction is determined by fluorescence spectrometry using the excitation and emission wavelengths of 535 nm and 590 nm, respectively. For analysis, the extent of resazurin reduction by the treated cells is compared to that of the untreated control cells.

Example 34

In Vitro Cell Proliferation Assay

Efficacy of ADC can be measured by a cell proliferation assay employing the following protocol (Promega Corp. Technical Bulletin TB288; Mendoza et al., 2002, *Cancer Res.* 62:5485-5488):

1. An aliquot of 100 µl of cell culture containing about $10^4$ cells (e.g., SKBR-3, BT474, MCF7 or MDA-MB-468) in medium is deposited in each well of a 96-well, opaque-walled plate.
2. Control wells are prepared containing medium and without cells.
3. ADC is added to the experimental wells and incubated for 3-5 days.
4. The plates are equilibrated to room temperature for approximately 30 minutes.
5. A volume of CellTiter-Glo Reagent equal to the volume of cell culture medium present in each well is added.
6. The contents are mixed for 2 minutes on an orbital shaker to induce cell lysis.

7. The plate is incubated at room temperature for 10 minutes to stabilize the luminescence signal.
8. Luminescence is recorded and reported in graphs as RLU=relative luminescence units.

Table 7 shows in vitro activity of h1F6-antibody-MMAZ (h1F6-mc-vc-PAB-MMAZ) conjugates against CD70+ (U251, L428 and Caki-1) cell lines. Conjugates contain approximately 4 drugs per antibody.

TABLE 7

| IC$_{50}$ (ng/mL) of h1F6-MC-val-cit-PAB-MMAZ conjugates on CD70+ cell lines | | | |
|---|---|---|---|
| Z | U251 | Caki-1 | L428 |
| (L-2-Chlorophenylalanine) SP3-a | 8 | 4.4 | 8 |
| (L-Me-Phenylalanine) SP3-b | 8 | 6 | 6 |
| (L-Tic) SP3-c | 20 | 28 | Maximum inhibition = 12% @ 1000 ng/ml |
| (L-beta-homophenylalanine) SP3-d | 11 | 9 | 33 |
| (L-Met) SP3-j | 23 | 18 | 43 |
| (L-Leu) SP3-i | 14 | 16 | 105 |
| (3-Pyridyl-L-alanine) SP3-h | 16 | 16 | 12 |
| (L-4-thiazolylalanine) SP3-g | 6 | 7 | 4 |
| (L-Trp) SP3-k | 7.5 | 6 | 11 |

TABLE 7-continued

IC$_{50}$ (ng/mL) of h1F6-MC-val-cit-PAB-MMAZ conjugates on CD70+ cell lines

| Z | U251 | Caki-1 | L428 |
|---|---|---|---|
| (3-Cyclohexyl-L-alanine) 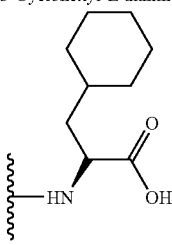 SP3-f | 8 | 10 | 105 |
| (Glu(OtBu) 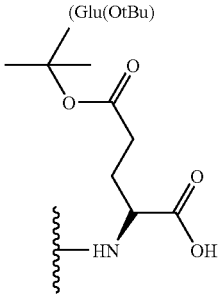 SP3-1 | 43 | 51 | Maximum inhibition = 12% @ 141 ng/ml |
| (p-aminophenylalanine) 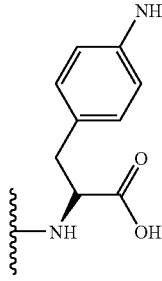 SP3-e | No effect | No effect | Maximum inhibition = 10% @ 100 ng/ml |
| Phenylalanine (MMAF) | 10 | 7 | 8 |

Example 35

Plasma Clearance in Rat

Plasma clearance pharmacokinetics of antibody drug conjugates and total antibody is studied in Sprague-Dawley rats (Charles River Laboratories, 250-275 grams each). Animals are dosed by bolus tail vein injection (IV Push). Approximately 300 µl whole blood is collected through jugular cannula, or by tail stick, into lithium/heparin anticoagulant vessels at each timepoint: 0 (predose), 10, and 30 minutes; 1, 2, 4, 8, 24 and 36 hours; and 2, 3, 4, 7, 14, 21, and 28 days post dose. Total antibody is measured by ELISA-ECD/GxhuFc-HRP. Antibody drug conjugate is measured by ELISA-MMAZ/ECD-Bio/SA-HRP.

Example 36

Plasma Clearance in Monkey

Plasma clearance pharmacokinetics of antibody drug conjugates and total antibody can be studied in cynomolgus monkeys, using a similar procedure to that described above.

Example 37

Tumor Volume In Vivo Efficacy in Transgenic Explant Mice

Animals suitable for transgenic experiments can be obtained from standard commercial sources such as Taconic (Germantown, N.Y.). Many strains are suitable, but FVB female mice are preferred because of their higher susceptibility to tumor formation. FVB males can be used for mating and vasectomized CD.1 studs can be used to stimulate pseudopregnancy. Vasectomized mice can be obtained from any commercial supplier. Founders can be bred with either FVB mice or with 129/BL6×FVB p53 heterozygous mice. The mice with heterozygosity at p53 allele can be used to potentially increase tumor formation. Some F1 tumors are of mixed strain. Founder tumors can be FVB only.

Animals having tumors (allograft propagated from Fo5 mmtv transgenic mice) can be treated with a single or multiple dose by IV injection of ADC. Tumor volume can be assessed at various time points after injection.

Example 38

In Vivo Efficacy of mcMMAZ Antibody-Drug Conjugates

The efficacy of cAC10-mcMMAZ can be evaluated in Karpas-299 ALCL xenografts. Chimeric AC10-mcMMAZ with an average of 4 drug moieties per antibody (cAC10-mcF4) is used. Karpas-299 human ALCL cells are implanted subcutaneously into immunodeficient C.B-17 SCID mice (5×10$^6$ cells per mouse). Tumor volumes are calculated using the formula (0.5×L×W$^2$) where L and W are the longer and shorter of two bi-directional measurements.

Efficacy of cBR96-mcMMAZ in L2987 NSCLC Xenografts:

cBR96 is a chimeric antibody that recognizes the Le$^Y$ antigen. To evaluate the in vivo efficacy of cBR96-mcMMAZ with 4 drugs per antibody (cBR96-mcF4) L2987 non-small cell lung cancer (NSCLC) tumor fragments are implanted into athymic nude mice. When the tumors average approximately 100 mm$^3$ the mice are divided into 3 groups: untreated and 2 therapy groups. The efficacy of the antibody drug conjugates is evaluated as described above.

ATCC Deposits

An ATCC deposit of monoclonal antibody S2C6 was made on May 25, 1999 pursuant to the terms of the Budapest Treaty on the international recognition of the deposit of microorganisms for purposes of patent procedure. This ATCC deposit was given an accession number of PTA-110.

An ATCC deposit of murine monoclonal antibody AC10 was made on Apr. 26, 2005 pursuant to the terms of the Budapest Treaty on the international recognition of the deposit of microorganisms for purposes of patent procedure. This ATCC deposit was given an accession number of PTA-6679.

An ATCC deposit of monoclonal antibody humanized AC10 was made on Aug. 23, 2005 pursuant to the terms of the Budapest Treaty on the international recognition of the deposit of microorganisms for purposes of patent procedure. This ATCC deposit was given an accession number of PTA-6951.

The ATCC is located at 10801 University Boulevard, Manassas, Va. 20110-2209, USA. Any deposit is provided as a convenience to those of skill in the art and is not an admission that a deposit is required under 35 U.S.C. Section 112. That described herein is not to be limited in scope by the antibody deposited, since the deposited embodiment is intended as a single illustration of certain aspects of the invention and any antibody that is functionally equivalent is within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety and for all purposes to the same extent as if each individual publication or patent or patent application was specifically and individually indicated to be incorporated by reference in its entirety for all purposes.

What is claimed is:

1. A compound having the formula:

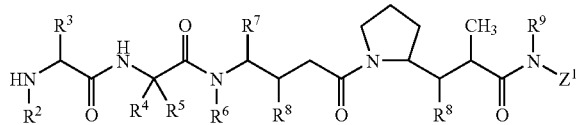

or a pharmaceutically acceptable salt thereof, wherein:

$R^2$ is $C_1$-$C_8$ alkyl;

$R^3$ is $C_1$-$C_8$ alkyl;

$R^4$ is $C_1$-$C_8$ alkyl;

$R^5$ is selected from the group consisting of H and methyl;

$R^6$ is $C_1$-$C_8$ alkyl;

$R^7$ is $C_1$-$C_8$ alkyl;

each $R^8$ is independently selected from O—($C_1$-$C_8$ alkyl); and the moiety —$NR^9Z^1$ is a phenylalanine bioisostere moiety selected from the group consisting of,

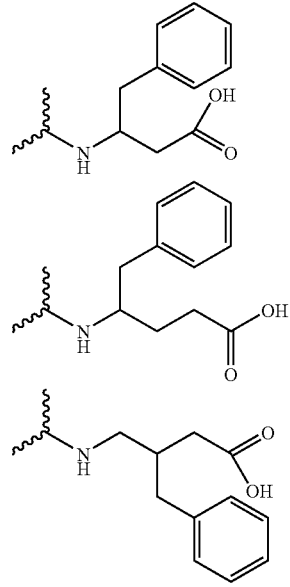

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: synthetic Amino Acid unit (W)

<400> SEQUENCE: 1

Gly Ser Val Glu
 1

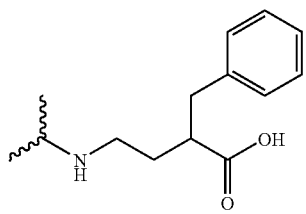

and

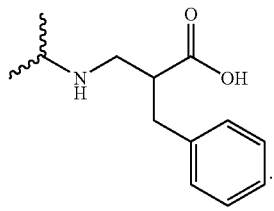

2. The compound of claim 1 or a pharmaceutically acceptable salt thereof, wherein $R^2$ is methyl.

3. The compound of claim 1 or a pharmaceutically acceptable salt thereof, wherein $R^3$ is isopropyl.

4. The compound of claim 1 or a pharmaceutically acceptable salt thereof, wherein $R^4$ is isopropyl.

5. The compound of claim 1, wherein the phenylalanine bioisostere moiety is

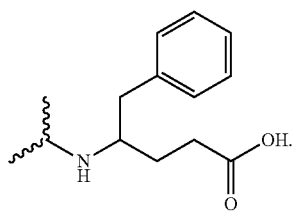 [SMILES: *NC(CCC(=O)O)Cc1ccccc1]

6. A compound having the formula:

L-((LU)-(D)$_{1-4}$)$_p$ or a pharmaceutically acceptable salt thereof
wherein,
L- is a Ligand Unit selected from the group consisting of a protein, polypeptide and peptide;
LU is a Linker Unit;
p is an integer of from 1 to about 20; and
D is a drug moiety having Formula D:

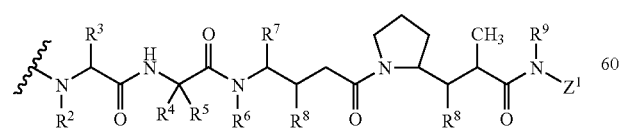

D wherein,
$R^2$ is $C_1$-$C_8$ alkyl;
$R^3$ is $C_1$-$C_8$ alkyl;

$R^4$ is $C_1$-$C_8$ alkyl;
$R^5$ is selected from the group consisting of H and methyl;
$R^6$ is $C_1$-$C_8$ alkyl;
$R^7$ is $C_1$-$C_8$ alkyl;
each $R^8$ is independently selected from O—($C_1$-$C_8$ alkyl); and
the moiety —NR$^9$Z$^1$ is a phenylalanine bioisostere moiety selected from the group consisting of

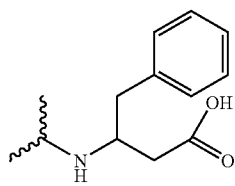

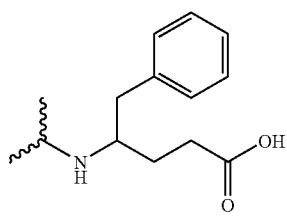

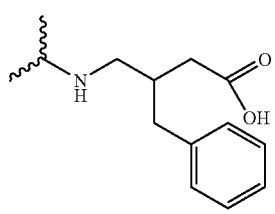

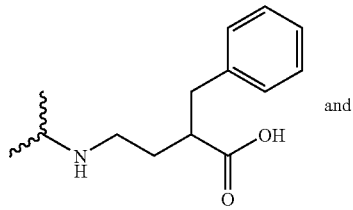

and

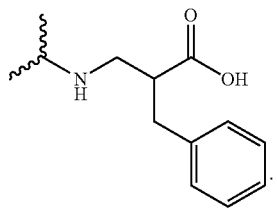

7. A compound of claim 6, having the formula:

L-[LU-D]$_p$ or a pharmaceutically acceptable salt thereof.

8. The compound according to claim 6, or a pharmaceutically acceptable salt thereof, wherein:
L is an antibody (Ab),
LU is a Linker Unit having the formula -$A_a$-$W_w$—$Y_y$—, wherein
A is a Stretcher unit,
a is 0 or 1,
each W is independently an Amino Acid unit,
w is an integer ranging from 0 to 12,
Y is a Spacer unit, and
y is 0, 1 or 2.

9. The compound of claim 8 or a pharmaceutically acceptable salt thereof having the formula:

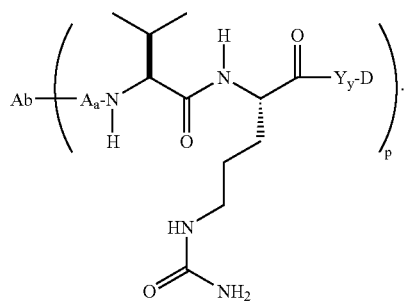

10. The compound of claim 8 having the formula:

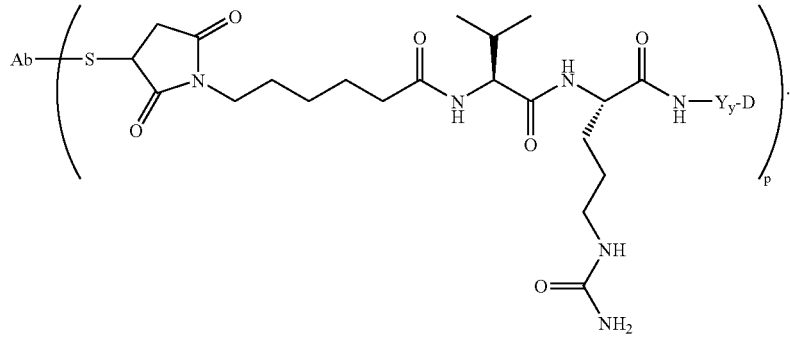

11. The compound of claim 8 having the formula:

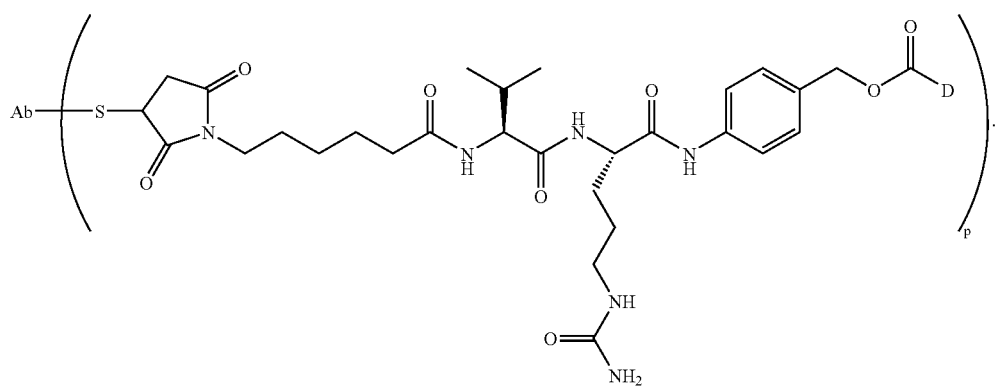

12. The compound of claim 8 or a pharmaceutically acceptable salt thereof wherein w is an integer ranging from 2 to 12.

13. The compound of claim 8 or a pharmaceutically acceptable salt thereof wherein w is 2.

14. The compound of claim 13 or a pharmaceutically acceptable salt thereof, wherein $W_w$ is -valine-citrulline-.

15. The compound of claim 8 wherein $W_w$ is selected from the group consisting of 5-aminovaleric acid, homophenylalanine-lysine, tetraisoquinolinecarboxylate-lysine, cyclohexylalanine-lysine, isonepecotic acid-lysine, beta-alanine-lysine, glycine-serine-valine-glutamine (SEQ ID NO:1) and isonepecotic acid.

16. The compound of claim 8 or a pharmaceutically acceptable salt thereof, wherein the antibody is a monoclonal antibody.

17. The compound of claim 8, wherein the antibody is an antibody fragment.

18. The compound of claim 8 having the formulae:
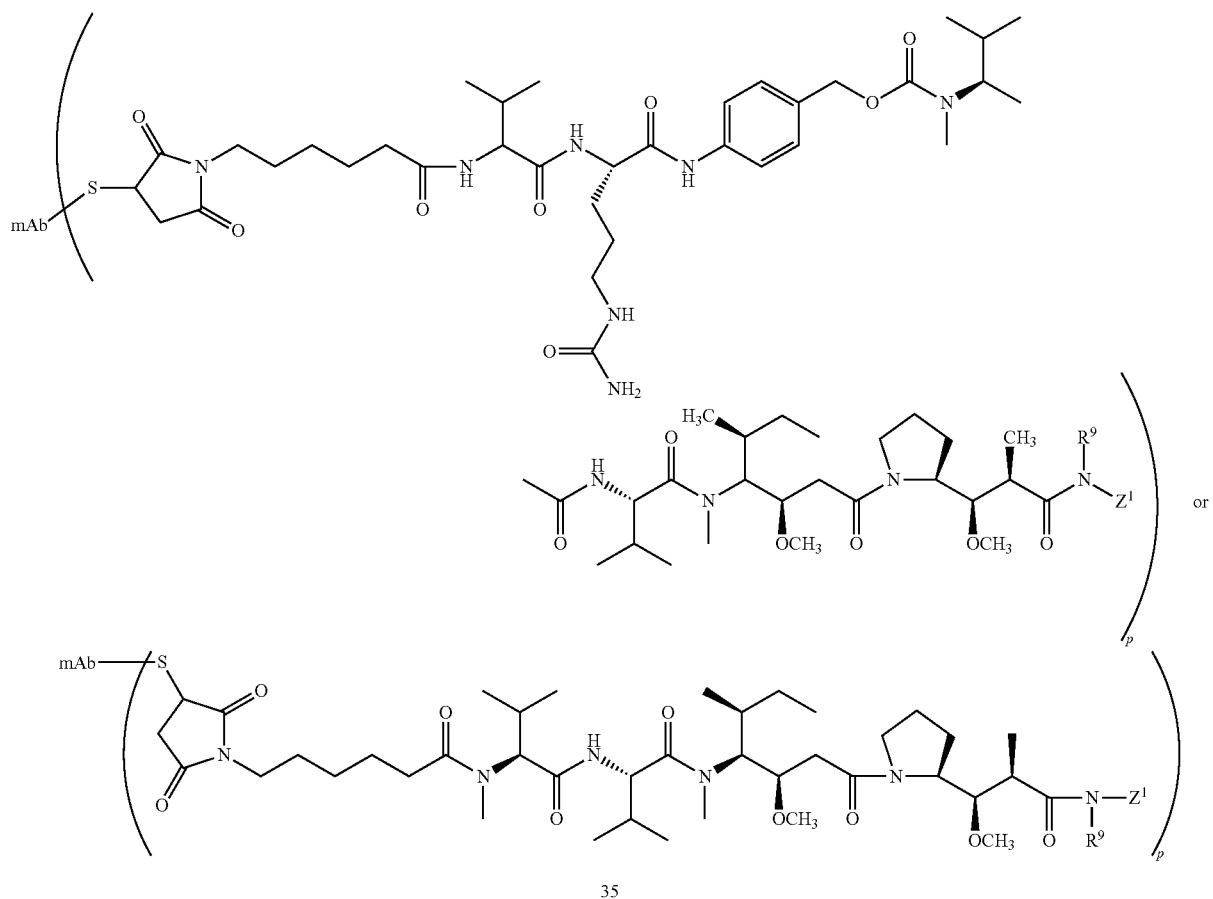
or a pharmaceutically acceptable salt thereof
wherein mAb is a monoclonal antibody and
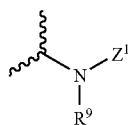
is a phenylalanine bioisostere moiety selected from the group consisting of
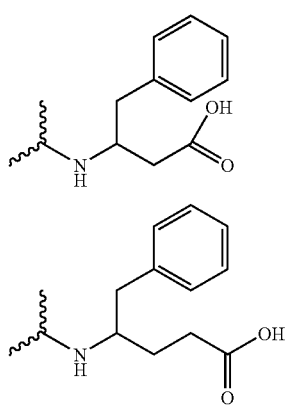
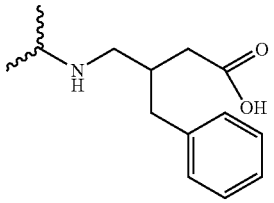
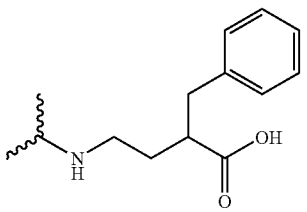 and
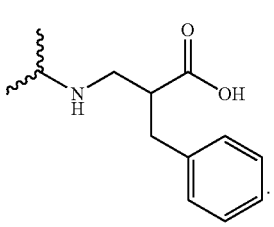
19. The compound of claim 8 or a pharmaceutically acceptable salt thereof, wherein the antibody specifically binds to CD20, CD30, CD33, CD40, CD70, or Lewis Y antigen.

20. A pharmaceutical composition comprising an effective amount of the compound of claim 6, or a pharmaceutically acceptable salt thereof, and a pharmaceutically acceptable diluent, carrier or excipient.

21. The compound of claim 12 or a pharmaceutically acceptable salt thereof wherein y is 1 or 2.

22. The compound of claim 6, wherein the phenylalanine bioisostere moiety is

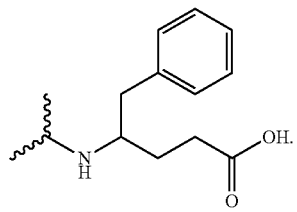 [SMILES: *NC(CCC(=O)O)Cc1ccccc1]

23. The compound of claim 8, wherein the phenylalanine bioisostere moiety is

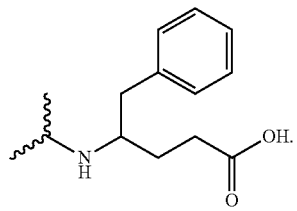 [SMILES: *NC(CCC(=O)O)Cc1ccccc1]

24. The compound of claim 18, wherein the phenylalanine bioisostere moiety is

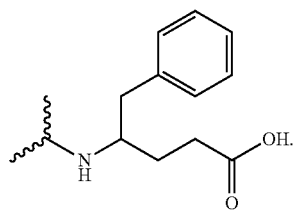 [SMILES: *NC(CCC(=O)O)Cc1ccccc1]

25. A compound having the formula:
LU-(D)$_{1-4}$
or a pharmaceutically acceptable salt thereof
wherein,
LU- is a Linker Unit; and
D is a drug moiety having the Formula D:

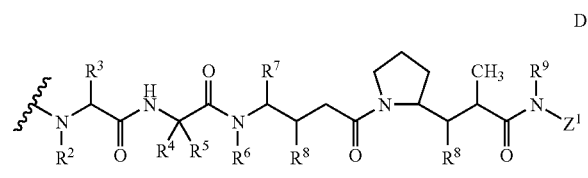

wherein
$R^2$ is $C_1$-$C_8$ alkyl;
$R^3$ is $C_1$-$C_8$ alkyl;
$R^4$ is $C_1$-$C_8$ alkyl;
$R^5$ is selected from the group consisting of H and methyl;
$R^6$ is $C_1$-$C_8$ alkyl;
$R^7$ is $C_1$-$C_8$ alkyl;
each $R^8$ is independently selected from O—($C_1$-$C_8$ alkyl); and
the moiety —NR$^9$Z$^1$ is a phenylalanine bioisostere selected from the group consisting of

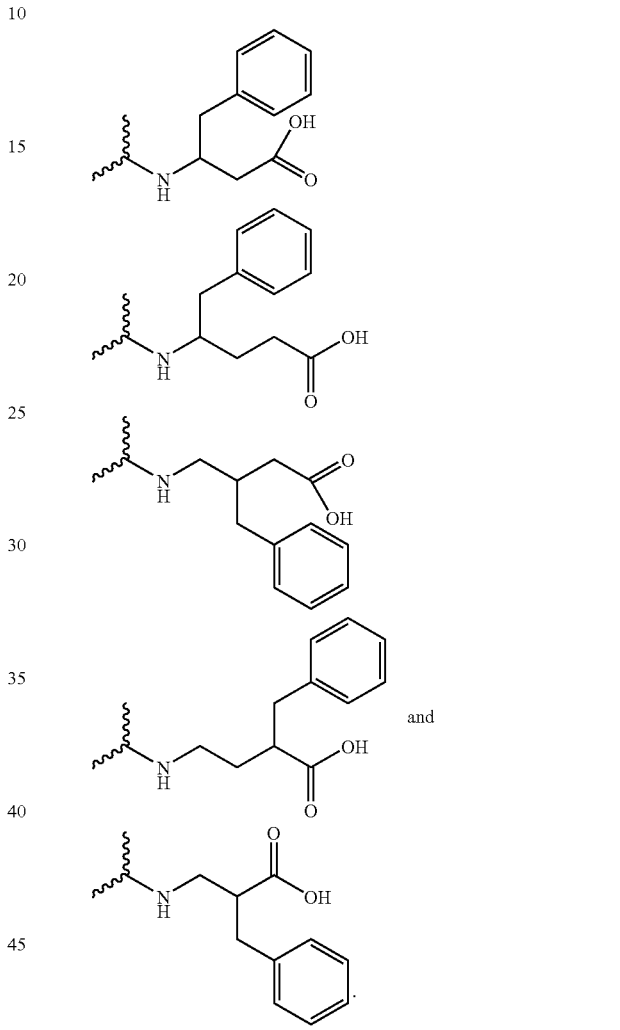

26. The compound of claim 25, wherein the phenylalanine bioisostere moiety is

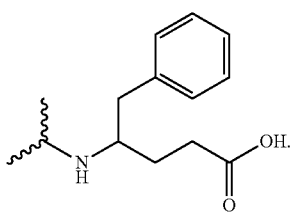 [SMILES: *NC(CCC(=O)O)Cc1ccccc1]

* * * * *